United States Patent
Zhao

(10) Patent No.: US 9,988,408 B2
(45) Date of Patent: Jun. 5, 2018

(54) CYTOTOXIC AGENTS FOR CONJUGATION TO A CELL BINDING MOLECULE

(71) Applicant: Hangzhou DAC Biotech Co., Ltd., Hangzhou (CN)

(72) Inventor: Robert Yongxin Zhao, Lexington, MA (US)

(73) Assignee: HANGZHOU DAC BIOTECH CO., LTD., Hangzhou (CN)

( * ) Notice: Subject to any disclaimer, the term of this patent is extended or adjusted under 35 U.S.C. 154(b) by 0 days. days.

(21) Appl. No.: 14/914,739

(22) PCT Filed: Sep. 2, 2013

(86) PCT No.: PCT/IB2013/058229
§ 371 (c)(1),
(2) Date: Feb. 26, 2016

(87) PCT Pub. No.: WO2015/028850
PCT Pub. Date: Mar. 5, 2015

(65) Prior Publication Data
US 2016/0207949 A1  Jul. 21, 2016

(51) Int. Cl.
| | |
|---|---|
| C07D 487/04 | (2006.01) |
| C07D 519/00 | (2006.01) |
| C07F 9/6561 | (2006.01) |
| C07F 9/553 | (2006.01) |
| C07F 9/6558 | (2006.01) |
| A61K 31/675 | (2006.01) |
| A61K 39/395 | (2006.01) |
| A61K 45/06 | (2006.01) |
| C07K 16/28 | (2006.01) |
| A61K 47/55 | (2017.01) |
| A61K 47/68 | (2017.01) |

(52) U.S. Cl.
CPC .......... *C07F 9/6561* (2013.01); *A61K 31/675* (2013.01); *A61K 39/3955* (2013.01); *A61K 45/06* (2013.01); *A61K 47/55* (2017.08); *A61K 47/6803* (2017.08); *A61K 47/6849* (2017.08); *C07F 9/5535* (2013.01); *C07F 9/65583* (2013.01); *C07K 16/2803* (2013.01); *C07K 16/2887* (2013.01); *C07K 2317/24* (2013.01); *C07K 2317/54* (2013.01); *C07K 2317/55* (2013.01); *C07K 2317/622* (2013.01); *C07K 2317/626* (2013.01); *C07K 2317/76* (2013.01)

(58) Field of Classification Search
CPC .......................... C07D 519/00; C07D 487/04
See application file for complete search history.

(56) References Cited

U.S. PATENT DOCUMENTS

| | | |
|---|---|---|
| 9,242,013 B2 | 1/2016 | Howard et al. |
| 2009/0036431 A1 | 2/2009 | Gauzy et al. |
| 2012/0244171 A1 | 9/2012 | Li et al. |

FOREIGN PATENT DOCUMENTS

| | | |
|---|---|---|
| CN | 101374846 A | 2/2009 |
| EP | 1 813 614 A1 | 8/2007 |
| JP | 2009-524636 A | 7/2009 |
| WO | 2005/040170 A2 | 5/2005 |
| WO | 2012/112687 A1 | 8/2012 |
| WO | 2012/112708 A1 | 8/2012 |
| WO | 2012/128868 A1 | 9/2012 |
| WO | 2013/041606 A1 | 3/2013 |

OTHER PUBLICATIONS

International Search Report (Form PCT/ISA/210) dated Jun. 5, 2014 by the State Intellectual Property Office of the People's Republic of China in corresponding International Patent Application No. PCT/IB2013/058229. (6 pages).
Written Opinion of the International Searching Authority (Form PCT/ISA/237) dated Jun. 5, 2014 by the State Intellectual Property Office of the People's Republic of China in corresponding International Patent Application No. PCT/IB2013/058229. (7 pages).
International Preliminary Report on Patentability (Form PCT/IPEA/409) dated Dec. 28, 2015 by the European Patent Office in corresponding International Patent Application No. PCT/IB2013/058229. (6 pages).
Supplementary International Search Report (Form PCT/SISA/501) dated Jan. 3, 2016 by the European Patent Office in corresponding International Patent Application No. PCT/IB2013/058229. (7 pages).
Adams et al., "Generating Improved Single-Chain Fv Molecules for Tumor Targeting," Journal of Immunological Methods, (1999), vol. 231, No. 1-2, pp. 249-260.
Almagro et al., "Humanization of Antibodies," Frontiers in Bioscience, (Jan. 1, 2008), vol. 13, pp. 1619-1633.
Almutairi et al., "Biodegradable Dendritic Positron-Emitting Nanoprobes for the Noninvasive Imaging of Angiogenesis," PNAS, (Jan. 20, 2009), vol. 106, No. 3, pp. 685-690.
Amsberry et al., "The Lactonization of 2'-Hydroxyhydrocinnamic Acid Amides: A Potential Prodrug for Amines," The Journal of Organic Chemistry, (1990), vol. 55, No. 23, pp. 5867-5877.
Antonow et al., "Synthesis of DNA-Interactive Pyrrolo[2,1-c][1,4]benzodiazepines (PBDs)," Chemical Reviews, (2011), vol. 111, No. 4, pp. 2815-2864.
Brannigan et al., "Protein Engineering 20 Years on," Nature Reviews Molecular Cell Biology, (Dec. 2002), vol. 3, No. 12, pp. 964-970.
Bross et al., "Approval Summary: Gemtuzumab Ozogamicin in Relapsed Acute Myeloid Leukemia," Clinical Cancer Research, (Jun. 2001), vol. 7, No. 6, pp. 1490-1496.
Burgess, "The Complex Mediators of Cell Growth and Differentiation," Immunology Today, (Jun. 1984), vol. 5, No. 6, pp. 155-158.
Burmeister Getz et al., "A Comparison between the Sulfhydryl Reductants Tris(2-carboxyethyl)phosphine and Dithiothreitol for Use in Protein Biochemistry," Analytical Biochemistry, (1999), vol. 273, No. 1, pp. 73-80.

(Continued)

*Primary Examiner* — Bruck Kifle
(74) *Attorney, Agent, or Firm* — Buchanan Ingersoll & Rooney PC

(57) ABSTRACT

The present invention is related to novel cytotoxic agents, pyrrolo[2,1-c][1,4]benzodiazepine (PBD) derivatives, their conjugates with a cell-binding agent, the preparation and the therapeutic uses in the targeted treatment of cancers, autoimmune disorders, and infectious diseases.

18 Claims, 23 Drawing Sheets

(56) References Cited

OTHER PUBLICATIONS

Cipolla et al., "Pyrrolo[2,1-c][1,4]benzodiazepine as a Scaffold for the Design and Synthesis of Anti-Tumour Drugs," Anti-Cancer Agents in Medicinal Chemistry, (2009), vol. 9, No. 1, pp. 1-31.
Clackson et al., "Making antibody fragments using phage display libraries," Nature, (Aug. 15, 1991), vol. 352, pp. 624-628.
Coiffier et al., "Safety and Efficacy of Ofatumumab, a fully Human Monoclonal Anti-CD20 Antibody, in patients with Relapsed or Refractory B-cell Chronic Lymphocytic Leukemia: a phase 1-2 study," Blood, (Feb. 1, 2008), vol. 111, No. 3, pp. 1094-1100.
Damayanthi et al., "Design and Synthesis of Novel Pyrrolo[2,1-c][1,4]benzodiazepine-Lexitropsin Conjugates," Journal of Organic Chemistry, (1999), vol. 64, No. 1, pp. 290-292.
Dente et al., "Monoclonal Antibodies that Recognise Filamentous Phage: Tools for Phage Display Technology," Gene, (Oct. 11, 1994), vol. 148, Issue 1, pp. 7-13.
Dervan, "Design of Sequence-Specific DNA-Binding Molecules," Science, (Apr. 25, 1986), vol. 232, No. 4749, pp. 464-471.
Dhar et al., "Targeted Delivery of Cisplatin to Prostate Cancer Cells by Aptamer Functionalized Pt(IV) Prodrug-PLGA-PEG Nanoparticles," PNAS, (Nov. 11, 2008), vol. 105, No. 45, pp. 17356-17361.
Dijoseph et al., "Antibody-Targeted Chemotherapy with CMC-544: a CD22-Targeted Immunoconjugate of Calicheamicin for the Treatment of B-Lymphoid Malignancies," Blood, (Mar. 1, 2004), vol. 103, No. 5, pp. 1807-1814.
Dubowchik et al., "Receptor-Mediated and Enzyme-Dependent Targeting of Cytotoxic Anticancer Drugs," Pharmacology & Therapeutics, (1999), vol. 83, No. 2, pp. 67-123.
Dulbecco et al., "A Plaque Assay for the Polyoma Virus," Letters to the Editors, (1959), Virol. 8, pp. 396-397.
Garnett, "Targeted Drug Conjugates: Principles and Progress," Advanced Drug Delivery Reviews, (2001), vol. 53, No. 2, pp. 171-216.
Geoghegan et al., "Site-Directed Conjugation of Nonpeptide Groups to Peptides and Proteins via Periodate Oxidation of a 2-Amino Alcohol. Application to Modification at N-Terminal Serine," Bioconjugate Chem., (1992), vol. 3, No. 2, pp. 138-146.
Geysen et al., "Small Peptides Induce Antibodies with a Sequence and Structural Requirement for Binding Antigen Comparable to Antibodies Raised Against the Native Protein," PNAS, (Jan. 1985), vol. 82, No. 1, pp. 178-182.
Gregson et al., "Linker Length Modulates DNA Cross-Linking Reactivity and Cytotoxic Potency of C8/C8¢ Ether-Linked C2-exo-Unsaturated Pyrrolo[2,1-c][1,4]benzodiazepine (PBD) Dimers," Journal of Medicinal Chemistry, (2004), vol. 47, No. 5, pp. 1161-1174.
Gregson et al., "Synthesis of the First Example of a C2-C3/C2'-C3'-endo Unsaturated Pyrrolo[2,1-c][1,4] benzodiazepine Dimer," Bioorganic & Medicinal Chemistry Letters, (2001), vol. 11, pp. 2859-2862.
Griffin et al., "A Monoclonal Antibody Reactive with Normal and Leukemic Human Myeloid Progenitor Cells," Leukemia Research, (1984), vol. 8, No. 4, pp. 521-534.
Harrison et al., "Compendium of Organic Synthetic Methods," vol. 1, (1971), A Wiley-Interscience Publication, by John Wiley & Sons, Inc., (540 pages).
Harrison et al., "Compendium of Organic Synthetic Methods," vol. 2, (1974), A Wiley-Interscience Publication, by John Wiley & Sons, Inc., (450 pages).
Hartley et al., "SG2285, a Novel C2-Aryl-Substituted Pyrrolobenzodiazepine Dimer Prodrug That Cross-links DNA and Exerts Highly Potent Antitumor Activity," Cancer Research, (Sep. 1, 2010), vol. 70, No. 17, pp. 6849-6858.
Hartley, "The Development of Pyrrolobenzodiazepines as Antitumour Agents," Expert Opinion on Investigational Drugs, (2011), vol. 20, No. 6, pp. 733-744.
Hartley et al., "DNA interstrand cross-linking and in vivo antitumor activity of the extended pyrrolo[2,1-c][1,4] benzodiazepine dimer SG2057," Investigational New Drugs, (2012), vol. 30, No. 3, pp. 950-958.
Hay et al., "A 2-Nitroimidazole Carbamate Prodrug of 5-Amino-1-(Chloromethyl)-3-[(5,6,7-Trimethoxyindol-2-YL) Carbonyl]-1,2-Dihydro-3H-Benz[E]Indole (Amino-SECO-CBI-TMI) for use with ADEPT and GDEPT," Bioorganic & Medicinal Chemistry Letters, (1999), vol. 9, No. 15, pp. 2237-2242.
Hegedus et al., "Compendium of Organic Synthetic Methods," vol. 3 in the series originated by I.T. Harrison and S. Harrison, (1977), A Wiley-Interscience Publication, by John Wiley & Sons, Inc., (509 pages).
Hermanson, "Bioconjugate Techniques," Third Edition, Academic Press is an imprint of Elsevier, (2013), (200 pages).
Hoogenboom, "Overview of Antibody Phage-Display Technology and Its Applications," From: Methods in Molecular Biology, vol. 178: Antibody Phage Display: Methods and Protocols, (2002), pp. 1-37.
Hopton et al., "Nuclear Magnetic Resonance Solution Structures of Inter- and Intrastrand Adducts of DNA Cross-Linker SJG-136," Biochemistry, (2011), vol. 50, No. 21, pp. 4720-4732.
Houdebine, "Antibody Manufacture in Transgenic Animals and Comparisons with other Systems," Current Opinion in Biotechnology, (Dec. 1, 2002), vol. 13, Issue 6, pp. 625-629.
Howard et al., "Synthesis of a novel C2/C2'-aryl-substituted pyrrolo[2,1-c][1,4]benzodiazepine dimer prodrug with improved water solubility and reduced DNA reaction rate," Bioorganic & Medicinal Chemistry Letters, (2009), vol. 19, No. 22, pp. 6463-6466.
Hsieh et al., "A DC-81-indole conjugate agent suppresses melanoma A375 cell migration partially via interrupting VEGF production and stromal cell-derived factor-1α-mediated signaling," Toxicology and Applied Pharmacology, (2011), vol. 255, No. 2, pp. 150-159.
Hurley, "Pyrrolo(1,4)Benzodiazepine Antitumor Antibiotics. Comparative Aspects of Anthramycin, Tomaymycin and Sibiromycin," The Journal of Antibiotics, (May 1977), vol. 30, No. 5, pp. 349-370.
Hurley, "DNA and Associated Targets for Drug Design," Journal of Medicinal Chemistry, (Sep. 1989), vol. 32, No. 9, pp. 2027-2033.
Huse et al., "Generation of a Large Combinatorial Library of the Immunoglobulin Repertoire in Phage Lambda," Science, (Dec. 8, 1989), vol. 246, No. 4935, pp. 1275-1281.
Javier et al., "Aptamer-Targeted Gold Nanoparticles as Molecular-Specific Contrast Agents for Reflectance Imaging," Bioconjugate Chemistry, (Jun. 2008), vol. 19, No. 6, pp. 1309-1312.
Jenkins et al., "Structure of a Covalent DNA Minor Groove Adduct with a Pyrrolobenzodiazepine Dimer: Evidence for Sequence-Specific Interstrand Cross-Linking," Journal of Medicinal Chemistry, (1994), vol. 37, No. 26, pp. 4529-4537.
Kamal et al., "A new route for the synthesis of pyrrolo[2,1-c][1,4]benzodiazepine antibiotics via oxidation of cyclic secondary amine," Chemical Communications, (1996), pp. 385-386.
Kamal et al., "Synthesis of Pyrrolo[2,1-c][1,4]benzodiazepine Antibiotics via Azido Reductive Cyclization with HMDST," Tetrahedron Letters, (1996), vol. 37, No. 37, pp. 6803-6806.
Kamal et al., "Recent Developments in the Design, Synthesis and Structure-Activity Relationship Studies of Pyrrolo [2,1-c][1,4]benzodiazepines as DNA Interactive Antitumour Antibiotics," Current Medicinal Chemistry—Anti-Cancer Agents, (2002), vol. 2, No. 2, pp. 215-254.
Kamal et al., "Design, synthesis, and evaluation of mixed imine—amine pyrrolobenzodiazepine dimers with efficient DNA binding affinity and potent cytotoxicity," Bioorganic & Medicinal Chemistry, (2004), vol. 12, No. 20, pp. 5427-5436.
Kamal et al., "DNA binding potential and cytotoxicity of newly designed pyrrolobenzodiazepine dimers linked through a piperazine side-armed-alkane spacer," Bioorganic & Medicinal Chemistry, (2006), vol. 14, No. 2, pp. 385-394.
Kamal et al., "Carbazole—pyrrolo[2,1-c][1,4]benzodiazepine conjugates: design, synthesis, and biological evaluation," Med. Chem. Commun., (2011), vol. 2, pp. 780-788.
Kamal et al., "Synthesis, anticancer activity and apoptosis inducing ability of bisindole linked pyrrolo[2,1-c][1,4] benzodiazepine conjugates," Bioorganic & Medicinal Chemistry Letters, (2012), vol. 22, No. 1, pp. 571-578.

(56) References Cited

OTHER PUBLICATIONS

Kingsbury et al., "A Novel Peptide Delivery System Involving Peptidase Activated Prodrugs as Antimicrobial Agents. Synthesis and Biological Activity of Peptidyl Derivatives of 5-Fl uorouracil," Journal of Medicinal Chemistry, (1984), vol. 27, No. 11, pp. 1447-1451.
Kipriyanov et al., "Generation and Production of Engineered Antibodies," Molecular Biotechnology, (2004), vol. 26, No. 1, pp. 39-60.
Kumar et al., "Recent Developments in Novel Pyrrolo[2,1-c][1,4]Benzodiazepine Conjugates: Synthesis and Biological Evaluation," Mini Reviews in Medicinal Chemistry, (2003), vol. 3, No. 4, pp. 323-339.
Kumar et al., "Design, synthesis and in vitro cytotoxic studies of novel bis-pyrrolo[2,1][1,4] benzodiazepine-pyrrole and imidazole polyamide conjugates," European Journal of Medicinal Chemistry, (2005), vol. 40, No. 7, pp. 641-654.
Lazar et al., "A molecular immunology approach to antibody humanization and functional optimization," Molecular Immunology, (2007), vol. 44, No. 8, pp. 1986-1998.
Lee et al., "Designing Dendrimers for Biological Applications," Nature Biotechnology (Dec. 2005), vol. 23, No. 12, pp. 1517-1526.
Lee et al., "High-affinity Human Antibodies from Phage-displayed Synthetic Fab Libraries with a Single Framework Scaffold," Journal of Molecular Biology, (2004), vol. 340, No. 5, pp. 1073-1093.
Lee et al., "Pyrrolo[2,1-c][1,4]benzodiazepine and indole conjugate (IN6CPBD) has better efficacy and superior safety than the mother compound DC-81 in suppressing the growth of established melanoma in vivo," Chemico-Biological Interactions, (2009), vol. 180, No. 3, pp. 360-367.
Lei et al., "Binding of Monoclonal Antibodies against the Carboxyl Terminal Segment of the Nicotinic Receptor δ Subunit Suggests an Unusual Transmembrane Disposition of This Sequence Region," Biochemistry (1995), vol. 34, No. 20, pp. 6675-6688.
Leonard et al., "Epratuzumab, a Humanized Anti-CD22 Antibody, in Aggressive Non-Hodgkin's Lymphoma: Phase I/II Clinical Trial Results," Clinical Cancer Research, (Aug. 15, 2004), vol. 10, No. 16, pp. 5324-5334.
Li et al., "Human antibodies for immunotherapy development generated via a human B cell hybridoma technology," PNAS, (Mar. 7, 2006), vol. 103, No. 10, pp. 3557-3562.
Little et al., "Surface Display of Antibodies," Biotechnology Advances, (1994), vol. 12, Issue 3, pp. 539-555.
Liu et al., "Engineering Therapeutic Monoclonal Antibodies," Immunological Reviews, (2008), vol. 222, No. 1, pp. 9-27.
Lown et al., "Molecular Mechanism of Binding of Pyrrolo(1,4)Benzodiazepine Antitumour Agents to Deoxyribonucleic Acid—: Anthramycin and tomaymycin," Biochemical Pharmacology, (1979), vol. 28, No. 13, pp. 2017-2026.
Mansfield et al., "Recombinant RFB4 Immunotoxins Exhibit Potent Cytotoxic Activity for CD22-Bearing Cells and Tumors," Blood, (Sep. 1, 1997), vol. 90, No. 5, pp. 2020-2026.
Martin et al., "Sequence-Selective Interaction of the Minor-Groove Interstrand Cross-Linking Agent SJG-136 with Naked and Cellular DNA: Footprinting and Enzyme Inhibition Studies," Biochemistry, (Mar. 22, 2005), vol. 44, No. 11, pp. 1435-4147.
Masterson et al., "Synthesis and biological evaluation of novel pyrrolo[2,1-c][1,4]benzodiazepine prodrugs for use in antibody-directed enzyme prodrug therapy," Bioorganic & Medicinal Chemistry Letters, (2006), vol. 16, No. 2, pp. 252-256.
Medarova et al., "In vivo Imaging of siRNA Delivery and Silencing in Tumors," Nature Medicine, (Mar. 2007), vol. 13, No. 3, pp. 372-377.
Medina et al., "Targeted Liposomal Drug Delivery in Cancer," Current Pharmaceutical Design, (2004), vol. 10, No. 24, pp. 2981-2989.
Molina et al., "Synthesis of Pyrrolo[2,1-c][1,4]benzodiazepines via an Intramolecular Aza-Wittig Reaction. Synthesis of the Antibiotic DC-81," Tetrahedron, (1995), vol. 51, No. 19, pp. 5617-5630.

Nadler et al., "B4, A Human B Lymphocyte-Associated Antigen Expressed on Normal, Mitogen-Activated, and Malignant B Lymphocytes," The Journal of Immunology, (Jul. 1983), vol. 131, No. 1, pp. 244-250.
Niman et al., "Generation of Protein-Reactive Antibodies by Short Peptides is an Event of High Frequency: Implications for the Structural Basis of Immune Recognition," Proceedings of the National Academy of Sciences, (Aug. 1983), vol. 80, No. 16, pp. 4949-4953.
Nisonoff et al., "Separation of Univalent Fragments from the Bivalent Rabbit Antibody Molecule by Reduction of Disulfide Bonds," Archives of Biochemistry and Biophysics, (1960), vol. 89, No. 2, pp. 230-244.
O'Keefe et al., "Characterization of a Transferrin-Diphtheria Toxin Conjugate," The Journal of Biological Chemistry, (Jan. 25, 1985), vol. 260, No. 2, pp. 932-937.
O'Neil et al., "The synthesis and biological activity of C2-fluorinated pyrrolo[2,1-c][1,4]benzodiazepines," Tetrahedron Letters, (2003), vol. 44, No. 42, pp. 7809-7812.
Parham, "On the Fragmentation of Monoclonal IgG1, IgG2a, and IgG2b from BALB/c mice," The Journal of Immunology, (Dec. 1983), vol. 131, No. 6, pp. 2895-2902.
Pawlak-Byczkowska et al., "Two New Monoclonal Antibodies, EPB-1 and EPB-2, Reactive with Human Lymphoma," Cancer Research, (Aug. 15, 1989), vol. 49, No. 16, pp. 4568-4577.
Plückthun, "Mono-and Bivalent Antibody Fragments Produced in *Escherichia coli*: Engineering, Folding and Antigen Binding," Immunological Reviews, (1992), vol. 130, No. 1, pp. 151-188.
Purnell et al., "DNA interstrand crosslinking agents: Synthesis, DNA interactions, and cytotoxicity of dimeric achiral seco-amino-CBI and conjugates of achiral seco-amino-CBI with pyrrolobenzodiazepine (PBD)," Bioorganic & Medicinal Chemistry Letters, (2006), vol. 16, No. 21, pp. 5677-5681.
Rahman et al., "The Pyrrolobenzodiazepine Dimer SJG-136 Forms Sequence-Dependent Intrastrand DNA Cross-Links and Monoalkylated Adducts in Addition to Interstrand Cross-Links," Journal of the American Chemical Society, (2009), vol. 131, No. 38, pp. 13756-13766.
Rahman et al., "Antistaphylococcal activity of DNA-interactive pyrrolobenzodiazepine (PBD) dimers and PBD-biaryl conjugates," Journal of Antimicrobial Chemotherapy, (2012), vol. 67, No. 7, pp. 1683-1696.
Rahman et al., "GC-Targeted C8-Linked Pyrrolobenzodiazepine-Biaryl Conjugates with Femtomolar in Vitro Cytotoxicity and in Vivo Antitumor Activity in Mouse Models," Journal of Medicinal Chemistry, (2013), vol. 56, No. 7, pp. 2911-2935.
Rodrigues et al., "Synthesis and β-Lactamase-Mediated Activation of a Cephalosporin-taxol Prodrug," Chemistry & Biology, (Apr. 1995), vol. 2, No. 4, pp. 223-227.
Sagnou et al., "Design and Synthesis of Novel Pyrrolobenzodiazepine (PBD) Prodrugs for ADEPT and GDEPT," Bioorganic & Medicinal Chemistry Letters, (2000), vol. 10, No. 18, pp. 2083-2086.
Seifert et al., "Inter- and intrastrand DNA crosslinks by 2-fluoro-substituted pyrrolobenzodiazepine dimers: stability, stereochemistry and drug orientation," Organic & Biomolecular Chemistry, (2012), vol. 10, pp. 6850-6860.
Shimizu et al., "Prothracarcin, A Novel Antitumor Antibiotic," The Journal of Antibiotics, (Aug. 1982), vol. 35, No. 8, pp. 972-978.
Skerra, "Bacterial Expression of Immunoglobulin Fragments," Current Opinion in Immunology, (1993), vol. 5, No. 2, pp. 256-262.
Smellie et al., "Sequence-Selective Recognition of Duplex DNA through Covalent Interstrand Cross-Linking: Kinetic and Molecular Modeling Studies with Pyrrolobenzodiazepine Dimers," Biochemistry, (2003), vol. 42, No. 27, pp. 8232-8239.
Smith, "Compendium of Organic Synthetic Methods," vol. 13, 2014 by John Wiley & Sons, Inc., (128 pages).
Spring et al., "Allotypic Markers on Fab Fragments of Mouse Immunoglobulins," The Journal of Immunology, (Aug. 1974), vol. 113, No. 2, pp. 470-478.
Strom et al., "Effect of Small Changes in Orientation on Reaction Rate," Journal of the American Chemical Society, (Aug. 9, 1972), vol. 94, No. 16, pp. 5815-5825.

(56) References Cited

OTHER PUBLICATIONS

Szardenings, "Phage Display of Random Peptide Libraries: Applications, Limits, and Potential," Journal of Receptors and Signal Transduction, (2003), vol. 23, No. 4, pp. 307-349.
Thurston et al., "Synthesis of DNA-Interactive Pyrrolo[2,1-c][1,4]benzodiazepines," Chemical Reviews, (1994), vol. 94, No. 2, pp. 433-465.
Thurston et al., "Synthesis of Sequence-Selective C8-Linked Pyrrolo[2,1-c][1,4]benzodiazepine DNA Interstrand Cross-Linking Agents," The Journal of Organic Chemistry, (1996), vol. 61, No. 23, pp. 8141-8147.
Tiberghien et al., "An asymmetric C8/C8'-tripyrrole-linked sequence-selective pyrrolo[2,1-c][1,4]benzodiazepine (PBD) dimer DNA interstrand cross-linking agent spanning 11 DNA base," Bioorganic & Medicinal Chemistry Letters, (2008), vol. 18, No. 6, pp. 2073-2077.
Wilkinson et al., "Preliminary pharmacokinetic and bioanalytical studies of SJG-136 (NSC 694501), a sequence-selective pyrrolobenzodiazepine dimer DNA-cross-linking agent," Investigational New Drugs, (Sep. 2004), vol. 22, No. 3, pp. 231-240.
Zhang, "Ofatumumab," mAbs, (2009), vol. 1, No. 4, pp. 326-331.
Zhilina et al., "Synthesis and Evaluation of a Triplex-Forming Oligonucleotide-Pyrrolobenzodiazepine Conjugate," Bioconjugate Chemistry, (2004), vol. 15, No. 6, pp. 1182-1192.
Office Action (Communication pursuant to Article 94(3) EPC) dated Jan. 26, 2017 by the European Patent Office in corresponding European Patent Application No. 13 892 435.2-1452. (5 pages).
Notice of grant for your patent issued Feb. 9, 2017, by the Australian Patent Office in corresponding Australian Patent Application No. 2012395148. (2 pages).
Examination Report No. 1 dated Oct. 3, 2017, by IP Australia in corresponding Australian Patent Application No. 2013399485. (4 pages).
Notification of Reasons for Refusal dated May 30, 2017, by the Japanese Patent Office in corresponding Japanese Patent Application No. 2016-537393 and an English Translation of the Notification. (4 pages).
Communication pursuant to Article 94(3) EPC dated Jul. 20, 2017, by the European Patent Office in corresponding European Patent Application No. 13 892 435.2. (3 pages).

CYTOTOXIC AGENTS FOR CONJUGATION TO A CELL BINDING MOLECULE

FIELD OF THE INVENTION

The present invention relates to novel cytotoxic agents, pyrrolo[2,1-c][1,4]benzodiazepine (PBD) derivatives and their therapeutic use. These novel cytotoxic agents have therapeutic use as a result of delivering the pyrrolo[2,1-c][1,4]benzodiazepine (PBD) derivatives to a specific targeted cell population by chemically linking these derivatives to a cell binding agent.

BACKGROUND OF THE INVENTION

Since the successful launches of Brentuximab vedotin (Adcetris) and Trastuzuinab emtansineo (Kadcyla), Antibody-drug conjugates (ADCs) have currently become a promising therapeutic modality for the clinical management of cancer. The new ADC compounds, which covalently incorporate the antitumor activity of a cytotoxic agent to a monoclonal antibody, have ability to deliver cytotoxic agents specifically to antigen-expressing tumor cells and then kill the tumor cells. The ADC platform includes a growing repertoire of cytotoxic agents, linker technologies, antibody properties, and conjugation methods. An important key factor in generating an optimal ADC is the cytotoxic agents.

Pyrrolo[2,1-c][1,4]benzodiazepines (PBDs) are a well-known class of sequence-selective DNA-binding agents derived from various *Streptomyces* species. Well-known members of this include DC-81, tomaymycin, porothramycin B, prothracarcin, mazethramycin, porothramycin, prothracarcin, sibanomycin, neothramycin, chicamycin, abbemycin, sibiromycin and anthramycin (I. O'Neil et al. Tetrahedron Letters 2003, 44, 7809-7812; L. Cipolla, et al, Anti-Cancer Agents in Medicinal Chemistry, 2009, 9, 1-31; L. Hurley, J. Antibiot. 1977, 30, 349; K. Schim/zu, et al. J. Antibiot 1982, 35, 992; J. Lown, et al. Biochem. Pharmacol. 1979, 28, 2017; D. Thurston, et al. Chem. Rev. 1994, 94, 433; P. Molina, et al. Tetrahedron 1995, 51, 5617; A. Kamal, et al. Chem. Commun. 1996, 385; A. Kamal, et al. Tetrahedron Lett. 1996, 37, 6803). These agents exert their antitumor antibiotics activity by the formation of a covalent adduct in the minor groove of a DNA with preference of a three base pairs of Pu-G-Pu (where Pu=purine; G=guanine) sequences, wherein their C11-position is electrophilic, enabling the molecules to alkylate the $NH_2$ group of a guanine in the minor groove of DNA (Thurston, D. Molecular Aspects of Anticancer Drug-DNA Interactions; The Macmillan Press Ltd.: London, UK, 1993, pp 54-88, D. Antonow and D. Thurston, Chem. Rev. 2011, 111, 2815-2864; P. Dervan, Science 1989, 232, 464; L. Hurley, J. Med. Chem. 1989, 32, 2027; D. Thurston, Chem. Br. 1990, 26, 767). Moreover, PBDs have potential not only as antitumor agents but also as gene regulators and probes of DNA structure (Hurley, L. J. Med. Chem. (1989), 32: 2027-2033).

Thurston and co-workers reported the first C8/C8'-linked PBD dimer (DSB-120) in which two DC-81 subunits are joined through their aromatic A-ring at phenol positions by an inert propyldioxy linkage (D. Thurston, et al., J. Org. Chem. 1996, 61, 8141). These C8/C8'-diether-linked PBD dialers exhibit higher DNA binding affinity, at least twice compared to the monomer DC-81. The three carbon space ((n=3) C8/C8'-linked PBD dimer analog (DSB-120) covalently bind to a 5'-Pu-GATC-Py sequence by crosslinking opposite-strand guanines separately by 2 base pairs, span six DNA base pairs (Rahman, K. et al J. Am. Chem. Soc. (2009), 131(38), 13756-13766; Martin, C. et al Biochemistry (2005), 44(11), 4135-4147). The more extended PBD dimer (n=5) can span an extra base pair and cross-link the 5'-Pu-GA(T/A)TC-Py sequence (S. Hopton and A. Thompson, Biochemistry 2011, 50(21), 4720-4732, M. Smellie, et al, Biochemistry 2003, 42(27), 8232-8239; Gregson, S. et al J. Med. Chem. (2004), 47(5), 1161-1174). Among the C8/C8'-linked dimmers, the one with five carbon chain showed the highest cytotoxicities in most of the tested cell lines (Thurston, D. et al., J. Org. Chem. 1996, 61, 8141; Kamal, A. et al., Curr. Med. Chem.—Anti-cancer Agents, 2002, 2, 215-254, Gregson, S. et al J. Med. Chem. (2004), 47(5), 1161-1174). Since the introduction of C8/C8'-linked PBD dimer, a number of structurally modified PBD dimers have been synthesized and evaluated for their biological activity, particularly for their DNA binding ability and antitumor activity (see U.S. Pat. Nos. 8,383,618; 8,372,831; 8,217,167; 8,318,726; 8,153,627; 7,754,694; 7,741,319; 7,704,924; 7,612,062; 7,608,615; 7,557,099; 7,528,128; 7,528,126; 7,476,664; 7,465,724; 7,429,658; 7,407,951; 7,312,210; 7,265,105; 7,189,710; 7,183,054; 7,173,026; 7,067,511; 7,056,913; 7,049,311; 7,015,215; 6,979,684; 6,951,853; 6,939,869; 6,884,799; 6,800,622; 6,683,073; 6,660,856; 6,562,806; 6,362,331; Seifert, J. et al, Org. Biomol. Chem. (2012), 10(34), 6850-6860; Rahman, K et al J. Antimicro. Chem. (2012), 67(7), 1683-1696. Hartley, J. et al Cancer Research (2010), 70(17), 6849-6858; Hartley, J. et al Invest. New Drugs (2012), 30(3), 950-958; Howard, P. et al WO 2011130613; Hartley, J. et al Expert Opin. Invest. Drugs (2011), 20(6), 733-744; Howard, P. et al Bioorg. Med. Chem. Lett. (2009), 19(22), 6463-6466; Cipolla, L. et al Anti-Cancer Agents Med. Chem. (2009), 9(1), 1-31; Tiberghien, Ar. Bioorg. Med. Chem. Lett. (2008), 18(6), 2073-2077; Purnell, B. et al Bioorg. Med. Chem. Lett. (2006), 16(21), 5677-5681; Kamal, A. Bioorg. Med. Chem. (2006), 14(2), 385-394; Howard, P. et al WO 2005085259; Kumar, R. et al Eur. J. Med. Chem, (2005), 40(7), 641-654; Kamal, A. et al Bioorg. Med. Chem. (2004), 12(20), 5427-5436; Wilkinson, G. Invest. New Drugs (2004), 22(3), 231-240; Kumar, R. et al Mini-Reviews Med. Chem. (2003), 3(4), 323-339; Gregson, S. et al Bioorg. Med. Chem. Lett. (2001), 11(21), 2859-2862; Reddy, B. et al Anti-Cancer Drug Design (2000), 15(3), 225-238; Damayanthi, Y. et al J Org Chem 1999, 64, 290-292). Some structures of these dimers are shown in the Table 1. Interestingly, only the PBD dimers which have flexible linkers between two PBD subunits to form none distorting interstrand cross-links within the minor groove of DNA have been shown significantly increased the potency comparing to the PBD monomer. So far, a number of these compounds have been selected for preclinical studies but unfortunately most of them did not proceed beyond that stage mainly because of problems related to poor bioavailability. Therefore some of these PBD dimers have been conjugated to a cell binding agent, such as an antibody to enhance their bioavailability and therapeutic efficacy (see U.S. Pat. Nos. 8,426,402; 8,404,678; 8,163,736; 8,097,238; Commercon, A., et al. WO 2012014147; FR 2963007, Howard, P., et al WO 2011130598; Howard, P. et al WO 2011130613; Howard, P. et al WO 2011130616; Commercon, A. et al WO 2011023883; Bouchard, H. et al WO 2009016516 Gauzy, L. et al Eur. Pat. Appl. EP 2019104; Gauzy, L.; Zhao, Robert; et al WO 2007085930; Masterson, L. Bioorg. Med. Chem. Let. (2006), 16(2), 252-256; Li, W. et al WO 2012128868; Fishkin, N. et al WO 2012112687; Chari, R. WO 2012112708; Zhilina, Z. et al Bioconj. Chem. (2004), 15(6), 1182-1192; Kamal, A. et al Med Chem Comm (2011), 2(8), 780-8. Masterson, L. et al Bioorg. Med. Chem. Lett. (2006), 16(2), 252-6; Sagnou, M. et al Bioorg. Med. Chem. Lett. (2000), 10(18), 2083-2086; Rahman, K. M., et al. J Med Chem 2013, 56, 2911-35; Kamal, A. et al. Bioorg Med Chem Lett 2012, 22, 571-8; Hsieh, M. C, et al. Toxicol Appl Pharmacol 2011, 255, 150-9; Lee, C. et al, Chem Biol Interact 2009, 180, 360-7; Reddy, B. et at Anticancer Drug Des 2000, 15, 225-38). However, the PBD dimers, even some of them have been modified as a prodrug in antibody drug conjugates (WO 2012014147; WO 2012128868, WO 2012112687; WO 2011130616; Howard, P. et al Bioorg. Med. Chem. Lett. (2009), 19, 6463-6), are hardly soluble in a water based buffer solution, resulting in significant amount of antibody or protein aggregation. Here we disclose novel PBD dimer derivatives which have good antitumor antibiotic activities and especially they are linkable and can facilitate conjugation to a cell surface binding ligand in a water based medium without leading to protein aggregation. Thus they can be used effectively in a conjugate with a cell binding molecule for treating cancers and immune disorders.

TABLE 1

Some of the published Pyrrolo[2,1-c][1,4]benzodiazepine (PBD) dimers

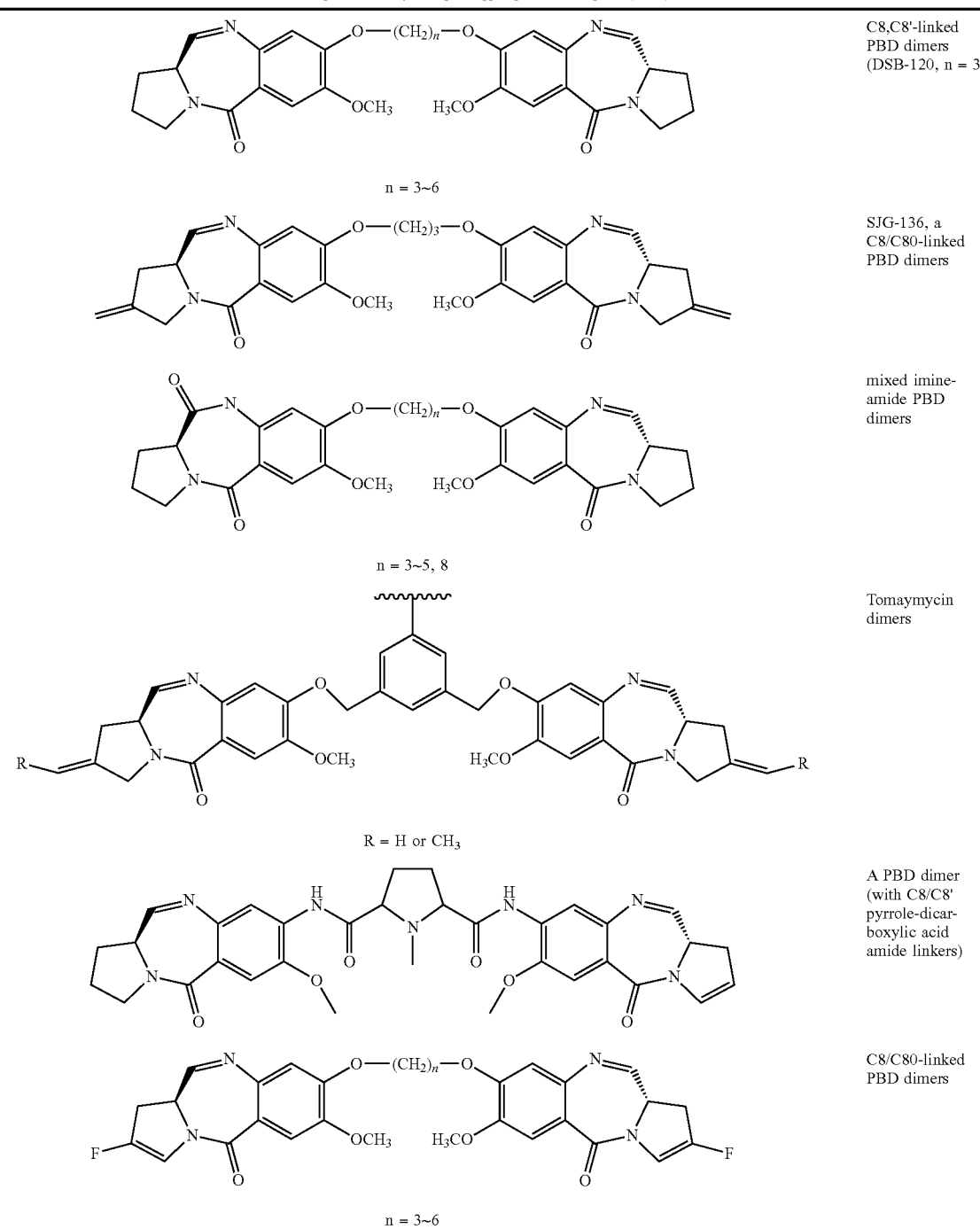

TABLE 1-continued

Some of the published Pyrrolo[2,1-c][1,4]benzodiazepine (PBD) dimers

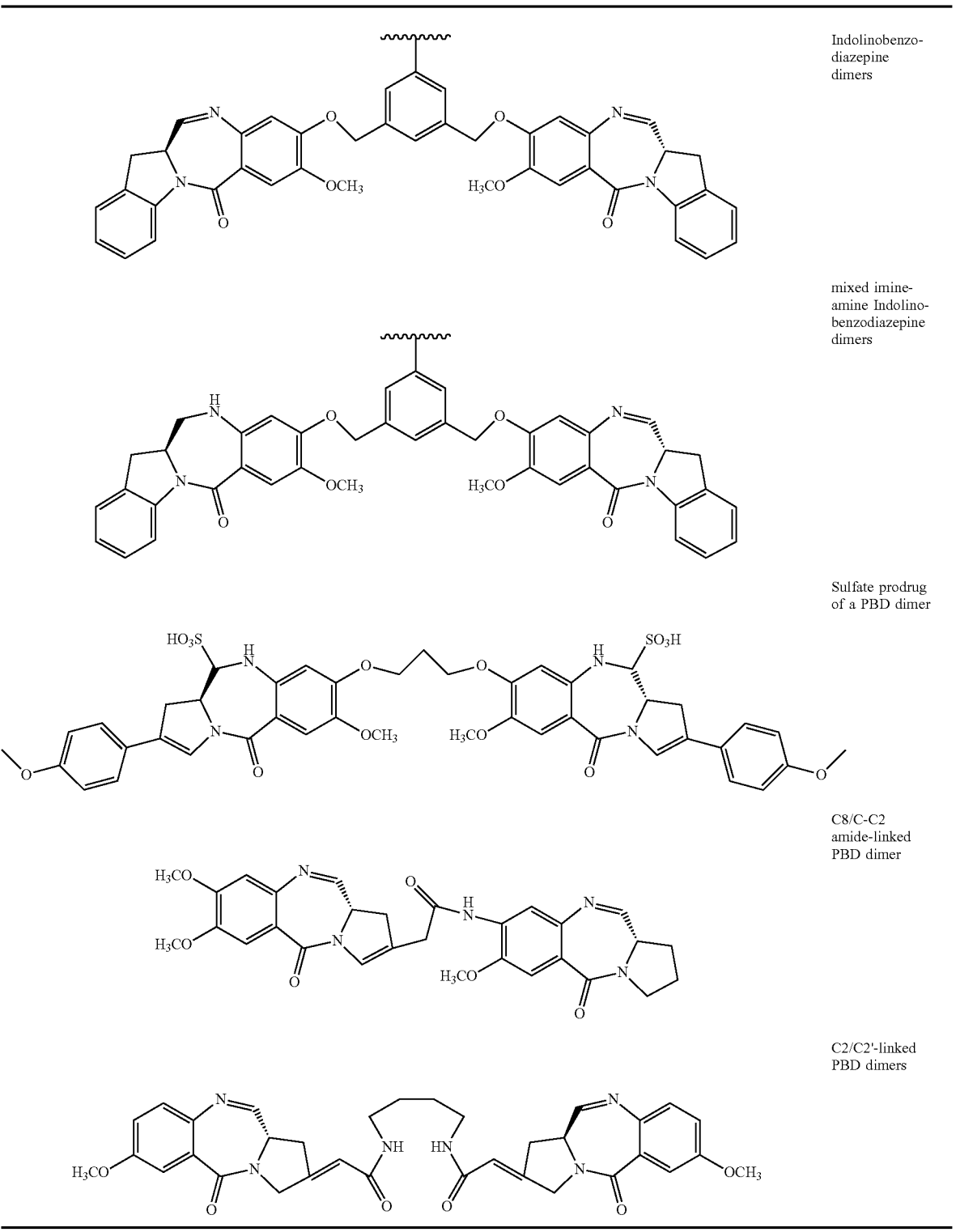

Indolinobenzo-
diazepine
dimers mixed imine-
amine Indolino-
benzodiazepine
dimers Sulfate prodrug
of a PBD dimer C8/C-C2
amide-linked
PBD dimer C2/C2'-linked
PBD dimers

SUMMARY OF THE INVENTION

The first embodiment of this invention is to disclose cytotoxic agents, specifically, pyrrolo[2,1-c][1,4]benzodiazepine derivatives which are potent cytotoxic agents and can be effectively used to block cell proliferation. In particular, this invention is to disclose novel pyrrolo[2,1-c][1,4]benzodiazepine derivatives, optionally linkable or linked to a cell binding agent to block cell proliferation. The novel cytotoxic agents and their conjugates to a cell binding agent of this invention are illustrated in the following formula (I):

(I)

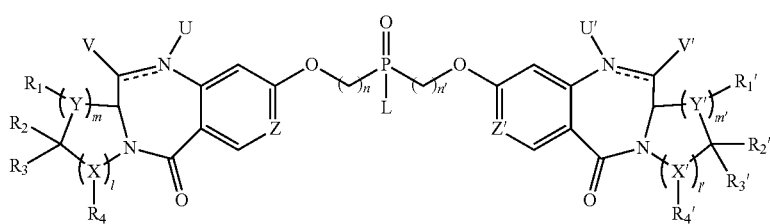

or their pharmaceutically acceptable salts, hydrates, or hydrated salts, or the polymorphic crystalline structures of these compounds or their optical isomers, racemates, diastereomers or enantiomers.

wherein

---- represents an optional single bond;

═══ represents either a single bond or a double bond;

It provided that when ═══ represents a single bond, U and U', the same or different, independently represent H; or the linking group (L') with the reactive group or a cell binding agent bonded thereto.

V and V', the same or different, are independently selected from the group consisting of H, OH, —NHOH; an ether (—OR$_5$); an ester (—OCOR$_5$, e.g. an acetate); a carbonate (—OCOOR$_5$); an amine (—NR$_5$R$_5$', —NR$_5$COR$_5$', —NR$_5$NR$_5$'NR$_5$''); a carbamate (—OCONR$_5$R$_5$'); a guanidinum (—NR$_5$(C═NH)NR$_5$'R$_5$''); an amino acid, or peptide (—NR$_5$CO(Aa)$_t$, wherein Aa is an amino acid or a polypeptide containing between t=1~100 amino acid units; a optionally substituted 5- or 6-membered nitrogen-containing heterocycle (such as piperidine, tetrahydropyrrole, pyrazole, morpholine); a cyclic carbamate, such that U and V, and/or U' and V' are a part of the cycle; a urea (—NR$_5$CONR$_5$'R$_5$''); a thiocarbamate (—OCSNHR$_5$); a cyclic thiocarbamate such that U and V, and U' and V' are a part of the cycle; a thiol (—SH); a sulfide such as —SR$_5$; a sulphoxide (—SOR$_5$); a sulfone (—SOOR$_5$); a sulphite (—SO$_3$, HSO$_3$, HSO$_2$, or a salt of HSO$^{3-}$, SO$_3^{2-}$ or —HSO$_2^-$); a bisulphite (—OSO$_3$); a sulfonamide (—NR$_5$SOOR$_5$'); metabisulfite (H$_2$S$_2$O$_5$ or a salt of S$_2$O$_5^{2-}$); Mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$, PS$_4^{3-}$); thiophosphate ester (R$_5$O)$_2$POSR$_5$'); thiosulfate (HS$_2$O$_3$ or a salt of S$_2$O$_3^{2-}$); dithionite (HS$_2$O$_4$ or a salt of S$_2$O$_4^{2-}$); phosphorodithioate (P(═S)(OR$_5$)(S)(OH) or a salt thereof form with a cation); optionally cyclic amine such that U and V, and U' and V' are a part of the cycle; a hydroxylamine derivative (—NR$_5$OR$_5$'); hydroxamic acid (R$_5$C(═O)NOH or a salt formed with a cation); formaldehyde sulfoxylate (HOCH$_2$SO$_2^-$, or its salts); an amide (—NR$_5$COR$_5$); an azido (—N$_3$); a cyano; a halo; a trialkyl, a phosphoramidate (phosphoramidic acid), or triarylphosphonium; an amino-acid-derived group; or the linking group (L') with the reactive group or a cell binding agent bonded thereto. The R$_5$, R$_5'$ and R$_5$'' are described below.

and when ═══ represents a double bond, U and U' are absent; V and V' represent H;

l, m, n, l', m' and n' are the number 0, 1, 2, 3, 4, 5 or 6.

X, X', Y and Y' the same or different, independently, represent N, O, S, an alkyl, such as CH$_2$ or CHR$_5$, an alkene, such as ═CH— or ═CR$_5$—, an ether, such as —C(OR$_5$)H—.

Z and Z' the same or different, independently, represent N, CH, CR$_5$, COH or COR$_5$. R$_5$ is independently selected from C$_1$~C$_8$ alkyl and aryl.

R$_1$, R$_2$, R$_3$, R$_4$, R$_1$', R$_2$', R$_3$', and R$_4$' are the same or different and independently chosen from —H, an optionally substituted linear, branched or cyclic alkyl, alkenyl or alkynyl having from 1 to 10 carbon atoms, a polyethylene glycol unit —(OCH$_2$CH$_2$)$_r$R$_5$, halogen, guanidinium [—NH(C═NH)NH$_2$], —OR$_5$, —NR$_5$R$_5$', —NO$_2$, —NCO, —NR$_5$COR$_5$', —SR$_5$, a sulfoxide represented by —SOR$_5$, a sulfone represented by —SO$_2$R$_5$, a sulfonate —SO$_3^-$M$^+$, —SO$_3$H, a sulfate —OSO$_3^-$M$^+$, OSO$_3$H, a sulfonamide represented by —SO$_2$NR$_5$R$_5$', cyano, an azido, —COR$_5$, —OCOR$_5$, —OCONR$_5$R$_5$', CF$_3$, OR$_5$, Aryl, heterocycle, or P(O)R$_5$R$_5$'R$_5$'' and the linking group (L') with the reactive group or a cell binding agent bonded thereto;

R$_5$, R$_5$' and R$_5$'' are independently selected from H, C$_1$~C$_8$ of alkyl, alkenyl, alkinyl, heteroalkyl, aryl, arylalkyl, carbonylalkyl, or pharmaceutical salts. R$_5$, R$_5'$ and R$_5$'' can further be substituted with at least one substituent selected from —N(R$_1$)(R$_2$), —CO$_7$H, —SO$_3$H, —PO$_2$R$_1$R$_2$, POR$_1$R$_2$R$_3$ and —PO$_3$H.

q=0, 1 or 2.

In addition, R$_2$ and R$_3$ join together, or R$_2$' and R$_3$' join together to form a ═ (double bond), ═O (ketone), ═S, ═NR$_5$, —C(═O)R$_5$, or a double bond containing group ═CR$_5$R$_5$'; and R$_1$ and R$_2$ join together, or and R$_2$' join together, or R$_3$ and R$_4$ join together, or R$_3$' and R$_4$' join together form an aromatic, heterocyclic, or heteroaryl ring.

L and L' are the same or independently a linker or a linker-cell binding molecule (Q) covalently bound cluster, or a linker which has a functional group on the linker that enables reaction with a cell-binding agent (CBA). L, when is a linker, is preferred a releasable linker, which has the formula of: -Ww-(Aa)r-Tt-; or -Ww-(Aa)r-Tt-Q; or Q-Ww-(Aa)r-Tt-; wherein: W is a Stretcher unit; w is 0 or 1; Aa is independently an Amino Acid unit; r is independently an integer ranging from 0 to 100;

The Stretcher unit W independently contains a self-immolative or a non-self-immolative component, peptidyl units, a hydrazone bond, a disulfide, an ester, an oxime, an amide, or a thioether bond. The self-immolative unit includes, but is not limited to, aromatic compounds that are electronically similar to the para-aminobenzylcarbamoyl (PAB) groups such as 2-aminoimidazol-5-methanol derivatives, heterocyclic PAB analogs, beta-glucuronide, and ortho or para-aminobenzylacetals. Preferably, the self-immolative linker component has any one of the following structures:

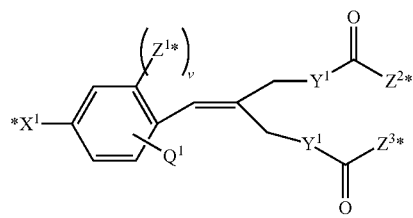

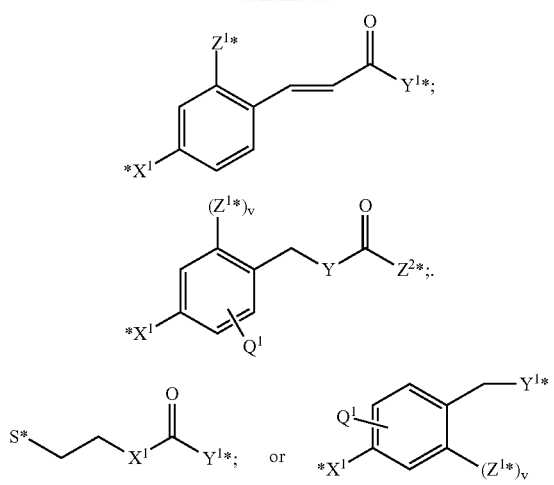

wherein the (*) atom is the point of attachment of additional spacer or releasable linker units, or the cytotoxic agent, and/or the binding molecule (CBA); $X^1$, $Y^1$, $Z^2$ and $Z^3$ are independently NH, or O, or S; $Z^1$ is H, or NH, or O or S independently. v is 0 or 1; $Q^1$ is independently H, OH, $C_1$~$C_6$ alkyl, $(OCH_2CH_2)_nF$, Cl, Br, I, $OR_5$, or $SR_5$, $NR_5R_5'$, $N{=}NR_5$, $N{=}R_5$, $NR_5R_5'$, $NO_2$, $SOR_5R_5'$, $SO_2R_5$, $SO_3R_5$, $OSO_3R_5$, $PR_5R_5'$, $POR_5R_5'$, $PO_2R_5R_5'$, $OPO(OR_5)(OR_5')$, or $OCH_2PO(OR_5(OR_5')$ wherein $R_5$ and $R_5'$ are as defined above, preferably $R_5$ and $R_5'$ are independently selected from H, $C_1$~$C_8$ of alkyl; $C_2$~$C_8$ of alkenyl, alkynyl, heteroalkyl; $C_3$~$C_8$ of aryl, heterocyclic, carbocyclic, cycloalkyl, heterocycloalkyl, heteroaralkyl, alkylcarbonyl; or pharmaceutical cation salts.

The non-self-immolative linker component is any one of the following structures:

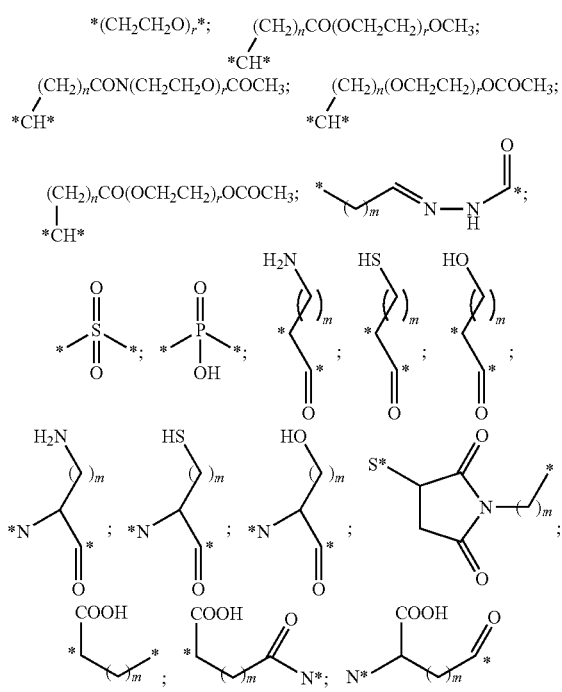

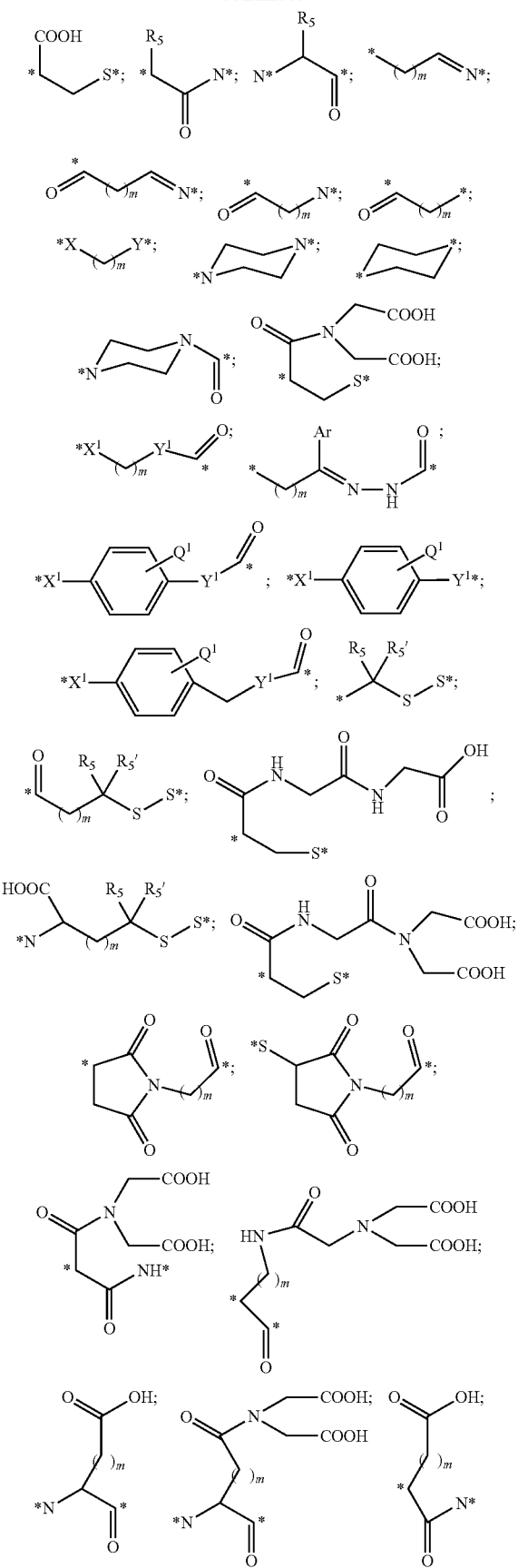

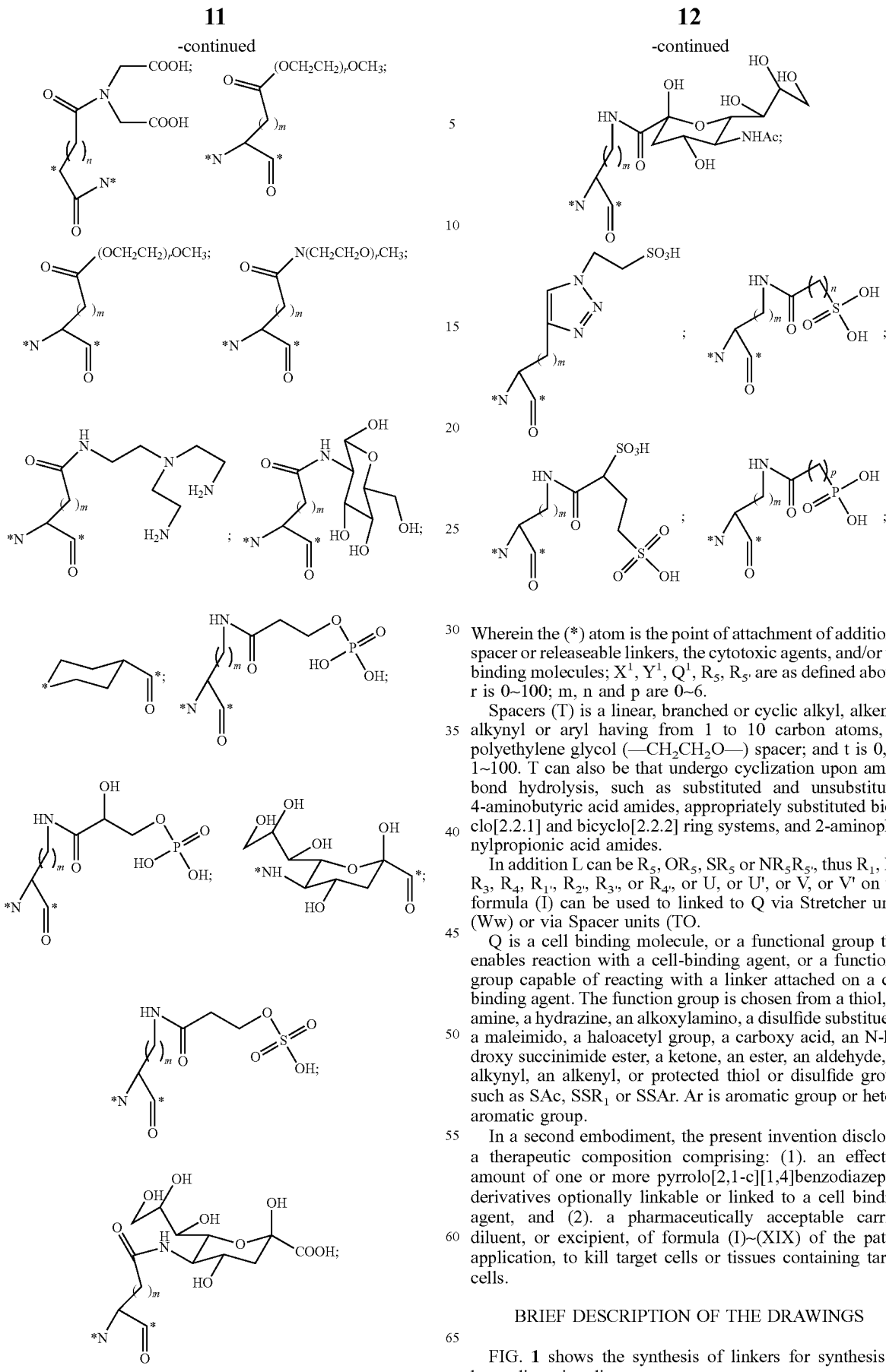

Wherein the (*) atom is the point of attachment of additional spacer or releaseable linkers, the cytotoxic agents, and/or the binding molecules; $X^1$, $Y^1$, $Q^1$, $R_5$, $R_{5'}$ are as defined above; r is 0~100; m, n and p are 0~6.

Spacers (T) is a linear, branched or cyclic alkyl, alkenyl, alkynyl or aryl having from 1 to 10 carbon atoms, or polyethylene glycol ($-CH_2CH_2O-$) spacer; and t is 0, or 1~100. T can also be that undergo cyclization upon amide bond hydrolysis, such as substituted and unsubstituted 4-aminobutyric acid amides, appropriately substituted bicyclo[2.2.1] and bicyclo[2.2.2] ring systems, and 2-aminophenylpropionic acid amides.

In addition L can be $R_5$, $OR_5$, $SR_5$ or $NR_5R_{5'}$, thus $R_1$, $R_2$, $R_3$, $R_4$, $R_{1'}$, $R_{2'}$, $R_{3'}$, or $R_{4'}$, or U, or U', or V, or V' on the formula (I) can be used to linked to Q via Stretcher units (Ww) or via Spacer units (TO.

Q is a cell binding molecule, or a functional group that enables reaction with a cell-binding agent, or a functional group capable of reacting with a linker attached on a cell binding agent. The function group is chosen from a thiol, an amine, a hydrazine, an alkoxylamino, a disulfide substituent, a maleimido, a haloacetyl group, a carboxy acid, an N-hydroxy succinimide ester, a ketone, an ester, an aldehyde, an alkynyl, an alkenyl, or protected thiol or disulfide group, such as SAc, $SSR_1$ or SSAr. Ar is aromatic group or hetero aromatic group.

In a second embodiment, the present invention discloses a therapeutic composition comprising: (1). an effective amount of one or more pyrrolo[2,1-c][1,4]benzodiazepine derivatives optionally linkable or linked to a cell binding agent, and (2). a pharmaceutically acceptable carrier, diluent, or excipient, of formula (I)~(XIX) of the patent application, to kill target cells or tissues containing target cells.

DETAILED DESCRIPTION OF THE INVENTION

Definitions

Figure 1:
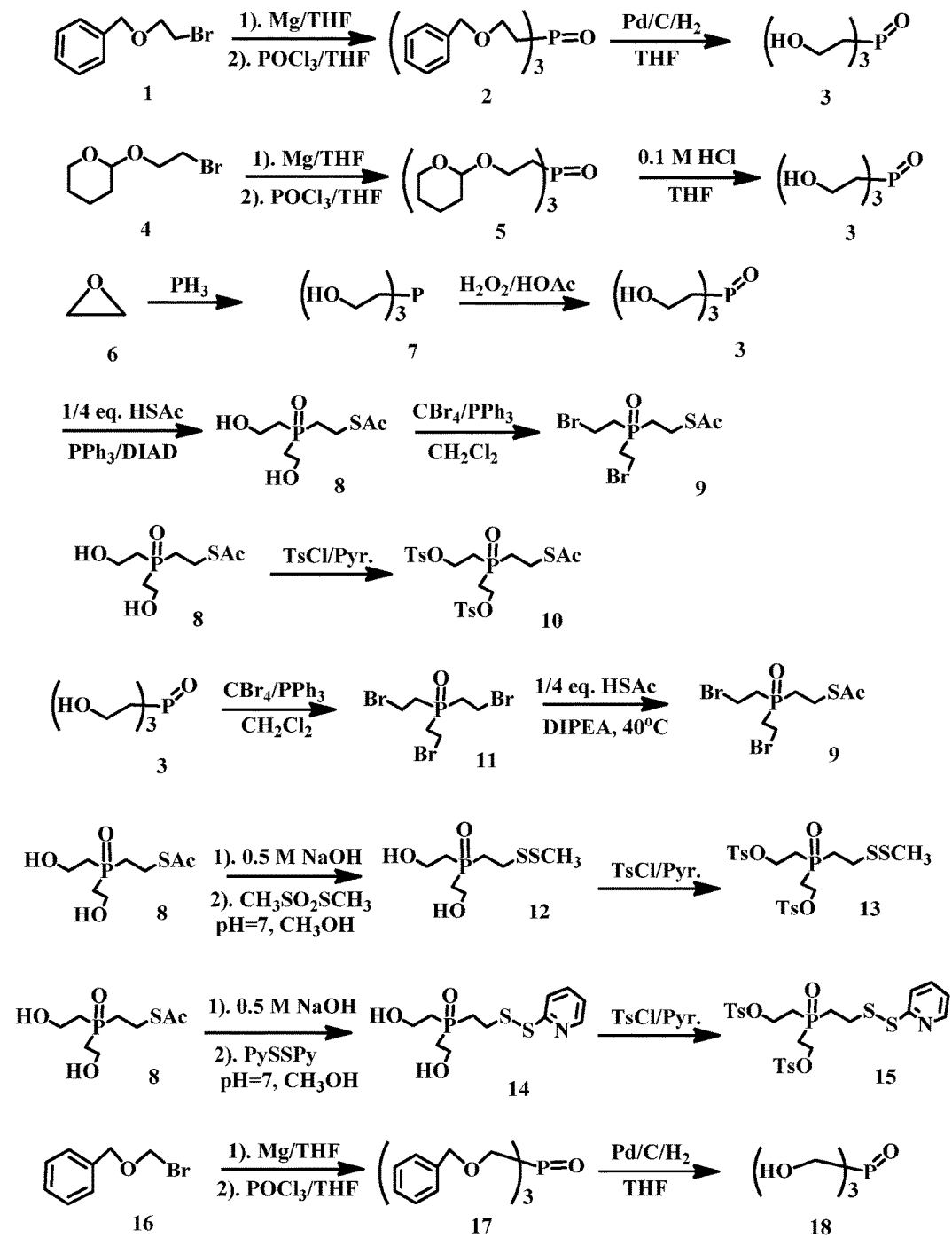
FIG. 1 shows the synthesis of linkers for synthesis of benzodiazepine dimers.

"Alkyl" means an aliphatic hydrocarbon group which may be straight or branched having 1 to 8 carbon atoms in the chain or cyclic. "Branched" means that one or much lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$~$C_8$ alkyl, —O—($C_1$~$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen (F, Cl, Br or I), —N$_3$, —NH$_2$, —NH(R'), —N(R')$_2$ and —CN; where each R' is independently selected from —$C_1$~$C_8$ alkyl and aryl.

A "cyclic alkyl", "cycloalkyl" and "$C_3$-$C_8$ carbocycle" can be used interchangeably. They mean a 3-, 4-, 5-, 6-, 7- or 8-membered saturated or unsaturated non-aromatic carbocyclic ring. Representative $C_3$-$C_8$ carbocycles include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatienyl, cyclooctyl, and cyclooctadienyl. A $C_3$~$C_8$ carbocycle group can be unsubstituted or substituted with one or more groups including, but not limited to, —$C_1$~$C_8$ alkyl, —OR$_5$, -aryl, —C(O)R$_5$, —OC(O)R$_5$, —C(O)OR$_5$, —C(O)NH$_2$, —C(O)NHR$_5$, —C(O)NR$_5$R$_5'$—NHC(O)R$_5$, —S(O)$_2$R$_5$, —S(O)R$_5$, —OH, -halogen, —N$_3$, —NH$_2$, —NHR$_5$, —NR$_5$R$_5'$ and —CN; wherein R$_5$ and R$_5'$ are independently H; $C_1$~$C_8$ of alkyl, alkenyl, alkynyl, heteroalkyl, aryl, arylalkyl, or carbonylalkyl; or pharmaceutical salts. R$_5$ and R$_5'$ can further be substituted with at least one substituent selected from —N(R$_5$)(R$_5'$), —CO$_2$H, —SO$_3$H, —OR$_5$, —CO$_2$R$_5$, —CONR$_5$, and —PO$_3$H.

A "$C_3$~$C_8$carbocyclo" refers to a $C_3$~$C_8$ carbocycle group defined above wherein one of hydrogen atoms on the carbocycle is replaced with a bond.

Alkenyl refers to an aliphatic hydrocarbon group containing a carbon-carbon double bond and which may be straight or branched having 2 to 8 carbon atoms in the chain. The alkenyl double bond may have "cis" and "trans" orientations, or alternatively, "E" and "Z" orientations. Exemplary alkenyl groups include, but are not limited to, ethylenyl or vinyl, propenyl or allyl, n-butenyl, i-butenyl, 3-methylbut-2-enyl, n-pentenyl, hexylenyl, heptenyl, octenyl.

"Alkynyl" or "alkinyl" means an aliphatic hydrocarbon group containing a carbon-carbon triple bond and which may be straight or branched having 2 to 8 carbon atoms in the chain. Exemplary alkynyl groups include ethynyl, propynyl, n-butynyl, 2-butynyl, 3-methylbutynyl, pentynyl, n-pentynyl, hexylynyl, heptynyl, and octynyl.

"Heteroalkyl" is $C_2$~$C_8$ alkyl in which one to four carbon atoms are independently replaced with a heteroatom from the group consisting of O, S and N.

"Heterocycle" refers to an aromatic or non-aromatic $C_3$~$C_{14}$ carbocycle in which one to four of the ring carbon atoms are independently replaced with a heteroatom from the group of O, N, P, S and Se. Preferable heteroatoms are oxygen, nitrogen and sulphur. Suitable heterocyclics are also disclosed in The Handbook of Chemistry and Physics, 76th Edition, CRC Press, Inc., 1995-1996, p 2-25 to 2-26, the disclosure of which is hereby incorporated by reference. Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrinidinyl, dihydrothiopyranyl, azepanyl, as well as the fused systems resulting from the condensation with a phenyl group.

"Aryl" or Ar refers to an aromatic or hetero aromatic group, composed of one or several rings, comprising three to fourteen carbon atoms, preferentially six to ten carbon atoms. The term of hetero aromatic group refers one or several carbon on aromatic group, preferentially one, two, three or four carbon atoms are replaced by O, N, Si, Se, P or S, preferentially by O, S, N. The term aryl or Ar also refers to a aromatic group, wherein one or several H atoms are replaced independently by alkyl, F, Cl, Br, I, O $R_5$, or $SR_5$, $NR_5R_{5'}$, N=$NR_5$, N=$R_5$, $NR_5R_{5'}$, $NO_2$, $SOR_5R_{5'}$, $SO_2R_5$, $SO_3R_5$, $OSO_3R_5$, $PR_5R_{5'}$, $POR_5R_{5'}$, $PO_5R_{5'}$, $OPO_3R_5R_{5'}$, or $PO_3R_5R_{5'}$ wherein $R_5$ and $R_{5'}$ are independently H, alkyl, alkenyl, alkinyl, heteroalkyl, aryl, arylalkyl, carbonyl, or pharmaceutical salts.

The term "heteroaryl" or aromatic heterocycles refers to a 5 to 14, preferably 5 to 10 membered aromatic hetero, mono-, bi- or multicyclic ring. Examples include pyrrolyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Halogen atom" refers to fluorine, chlorine, bromine or iodine atom; preferably bromine and chlorine atom.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, lactic and the like. Further addition salts include ammonium salts such as tromethamine, triethanolamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared by reaction of the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p 1418, the disclosure of which is hereby incorporated by reference.

The term "compound", "cytotoxic agent", "cytotoxic compound," "cytotoxic dimer" and "cytotoxic dimer compound" are used interchangeably. They are intended to include compounds for which a structure or formula or any derivative of thereof has been disclosed in the present invention or a structure or formula or any derivative thereof that has been incorporated by reference. The term also includes, stereoisomers, geometric isomers, tautomers, solvates, metabolites, salts pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "mine reactive reagent" refers to a reagent that is capable of reacting with an imine group. Examples of imine reactive reagent includes, but is not limited to, sulfites ($H_2SO_3$, $H_2SO_2$ or a salt of $HSO_3^-$, $SO_3^{2-}$ or $HSO_2$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R_5O)_2PS(OR_5$), $R_5SH$, $R_5SOH$, $R_5SO_2H$, $R_5SO_3H$), various amines (hydroxyl amine ($NH_2OH$), hydrazine ($NH_2NH_2$), $NH_2OR_5$, $R_5NHR_{5'}$, $NH_2R_5$), $NH_2$—CO—$NH_2$, $NH_2$—C(=S)—$NH_2$), thiosulfate ($H_2S_2O_3$ or a salt of $S_2O_3^{2-}$ formed with a cation), dithionite ($H_2S_2O_4$ or a salt of $S_2O_4^-$ formed with a cation), phosphorodithioate (P(=S)($OR_5$)(SH)(OH) or a salt thereof formed with a cation), hydroxamic acid ($R_5C$(=O)NHOH or a salt formed with a cation), hydrazide ($R_5CONHNH_2$), formaldehyde sulfoxylate ($HOCH_2SO_2H$ or a salt of $HOCH_2SO_2^-$ formed with a cation, such as $HOCH_2SO_2^-Na^+$), glycated nucleotide (such as GDP-mannose), fludarabine or a mixture thereof, wherein $R_5$ and $R_{5'}$ are each independently a linear or branched alkyl having 1 to 8 carbon atoms and can be substituted with at least one substituent selected from N($R_5$)($R_{5'}$), —$CO_2H$, —$SO_3H$, —$OR_5$, —$CO_2R_5$, —$CONR_5$, and —$PO_5H$; $R_5$ and $R_{5'}$ can be further optionally substituted with a substituent for an alkyl described herein; Preferably, the cation is a monovalent cation, such as $Na^+$ or $K^+$. Preferably, the imine reactive reagent is selected from sulfites, hydroxyl amine, urea and hydrazine. More preferably, the imine reactive reagent is $NaHSO_3$ or $KHSO_3$.

"Cell binding agents" or "Cell binding molecules" may be of any kind presently known, or those become known, and include peptides and non-peptides. Generally, these can be antibodies (especially monoclonal antibodies) or a fragment of an antibody that contains at least one binding site, lymphokines, hormones, growth factors, nutrient-transport molecules (such as transferrin), or any other cell binding molecule or substance (such as vitamins).

More specific examples of cell binding agents that can be used include:
monoclonal antibodies (mAb);
single chain antibodies;

fragments of antibodies such as Fab, Fab', F(ab')$_2$, F$_v$, {Parham, J. Immunol. 131, 2895-2902 (1983); Spring et al, J. Immunol. 113, 470-478 (1974); Nisonoff et al, Arch. Biochem. Biophys. 89, 230-244 (1960)}, fragments produced by a Fab expression library, anti-idiotypic (anti-Id) antibodies, CDR's, and epitope-binding fragments of any of the above which immunospecifically bind to cancer cell antigens, viral antigens or microbial antigens.

interferons;
peptides; or conjugated proteins or peptides;
lymphokines such as IL-2, IL-3, IL-4, IL-6;
hormones such as insulin, TRH (thyrotropin releasing hormones), MSH (melanocyte-stimulating hormone), steroid hormones, such as androgens and estrogens;
growth factors and colony-stimulating factors such as EGF, TGFα, insulin like growth factor (IGF-I, IGF-II) G-CSF, M-CSF and GM-CSF {Burgess, Immunology Today 5, 155-158 (1984)}; vitamins, such as folate and transferrin {O'Keefe et al, J. Biol. Chem. 260, 932-937 (1985)}.

Monoclonal antibodies (mAb), mAb single chain or fragments can be produced in the well known state of art technology. The technology permits the production of extremely selective cell binding agents in the form of specific monoclonal antibodies. The well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins.

Selection of appropriate cell binding agents is a matter of choice that depends upon the particular cell population that is to be targeted, but in general monoclonal antibodies are preferred if an appropriate one is available.

For example, an anti-CD20 antigen monoclonal antibody, known as Rituximab is a chimeric (mouse/human) monoclonal antibody and it was the first therapeutic antibody approved by the United States Food and Drug Administration for treatment of relapsed or refractory low-grade or follicular NHL (Leonard, J. P. et al., Clin. Canc. Res. 10:5327-5334 (2004)). Another anti-CD20 antibody, known as Ofatumumab, is a human monoclonal antibody targeting an epitope different from that of rituximab and most other CD20 directed antibodies. It was approved by US FDA for treating chronic lymphocytic leukemia and has also shown potential in treating Follicular non-Hodgkin's lymphoma, Diffuse large B cell lymphoma, rheumatoid arthritis and relapsing remitting multiple sclerosis (Coiffier, B. et al Blood 111: 1094-100 (2008); Zhang, B. MAbs 1 (4): 326-31 (2009)). A third-generation, humanized and glyco-engineered anti-CD20 mAb for the treatment of B-cell lymphoid malignancies named Afutuzumab (now called obinutuzumab) has been developed (Robak, T (2009) Current opinion in investigational drugs (London, England: 2000) 10 (6): 588-96). Obinutuzumab is fully humanized IgG1 type II anti-CD20 antibody and it selectivity binds to the extracellular domain of the human CD20 antigen on malignant human B cells. Similarly, an anti-CD19 antigen monoclonal antibody B4 is a murine IgG$_1$, that binds to the CD19 antigen on B cells {Nadler et al, 131 J. Immunol. 244-250 (1983)} and can be used if the target cells are B cells or diseased cells that express CD19 antigen such as in non-Hodgkin's lymphoma or chronic lymphoblastic leukemia. In addition, the anti-CD22 antibodies that include RFB4 (Mansfield, E. et al., Blood 90:2020-2026 (1997)), CMC-544 (DiJoseph, J. F., Blood 103:1807-1814 (2004)) and LL2 (Pawlak-Byczkowska, E. J. et al., Cancer Res. 49:4568-4577 (1989)) can be used as potential therapies for B cell cancers and other B cell proliferative diseases. The LL2 antibody (formerly called HPB-2) is an IgG2a mouse monoclonal antibody directed against the CD22 antigen (Pawlak-Byczkowska, E. J. et. al. Cancer Res. 49:4568-77 (1989)). Furthermore, the anti CD33 antigen monoclonal antibody, named Gemtuzumab was first monoclonal antibody conjugated with a cytotoxic drug to treat acute myelogenous leukemia (AML) (P. F. Bross et al Clin Cancer Res 7 (6): 1490-6). A similar anti CD33 antigen antibody, named My9-6 is a murine IgG$_1$ antibody that binds specifically to the CD33 Antigen {J. D. Griffin et al 8 Leukemia Res., 521 (1984)} and can be used to target cells express CD33 as in the disease of acute myelogenous leukemia (AML). Additionally, GM-CSF antibody which binds to myeloid cells can be used as a cell binding agent to diseased cells from acute myelogenous leukemia. IL-2 antibody, which binds to activated T-cells, can be used for prevention of transplant graft rejection, for therapy and prevention of graft-versus-host disease, and for the treatment of acute T-cell leukemia. MSH antibody, which binds to melanocytes, can be used for the treatment of melanoma.

Novel Cytotoxic Agents and their Conjugation of the Invention.

The PBD dimer derivatives according to the present invention comprises one or more pyrrolo[2,1-c][1,4]benzodiazepine derivatives, optionally linkable or linked to a cell binding agent via a linking group. The linking group is part of a chemical moiety that is covalently bound to a pyrrolo [2,1-c][1,4]benzodiazepine derivative through conventional methods.

The PBD dimer derivatives disclosed in the present invention have the formula (I) shown below:

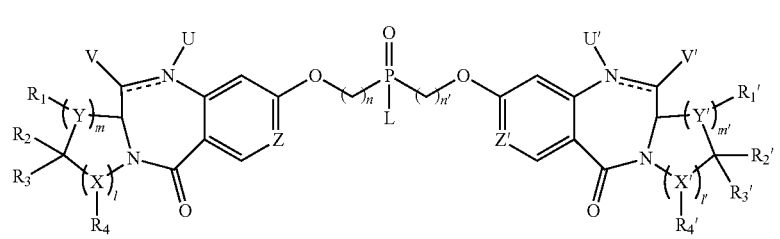

or their pharmaceutically acceptable salts, hydrates, or hydrated salts, or the polymorphic crystalline structures of these compounds or their optical isomers, racemates, diastereomers or enantiomers.

wherein
---- represents an optional single bond;
══ represents either a single bond or a double bond;

It provided that when ═ represents a single bond, U and U', the same or different, independently represent H; or the linking group (L') with the reactive group or a cell binding agent bonded thereto.

V and V', the same or different, are independently selected from the group consisting of OH, —NHOH; an ether (—$OR_5$); an ester (—$OCOR_5$ e.g. an acetate); a carbonate (—$OCOOR_5$); an amine (—$NR_5R_5'$, —$NR_5COR_5'$, —$NR_5NR_5'NR_5''$); a carbamate (—$OCONR_5R_5'$); a guanidinum (—$NR_5(C=NH)NR_5'R_5''$); an amino acid, or peptide (—$NR_5CO(Aa)_t$, wherein Aa is an amino acid or a polypeptide containing between t=1~100 amino acid units; a optionally substituted 5- or 6-membered nitrogen-containing heterocycle (such as piperidine, tetrahydropyrrole, pyrazole, morpholine); a cyclic carbamate, such that U and V, and/or U' and V' are a part of the cycle; a urea (—$NR_5CONR_5'R_5''$); a thiocarbamate (—$OCSNHR_5$); a cyclic thiocarbamate such that U and V, and U' and V' are a part of the cycle; a thiol (—SH); a sulfide such as —$SR_5$; a sulphoxide (—$SOR_5$); a sulfone (—$SOOR_5$); a sulphite (—$SO_3$, $HSO_3$, $HSO_2$, or a salt of $HSO^{3-}$, $SO_3^{2-}$ or —$HSO_2^-$); a bisulphite (—$OSO_3$); a sulfonamide (—$NR_5SOOR_5'$); metabisulfite ($H_2S_2O_5$ or a salt of $S_2O_5^{2-}$); Mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$, $PS_4^{3-}$); thiophosphate ester ($R_5O)_2POSR_5'$); thiosulfate ($HS_2O_3$ or a salt of $S_2O_3^{2-}$); dithionite ($HS_2O_4$ or a salt of $S_2O_4^{2-}$); phosphorodithioate (P(=S)($OR_5$)(S)(OH) or a salt thereof form with a cation); optionally cyclic amine such that U and V, and U' and V' are a part of the cycle; a hydroxylamine derivative (—$NR_5OR_5'$); hydroxarnic acid ($R_5C$(=O)NOH or a salt formed with a cation); formaldehyde sulfoxylate ($HOCH_2SO_2$, or its salts); an amide (—$NR_5COR_5$); an azido (—$N_3$); a cyano; a halo; a trialkyl, a phosphoramidate (phosphoramidic acid), or triarylphosphonium; an amino-acid-derived group; or the linking group (L') with the reactive group or a cell binding agent bonded thereto. The $R_5$, $R_5'$ and $R_5''$ are described below.

and when ═ represents a double bond, U and U' are absent; V and V' represent H;

l, m, n, l', m' and n' are the number 0, 1, 2, 3, 4, 5 or 6.

X, X', Y and Y' the same or different, independently, represent N, O, S, an alkyl, such as $CH_2$ or $CHR_5$, an alkene, such as =CH— or =$CR_5$—, an ether, such as —C($OR_5$) H—.

Z and Z' the same or different, independently, represent N, CH, $CR_5$, COH or $COR_5$. $R_5$ is independently selected from $C_1$~$C_8$ alkyl and aryl.

$R_1$, $R_2$, $R_3$, $R_4$, $R_1'$, $R_2'$, $R_3'$, and $R_4'$ are the same or different and independently chosen from —H, an optionally substituted linear, branched or cyclic alkyl, alkenyl or alkynyl having from 1 to 10 carbon atoms, a polyethylene glycol unit —($OCH_2CH_2)_nR_5$, halogen, guanidinium [—NH(C=NH)$NH_2$], —$OR_5$, —$NR_5R_5'$, —$NO_2$, —NCO, —$NR_5COR_5'$, —$SR_5$, a sulfoxide represented by —$SOR_5$, a sulfone represented by —$SO_2R_5$, a sulfonate —$SO_3^-M^+$, —$SO_3H$, a sulfate —$OSO_3^-M^+$, $OSO_3H$, a sulfonamide represented by —$SO_2NR_5R_5'$, cyano, an azido, —$COR_5$, —$OCOR_5$, —$OCONR_5R_5'$, $CF_3$, $OR_5$, Aryl, heterocycle, or P(O)$R_5R_5'R_5''$ and the linking group (L') with the reactive group or a cell binding agent bonded thereto;

$R_5$, $R_5'$ and $R_5''$ are independently selected from H, $C_1$~$C_8$ of alkyl, alkenyl, alkinyl, heteroalkyl, aryl, arylalkyl, carbonylalkyl, or pharmaceutical salts. $R_5$, $R_5'$ and $R_5'$ can further be substituted with at least one substituent selected from —N($R_1$)($R_2$), —$CO_2H$, —$SO_3H$, —$OR_1$, —$CO_2R_1$, —$CONR_1$, —$PO_2R_1R_2$, $POR_1R_2R_3$ and —$PO_3H$.

q=0, 1 or 2.

In addition, $R_2$ and $R_3$ join together, or $R_2'$ and $R_3'$ join together to form a ═ (double bond), =O (ketone), =S, =$NR_5$, —C(=O)$R_5$, or a double bond containing group =$CR_5R_5'$; and $R_1$ and $R_2$ join together, or $R_1'$ and $R_2'$ join together, or $R_3$ and $R_4$ join together, or $R_3'$ and $R_4'$ join together form an aromatic, heterocyclic, or heteroaryl ring.

L is a linker, or a linker-cell binding molecule covalently bound cluster, or a linker has a functional group on the linker that enables reaction with a cell-binding agent. L, when is a linker, is preferred a releasable linker, which is a chain of atoms selected from C, N, O, S, Si, B and P that covalently connects the cell-surface binding ligand (CBA) to the PBD derivatives. The linker may have a wide variety of lengths, such as in the range from about 2 to about 100 atoms. The atoms used in forming the linker may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, acyloxylamines, oximes, aldoximes, ketoximes, amidoximes, hydroxamic acids, and many others. In addition, it is to be understood that the atoms forming the releasable linker (L) may be either saturated or unsaturated, or may be radicals, or may be cyclized upon each other to form divalent cyclic structures, including cyclo alkanes, cyclic ethers, cyclic amines, arylenes, heteroarylenes, and the like in the linker.

Preferably L has the formula of: -Ww-(Aa)r-Tt-; or -Ww-(Aa)r-Tt-Q; or Q-Ww-(Aa)r-Tt-; wherein: W is a Stretcher unit; w is 0 or 1; Aa is independently an amino acid unit; r is independently an integer ranging from 0 to 100; The Stretcher unit W may independently contain a self-immolative or a non-self-immolative component, peptidyl units, a hydrazone bond, a disulfide, an ester, oxime, or thioether bonds. The examples of self-immolative units include, but are not limited to, aromatic compounds that are electronically similar to the para-aminobenzylcarbamoyl (PAB) group such as 2-aminoimidazol-5-methanol derivatives (Hay et al. (1999) Bioorg. Med. Chem. Lett. 9, 2237), heterocyclic PAB analogs, beta-glucuronide, and ortho or para-aminobenzylacetals.

Preferably, the self-immolative linker component has any one of the following structures:

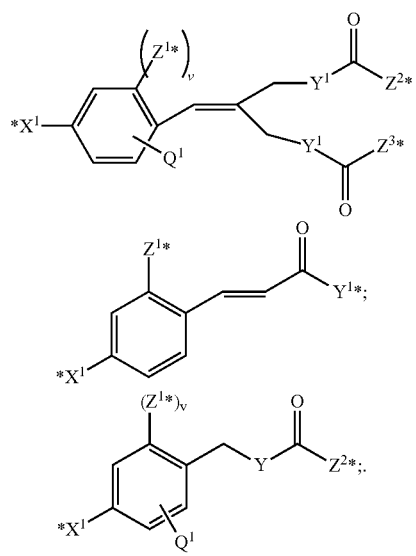

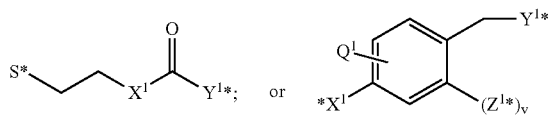

wherein the (*) atom is the point of attachment of additional spacer or releasable linker units, or the cytotoxic agent, and/or the binding molecule (CBA); $X^1$, $Y^1$, $Z^2$ and $Z^3$ are independently NH, or O, or S; $Z^1$ is H, or NH, or O or S independently. v is 0 or 1; $Q^1$ is independently H, OH, $C_1$~$C_6$ alkyl, $(OCH_2CH_2)_nF$, Cl, Br, I, $OR_5$, or $SR_5$, $NR_5R_{5'}$, $N=NR_5$, $N=R_5NR_5R_{5'}$, $NO_2$, $SOR_5R_{5'}$, $SO_2R_5$, $SO_3R_5$, $OSO_3R_5$, $PR_5R_{5'}$, $POR_5R_{5'}$, $PO_2R_5R_{5'}$, $OPO(OR_5)(OR_{5'})$, or $OCH_2PO(OR_5(OR_{5'})$ wherein $R_5$ and $R_{5'}$ are as defined above, preferably $R_5$ and $R_{5'}$ are independently selected from H, $C_1$~$C_8$ of alkyl; $C_2$~$C_8$ of alkenyl, alkynyl, heteroalkyl; $C_3$~$C_8$ of aryl, heterocyclic, carbocyclic, cycloalkyl, heterocycloalkyl, heteroaralkyl, alkylcarbonyl; or pharmaceutical cation salts.

The non-self-immolative linker component is any one of the following structures:

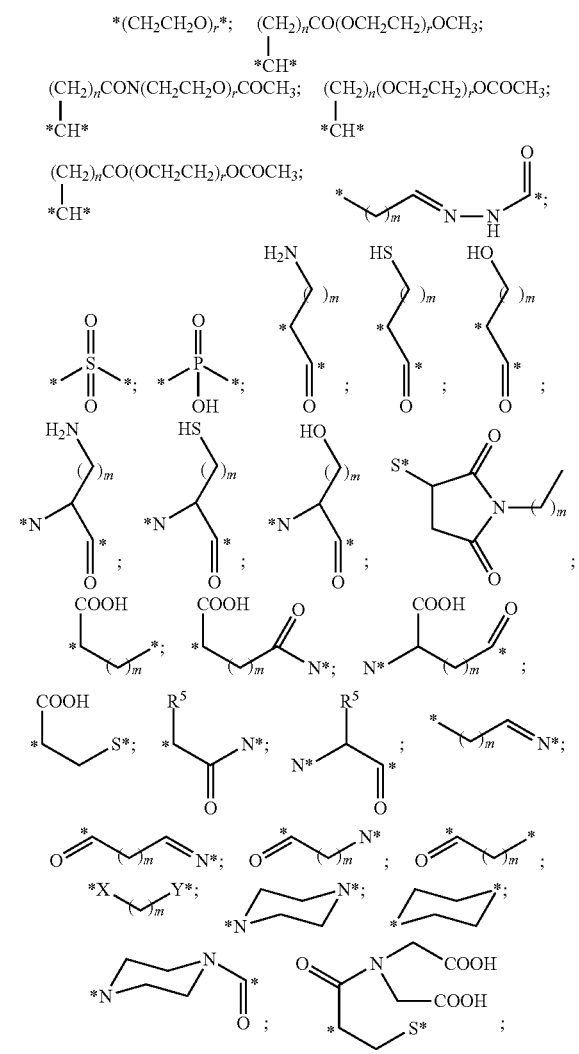

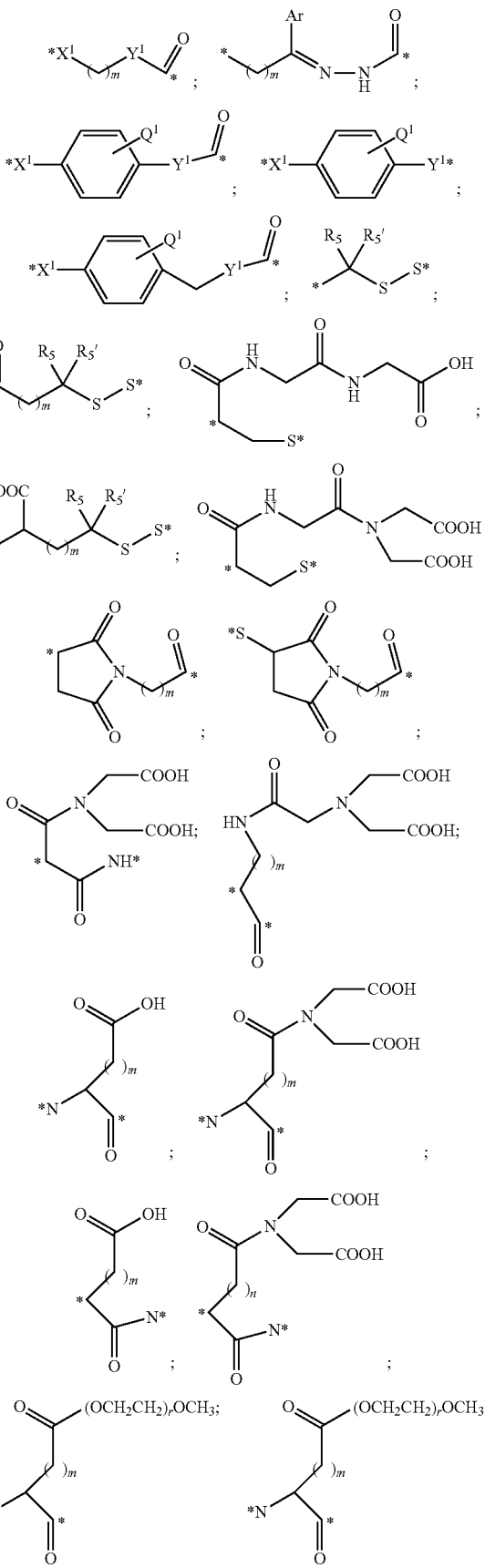

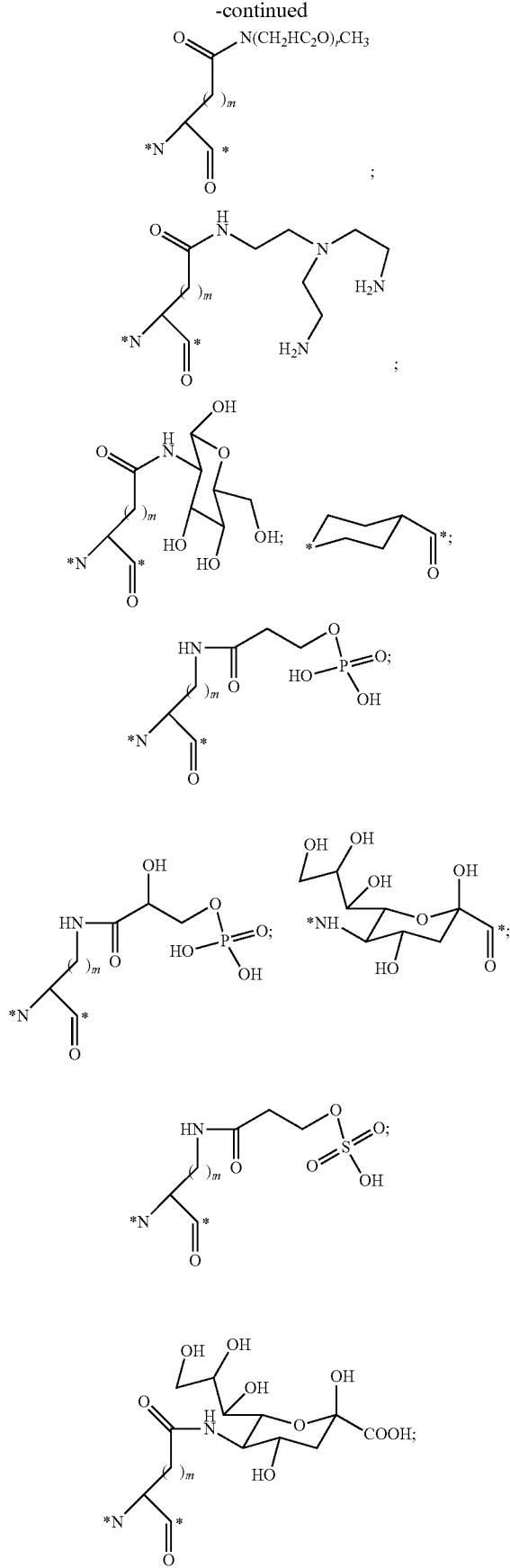
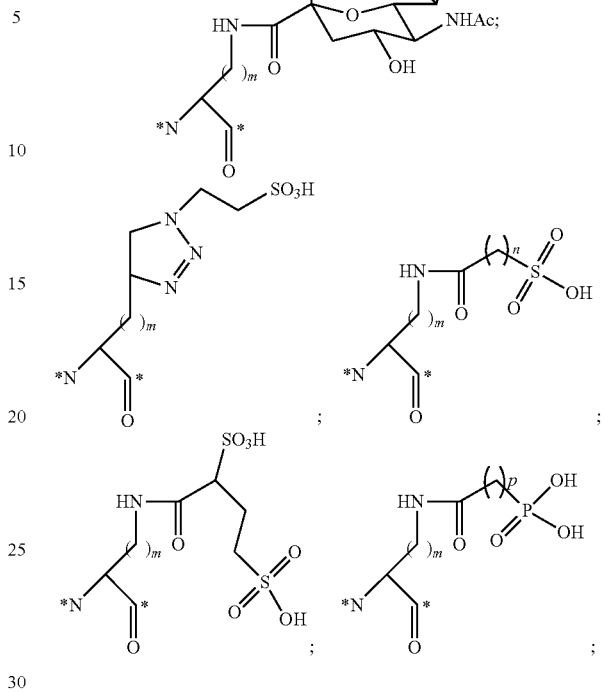

Wherein the (*) atom is the point of attachment of additional spacer or releaseable linkers, the cytotoxic agents, and/or the binding molecules; $X^1$, $Y^1$, $Q^1$, $R_5$, $R_5'$ are as defined above; r is 0~100; m, n and p are 0~6.

Spacers (T) is a linear, branched or cyclic alkyl, alkenyl, alkynyl or aryl having from 1 to 10 carbon atoms, or polyethylene glycol (—$CH_2CH_2O$—) spacer; and t is 0, or 1~100.

Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et at (1990) J. Org. Chem. 55:5867). Elimination of amine-containing drugs that are substituted at glycine (Kingsbury et al (1984) J. Med. Chem. 27:1447) is also examples of self-immolative spacer useful in the cell-binding agent cytotoxic agent conjugates of the present invention.

In addition L can be $R_5$, $OR_5$, $SR_5$, $NHR_5$, or $NR_5R_5'$, thus $R_1$, $R_2$, $R_3$, $R_4$, $R_1'$, $R_2'$, $R_3'$, or $R_4'$, or U, or U', or V, or V' on the formula (I) can be used to linked to Q via Stretcher units (Ww) or via Spacer units (Tt) when the compound is used for conjugation to a cell binding agent.

Q is a cell binding molecule (CBA), or a functional group that enables reaction with a cell-binding agent or a functional group capable of reacting with a linker attached on a cell binding agent. The function group is chosen from a thiol, an amine, a hydrazine, an alkoxylamino, a disulfide substituent, a maleimido, a haloacetyl group, an N-hydroxy succinimide ester, or protected thiol or disulfide group, such as SAc, $SSR_5$ or SSAr.

The term releasable linker refers to a linker that includes at least one bond that can be broken under physiological conditions, such as a pH-labile, acid-labile, base-labile, oxidatively labile, metabolically labile, biochemically labile, or enzyme-labile bond. It is appreciated that such physiological conditions resulting in bond breaking do not necessarily include a biological or metabolic process, and instead may include a standard chemical reaction, such as a hydrolysis or substitution reaction, for example, an endosome having a lower pH than cytosolic pH, and/or disulfide bond exchange reaction with a intracellular thiol, such as a millimolar range of abundant of glutathione inside the malignant cells.

The Stretcher unit (—W—), when present, may link a targeted binding molecular unit (CBA) to an amino acid unit (-Aa-), or links T when an Aa is not present. The Stretcher unit W may independently contain a self-immolative spacer, peptidyl units, a hydrazone bond, disulfide or thiolether bonds. In this regard a binding molecular (CBA) has a functional group that can form a bond with a functional group of a Stretcher. Useful functional groups that can be present on a binding molecular, either naturally or via chemical manipulation include, but are not limited to, sulfhydryl (—SH), amino, hydroxyl, carbonyl, the anomeric hydroxyl group of a carbohydrate, and carboxyl. Preferred functional groups are sulfhydryl, carboxy and amino. Sulfhydryl groups can be generated by reduction of an intramolecular disulfide bond of a Ligand. Alternatively, sulfhydryl groups can be generated by reaction of an amino group of a lysine moiety of a binding molecular using 2-iminothiolane (Traut's reagent) or thiolactone or another sulfhydryl generating reagent, such as modifies T with a disulfide bond linker, or a thiol ester following by reduction or hydrolysis respectively.

Specific examples of the releasable linkers (L) include, but not limited:

—$(CR_5R_6)_m(Aa)r(CR_7R_8)_n(OCH_2CH_2)_rQ$, —$(CR_5R_6)_m(CR_7R_8)_n(Aa)_t(OCH_2CH_2)_rQ$, -$(Aa)r(CR_5R_6)_m(CR_7R_8)_n(OCH_2CH_2)_rQ$, —$(CR_5R_6)_m(CR_7R_8)_n(OCH_2CH_2)_r(Aa)_tQ$, —$(CR_5R_6)_m$—$(CR_7=CR_8)(CR_9R_{10})(Aa)_t(OCH_2CH_2)_rQ$, —$(CR_5R_6)_m(NR_{11}CO)(Aa)_t(CR_9R_{10})_n$—$(OCH_2CH_2)_rQ$, —$(CR_5R_6)_m(Aa)_t(NR_{11}CO)(CR_9R_{10})_n(OCH_2CH_2)_rQ$, —$(CR_5R_6)_m(OCO)(Aa)_t(CR_9R_{10})_n$—$(OCH_2CH_2)_rQ$, —$(CR_5R_6)_m(OCNR_7)(Aa)_t(CR_9R_{10})_n(OCH_2CH_2)_rQ$, —$(CR_5R_6)_m(CO)(Aa)_t$-$(CR_9R_{10})_n(OCH_2CH_2)_rQ$, —$(CR_5R_6)_m(NR_{11}CO)(Aa)_t(CR_9R_{10})_n(OCH_2CH_2)_rQ$, —$(CR_5R_6)_m$—$(OCO)(Aa)_t(CR_9R_{10})_n(OCH_2CH_2)_rQ$, —$(CR_5R_6)_m(OCNR_7)(Aa)_t(CR_9R_{10})_n(OCH_2CH_2)_rQ$, —$(CR_5R_6)_m(CO)(Aa)_t(CR_9R_{10})_n(OCH_2CH_2)_rQ$, —$(CR_5R_6)_m$-phenyl-CO$(Aa)_t(CR_7R_8)_nQ$, —$(CR_5R_6)_m$-furyl-CO$(Aa)_t(CR_7R_8)_nQ$, —$(CR_5R_6)_m$-oxazolyl-CO$(Aa)_t(CR_7R_8)_nQ$, —$(CR_5R_6)_m$-thiazolyl-CO$(Aa)_t(CCR_7R_8)_nQ$, —$(CR_5R_6)_t$-thienyl-CO$(CR_7R_8)_nQ$, —$(CR_5R_6)_t$-imidazolyl-CO$(CR_7R_8)_nQ$, —$(CR_5R_6)_t$-morpholino-CO$(Aa)_t(CR_7R_8)_nQ$, —$(CR_5R_6)_t$piperazino-CO$(Aa)_t(CR_7R_8)_nQ$, —$(CR_5R_6)_t$—N-methylpiperazin-CO$(Aa)_t(CR_7R_8)_nQ$, —$(CR_5R)_m$-$(Aa)_t$phenyl-Q, —$(CR_5R_6)_m$-$(Aa)_t$furyl-Q, —$(CR_5R_6)_m$-oxazolyl$(Aa)_t$-Q, $(CR_5R_6)_m$-thiazolyl$(Aa)_t$-Q, —$(CR_5R_6)_m$-thienyl-$(Aa)_tQ$, —$(CR_5R_6)_m$-imidazolyl-$(Aa)_t$-Q, —$(CR_5R_6)_m$-morpholino-$(Aa)_tQ$, —$(CR_5R_6)_m$-piperazino-$(Aa)_tQ$, —$(CR_5R_6)_m$—N-methylpiperazino-$(Aa)(Q$, —$K(CR_5R_6)_m(Aa)r(CR_7R_8)_n(OCH_2CH_2)_rQ$, —$K(CR_5R_6)_m(CR_7R_8)_n(Aa)_r(OCH_2CH_2)_rQ$, —$K(Aa)r(CR_5R_6)_m(CR_7R_8)_n(OCH_2CH_2)_rQ$, —$K(CR_5R_6)_m(CR_7R_8)_n(OCH_2CH_2)_t(Aa)_tQ$, —$K(CR_5R_6)_m(CR_7=CR_8)(CR_9R_{10})_n(Aa)_t(OCH_2CH_2)_rQ$, —$K(CR_5R_6)_m(NR_{11}CO)(Aa)_t(CR_9R_{10})_nOCH_2CH_2)_rQ$, —$K(C R_5R_6)_m(Aa)_t(NR_{11}CO)(CR_9R_{10})_n(OCH_2CH_2)_rQ$, —$K(CR_5R_6)_m(OCO)(Aa)_t(CR_9R_{10})_n(OCH_2CH_2)_rQ$, —$K(CR_5R_6)_m(OCNR_7)(Aa)_t(CR_9R_{10})_n(OCH_2CH_2)_rQ$, —$K(CR_5R_6)_m(CO)(Aa)_t(CR_9R_{10})_n(OCH_2CH_2)_rQ$, —$K(CR_5R_6)_m(NR_{11}CO)(Aa)_t(CR_9R_{10})_n(OCH_2CH_2)_rQ$, —$K(CR_5R_6)_m(OCO)(Aa)_t(CR_9R_{10})_n(OCH_2CH_2)_rQ$, —$K(CR_5R_6)_m(OCNR_7)(Aa)_t(CR_9R_{10})_n(OCH_2CH_2)_rQ$, —$K(CR_5R_6)_m(CO)(Aa)_t(CR_9R_{10})_n(OCH_2CH_2)_rQ$, —$K(CR_5R_6)_m$-phenyl-CO$(Aa)_t(CR_7R_8)_nQ$, —$K(CR_5R_6)_m$-furyl-CO$(Aa)_t(CR_7R_8)_nQ$, —$K(CR_5R_6)_m$-oxazolyl-CO$(Aa)_t(CR_7R_8)_nQ$, —$K(CR_5R_6)_m$-thiazolyl-CO$(Aa)_t(CCR_7R_8)_nQ$, —$K(CR_5R_6)_t$-thienyl-CO$(CR_7R_8)_nQ$, —$K(CR_5R_6)_t$-imidazolyl-CO$(CR_7R_8)_nQ$, —$K(CR_5R_6)_t$morpholino-CO$(Aa)_t(CR_7R_8)_nQ$, —$K(CR_5R_6)_t$piperazino-CO$(Aa)_t(CR_7R_8)_nQ$, —$K(CR_5R_6)_t$—N-methylpiperazin-CO$(Aa)_t(CR_7R_8)_nQ$, —$K(CR_5R)_m$-$(Aa)_t$phenyl-Q, —$K(CR_5R_6)_m$-$(Aa)_t$furyl-Q, —$K(CR_5R_6)_m$-oxazolyl$(Aa)_t$-Q, —$K(CR_5R_6)_m$-thiazolyl$(Aa)_t$-Q, —$K(CR_5R_6)_m$-thienyl-$(Aa)_tQ$, —$K(CR_5R_6)_m$-imidazolyl$(Aa)_t$-Q, —$K(CR_5R_6)_m$-morpholino-$(Aa)_tQ$, —$K(CR_5R_6)_m$-piperazino-$(Aa)_tQ$, —$K(CR_5R_6)_m$N-methylpiperazino-$(Aa)_tQ$.

Wherein m, Aa, t, n, Q, $R_3$, $R_4$, and $R_5$ are described above; $R_6$, $R_7$, and $R_8$ are the same or different and independently chosen from H; halide; $C_1$~$C_8$ of alkyl, aryl, alkenyl, alkynyl, ether, ester, amine or amide, which optionally substituted by one or more halide, CN, $NR_1R_2$, $CF_3$, $OR_1$, Aryl, heterocycle, $S(O)R_1$, $SO_2R_1$, —$CO_2H$, —$SO_3H$, —$OR_1$, —$CO_2R_1$, —$CONR_1$, —$PO_2R_1R_2$, —$PO_3H$ or $P(O)R_1R_2R_3$; K is $NR_1$, O, S, Se, B or Het.

The compounds of the general formula (I) having geometrical and stereoisomers are also a part of the invention.

A preferred stereoisomer of the formula (I) is presented by the following formula (Ia) (Ib) and (Ic):

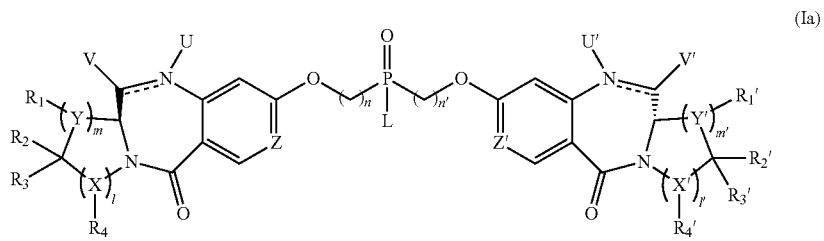

(Ia)

(Ib)

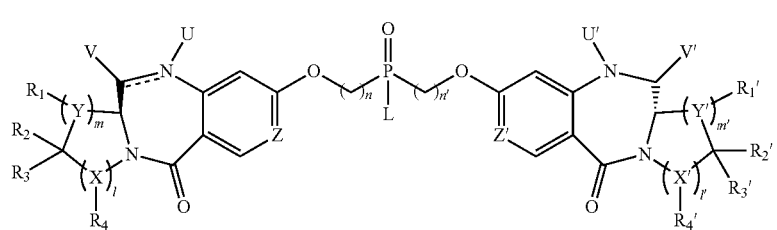

(Ic)

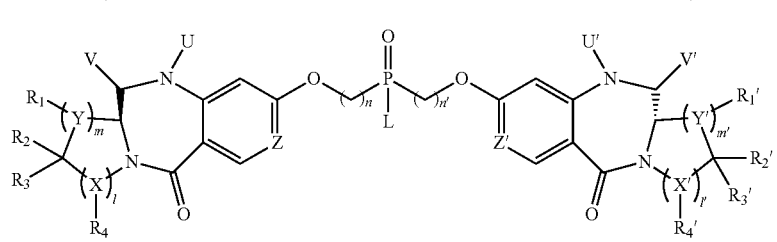

wherein X, X', Y, Y', Z, Z', l, l', m, m', n, n', R$_1$, R$_1$', R$_2$, R$_2$', R$_3$, R$_3$', R$_4$, R$_4$', L are the same as defined in formula (I).

In another preferred embodiment according to formula (I), the novel PBD derivatives of the invention have the formula (II), (III), and (IV).

(II)

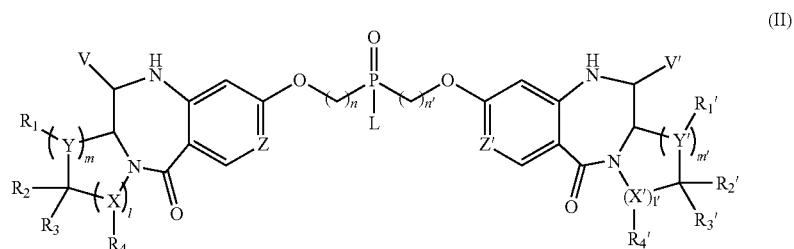

(III)

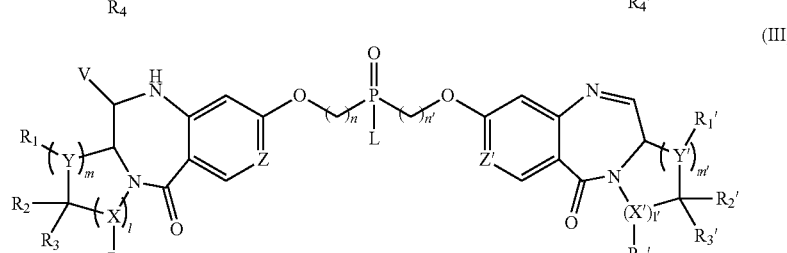

(IV)

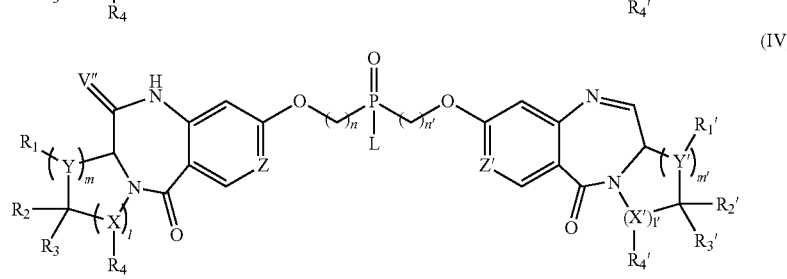

wherein X, X', Y, Y', Z, Z', l, l', m, m', n, n', R$_1$, R$_1$', R$_2$, R$_2$', R$_3$, R$_3$', R$_4$, R$_4$', L are the same as defined in formula (I)

V and V' the same or different are independently selected from the group consisting of OH, an ether such as —OR$_5$, an ester (e.g. an acetate), such as —OCOR$_5$, —COOR$_5$, a carbonate such as —OCOOR$_5$, a carbamate such as —OCONR$_5$R$_5$', a cyclic carbamate, such that N10 and C11 are a part of the cycle, a urea such as —NRCONR$_5$R$_5$', a thiocarbamate such as —OCSNHR$_5$, a cyclic thiocarbamate such that N10 and C11 are a part of the cycle, —SH, a sulfide such as —SR$_5$, a sulphoxide such as —SOR$_5$, a sulfone such as —SOOR$_5$, a sulphite (sulfite) such as —SO$_3$$^-$, a bisulphite such as —OSO$_3$$^-$, a sulfonamide such as —NRSOOR, an amine such as —NRR', optionally cyclic amine such that N10 and C11 are a part of the cycle, a hydroxylamine derivative such as —NR$_5$OR$_5$', an amide such as —NR$_5$COR$_5$', —NR$_5$CONR$_5$R$_5$'', an azido such as —N$_3$, a cyano, a halo, a triallyl or triarylphosphonium, an amino-acid-derived group.

V'' is (=)O, (=)NH, (=)N—CONR$_5$R$_5$', (=)N—COR$_5$, (=)N—COOR$_5$, (=)N—O—R$_5$ $R_5$, $R_5'$ and $R_5''$ are independently selected from H, $C_1 \sim C_8$ of alkyl, alkenyl, alkinyl, heteroalkyl, aryl, arylalkyl, carbonylalkyl, or pharmaceutical salts. $R_5$, $R_5'$ and $R_5''$ can further be substituted with at least one substituent selected from —$N(R_1)(R_2)$, —$CO_2H$, —$SO_3H$, —$OR_1$, —$CO_2R_1$, —$CONR_1$, —$PO_2R_1R_2$, $POR_1R_2R_3$ and —$PO_3H$ or M (Na, K, Ca, ammonium or the other pharmaceutically acceptable salt), or linked a cell binding agent via Stretcher units (Ww) or via. Spacer units (Tt).

In certain embodiments, the PBD derivatives of formula (I), (II), (III), and (IV) are represented by the following formulas (V), (VI), (VII), (VIII), (IX), (X), (XI), (XII), (XIII), (XIV), (XV), (XVI):

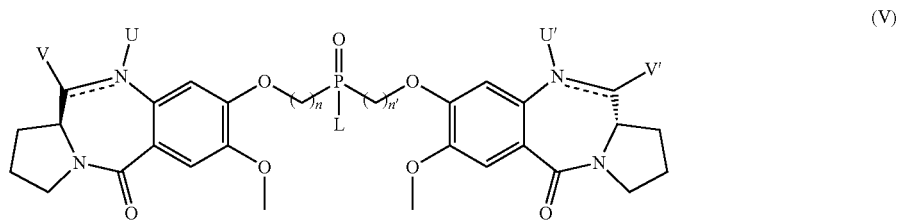
(V)

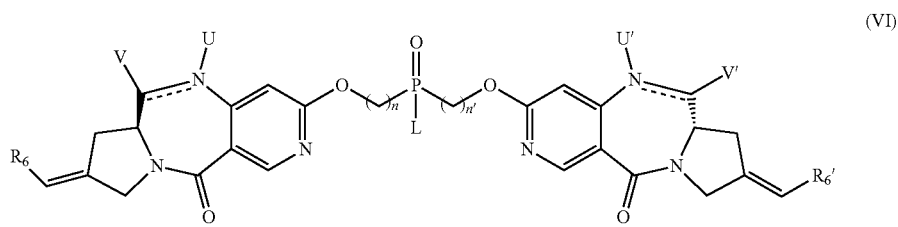
(VI)

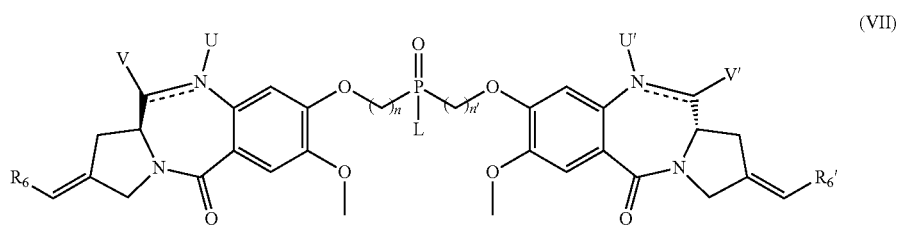
(VII)

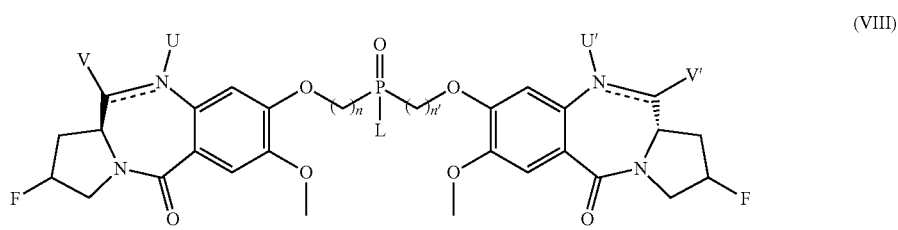
(VIII)

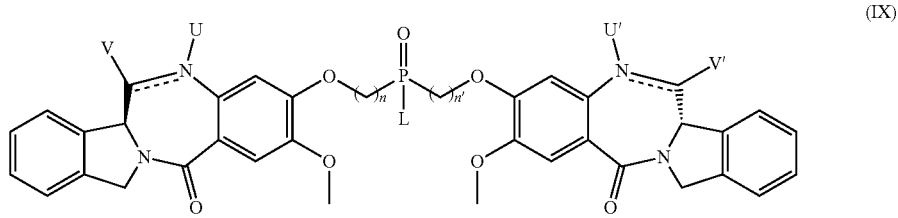
(IX)

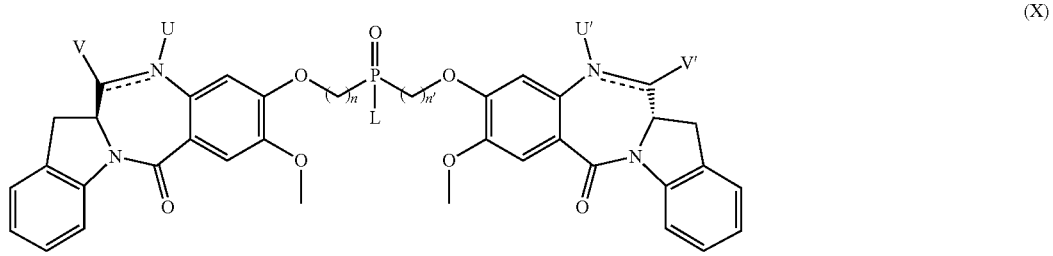
(X)

-continued
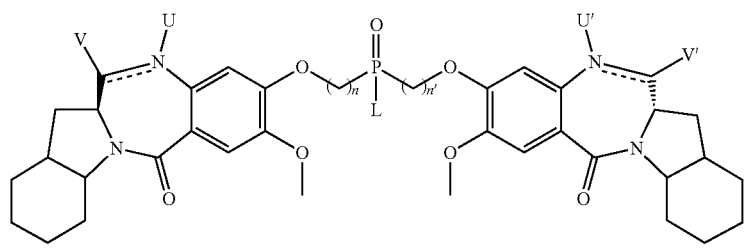
(XI)
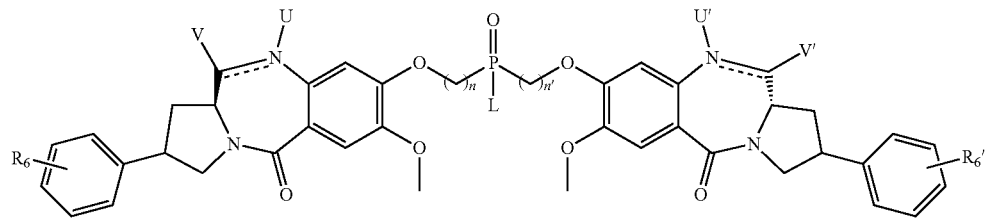
(XII)
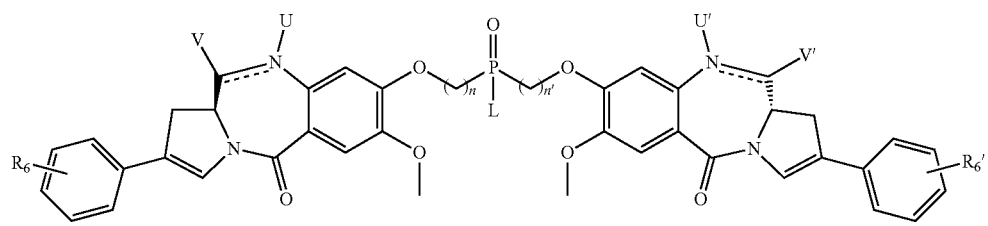
(XIII)
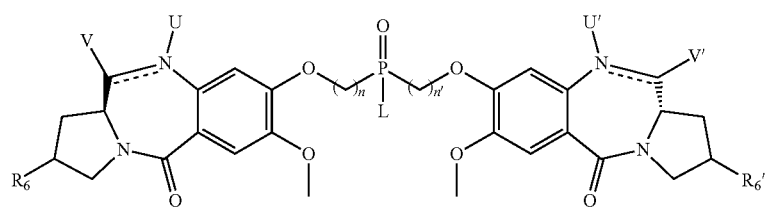
(XIV)
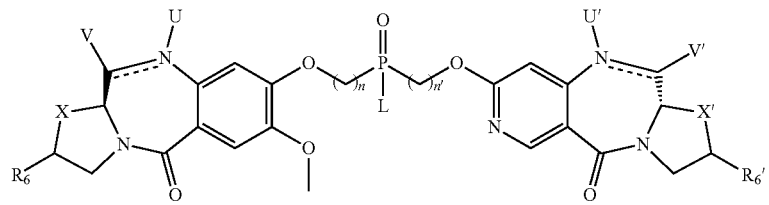
(XV)
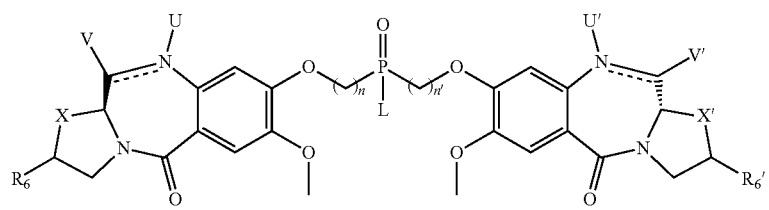
(XVI)
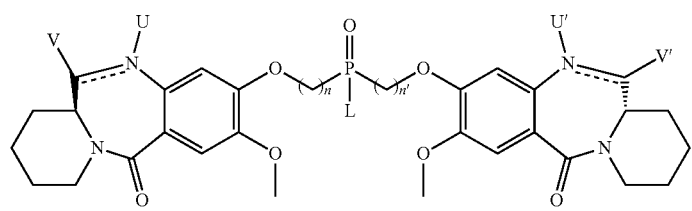
(XVII)

wherein U, U', V, V', n, n', X, X' and L are the same as defined in formula (I). $R_6$ and $R_6'$ are the same or independently as $R_5$ as described in formula (I), preferably $R_6$ and $R_6'$ are $C_1$~$C_8$ of alkyl, alkenyl, alkinyl, aryl, cyclic, cyclohetero, haloalkyl, alkoxy, haloalkoxy alkylamino; or halogen; or —$NO_2$; or —CN; or H; or linked a cell binding agent via Stretcher units (Ww) or via Spacer units (Tt). W, w, T, and t are as defined in Formula (I).

In certain embodiments, the cytotoxic agent and its conjugate of this invention are any one of the following structures:

(XVIII-1)
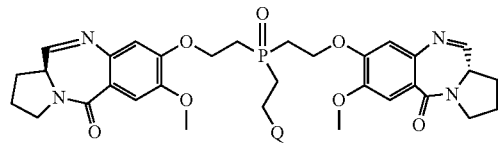

(XVIII-2)
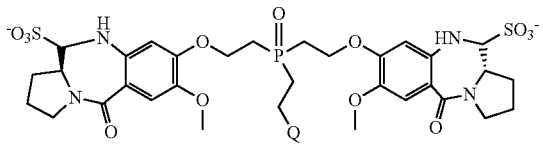

(XVIII-3)
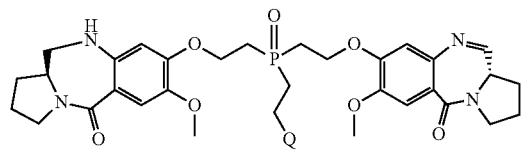

(XVIII-4)
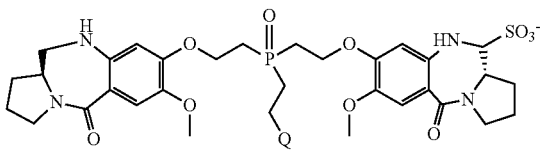

(XVIII-5)
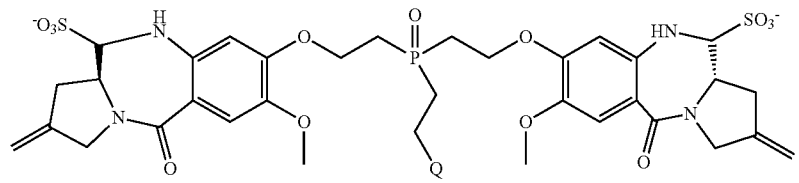

(XVIII-6)
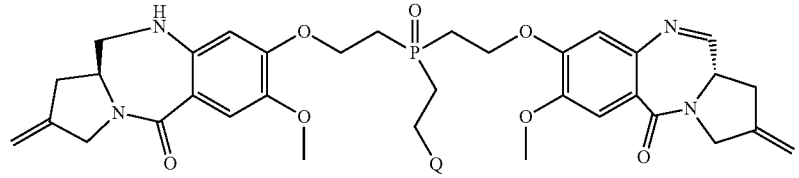

(XVIII-7)
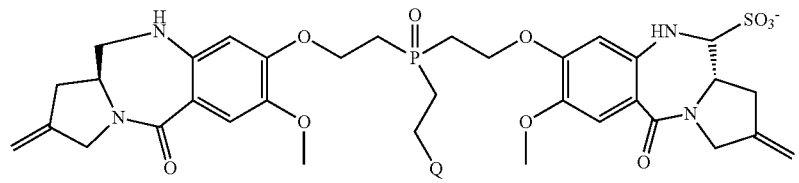

(XVIII-8)
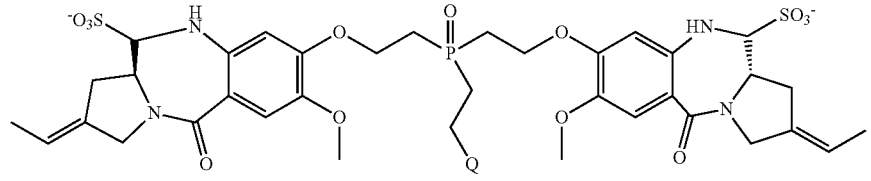

(XVIII-9)
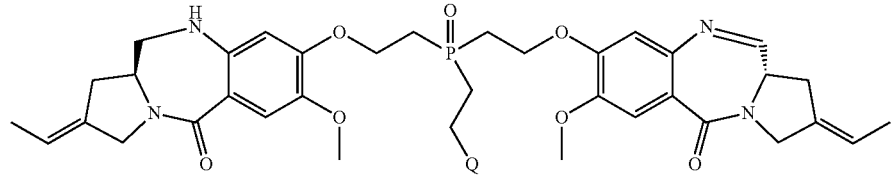

-continued
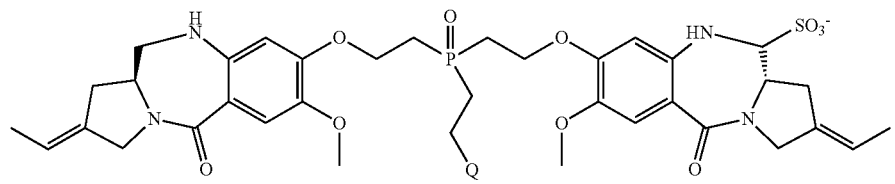
(XVIII-10)
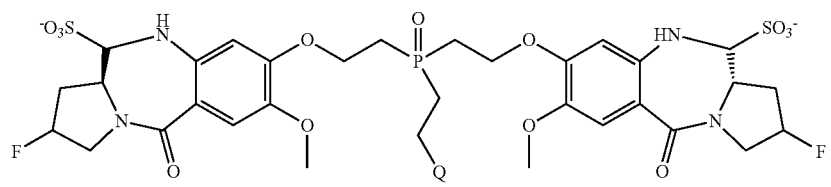
(XVIII-11)
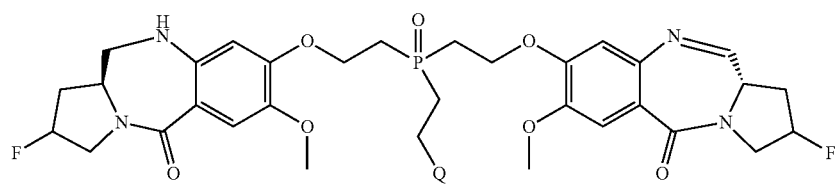
(XVIII-12)
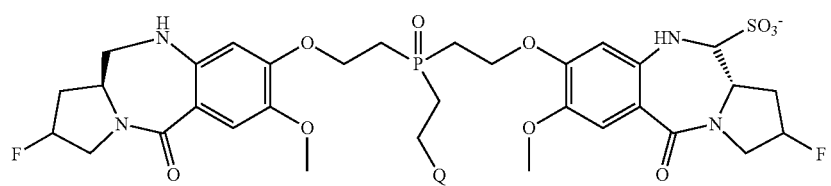
(XVIII-13)
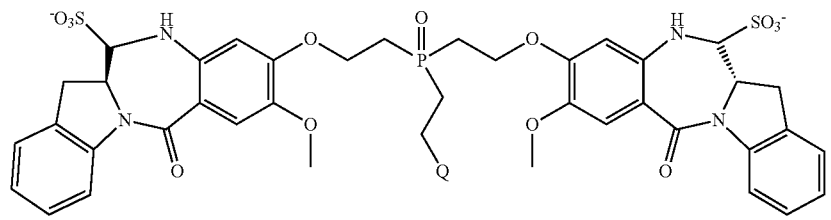
(XVIII-14)
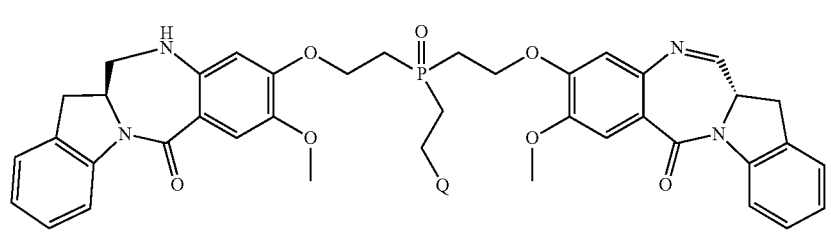
(XVIII-15)
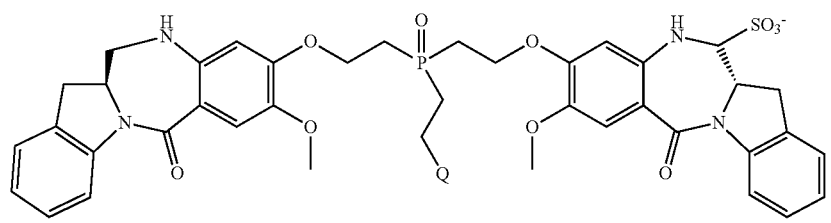
(XVIII-16)
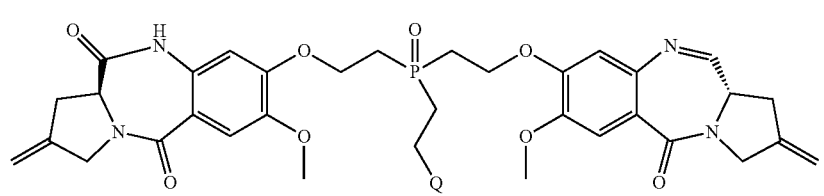
(XVIII-17)

-continued
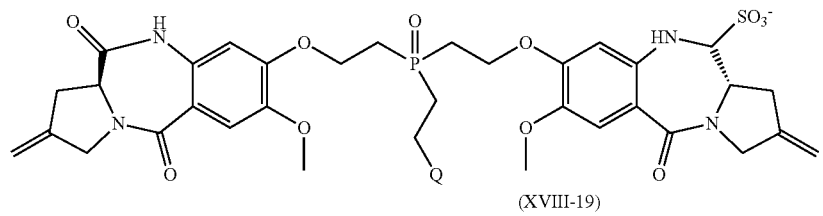
(XVIII-19)
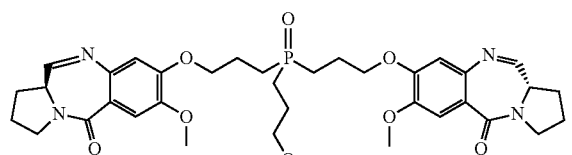
(XVIII-20)
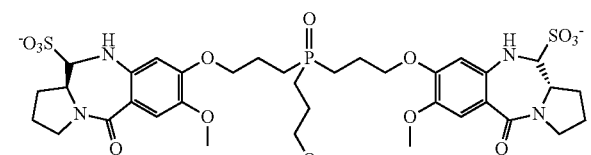
(XVIII-21)
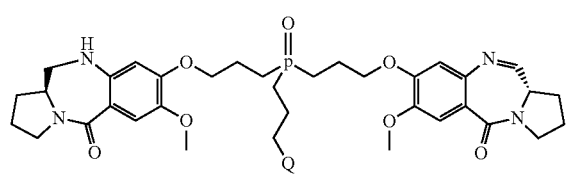
(XVIII-22)
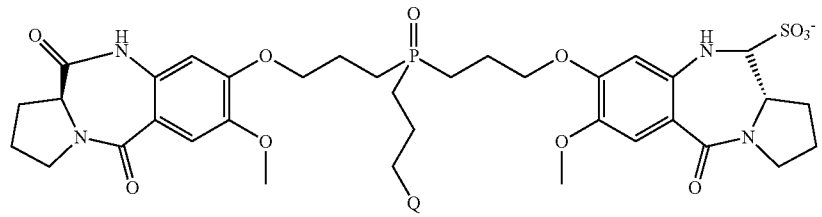
(XVIII-23)
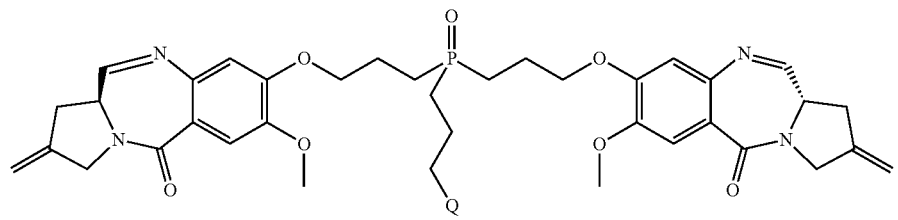
(XVIII-24)
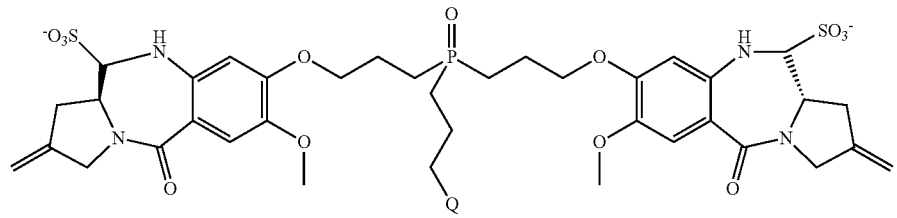
(XVIII-25)
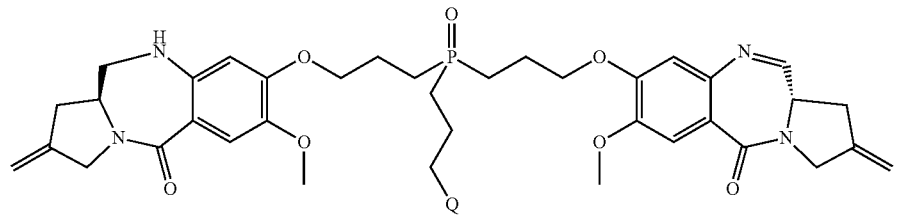
(XVIII-26)

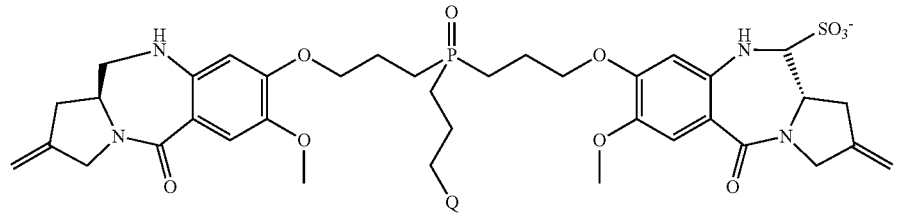
(XVIII-27)
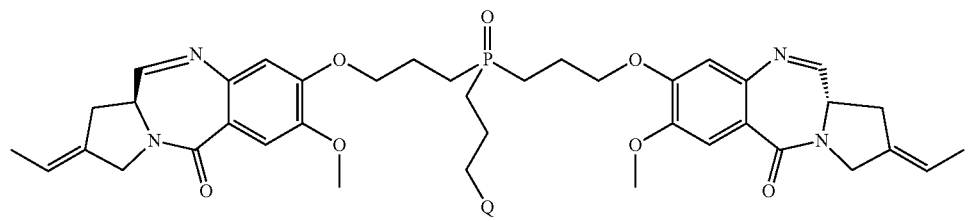
(XVIII-28)
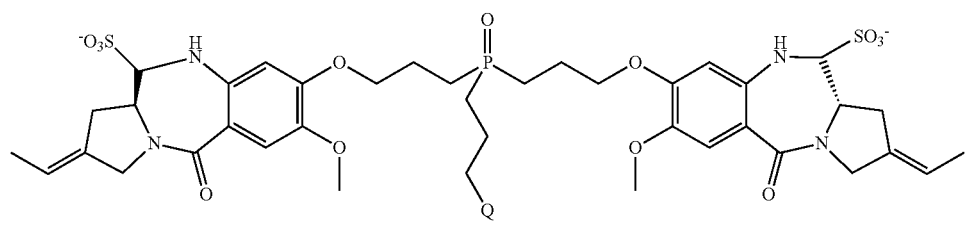
(XVIII-29)
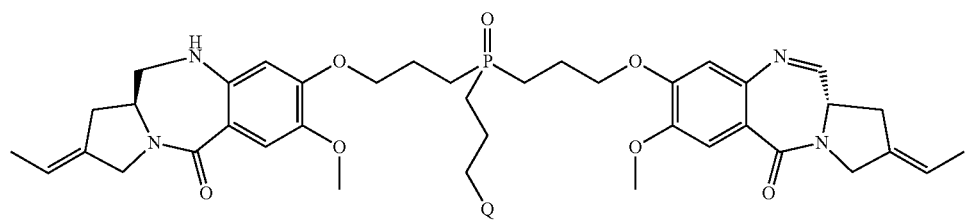
(XVIII-30)
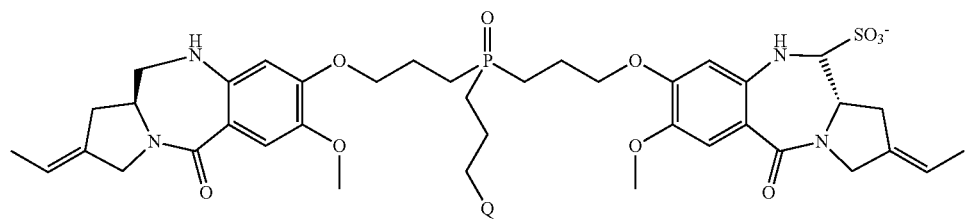
(XVIII-31)
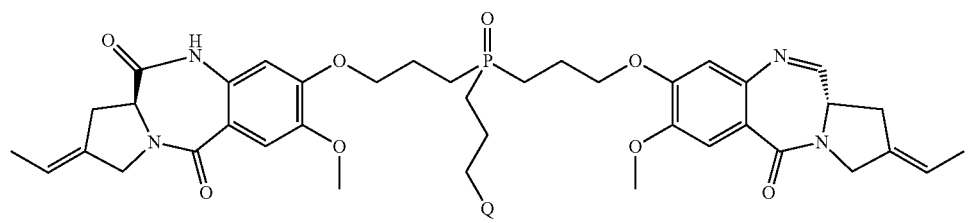
(XVIII-32)
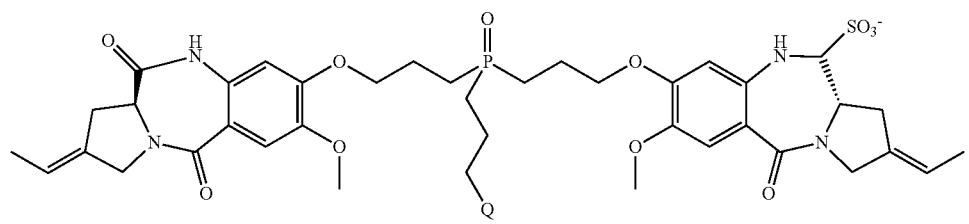
(XVIII-33)

-continued
(XVIII-34)
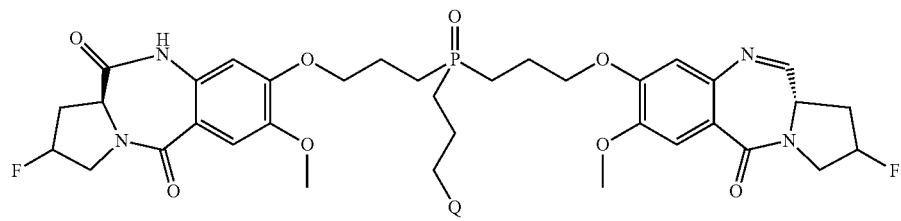
(XVIII-35)
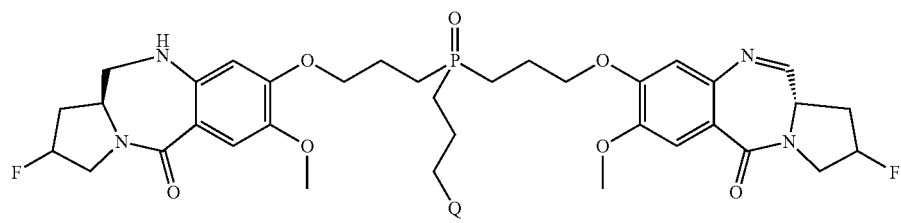
(XVIII-36)
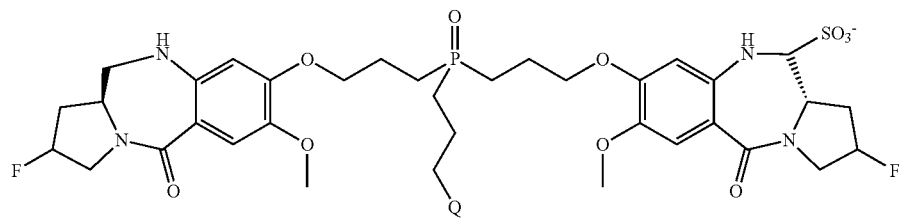
(XVIII-37)
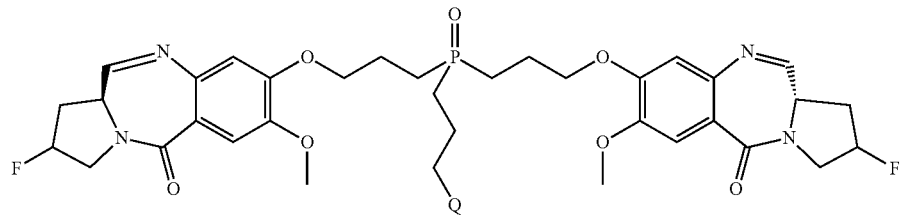
(XVIII-38)
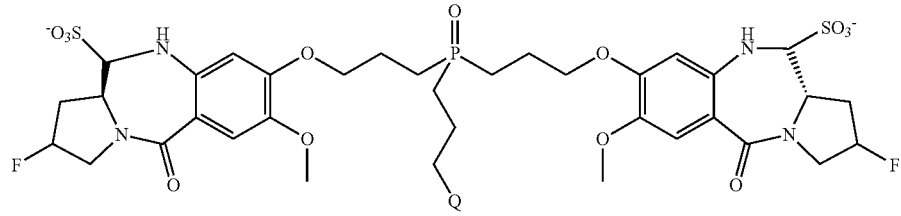
(XVIII-39)
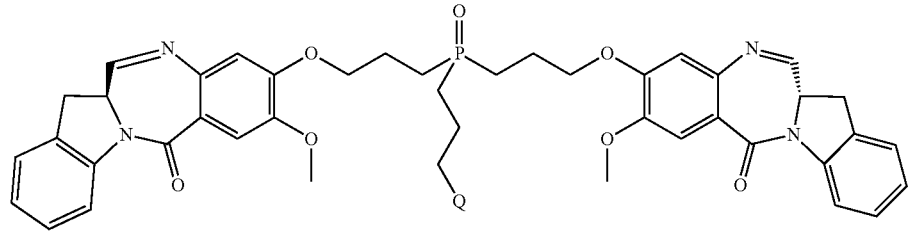
(XVIII-40)
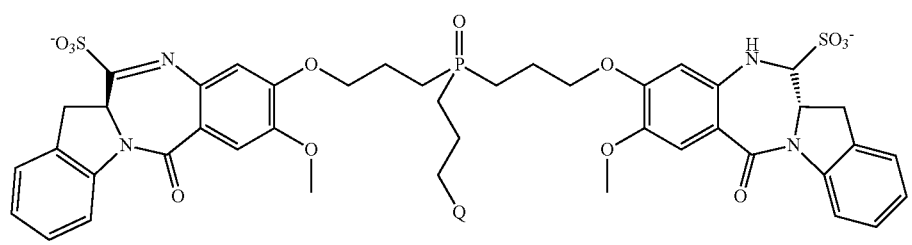

(XVIII-41)
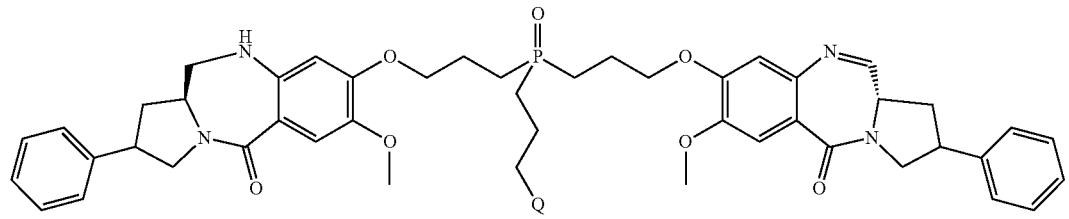
(XVIII-42)
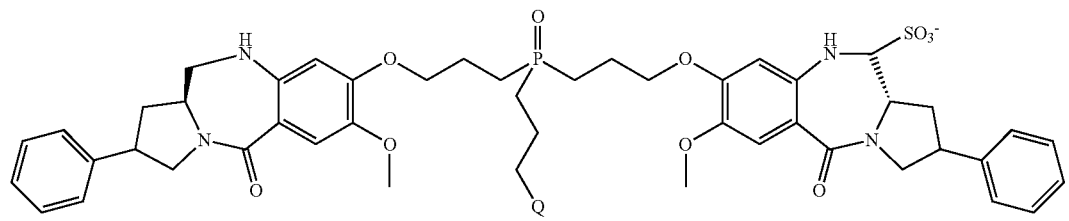
(XVIII-43)
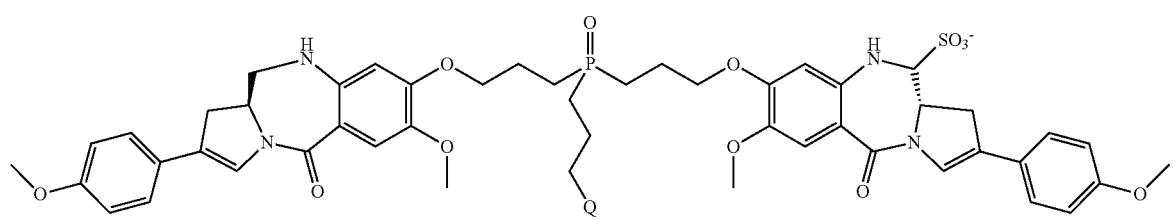
(XVIII-44)
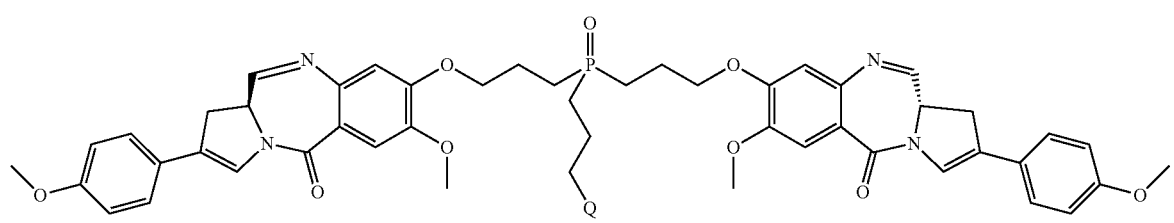
(XVIII-45)
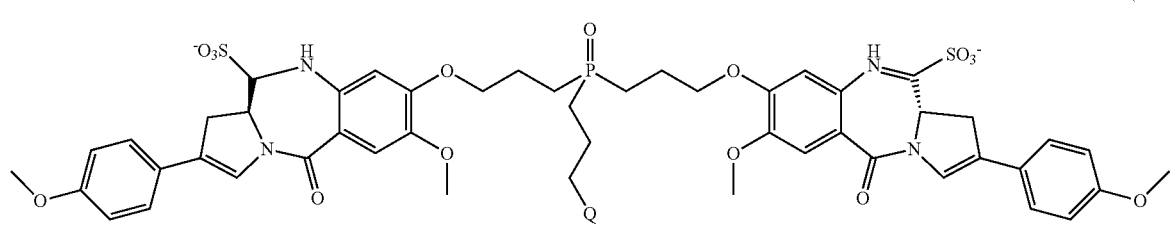
(XVIII-46)
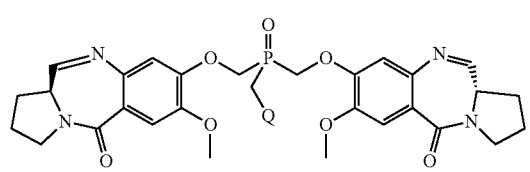
(XVIII-47)
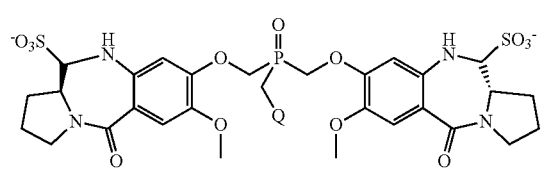
(XVIII-48)
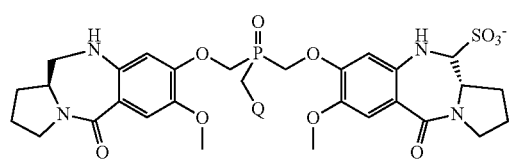
(XVIII-49)
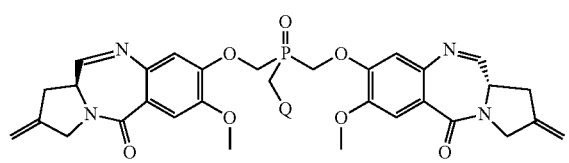

(XVIII-50)
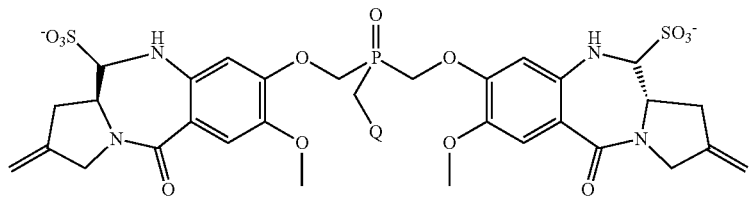
(XVIII-51)
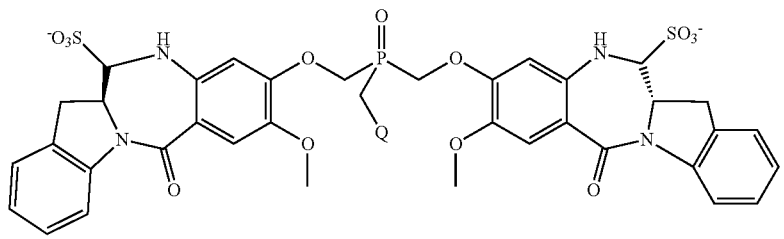
(XVIII-52)
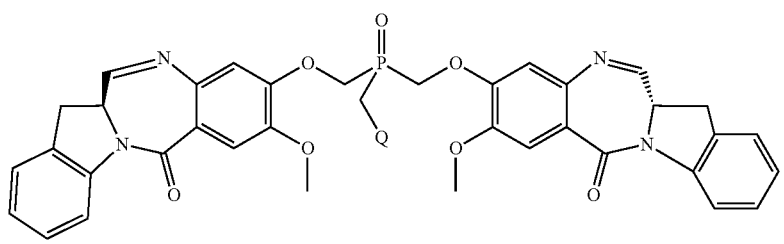
(XVIII-53)
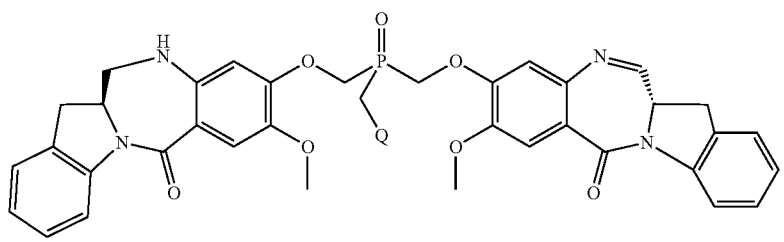
(XVIII-54)
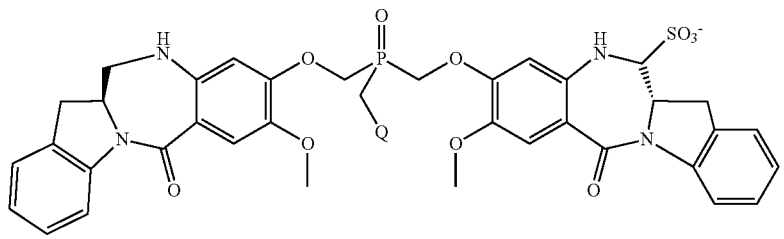
(XVIII-55)
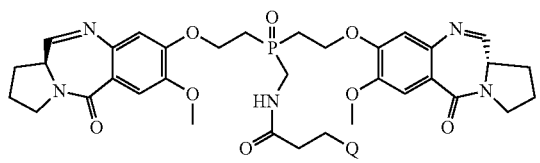
(XVIII-56)
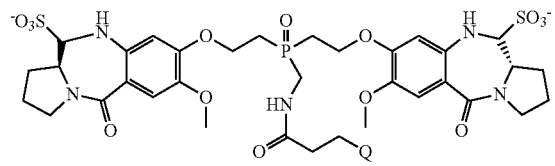
(XVIII-57)
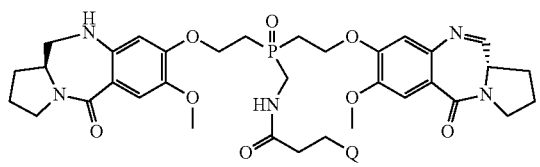
(XVIII-58)
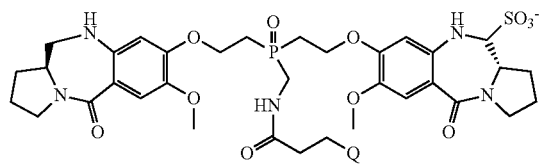

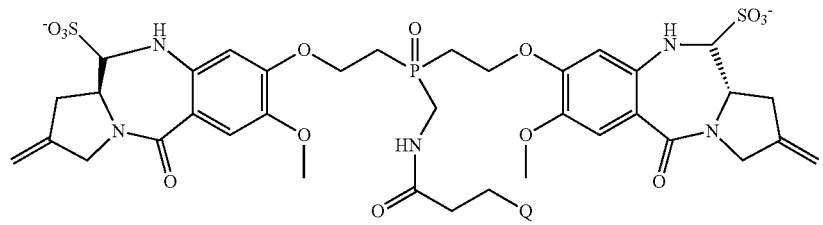
(XVIII-59)
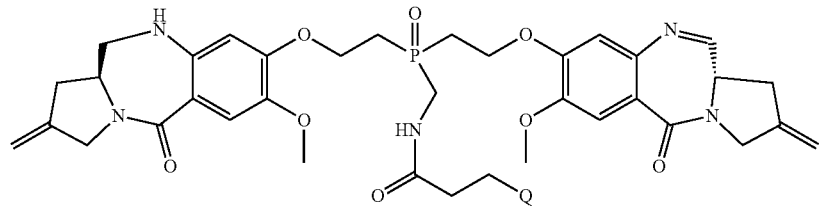
(XVIII-60)
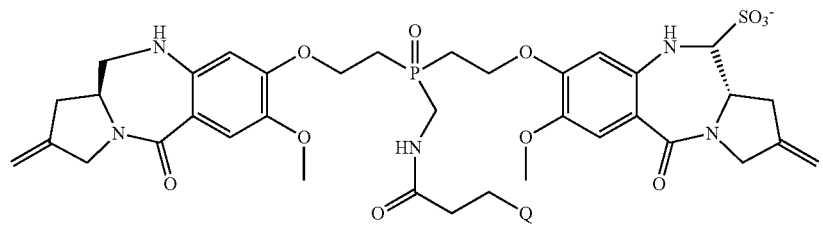
(XVIII-61)
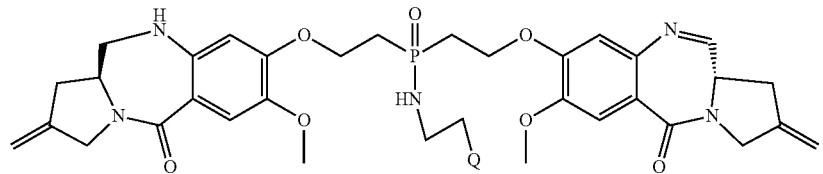
(XVIII-62)
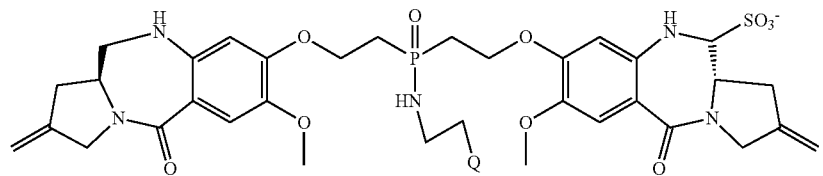
(XVIII-63)
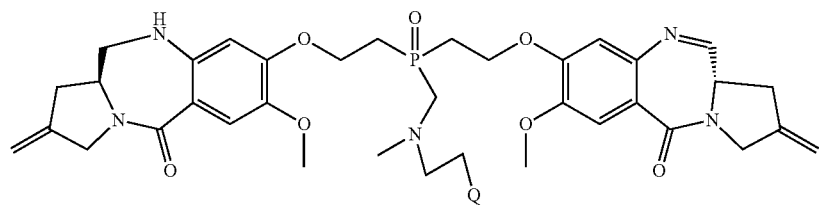
(XVIII-64)
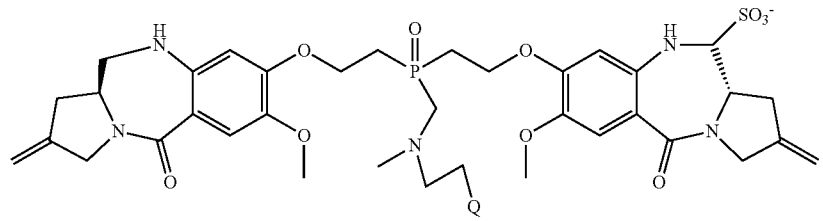
(XVIII-65)

-continued
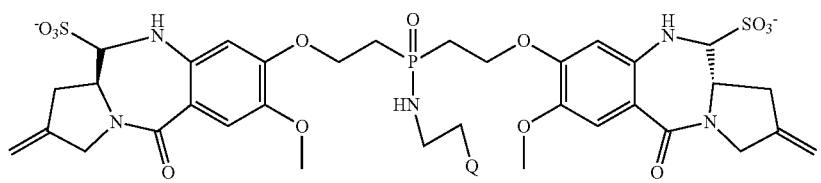
(XVIII-66)
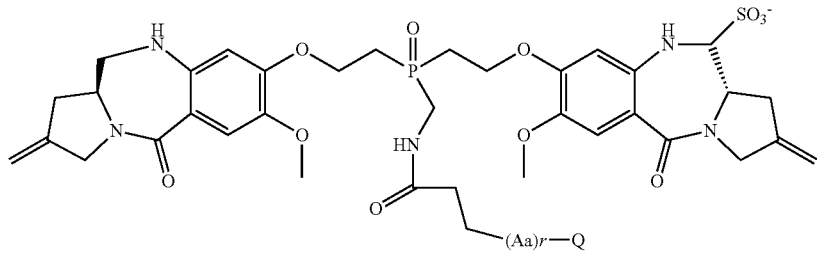
(XVIII-67)
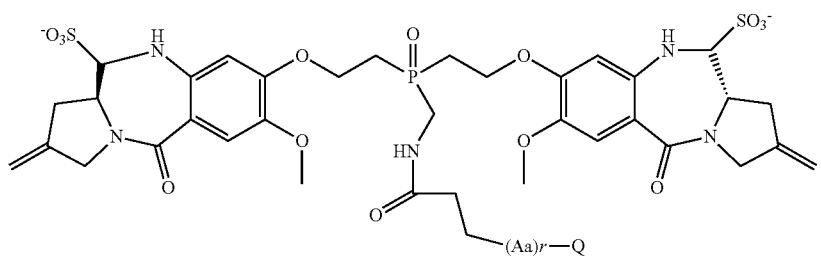
(XVIII-68)
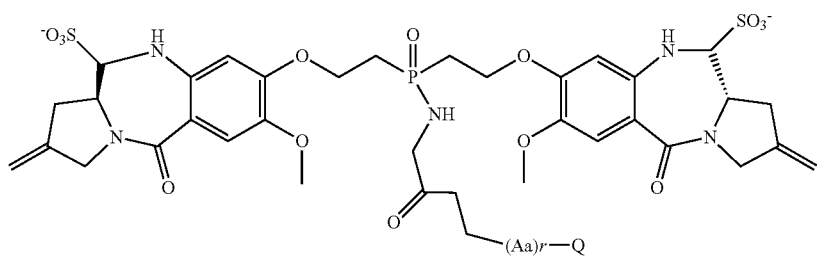
(XVIII-69)
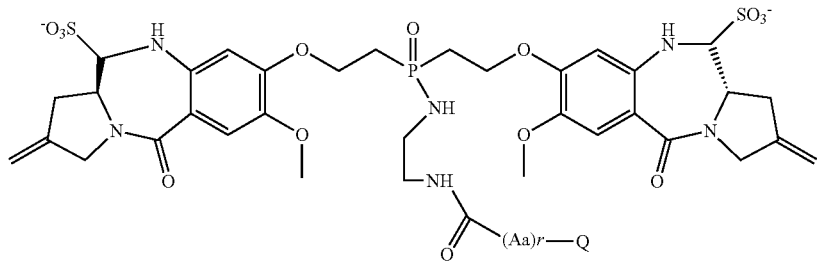
(XVIII-70)
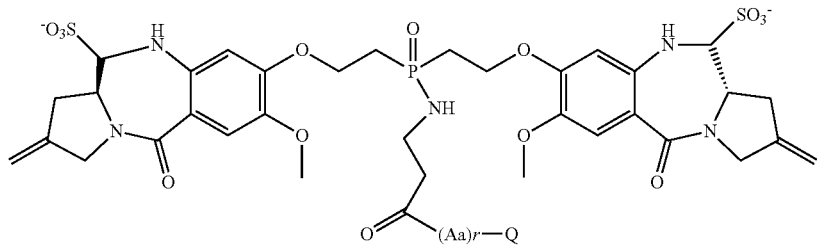
(XVIII-71)

-continued
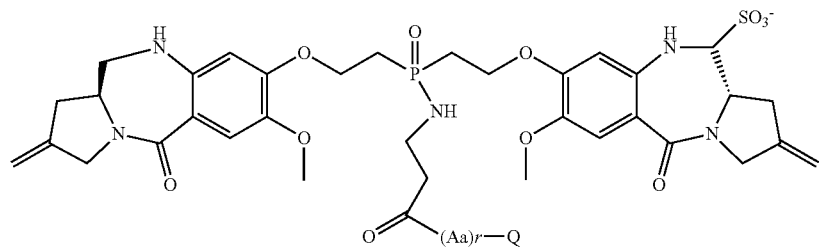 (XVIII-72)
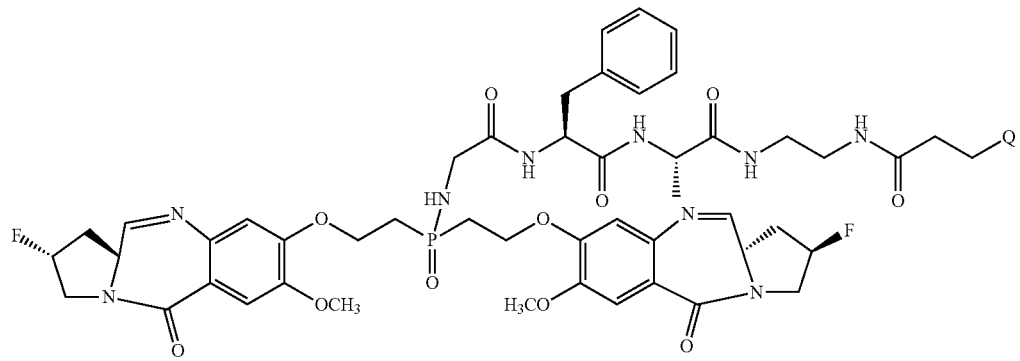 (XVIII-73)
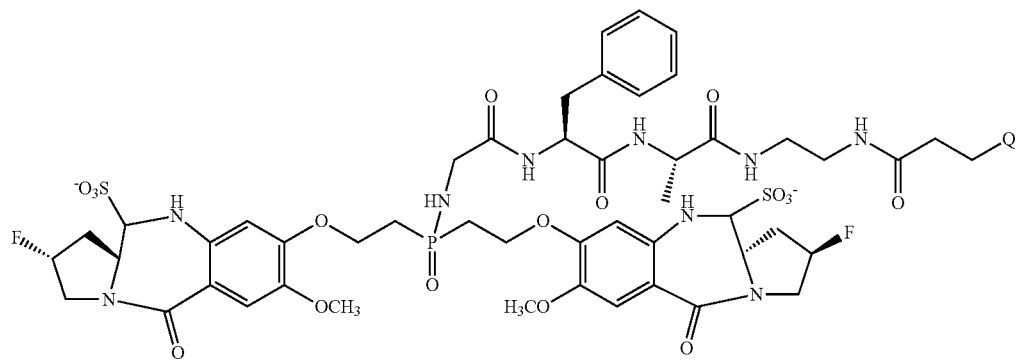 (XVIII-74)
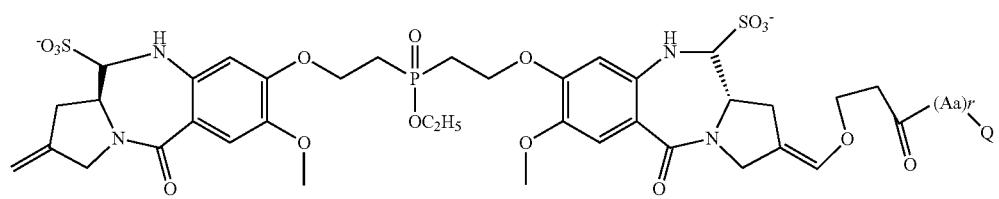 (XVIII-75)
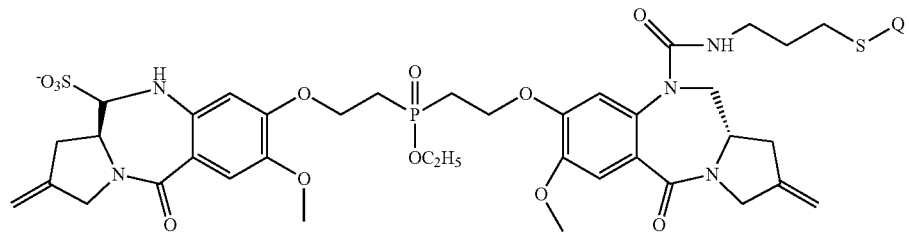 (XVIII-76)
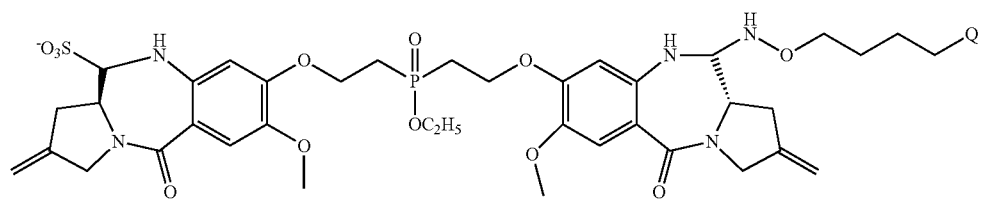 (XVIII-77)

(XVIII-78)

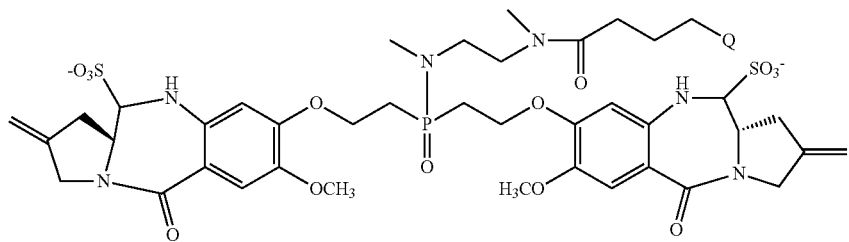

(XVIII-79)

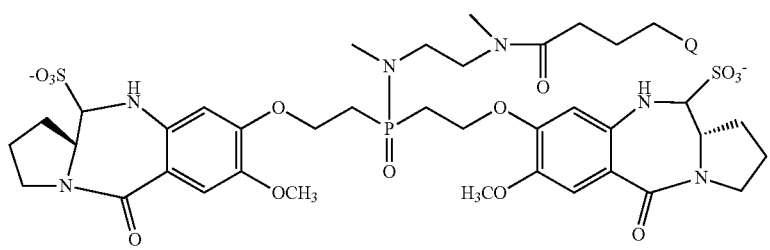

Wherein Aa, n, and Q are the same in the Formula (I) or (II). Preferably, Q is H, $C_1 \sim C_8$ of alkyl, alkenyl, alkinyl, aryl, cyclic, cyclohetero, haloalkyl, alkoxy, haloalkoxy alkylamino; or halogen; or —$NO_2$; or —CN; —SH; —$SSCH_3$; —SSAc; —SSAr; —SS-Pyridine; —SS—Ar(—$NO_2$); —S-cell binding agent; or a function group of NHS ester, pentafluorophenyl ester; alkyloxyamine; aldehyde; ketone; carboxyl acid; hydrazine; amine; or thiolactone; or linked a cell binding agent via Stretcher units (Ww) or via Spacer units (Tt). W, w, T, and t are as defined in Formula (I); or Q is selected from any one of the following formulas:

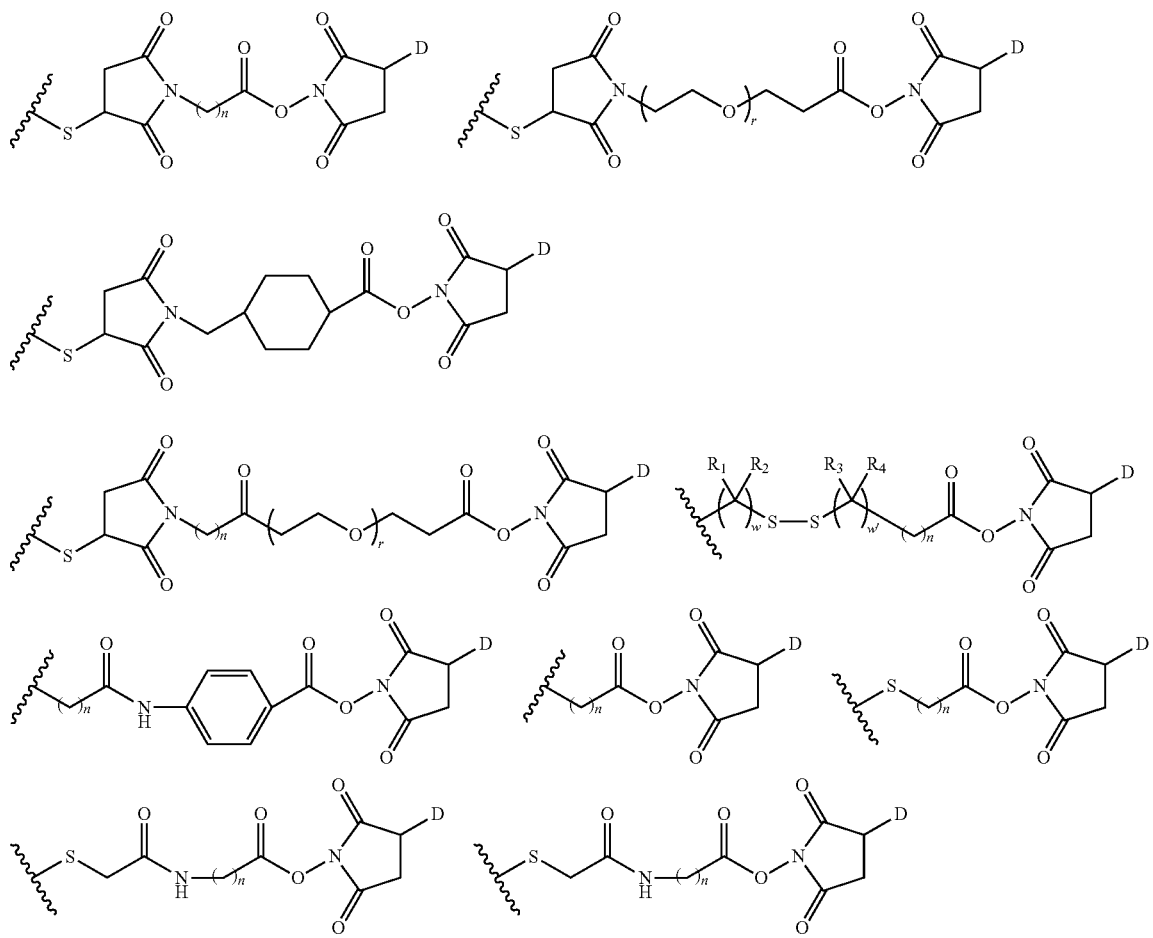

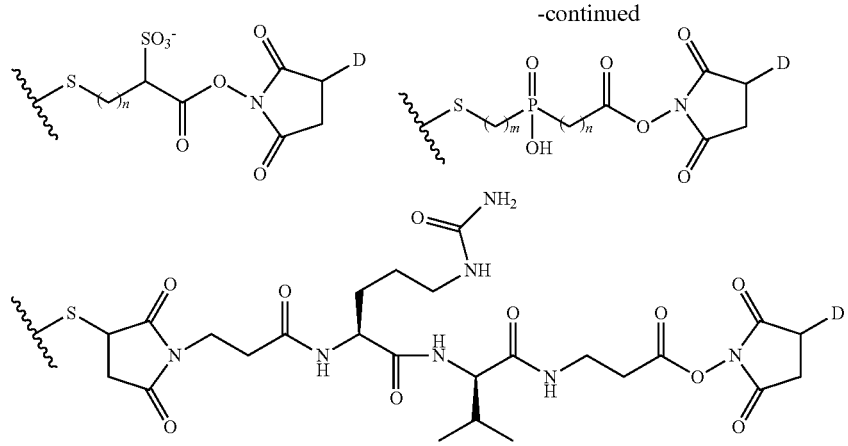

Wherein D is H, —NO$_2$, SO$_3^-$, CN, or F; R$_1$, R$_2$, R$_3$, R$_4$, r, m, and n are described in Formula (I); w and w' are 0 or 1 respectively.

Synthesis of Theses PBD Derivatives as Cytotoxic Agents.

The compounds and process of the present invention can be prepared in a number of ways well known to those skilled in the art. The compounds can be synthesized, for example, by application or adaptation of the methods described in the examples, or variations thereof as appreciated by the skilled artisan. The appropriate modifications and substitutions will be readily apparent and well known or readily obtainable from the scientific literature to those skilled in the art. In particular, such methods can be found in Richard C. Larock, Comprehensive Organic Transformations, A Guide to Functional Group Preparations, Two Volume Set, 2nd Edition, Wiley Publishers, 2010.

Because the cytotoxic agents of the present invention may contain one or more asymmetrically substituted carbon atoms, and may be isolated in optically active or racemic forms, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

The cytotoxic agents of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the synthetic reactions of the cytotoxic agents of the present invention, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see Peter G. M. Wuts, Theodora W. Greene in Greene's Protective Groups in Organic Synthesis, 4th Edition, John Wiley and Sons, 2006; Ian T. Harrison, Shuyen Harrison in Compendium of Organic Synthetic Methods, Vol 1, 2 Vols. 1.& 2 By Ian T. Harrison & Shuyen Harrison, Vols 3~5 by Louis S. Hegedus, Leroy Wade Vols 6~Vol 12 by Michael B. Smith, John Wiley and Sons, 2006~2012.

Normally the synthetic reactions are carried out in suitable solvents, temperatures and time. A variety of solvents which have no adverse effect on the reaction or on the reagents involved can be used in a synthetic reaction of the cytotoxic agent. Examples of suitable solvents include: hydrocarbons, which may be aromatic, aliphatic or cycloaliphatic hydrocarbons, such as hexane, cyclohexane, benzene, toluene and xylene; hydrocarbons containing halogens, such as chloroform, dichloromethane, dichloroethane; amides, such as dimethylactamide or dimethylformamide; alcohols such as ethanol and methanol and ethers, such as diethyl ether and tetrahydrofuran. The reactions can take place over a wide range of temperatures, from −100~300° C., preferably from 0° C. to 100° C. The time required for the synthetic reaction may also vary widely, depending on many factors, notably the reaction temperature and the nature of the reagents and can be from 5 second to 4 weeks, more preferably from 10 min to 20 hours. In addition, the cytotoxic agents prepared may be isolated or purified from the reaction mixture by conventional means, such as evaporating or distilling off the solvent from the reaction mixture, or after distilling off the solvent from the reaction mixture, pouring the residue into water followed by extraction with a water-immiscible organic solvent and then distilling off the solvent from the extract. It may also involve various well known techniques, such as re-crystallization re-precipitation or the various chromatography techniques, notably column chromatography, preparative thin layer chromatography, or high performance liquid chromatography.

Figure 2:
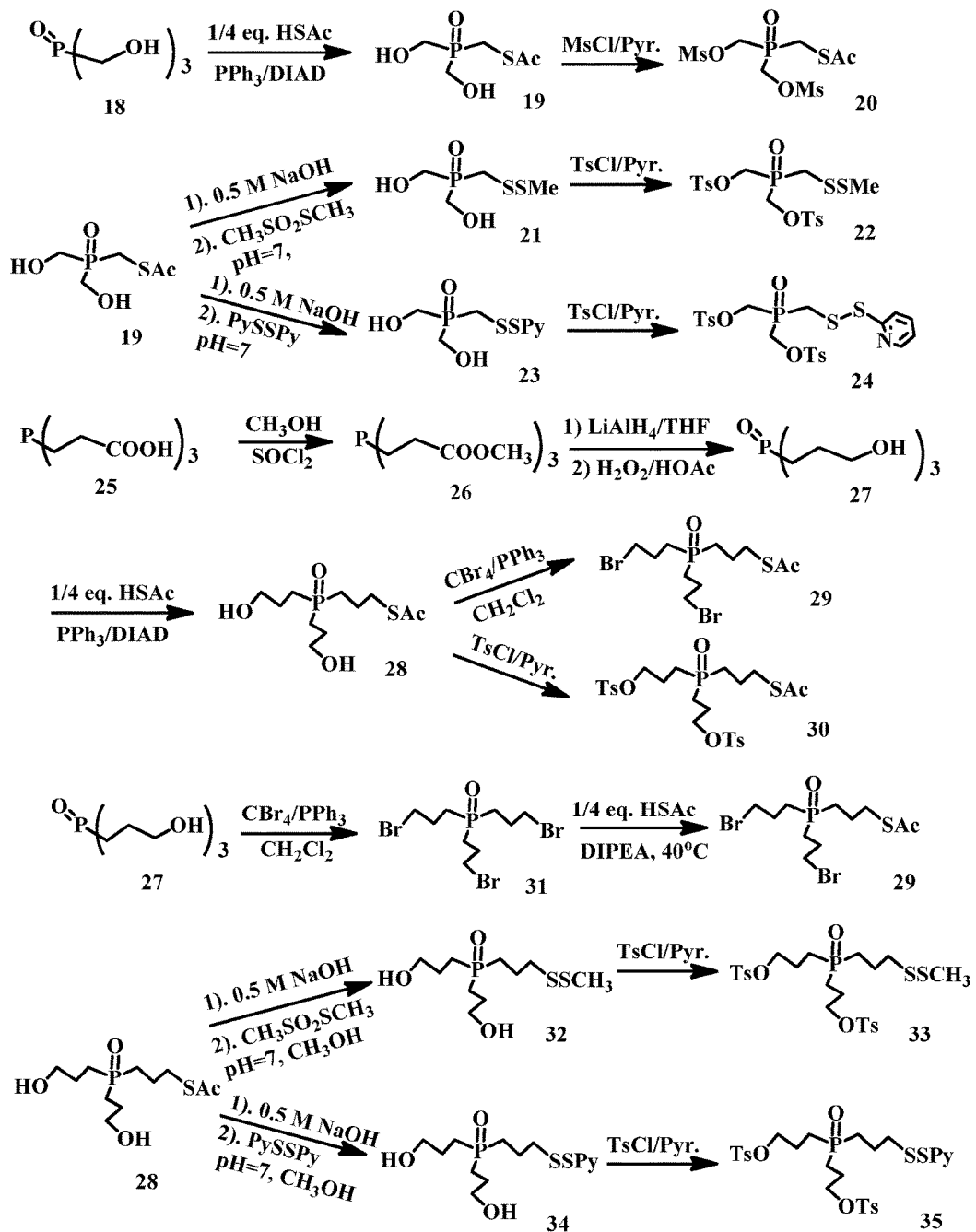
FIG. 2 shows the synthesis of linkers for synthesis of the conjugates of benzodiazepine dimers.
Figure 3:
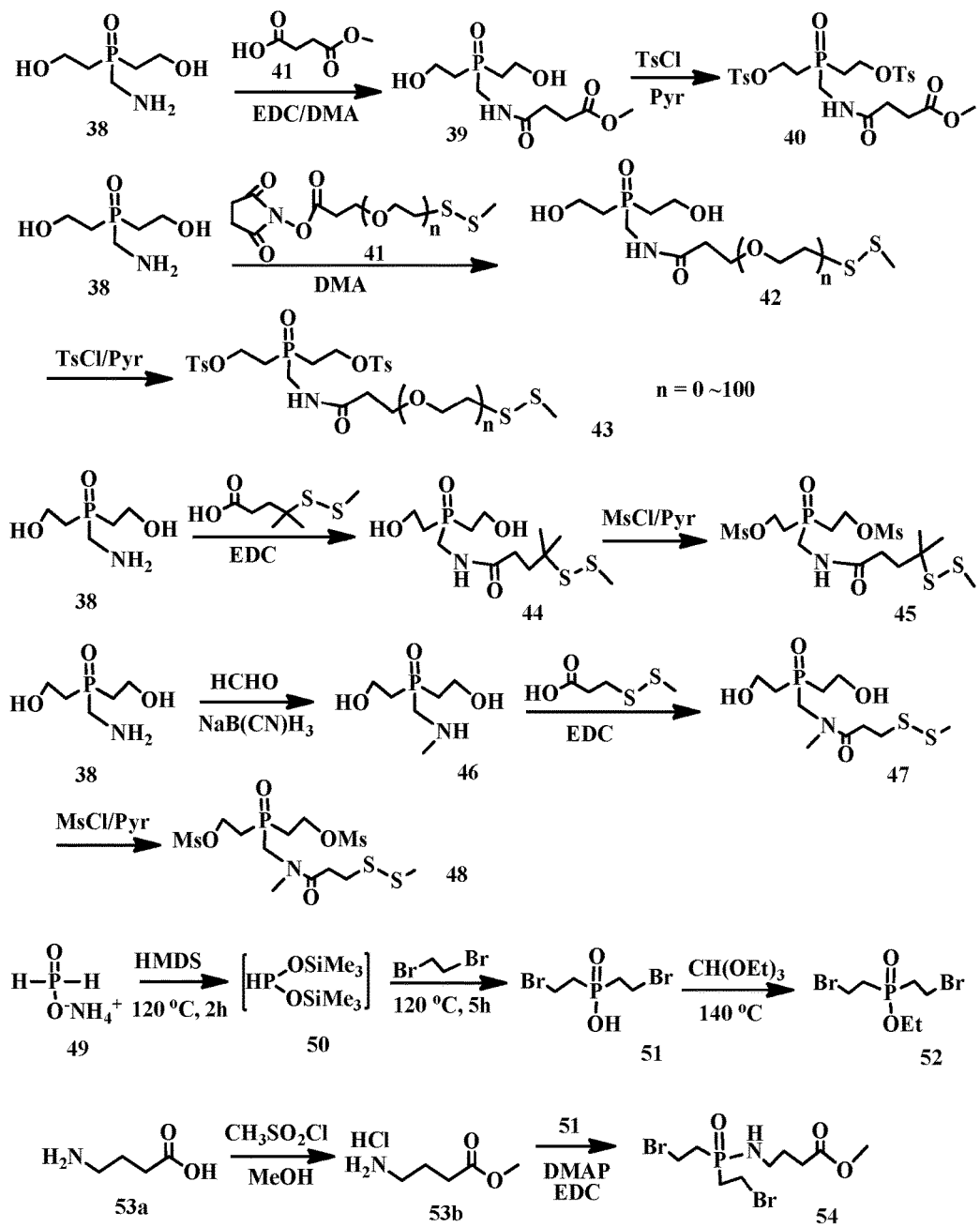
FIG. 3 shows synthesis of linkers for synthesis of the conjugates of benzodiazepine dimers.
Figure 4:
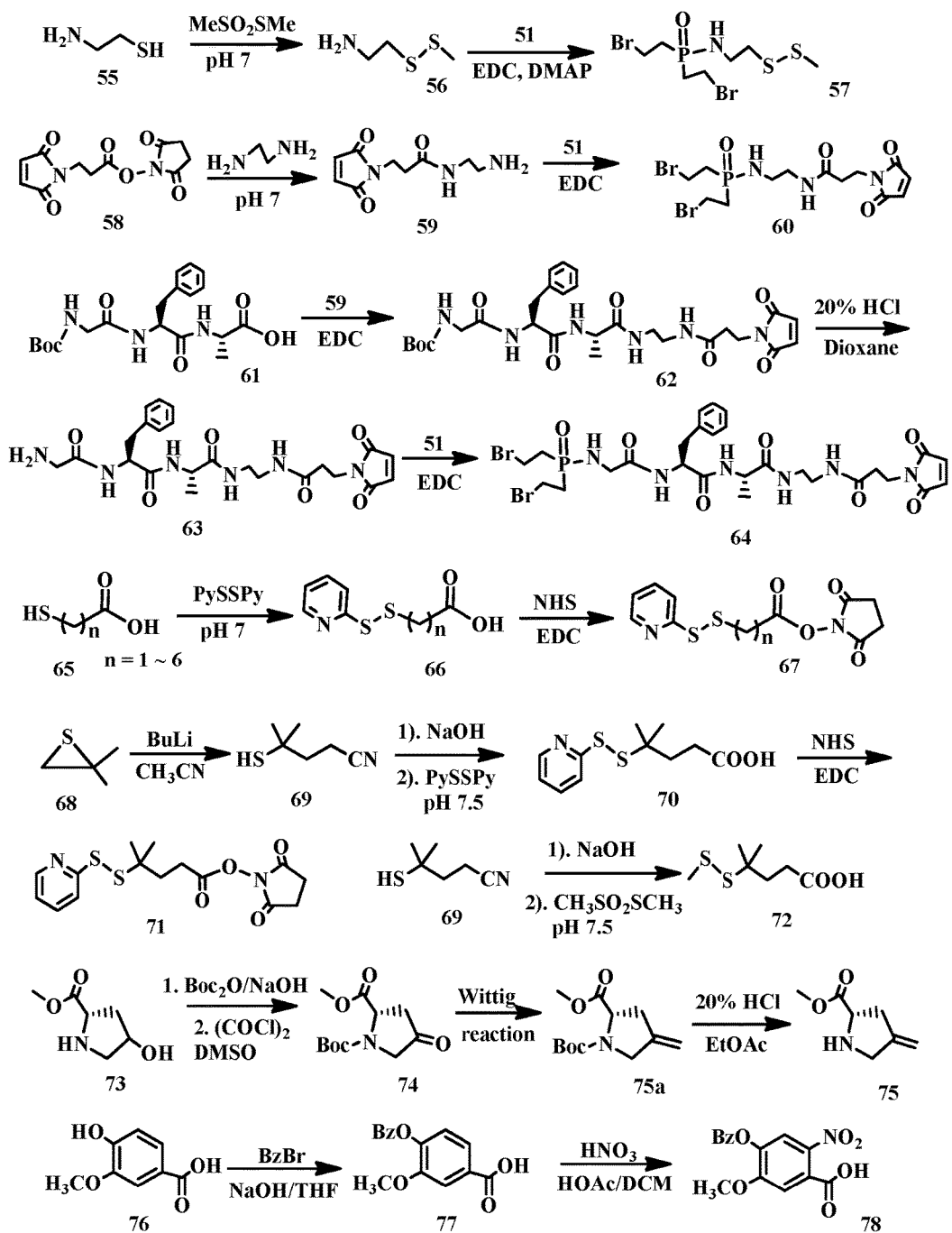
FIG. 4 shows the synthesis of linkers and intermediates for the conjugates of benzodiazepine dimers.
Figure 5:
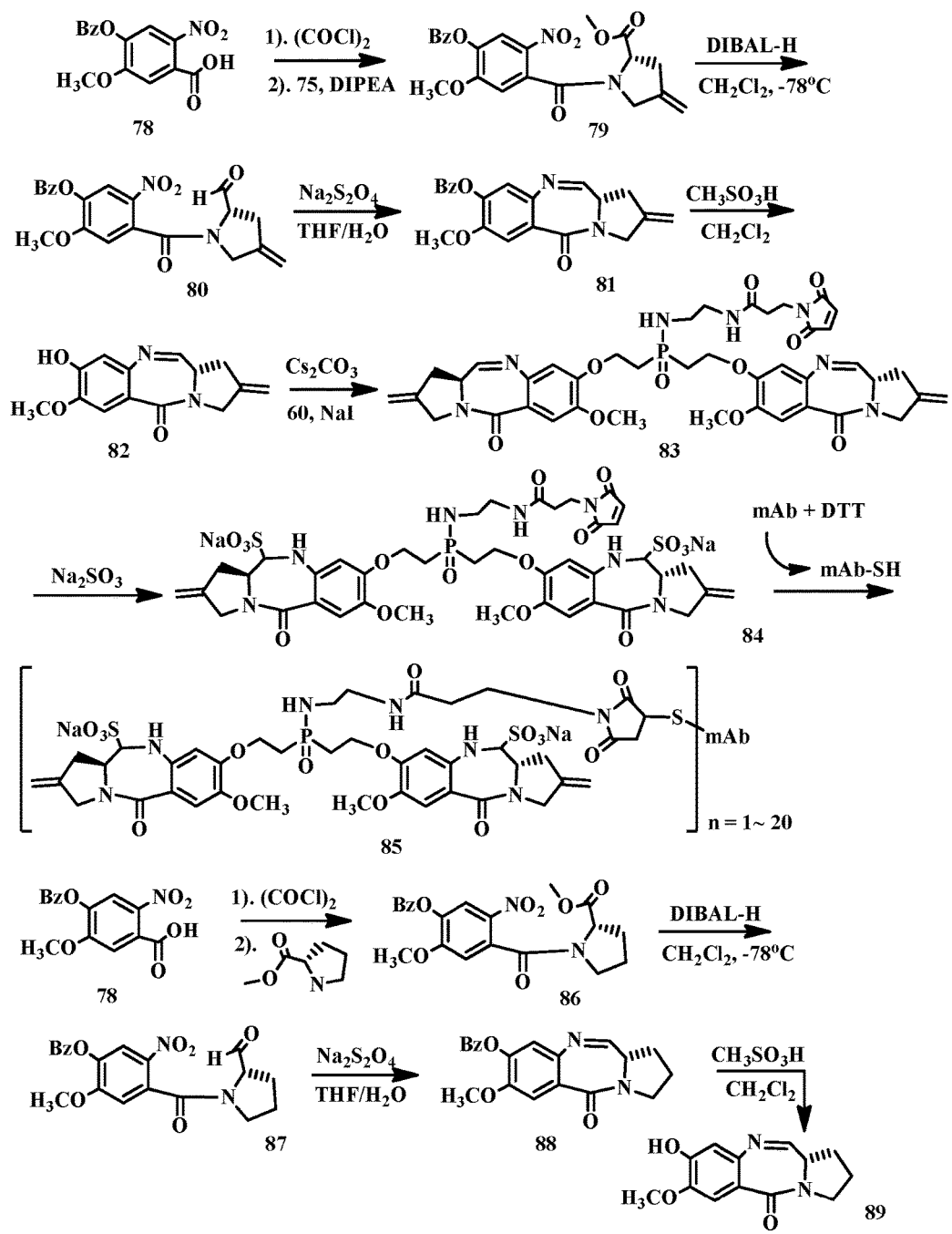
FIG. 5 shows synthesis of the intermediates and the conjugates of benzodiazepine dimers.
Figure 6:
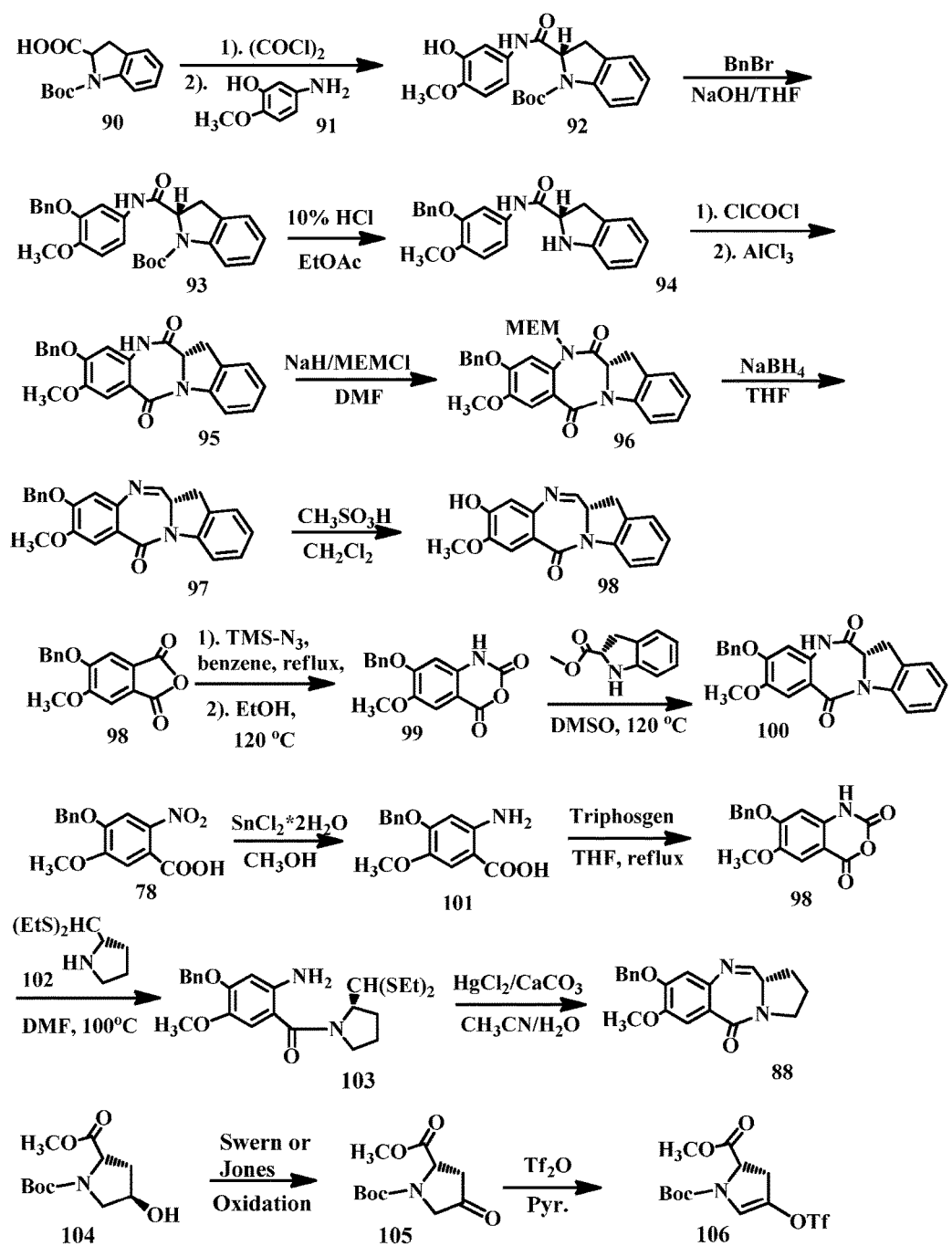
FIG. 6 shows the synthesis of intermediates for the synthesis of benzodiazepine dimers.
Figure 7:
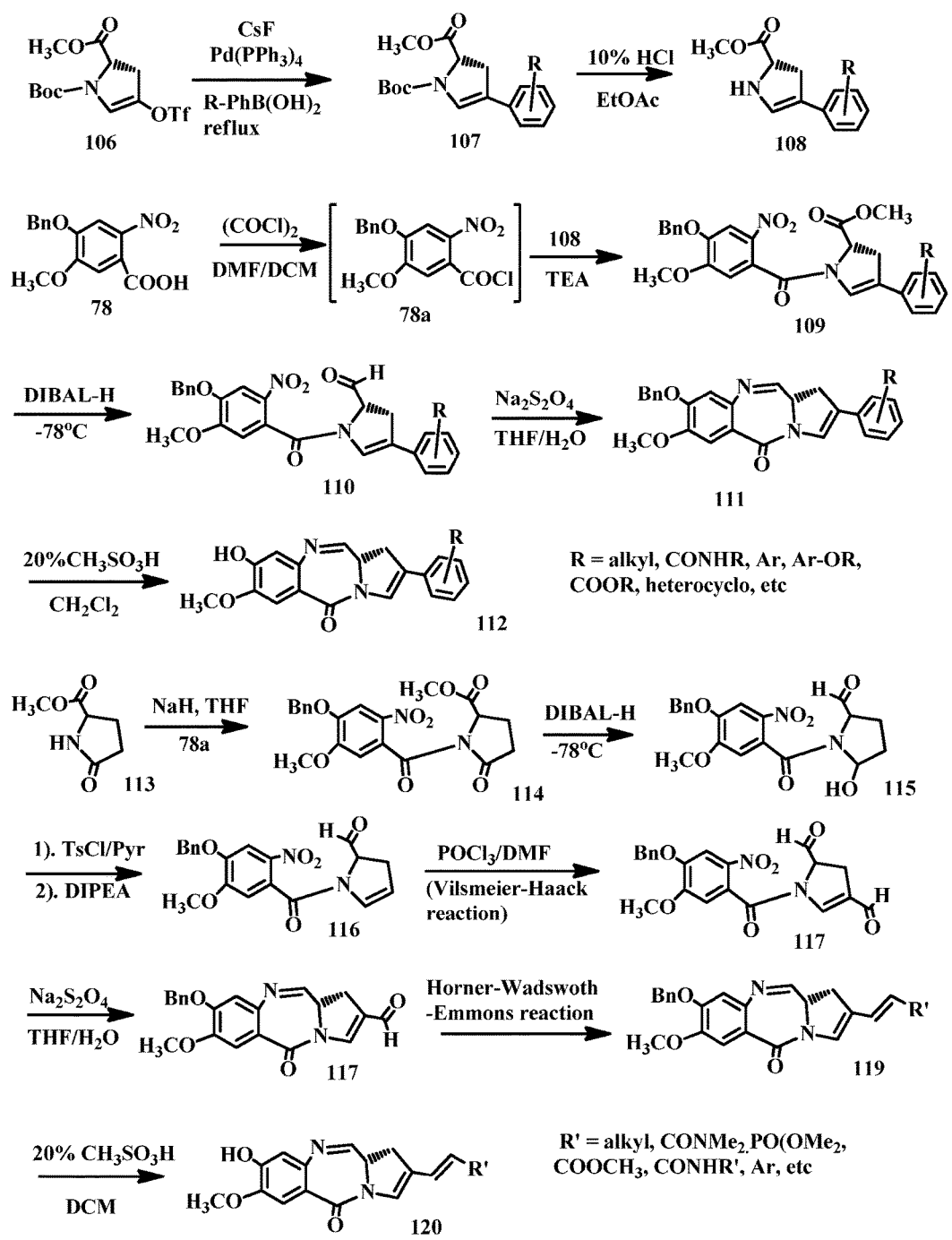
FIG. 7 shows the synthesis of intermediates for the synthesis of benzodiazepine dimers.
Figure 8:
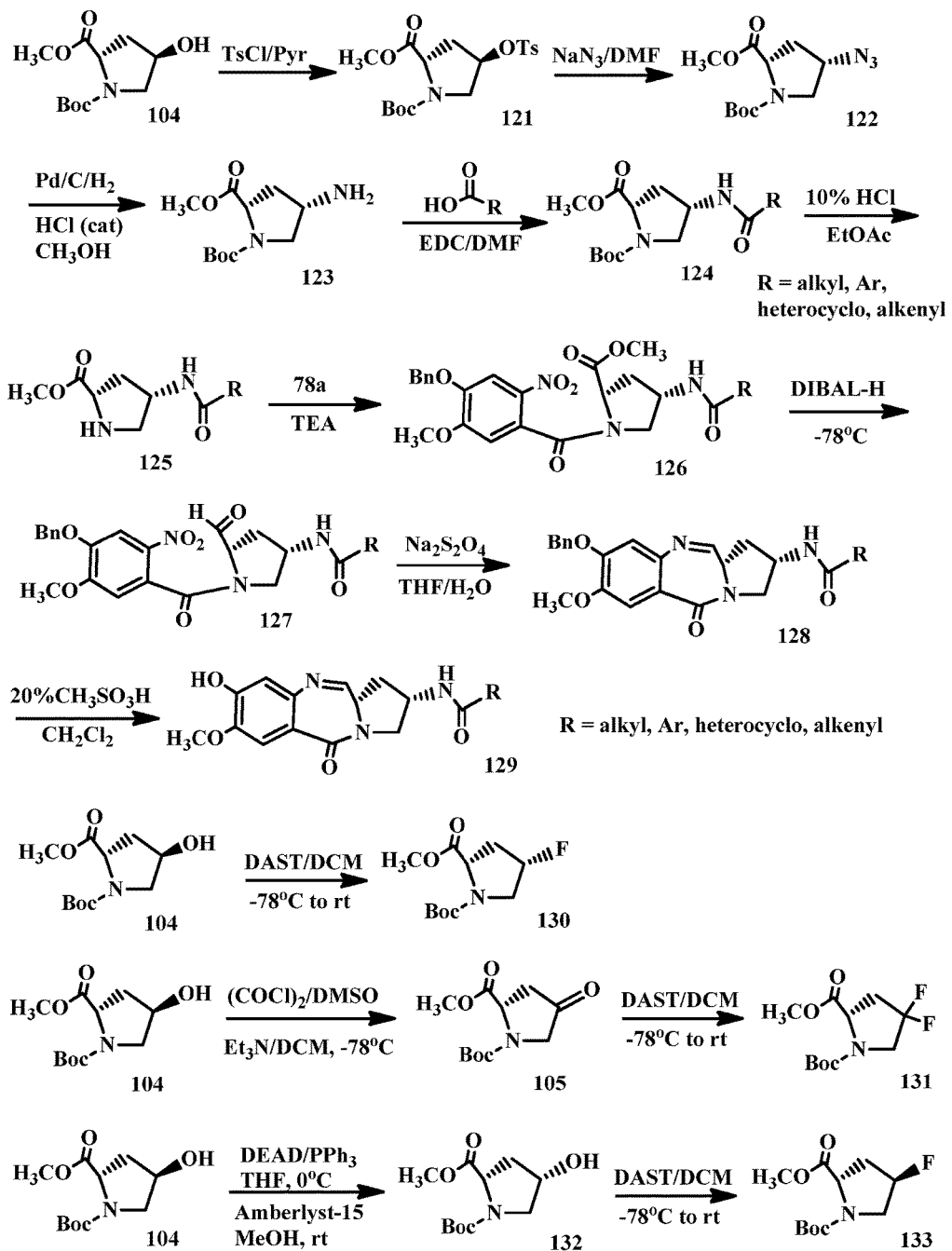
FIG. 8 shows the synthesis of intermediates for the synthesis of benzodiazepine dimers.
Figure 9:
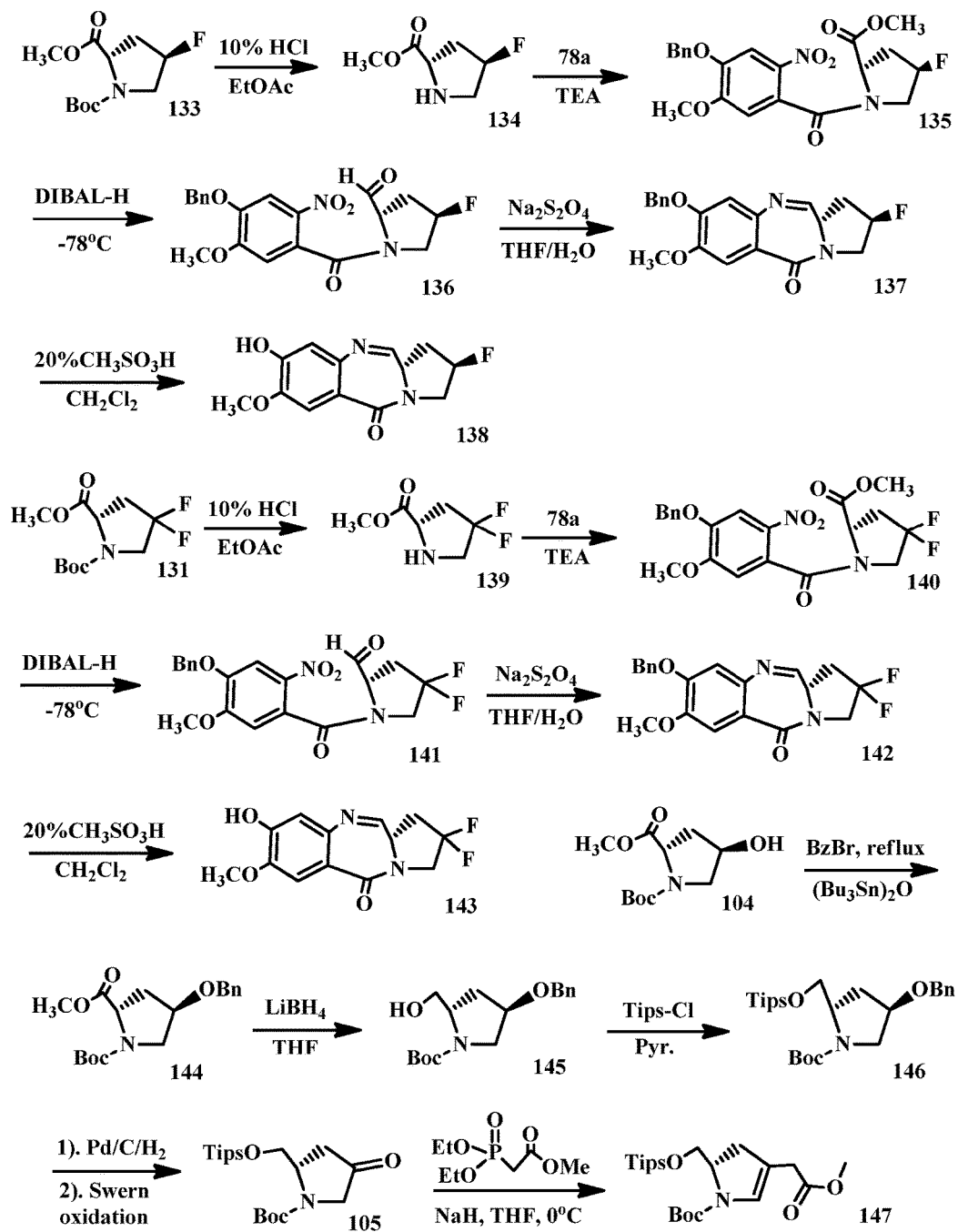
FIG. 9 shows the synthesis of intermediates for the synthesis of benzodiazepine dimers.
Figure 10:
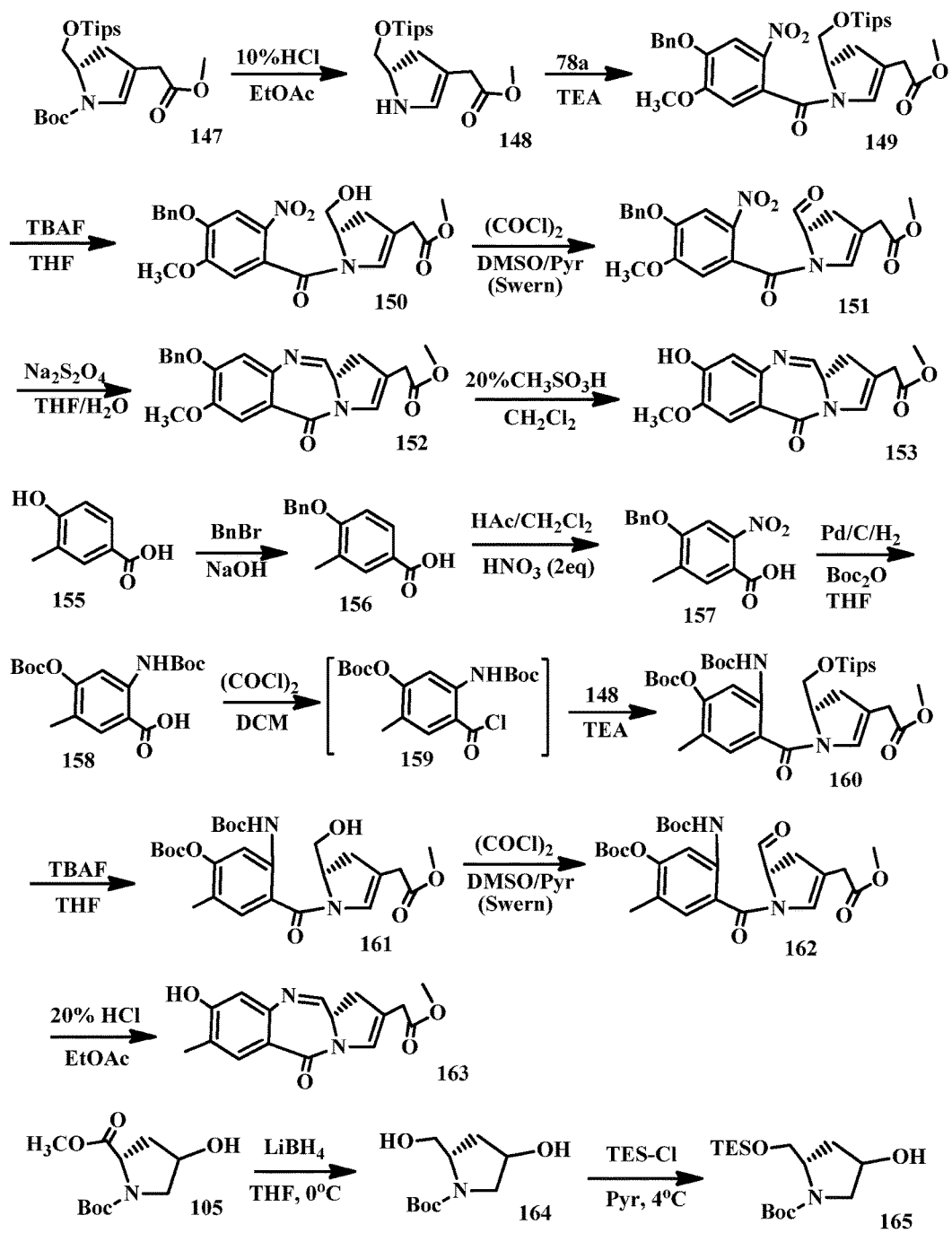
FIG. 10 shows the synthesis of intermediates for the synthesis of benzodiazepine dimers.
Figure 11:
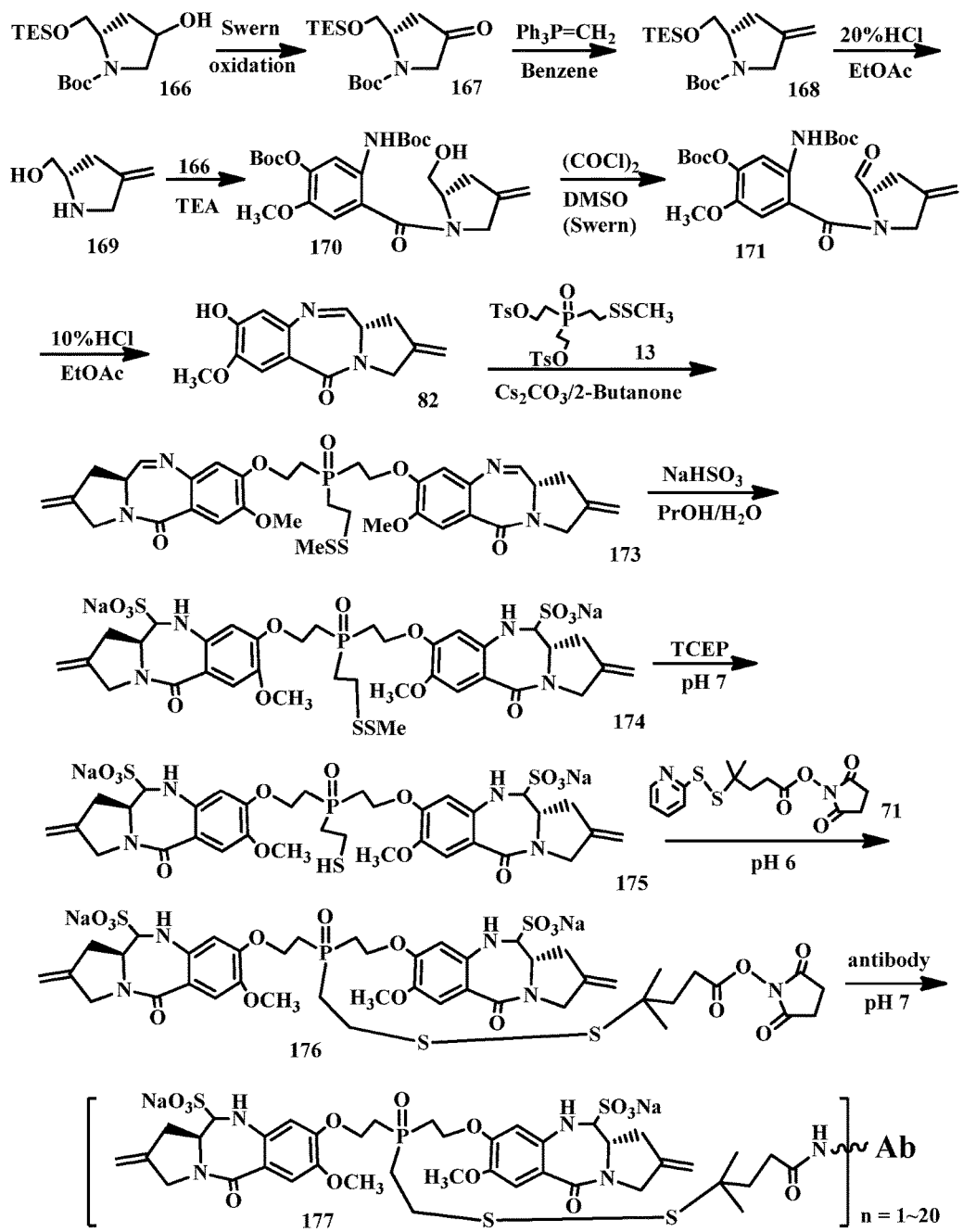
FIG. 11 shows the synthesis of intermediates and conjugates of benzodiazepine dimers.
Figure 12:
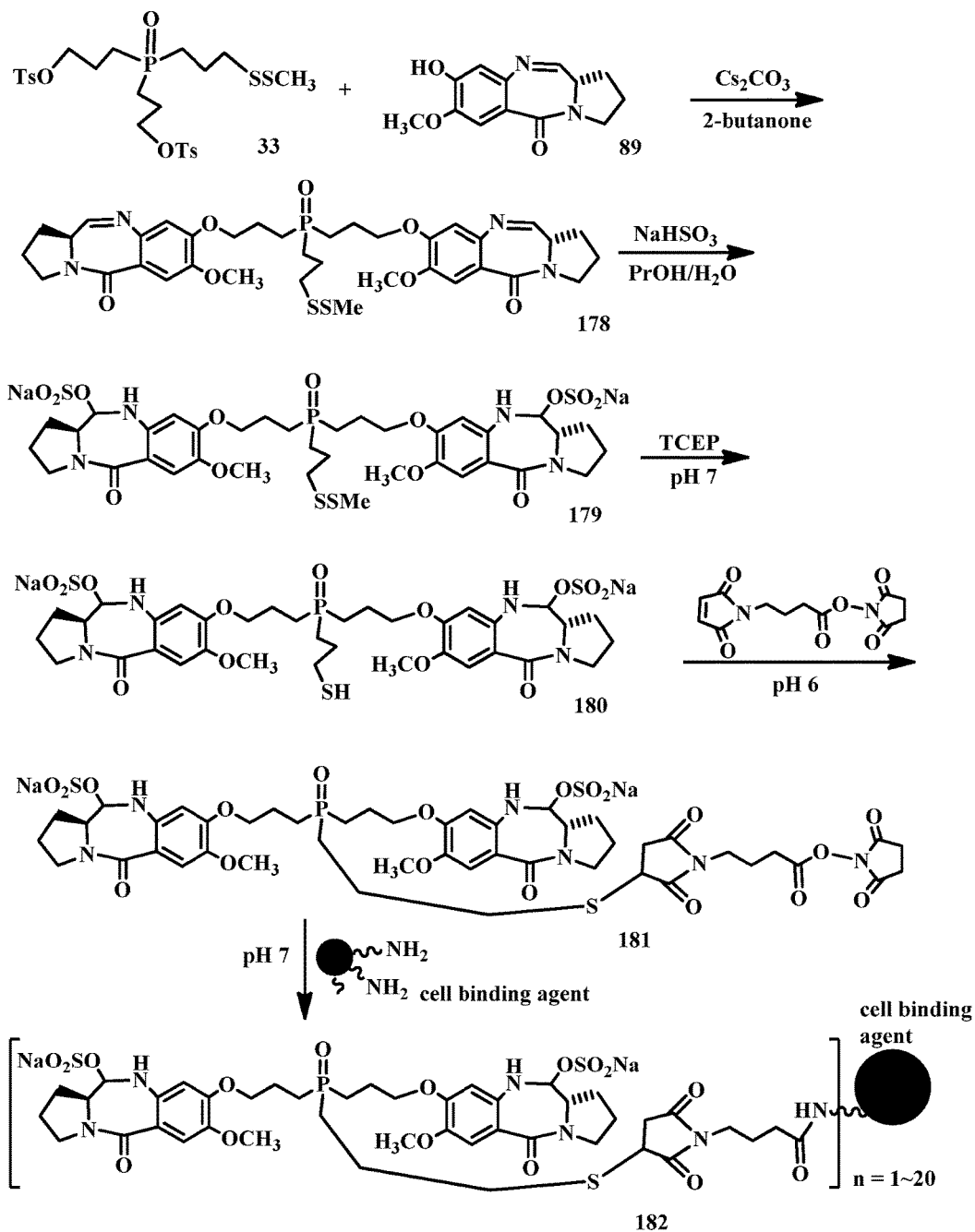
FIG. 12 shows the synthesis of conjugates of benzodiazepine dimers.
Figure 13:
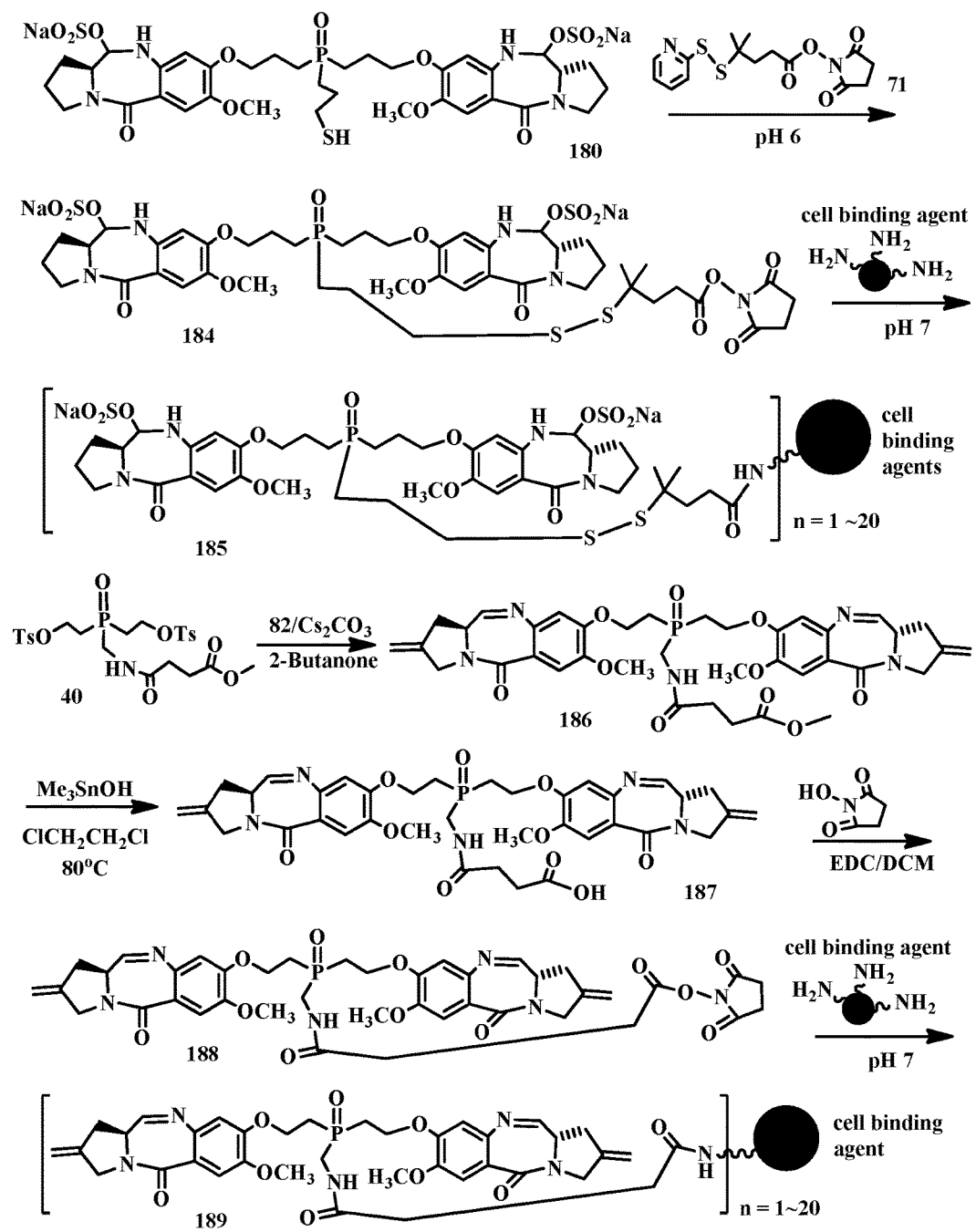
FIG. 13 shows the synthesis of conjugates of benzodiazepine dimers.
Figure 14:
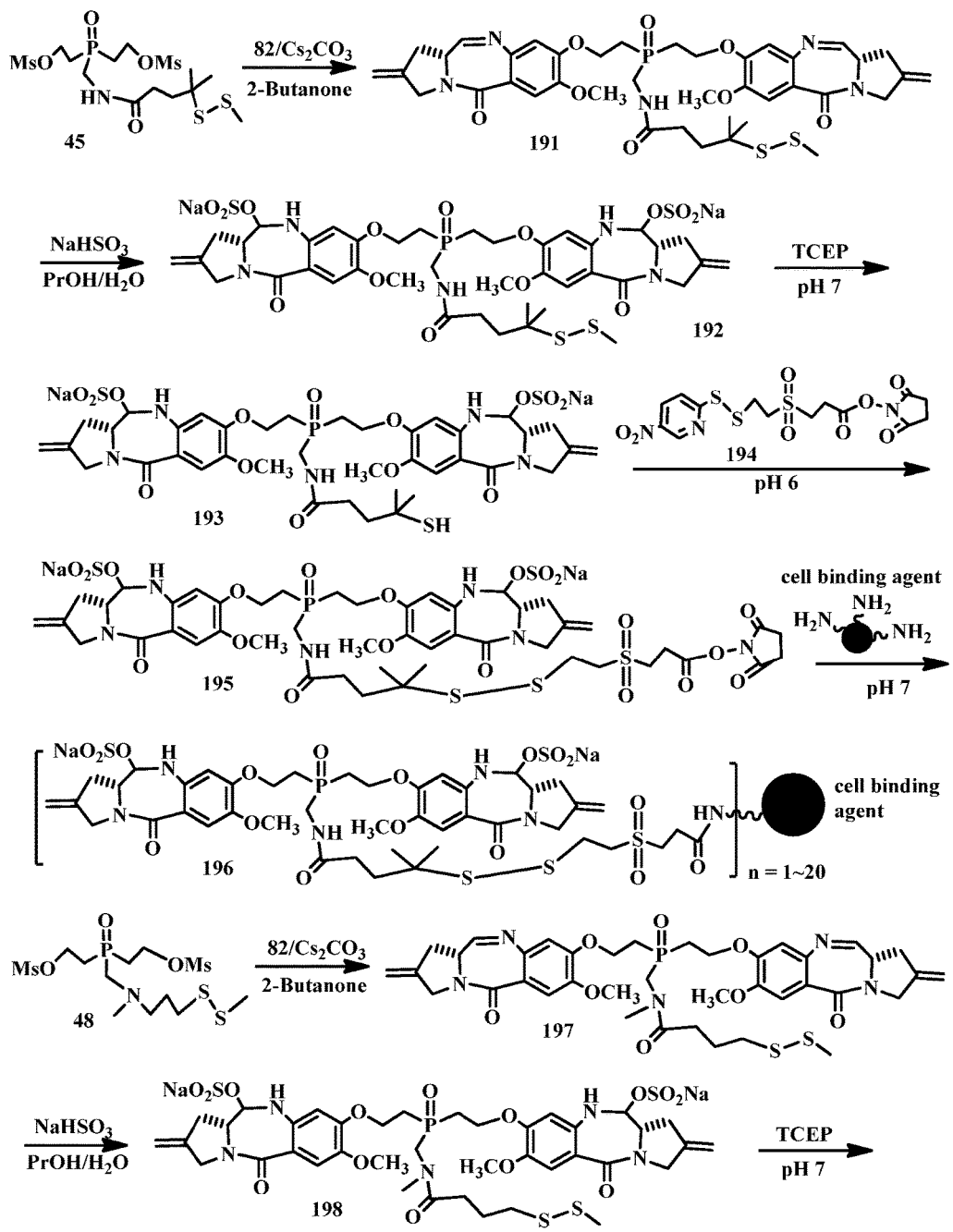
FIG. 14 shows the synthesis of conjugates of benzodiazepine dimers.
Figure 15:
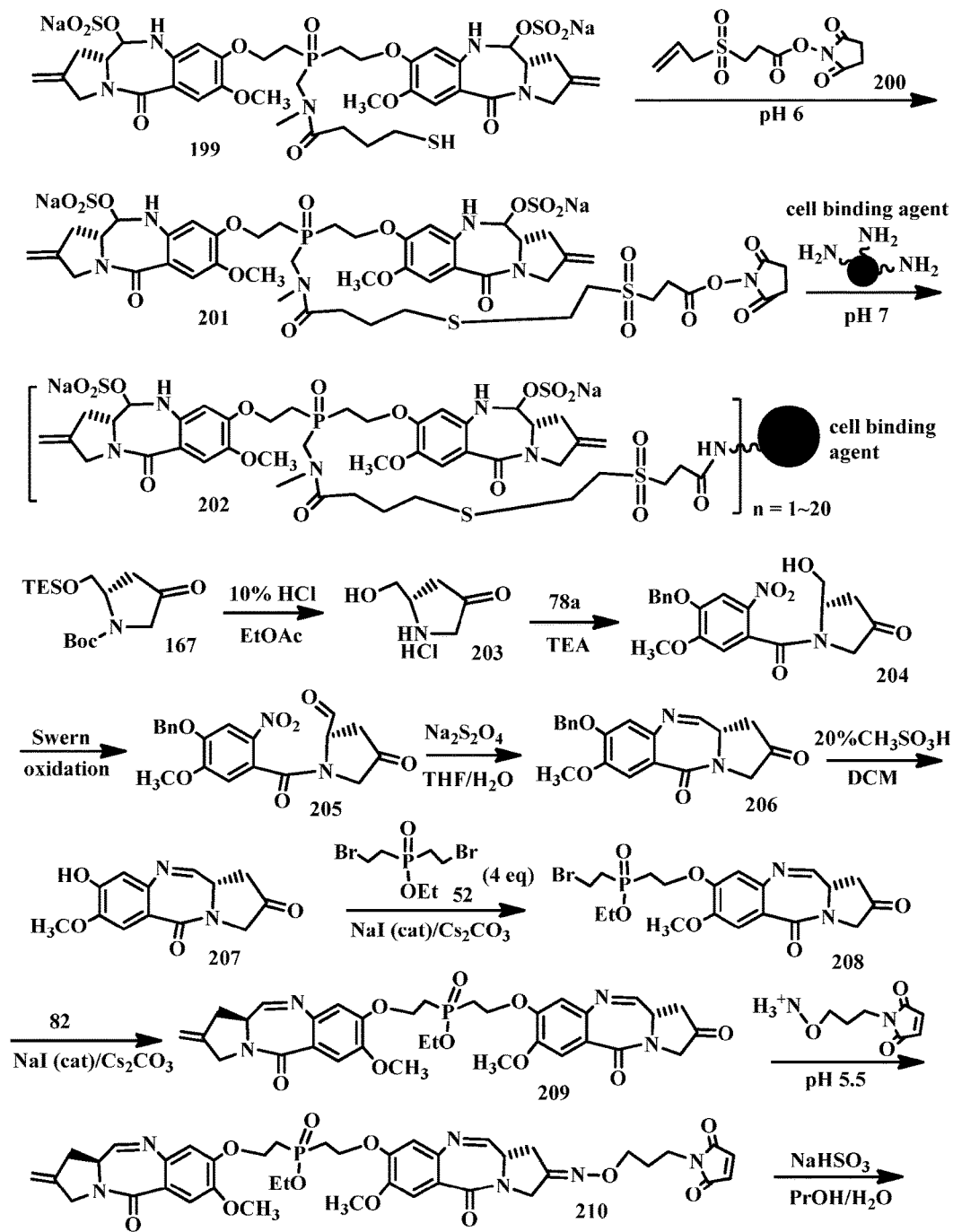
FIG. 15 shows the synthesis of conjugates of benzodiazepine dinners.
Figure 16:
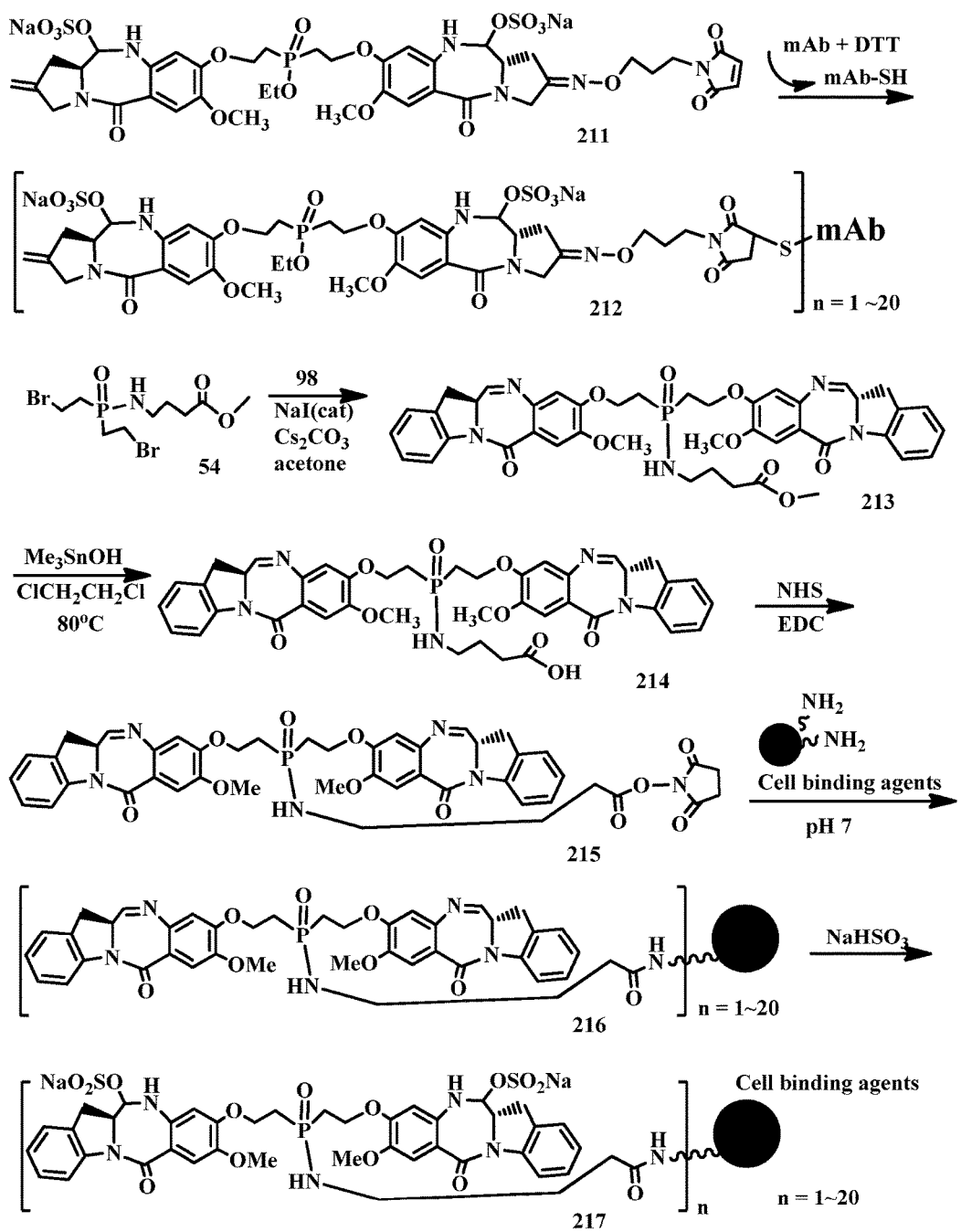
FIG. 16 shows the synthesis of conjugates of benzodiazepine dimers.
Figure 17:
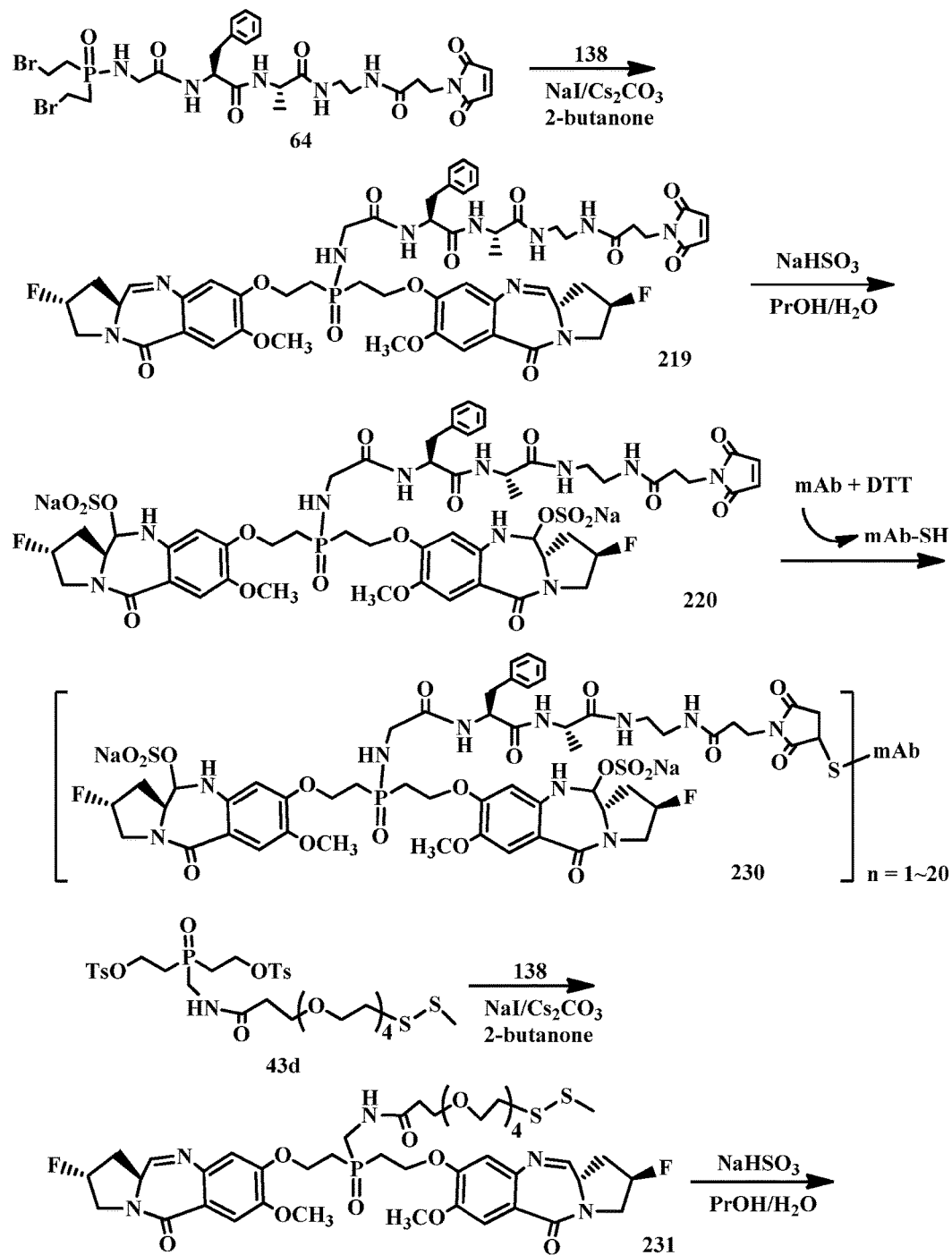
FIG. 17 shows the synthesis of conjugates of benzodiazepine dimers.
Figure 18:
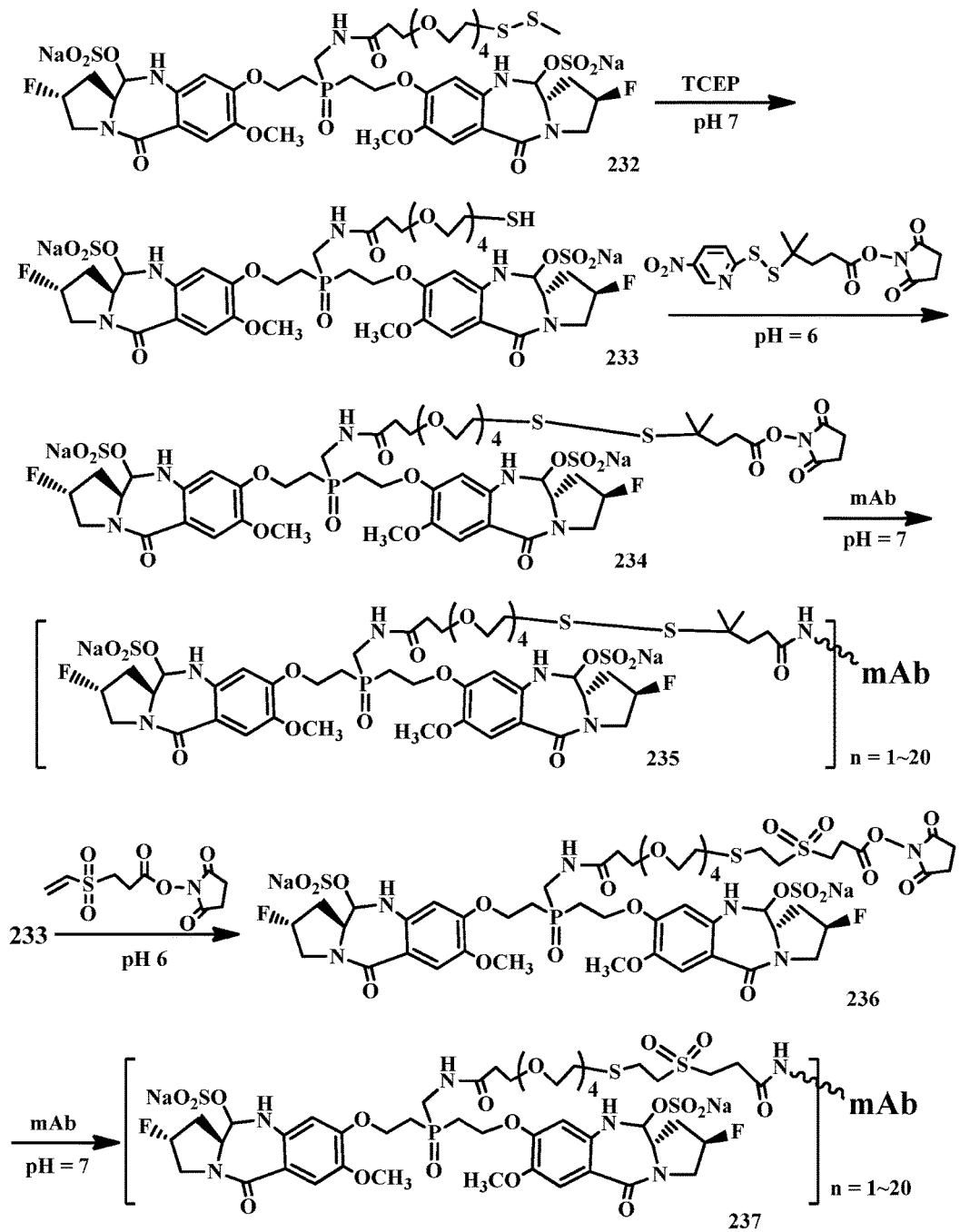
FIG. 18 shows the synthesis of conjugates of benzodiazepine dimers.
Figure 19:
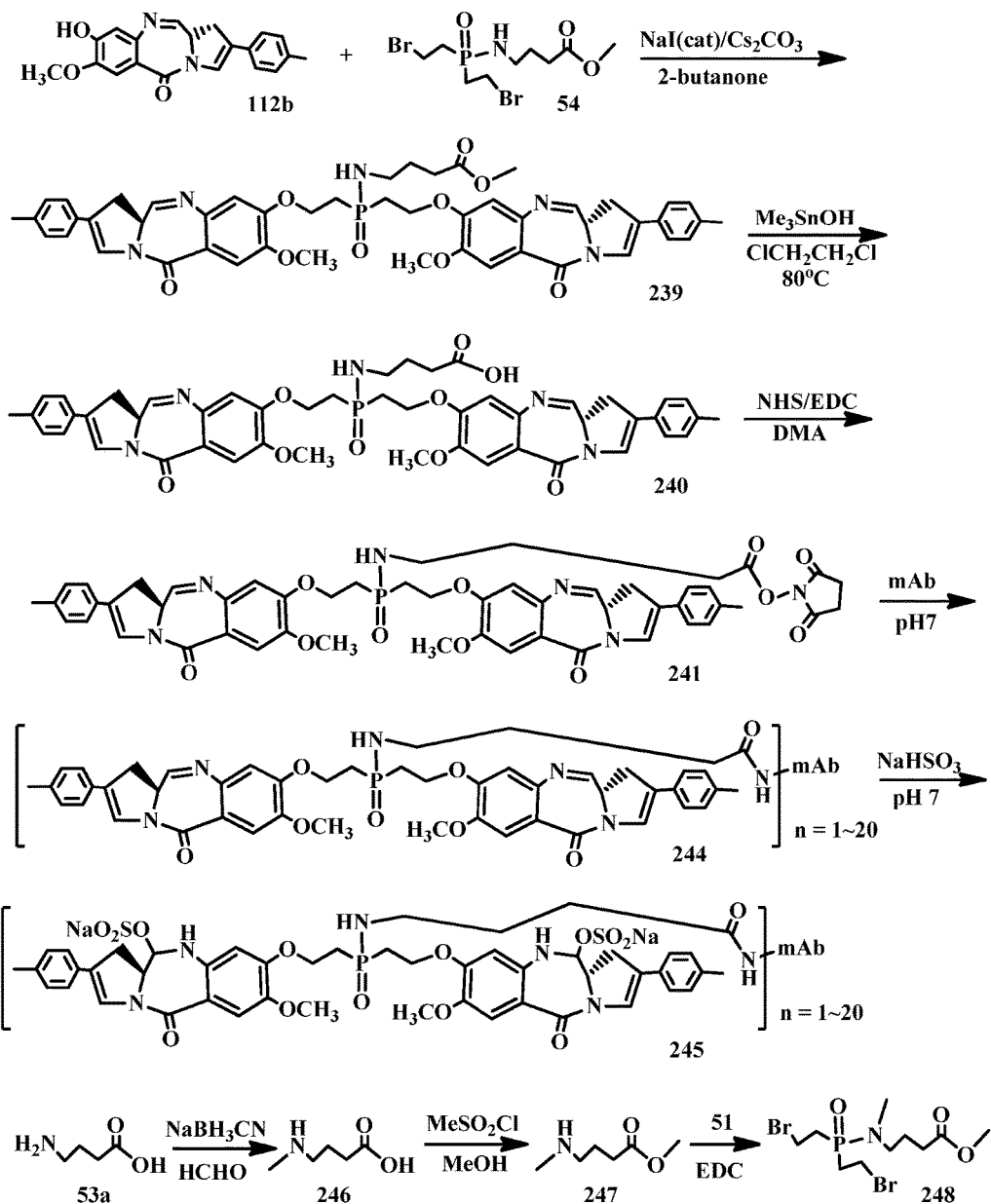
FIG. 19 shows the synthesis of conjugates of benzodiazepine dimers.
Figure 20:
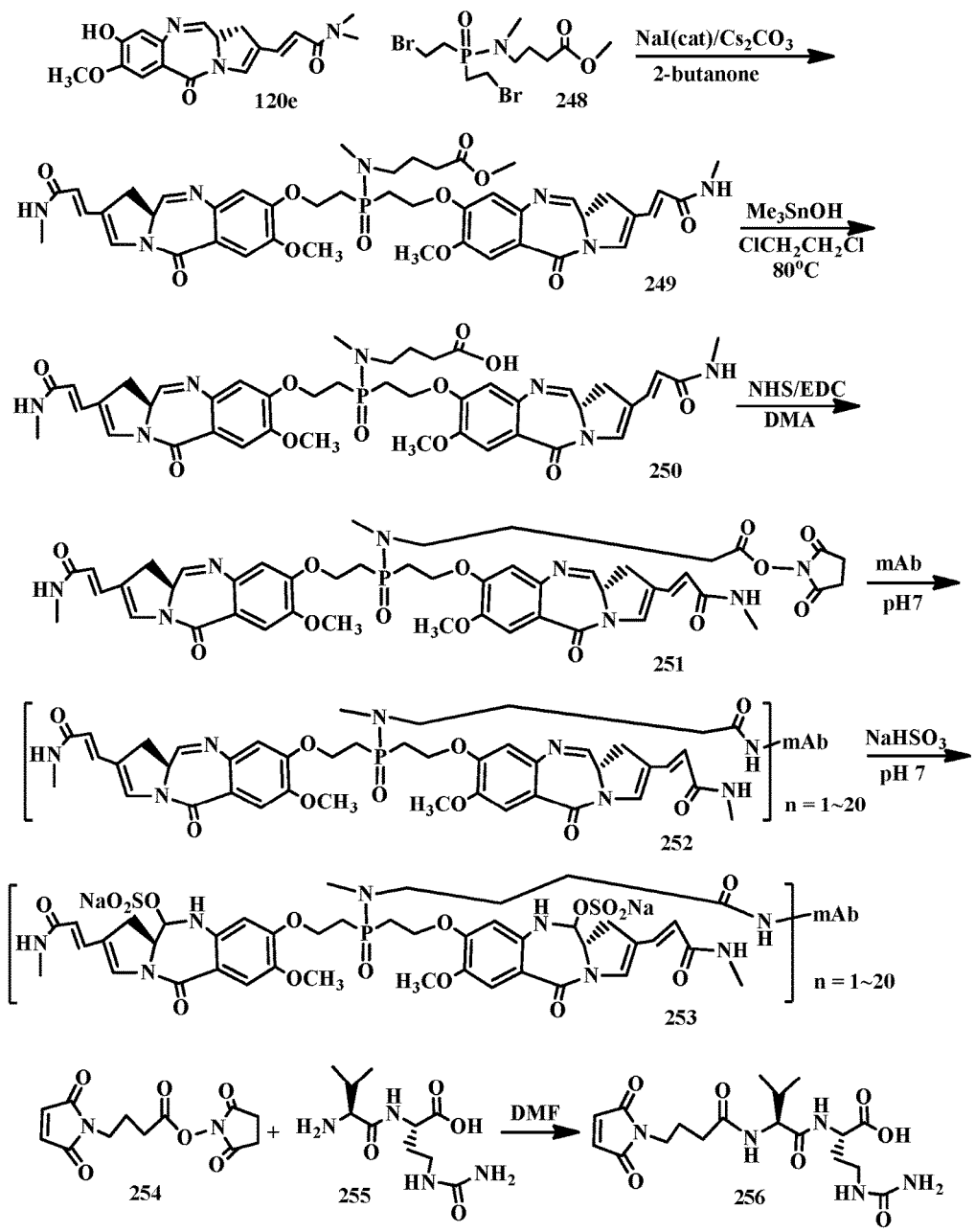
FIG. 20 shows the synthesis of conjugates of benzodiazepine dimers.
Figure 21:
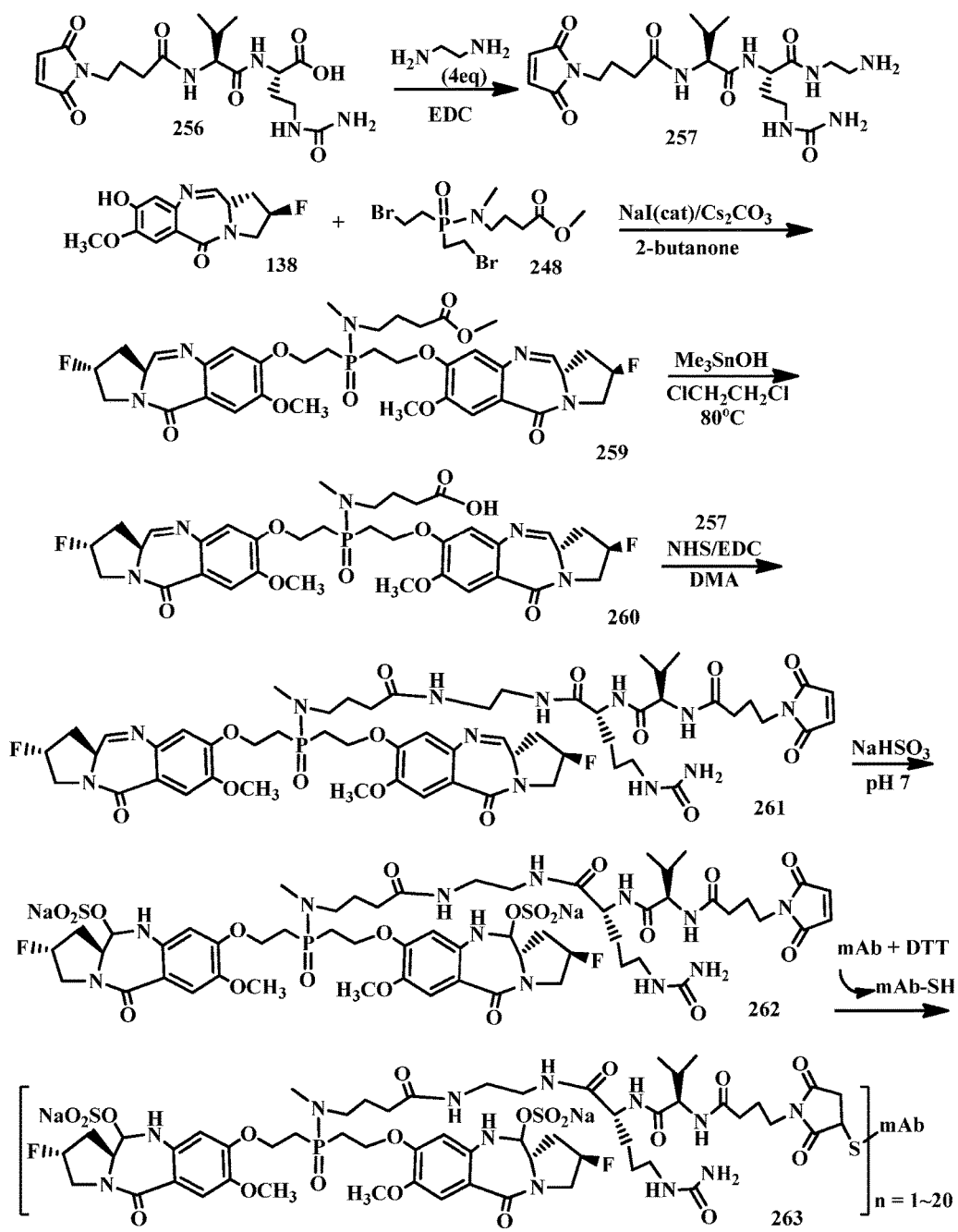
FIG. 21 shows the synthesis of conjugates of benzodiazepine dimers.
Figure 22:
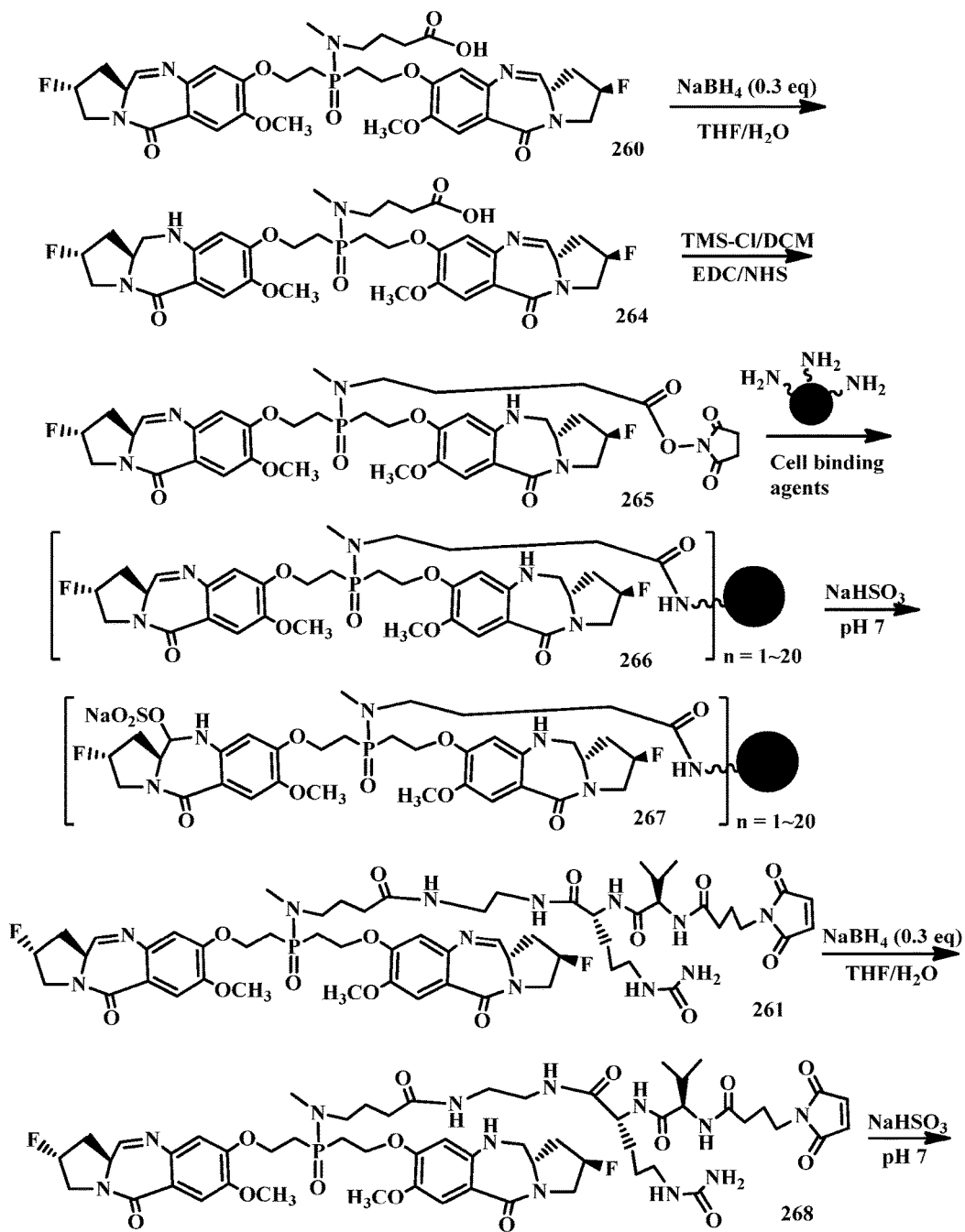
FIG. 22 shows the synthesis of conjugates of benzodiazepine dimers.
Figure 23:
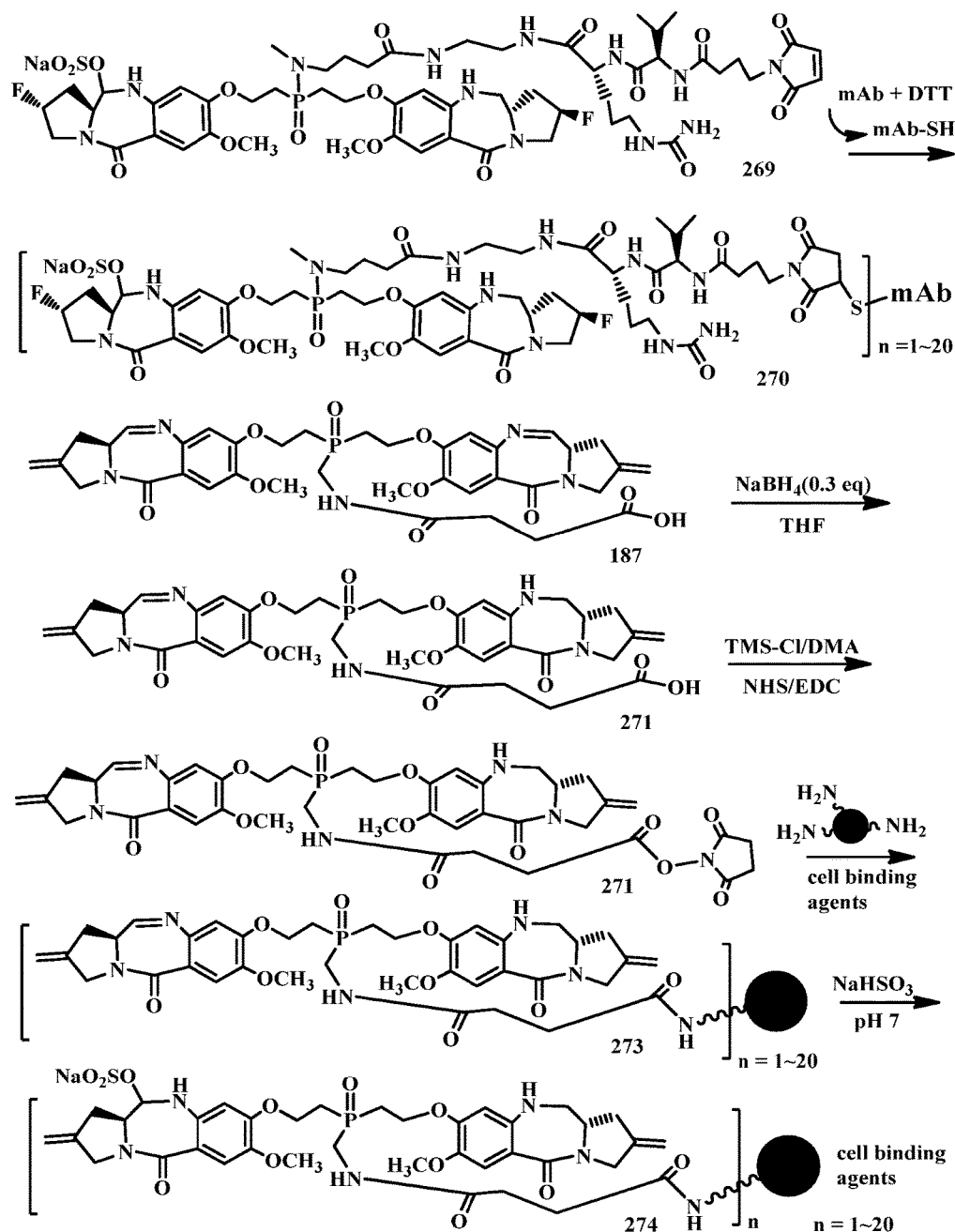
FIG. 23 shows the synthesis of conjugates of benzodiazepine dimers.

Some of the synthetic reactions of the cytotoxic agents and their conjugates to a cell binding agent are further exampled but not restricted in the FIGS. 1~23 and in the examples 1~73 of the description.

The Conjugates of Cell-Binding Agent—Cytotoxic Agent

The present invention also provides a conjugate molecule comprising at least one PBD derivative covalently linked to a cell binding agent (CBA) through the linking group of the crosslinker (L). Preferably said conjugate comprises one to twenty molecules of PBD derivatives according to the invention covalently linked to a cell binding agent through the linking group of the linker of the PBD derivatives.

As stated above, the conjugates of a cell surface binding molecule-cytotoxic agent are illustrated in the formula (I):

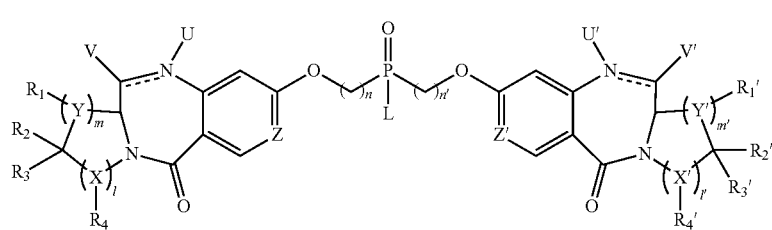
(I)

or their pharmaceutically acceptable salts, hydrates, or hydrated salts, or the polymorphic crystalline structures of these compounds or their optical isomers, racemates, diastereomers or enantiomers.

wherein U, U', V, V', m, m', n, n', X, X', Y, Y', Z, Z' $R_1$, $R_2$, $R_3$, $R_4$, $R_1{}'$, $R_2{}'$, $R_3{}'$, and $R_4{}'$, L are described above. L is preferred a linker-cell binding molecule covalently bound cluster, When L is $R_5$, $OR_5$, $SR_5$ or $NR_5R_{5'}$, then $R_1$, $R_2$, $R_3$, $R_4$, $R_1{}'$, $R_2{}'$, $R_3{}'$, $R_4{}'$, U, V, U' or V' on the formula (I) can be used to linked to a cell-binding molecule (CBA) via L', or via Stretcher units (Ww) or via. Spacer units (Tt). Wherein CBA, L', W, w, T, and t are as described through the patent application.

In certain embodiments, the conjugates of the invention are illustrated in the formula (XIX), (XX), (XXI), (XXII), (XXIII), and (XXIV)

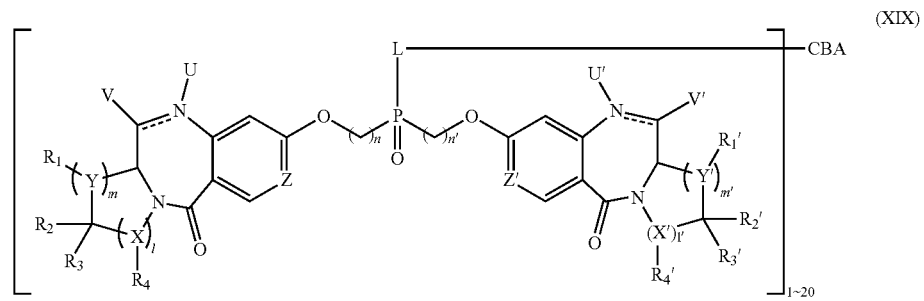
(XIX)

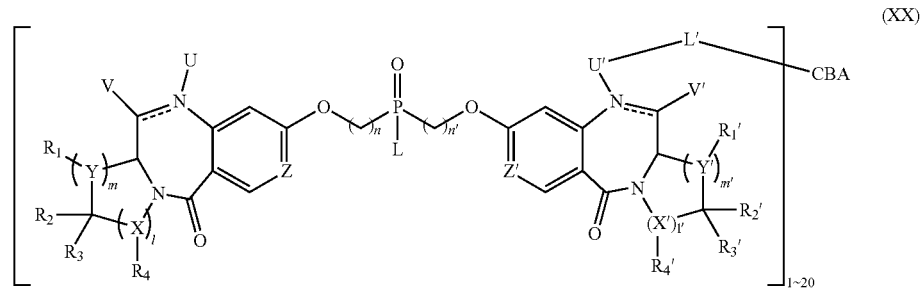
(XX)

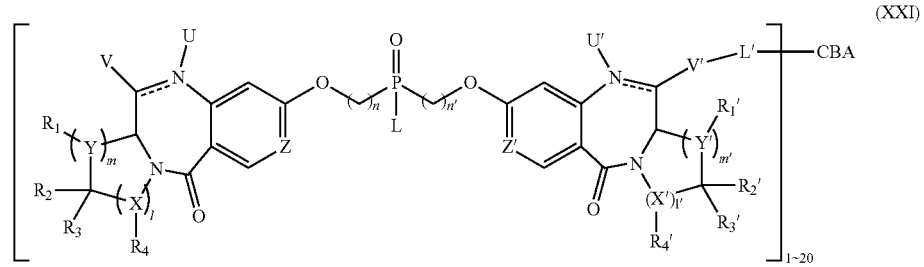
(XXI)

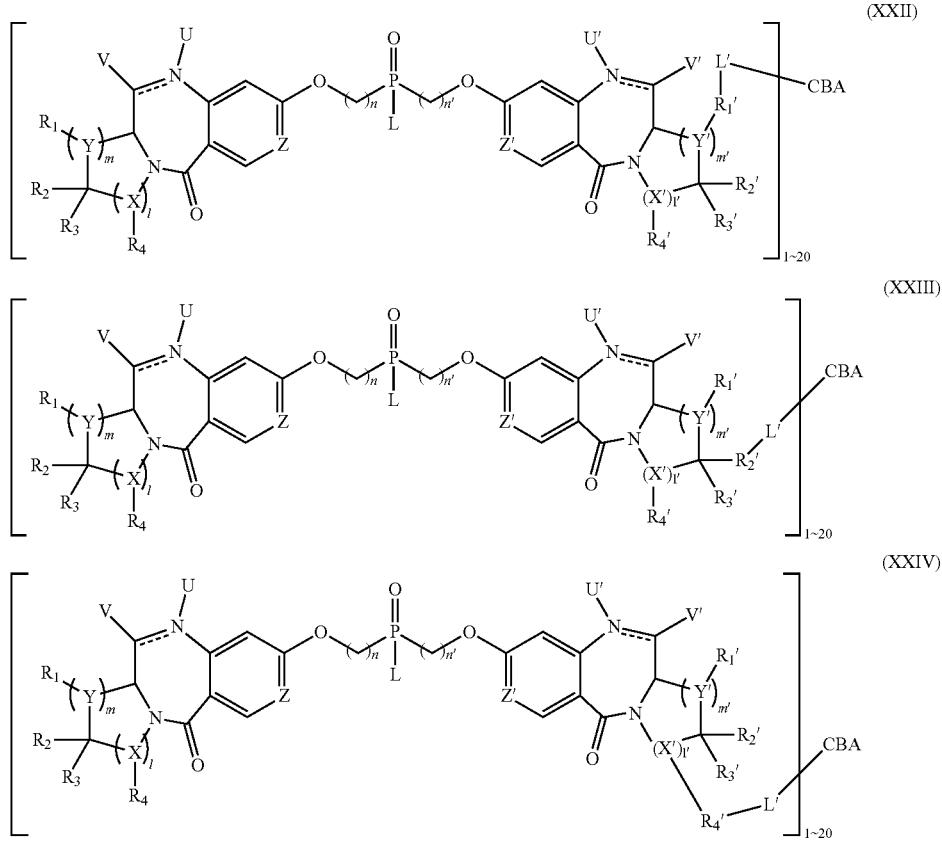

wherein U, U', V, V', m, m', n, n', X, X', Y, Y', Z, Z' $R_1$, $R_2$, $R_3$, $R_4$, $R_{1'}$, $R_{2'}$, $R_{3'}$, and $R_{4'}$, L are described above in Formula (I). L' is the same or independently L as defined in Formula (I).

Drug loading may range from 1 to 20 drug moieties (D) per cell binding agent and is preferred the average number of 2~8 drug moieties per cell binding agent in a molecule of Formula (IX)~(XIV). When CBA is antibody in preparations of ADC, the preferred drug loading is 3~6 drug per antibody andthe average number of drug moieties per antibody from conjugation reactions may be characterized by conventional means such as mass spectroscopy, ELISA assay, and HPLC. The quantitative distribution of the conjugates in terms of the drug loading may also be determined. In some instances, separation, purification, and characterization of homogeneous the conjugates where drug loading is a certain value from the conjugates with the drug loadings may be achieved by means such as reverse phase HPLC or electrophoresis.

The Cell binding agents (CBA) may be of any kind and include peptides and non-peptides. Generally, the cell binding agents include, but are not limited to, large molecular weight proteins such as, for example, full-length antibodies (polyclonal and monoclonal antibodies); single chain antibodies; fragments of antibodies such as Fab, Fab', F(ab')1, $F_v$, [Parham, J. Immunol. 131, 2895-2902 (1983)], fragments produced by a Fab expression library, anti-idiotypic (anti-Id) antibodies, CDR's, and epitope-binding fragments of any of the above which immuno-specifically bind to cancer cell antigens, viral antigens or microbial antigens; antibody mimetic, such as an affibody; domain antibodies (dAb); nanobodies; unibodies; DARPins; anticalins; versabodies; duocalins; lipocalins; vimers; interferons (such as type I, II, III); peptides; lymphokines such as IL-2, IL-3, IL-4, IL-6, GM-CSF, interferon-gamma (IFN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-158 (1984)]; vaccinia growth factors (VGF); fibroblast growth factors (FGFs); smaller molecular weight proteins, poly-peptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin {O'Keefe et al, 260 J. Biol. Chem. 932-937 (1985)}; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); dendrimers (Lee, et al, Nat. Biotechnol. 2005, 23, 1517-26; Ainiutairi, et al; Proc. Natl. Acad. Sci.

2009, 106, 685-90); nanoparticles (Liong, et al, ACS Nano, 2008, 19, 1309-12; Medarova, et al, Nat. Med. 2007, 13, 372-7; Javier, et al, Bioconjugate Chem, 2008, 19, 1309-12); liposomes (Medinai, et al, Curr. Phar. Des. 2004, 10, 2981-9); viral capsides (Flenniken, et al, Viruses Nanotechnol. 2009, 327, 71-93). In general monoclonal antibodies are preferred as a cell-surface binding agent if an appropriate one is available.

The linker used for the conjugation of this invention includes, but not limited to, a disulfide linker, a thioether linker, an amide bonded linker, a peptidase-labile linker, a photolabile linker, an acid-labile linkers (such as hydrazone liner), an esterase-labile linker, an oxidatively labile linker, a metabolically labile linker, a biochemically labile linker.

Preferably, the linker is linked to the cell binding agent via a function reactive towards for instance thiol and amino functions of the cell binding agent coming from reduced disulfide bonds and lysine residues respectively. More particularly, said derivative is linked through the —CO— group to the amino function of the lysine residue of said cell binding agent, so as to form an amide bond.

In addition, the linker may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), glycine-glycine, p-aminobenzyloxycarbonyl ("PAB"), N-succinimidyl 4-(2-pyridylthio)pentanoate ("SPP"), N-succinimidyl 4-(N-maleimidomethyl)cyclohexane-1 carboxylate ("SMCC"), N-Succinimidyl (4-iodoacetyl)aminobenzoate ("SIAB"), ethyleneoxy (—CH$_2$CH$_2$O—) as one or more repeating units ("EO" or "PEO"). The linker may be a "cleavable linker," facilitating release of a drug in the cell. Additional linker components are known in the art and some are illustrated below:

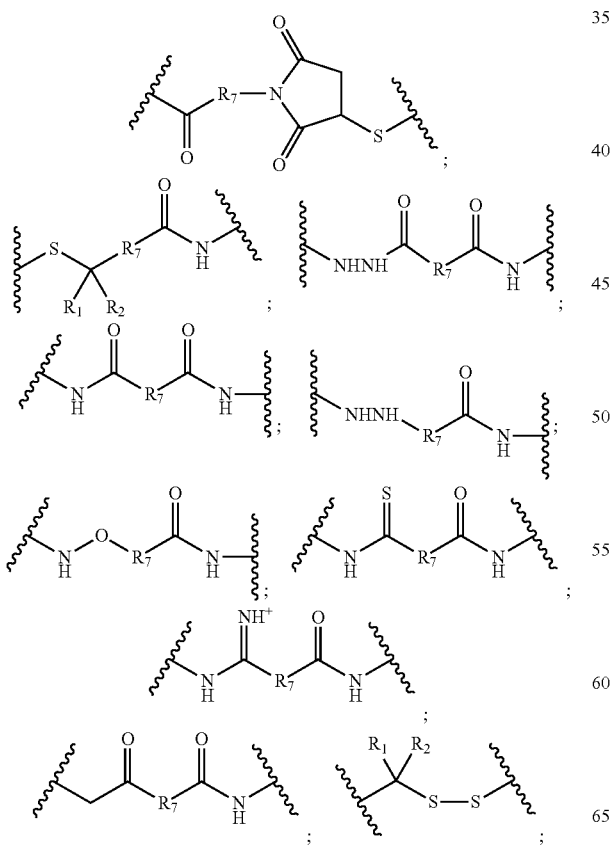

-continued

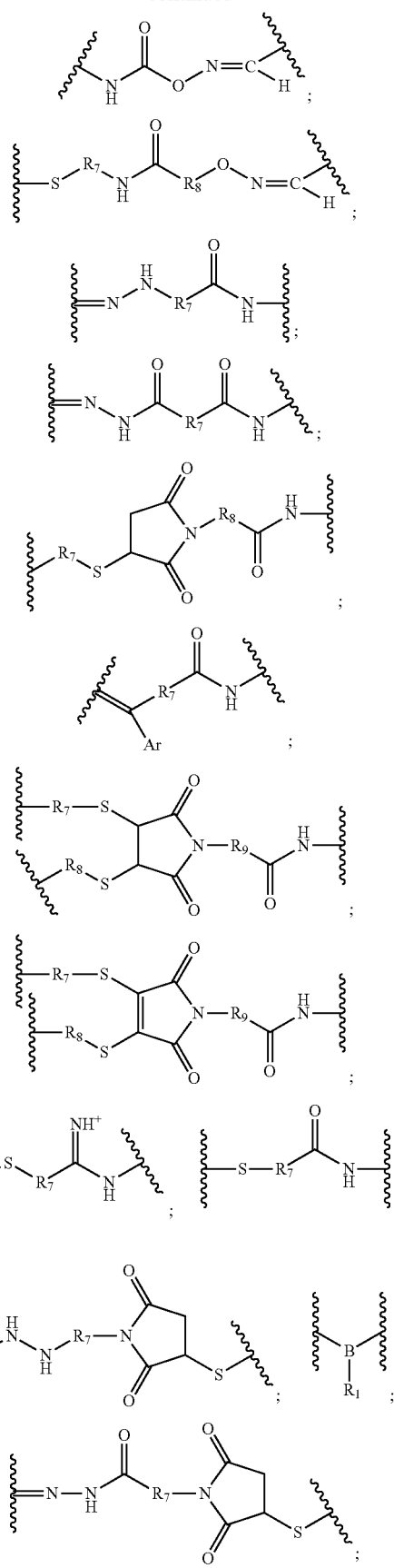

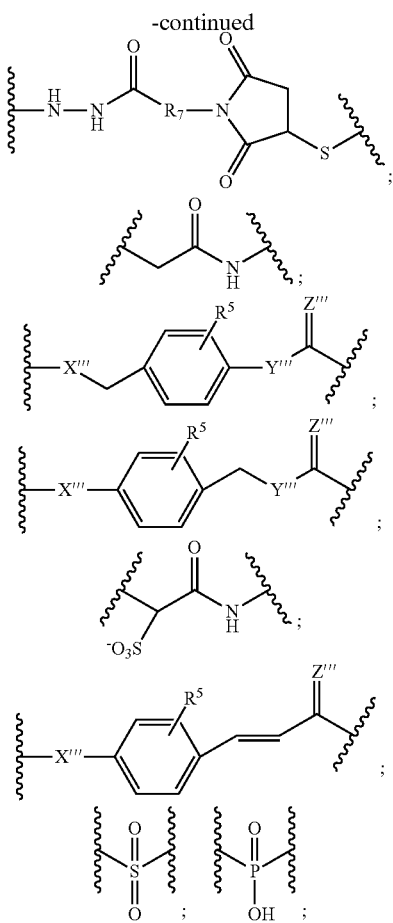

wherein $R_7$, $R_8$ and $R_9$ are defined as $R_5$, and more preferred independently selected from —$C_1$~$C_8$ alkyl or alkylene-, —$C_1$~$C_7$ carbocyclo-, —O—($C_1$<$C_8$ alkyl)-, -arylene-, —$C_1$~$C_8$ alkylene-arylene-, -arylene, —$C_1$~$C_8$ alkylene-, —$C_1$~$C_8$ alkylene-($C_1$~$C_8$ carbocyclo)-, —($C_3$~$C_7$ carbocyclo)-$C_1$~$C_8$ alkylene-, —$C_3$~$C_8$ heterocyclo-, —$C_1$~$C_8$ alkylene-($C_3$~$C_8$ heterocyclo)-, —($C_3$~$C_8$ heterocyclo)-$C_1$~$C_9$ alkylene-, —($CH_2CH_2O)_k$—, —($CH(CH_3)CH_2O)_k$—, and —($CH_2CH_2O)_k$—$CH_2$—; k is an integer ranging from 1-30; X''', Y''' and Z''' are independently selected from NH, O or S; $R_1$ and $R_2$ are described above.

In a preferred embodiment, conjugates of the invention are antibody/cytotoxic agent, antibody fragment/cytotoxic agent, diabody/cytotoxic agent, tri(a)body/cytotoxic agent, epidermal growth factor (EGF)/cytotoxic agent, prostate specific membrane antigen (PSMA) inhibitor/cytotoxic agent, melanocyte stimulating hormone (MSH)/cytotoxic agent, thyroid stimulating hormone (TSH)/cytotoxic agent, polyclonal antibody/cytotoxic agent, somatostatin/cytotoxic agent, folate/cytotoxic agent, matriptase inhibitor/cytotoxic agent, estrogen/cytotoxic agent, estrogen analogue/cytotoxic agent, designed ankyrin repeat proteins (DARPins)/cytotoxic agent, androgen/cytotoxic agent, and androgen analogue/cytotoxic agent.

In a more preferred embodiment, conjugates of the invention are monoclonal antibody/cytotoxic agent. Examples of antibodies used for conjugation of cyotoxic agents in this prevention include, but are not limited to, 3F8 (anti-GD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab anti-TAG-72), Anrukinzumab (IMA-638, anti-IL-13), Apolizumab (anti-HLA-DR), Arciturnornab (anti-CEA), Aselizumab (anti-L-selectin (CD62L), Atlizumab (tocilizumab, Acternra, RoActernra, anti-IL-6 receptor), Atorolimumab (anti-Rhesus factor), Bapineuzumab (anti-beta amyloid), Basiliximab (Simulect, antiCD25 (α chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Bads, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza. A hemagglutinin), Dacetuzumab (anti-CD40), Daclizumab (Zenapax, anti-CD25 (α chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Solids, anti-C5), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin $α_vβ_3$), Exbivirumab (anti-hepatitis B surface antigen), Fanolesomab (NeutroSpec, anti-CD15), Faralimomab (anti-interferon receptor), Farietuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-3), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (α chain of IL-2 receptor)), Inotuzumab (anti-CD22), ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizunriab (Bosatria, anti-IL-5), Metelimumab (anti-TGF beta 1), Milatuzuma) (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin $\alpha_4$. Nebacumab (anti-endotoxin), Necitumumab (anti-EGFR), Nerelimomab (anti-TNF-$\alpha$), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R $\alpha$), Omalizumab (Xolair, anti-IgE Fc region), Oportuzumab (anti-EpCA111), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtunrionriab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolyl-neuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab Rilotunriunriab (anti-HGF), Rituximab (MabThera, Rituxanmab, an 1-CD20), Robatumumab (anti-IGF-1 receptor), Rontalizumab (anti-IFN-$\alpha$), Rovelizumab (LeukArrest, anti-CD11, CD18), Ruplizumab (Antova, anti-CD154 (CD40L)), Satumomab (anti-TAG-72), Sevirumab (anti-cytomegalovirus), Sibrotuzumab (anti-PAP), Sifalimumab (anti-IFN-$\alpha$), Siltuximab Siplizumab (anti-CD2), (Smart) M195 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90 (granulocyte antigen), Tacatuzumab (anti-alpha-fetoprotein), Tadocizumab (anti-integrin $\alpha_{IIb}\beta_3$), Talizumab (anti-IgE), Tanezumab (anti-NGF), Taplitumomab (anti-CD19), Tefibazumab (Aurexis, (anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizurnab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzurnab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin $\alpha_4\beta_7$), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin $\alpha_5\beta_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591 (anti-PSMA, Weill Cornell Medical School for prostate cancers), 225.28S [anti-HMW-MAA (High molecular weight-melanoma-associated antigen), Sorin Radiofarmaci S.R.L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TR$\alpha\beta$ (T cell receptor alpha/beta), complex, from MedImmune Inc for Graft-versus-host disease], RING SCAN [anti-TAG 72 (tumour associated glycoprotein 72), from Neoprobe Corp. for Breast, Colon and Rectal cancers], Avicidin (anti-EP-CAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp. for Colon, Ovarian, Prostate cancers and NHL]; LymphoCide (Immunomedics, NJ), Smart ID10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone, NJ) and Cetuximab (ImClone, NJ).

Other antibodies as binding ligands include, but are not limited to, are antibodies against the following antigens: Aminopeptidase N (CD13), Annexin A1, B7-H3 (CD276, various cancers), CA125 (ovarian), CA15-3 (carcinomas), CA19-9 (carcinomas), L6 (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 (A-like-4), EGFR (Epidermal Growth Factor Receptor, various cancers), CTLA4 (melanoma), CXCR4 (CD184, Herneoncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins ($\alpha v \beta 3$, $\alpha 5 \beta 1$, $\alpha 6 \beta 4$, $\alpha 11 \beta 3$, $\alpha 5 \beta 5$, $\alpha v \beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-N-glycolylneuraminic acid (Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-253 (2009); Novellino et al, Cancer Immunol Immunother, 54(3), 187-207 (2005). Franke, et al, Cancer Biother Radiopharm. 2000, 15, 459-76). Examples of these antigens that antibodies against are: Many other Cluster of Differentiations (CD4, CD5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), Annexin A1, Nucleolin, Endoglin (CD105), ROBO4, Amino-peptidase N, Δ-like-4 (DLLA), VEGFR-2 (CD309), CXCR4 9CD184), Tie2, B7-H3, WT1, MUC1, LMP2, HPV E6 E7, EGFRvIII, HER-2/neu, Idiotype, MAGE A3, p53 nonmutant, NY-ESO-1, GD2, CEA, MelanA/MART1, Ras mutant, gp100, p53 mutant, Proteinase3 (PR1), bcr-abl, Tyrosinase, Survivin, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, Fos-related antigen 1.

Production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Köhler, G.; Milstein, C. (1975). *Nature* 256: 495-497). The detailed procedures are described in "Antibodies—A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after Protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8:396 (1959)) supplemented with 4.5 gm/l glucose, 20 mm glutamine, 20% fetal calf serum and with an anti-foaming agent, such as polyoxyethylene-polyoxypropylene block copolymer.

In addition, antibody-producing cell lines can also be created by techniques other than cell fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451,570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-4953 (1983); Geysen et al., Proc. Natl. Acad. Sci. USA, 82: 178-182 (1985); Lei et al. Biochemistry 34(20): 6675-6688, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3):539-55 (1994); Clackson et al., Nature 352: 264-628 (1991); Huse et al., Science 246:1275-1281 (1989); Hoogenboom et al. in Methods in Molecular Biology 178: 1-37 (2001) (O'Brien et al., ed., Human Press, Totowa, N.J.), and in certain embodiments, in Lee et al. J. Mol. Biol. 340:1073-1093 (2004).

Moncolonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859, 205 and 6,797,492; Liu et al, Immunol Rev. 222:9-27 (2008); Almagro et al, Front Biosci. 1; 13:1619-33 (2008); Lazar et al, Mol Immunol. 44(8):1986-98 (2007); Li et al, Proc. Natl. Acad. Sci. USA. 103(10):3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse (Abgenix/Amgen.), the HuMAb-Mouse (Medarex/BMS), the VelociMouse (Regeneron), see also U.S. Pat. Nos. 6,596, 541, 6,207,418, U.S. Pat. No. 6,150,584, U.S. Pat. No. 6,111,166, U.S. Pat. No. 6,075,181, U.S. Pat. No. 5,922,545, U.S. Pat. Nos. 5,661,016, 5,545,806, 5,436,149 and 5,569, 825. In human therapy, murine variable regions and human constant regions can also be fused to construct called "chimeric antibodies" that are considerably less immunogenic in man than murine mAbs (Kipriyanov et al, Mol Biotechnol. 26: 39-60 (2004); Houdebine, Curr Opin Biotechnol. 13: 625-9 (2002) each incorporated herein by reference). In addition, site-directed mutagenesis in the variable region of an antibody can result in an antibody with higher affinity and specificity for its antigen (Brannigan et Nat Rev Mol Cell Biol. 3: 964-70, (2002)); Adams et al, J Immunol Methods. 231: 249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immunospecific for a malignant cell antigen can be obtained commercially, e.g., from the GenBank database or a database like it, the literature publications, or by routine cloning and sequencing.

DNA encoding hybridoma-derived monoclonal antibodies or phage display Fv clones of the antibody can be readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells (Skerra et al., Curr. Opinion in Immunol., 5: 256 (1993) and Pluckthun, Immunol. Revs, 130: 151 (1992)). Antibodies can also be produced by using an expression system in which the quantitative ratio of expressed polypeptide components can be modulated in order to maxim/ze the yield of secreted and properly assembled antibodies. Such modulation is accomplished at least in part by simultaneously modulating translational strengths for the polypeptide components. After the fermentation which is known in the art, the produced antibody protein is further purified to obtain preparations that are substantially homogeneous for further assays and uses. Standard protein purification methods known in the art can be employed. The exemplary purification procedures: fractionation on immunoaffinity (such as Protein A columns) or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immunoglobulin family. These peptides can be isolated by similar techniques as for phage display antibodies (Szardenings, J Recept Signal Transduct Res, 23(4): 307-49, 2003). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, as long as such attachment permits the peptide or protein to retain its antigen binding specificity.

Any one of several different reactive groups on a cell binding agent, preferably on an antibody, can be a conjugation site, such as r-amino groups in lysine residues, pendant carbohydrate moieties, carboxylic acid groups, disulfide groups, and thiol groups. For reviews on antibody reactive groups suitable for conjugation, see, e.g., Hermanson, G. T. (2008). Bioconjugate Techniques, Academic Press; Garnett, Adv. Drug Delivery Rev. 53 (2001), 171-216 and Dubowchik and Walker, Pharmacology & Therapeutics 83 (1999), 67-123, the disclosures of which are incorporated herein by reference.

The cytotoxic agents of this invention can be directly conjugated (linked) to a cell binding agent, or via a bifunctional linker or a crosslinking agent to a cell binding agent. The bifunctional linker possess two reactive groups; one of which is capable of reacting with a cell binding agent while the other one reacts with one or more molecules of cytotoxic agent of the invention. The bifunctional crosslinkers are well known in the art (see, for example, U.S. Pat. No. 5,208,020; balm and Dent in Bioconjugation chapter 5, p 218-363, Groves Dictionaries Inc. New York, 1999). Examples of bifunctional linker are: N-succinimidyl-3-(2-pyridyldithio) propionate (SPDP), N-succinimidyl-4-(2-pyridyldithio)butyrate (SPDB), N-succinimidyl-4-(2-pyridyldithio)pentanoate (SPP), N-succinimidyl-3-(2-pyridyldithio)-butyrate (SDPB), 2-iminothiolane, N-succinimidyl-4-(5-nitro-2-pyridyldithio) butyrate (SNPB), N-succinimidyl 4-(5-nitro-2-pyridyldithio)-pentanoate (SNPP), N-sulfosuccinimidyl-4-(5-nitro-2-pyridyldithio) butyrate (SSNPB), N-succinimidyl-4-methyl-4-(5-nitro-2-pyridyldithio)pentanoate (SMNP), N-sulfosuccinimidyl 4-(5-nitro-2-pyridyldithio)-pentanoate (SSNPP), 4-succinimidyl-oxycarbonyl-α-methyl-α-(2-pyridyldithio)-toluene (SMPT), N-sulfosuccinimidyl-4-methyl-4-(5-nitro-2-pyridyldithio) pentanoate (SSMNP); N-succinimidyl-4-methyl-4-(2- pyridyldithio)pentanoate (SMPDP), N-succinimidyl-4-(5-N,N-dimethyl-carboxamido-2-pyridyldithio) butyrate (SCPB), N-sulfosuccinimidyl-4-(5-N,N-dimethyl-carboxamido-2-pyridyldithio) butyrate (SSCPB), N-succinimidyl-4,4-dimethyl-4-(2-pyridyldithio)pentanoate (SDMPDP), succinimidyl-4-(N-maleimidomethyl)cyclohexane-1-carboxylate (SMCC), N-succinimidyl-4-(iodoacetyl)-aminobenzoate (SIAB), bis-maleimidopolyethyleneglycol (BMPEG), BM(PEG)$_{1~20}$, N-(β-maleimidopropyloxy)-succinimide ester (BMPS), iminothiolane (IT), dimethyl adipimidate HCl or derivatives of imidoesters, active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene), gamma-maleimidobutyric acid N-succinimidyl ester (GMBS), E-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate) (a "long chain" analog of SMCC (LC-SMCC)), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), kappa-maleimidoundecanoic acid N-succinimidyl ester (KMUA), N-succinimidyl 4-(p-maleimidophenyl)-butyrate (SMPB), succinimidyl-6-(beta-maleimidopropionamido)-hexanoate (SMPH), succinimidyl-(4-vinylsulfonyl) benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfa-MBS), N-(gamma-maleimidobutryloxy)sulfosuccinimdeester (sulfo-GMBS), N-(epsilon-maleimidocaproyloxy)sulfosuccimido ester (sulfo-EMCS), N-(kappa-maleimidoundecanoyloxy)sulfosuccinimide ester (sulfo-KMUS), and sulfosuccinimidyl 4-(p-maleimidophenyl) butyrate (sulfo-SMPB); or the commercially available linkers (such as from Thermo Scientific's Pierce: Imidoester Crosslinkers: DMA (Dimethyl adipimidate.2 HCl), DMP (Dimethyl pimelimidate.2 HCl), DMS (Dimethyl Suberimidate.2 HCl), DTBP (Dimethyl 3,3'-dithiobispropionimidate.2 HCl); NHS-ester Crosslinkers-Amine Reactive: BS(PEG)$_5$ (Bis(succinimidyl) penta(ethylence glycol), BS(PEG)$_9$ (Bis(succinimidyl) nona(ethylence glycol), BS$^3$ (Bis[sulfosuccinimidyl] suberate), BSOCOES (Bis[2-(succinimidooxycarbonyloxy)ethyl]sulfone), DSG (Disuccinimidyl glutarate), DSP (Dithiobis[succinimidyl propionate]), DSS (Disuccinimidyl suberate), DST (Disuccinimidyl tartarate), DTSSP (3,3'-Dithiobis[sulfosuccinimidylpropionate]), EGS (Ethylene glycol bis[succinimidylsuccinate]), Sulfo-EGS (Ethylene glycol bis[sulfosuccinimidylsuccinate]), TSAT (Tris-succinimidyl aminotriacetate), DFDNB (1,5-Difluoro-2,4-dinitrobenzene); Amine-to-Sulthydryl Crosslinkers: Sulfo-SIAB (Sulfosuccinimidyl (4-iodoacetyl) aminobenzoate), SIAB (Succinimidyl (4-iodoacetyl)aminobenzoate), SBAP(Succinimidyl 3-(bromoacetamido)propionate), SIA (Succinimidyl iodoacetate), Sulfo-SMCC (Sulfosuccinimidyl-4-(N-maleimidomethyl)-cyclohexane-1-carboxylate), SM(PEG)n (NHS-PEG-Maleimide Crosslinkers: Succinimidyl-([N-maleimidopropionamido])-#ethyleneglycol)ester, #=1 2, 3, 4, 5, 6, 7, 8, 9, 10, 11, 12, 13, 14, 15, 16, 18, 20, 22, 24), LC-SMCC (Succinimidyl 4-(N-maleimidomethyl) cyclohexane-1-carboxy-(6-amidocaproate)), Sulfo-EMCS (N-epsilon-Maleimidocaproyl-oxysulfosuccinimide ester), EMCS (N-epsilon-Malemidocaproyl-oxysuccinimide ester), Sulfo-GMBS (N-gamma-Maleimidobutyryl-oxysulfosuccinimide ester), GMBS (N-gamma-Maleimidobutyryl-oxysuccinimide ester), Sulfo-KMUS (N-kappa-Maleimidoundecanoyl-oxysulfosuccinimide ester), Sulfo-MBS (m-Maleimidobenzoyl-N-hydroxysulfosuccinimide ester), MBS (m-Maleimidobenzoyl-N-hydroxysuccinimide ester), Sulfo-SMPB ((Sulfosuccinimidyl 4-(p-maleiimidophenyl)butyrate), SMPB (Succinimidyl 4-(p-maleimidophenyl)butyrate), AMAS N-(α-Maleimidoacetoxy) succinimide ester), BMPS (N-beta-Maleimidopropyl-oxysuccinimide ester), SMPH (Succinimidyl 6-[(beta-maleimidopropionamido)hexanoate]), PEG12-SPDP (2-Pyridyldithiol-tetraoxaoctatriacontane-N-hydroxysuccinimide), PEG4-SPDP (2-Pyridyldithiol-tetraoxatetradecane-N-hydroxysuccinimide), Sulfo-LC-SPDP (Sulfosuccinimidyl 6-[3'-(2-pyridyldithio) propionamido]hexanoate), LC-SPDP (Succinimidyl 6-[3-(2-pyridyldithio)propionamido]hexanoate), SMPT (4-Succinimidyloxycarbonyl-alpha-methyl-alpha(2-pyridyldithio)toluene); Carboxyl-to-Amine Crosslinkers: DCC (Dicyclohexylcarbodiimide), EDC (1-Ethyl-3-(3-dimethylaminopropyl) carbodiimide); Photoreactive Crosslinkers: ANB-NOS (N-5-Azido-2-nitrobenzoyloxysuccinimide), NHS-Diazirine (SDA) Crosslinkers: SDA (NHS-Diazirine) (Succinimidyl 4,4'-azipentanoate), LC-SDA (NHS-LC-Diazirine) (Succinimidyl 6-(4,4'-azipentanamido)hexanoate), SDAD (NHS-SS-Diazirine) (Succinimidyl 2-([4,4'-azipentanamido]ethyl)-1,3'-dithiopropionate), Sulfo-SDA (Sulfo-NHS-Diazirine) (Sulfosuccinimidyl 4,4'-azipentanoate), Sulfo-LC-SDA (Sulfo-NHS-LC-Diazirine) (Sulfosuccinimidyl 6-(4,4'-azipentanamido)hexanoate), Sulfo-SDAD (Sulfo-NHS-SS-Diazirine) (Sulfosuccinimidyl 2-([4,4'-azipentanamido]ethyl)-1,3'-dithiopropionate), Sulfo-SANPAH (Sulfosuccinimidyl 6-(4'-azido-2'-nitrophenylamino)-hexanoate), SPB (Succinimidyl-[4-(psoralen-8-yloxy)]-butyrate); Sulfhydryl-to-Carbohydrate Crosslinkers: BMPH (N-beta-Maleimidopropionic acid hydrazide-TFA), EMCH (N-epsilon-Maleimidocaproic acid hydrazide-TFA), KMUH (N-kappa-Maleimidoundecanoic acid hydrazide-TFA), MPBH (4-(4-N-Maleimidophenyl)butyric acid hydrazide-HCl), PDPH (3-(2-Pyridyldithio)propionyl hydrazide); Sulfhydryl-to-Hydroxyl Crosslinkers: PMPI (p-Maleimidophenyl isocyanate); Sulfhydryl-to-Sulfhydryl Crosslinkers: BM(PEG)2 (1,8-Bismaleimido-diethyleneglycol), BM(PEG)3 (1,11-Bismaleimido-triethyleneglycol), BMB (1,4-Bismaleimidobutane), BMDB (1,4-Bismaleimidyl-2,3-dihydroxybutane), BMH (Bismaleimidohexane), BMOE (Bismaleimidoethane), DTME (Dithiobismaleimido-ethane), TMEA (Tris(2-maleimidoethyl)amine) and SVSB (succinimidyl-(4-vinylsulfone)benzoate).

The bis-maleimide or bis-2-pridyldithiol reagents allow the attachment of the thiol group of a thiol-containing cell binding agent (such as antibody) to a thiol-containing drug moiety, label, or linker intermediate, in a sequential or concurrent fashion. Other functional groups besides maleimide and pyridyldithiol, which are reactive with a thiol group of a cell binding agent, drug moiety, label, or linker intermediate include iodoacetamide, bromoacetamide, vinyl pyridine, disulfide, pyridyl disulfide, isocyanate, and isothiocyanate.

In additional embodiments, the linker may be composed of one or more linker components. The exemplary linker components are:

1. The self-immolative linker components:

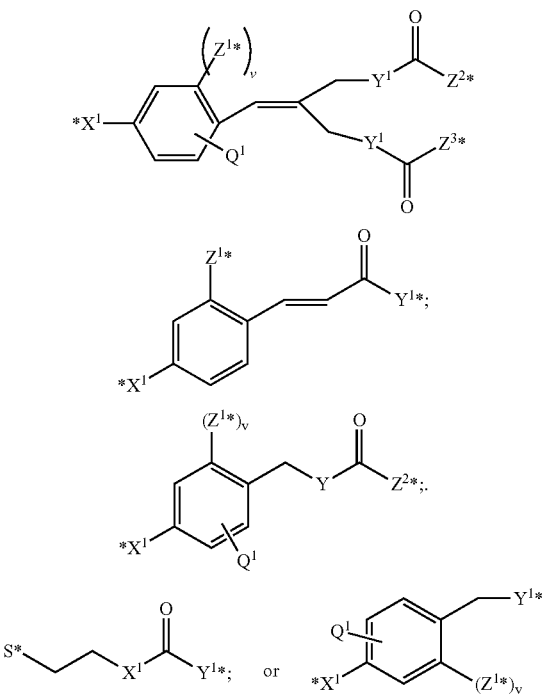

wherein the (*) atom is the point of attachment of additional spacer or releasable linker units, or the cytotoxic agent, and/or the binding molecule (CBA); $X^1$, $Y^1$, $Z^2$ and $Z^3$ are independently NH, or O, or S; $Z^1$ is H, or NH, or O or S independently. v is 0 or 1; $Q^1$ is independently H, OH, $C_1$~$C_6$ alkyl, $(OCH_2CH_2)$ F, Cl, Br, I, $OR_5$, or $SR_5$, $NR_5R_{5'}$, $N=NR_5$, $N=R_5$, $NR_5R_{5'}$, $NO_2$, $SOR_5R_{5'}$, $SO_2R_5$, $SO_3R_5$, $OSO_3R_5$, $PR_5R_{5'}$, $POR_5R_{5'}$, $PO_2R_5R_{5'}$, $OPO(OR_5)(OR_{5'})$, or $OCH_2PO(OR_5(OR_{5'})$ wherein $R_5$ and $R_{5'}$ are described in the Formula (I), preferably $R_5$ and $R_{5'}$ are independently selected from H, $C_1$~$C_8$ of alkyl; $C_2$~$C_8$ of alkenyl, alkynyl, heteroalkyl; $C_3$~$C_8$ of aryl, heterocyclic, carbocyclic, cycloalkyl, heterocycloalkyl, heteroaralkyl, alkylcarbonyl; or pharmaceutical cation salts 2. The examples of non-self-immolative linker components:

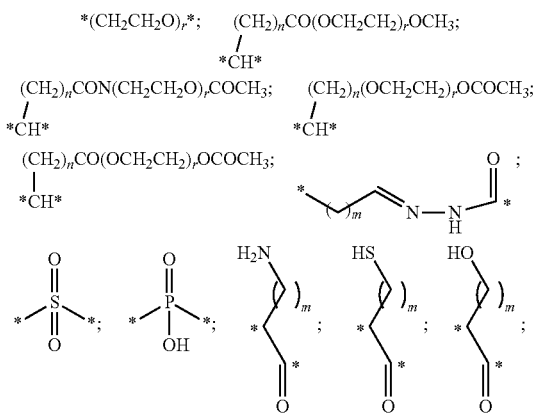

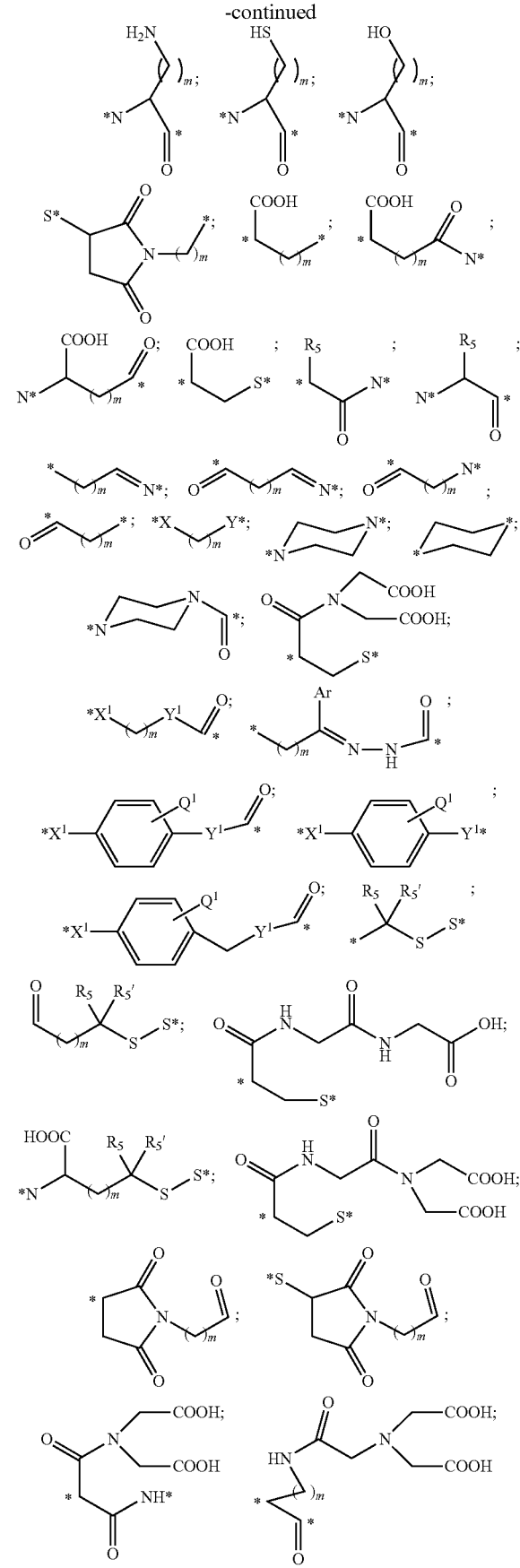

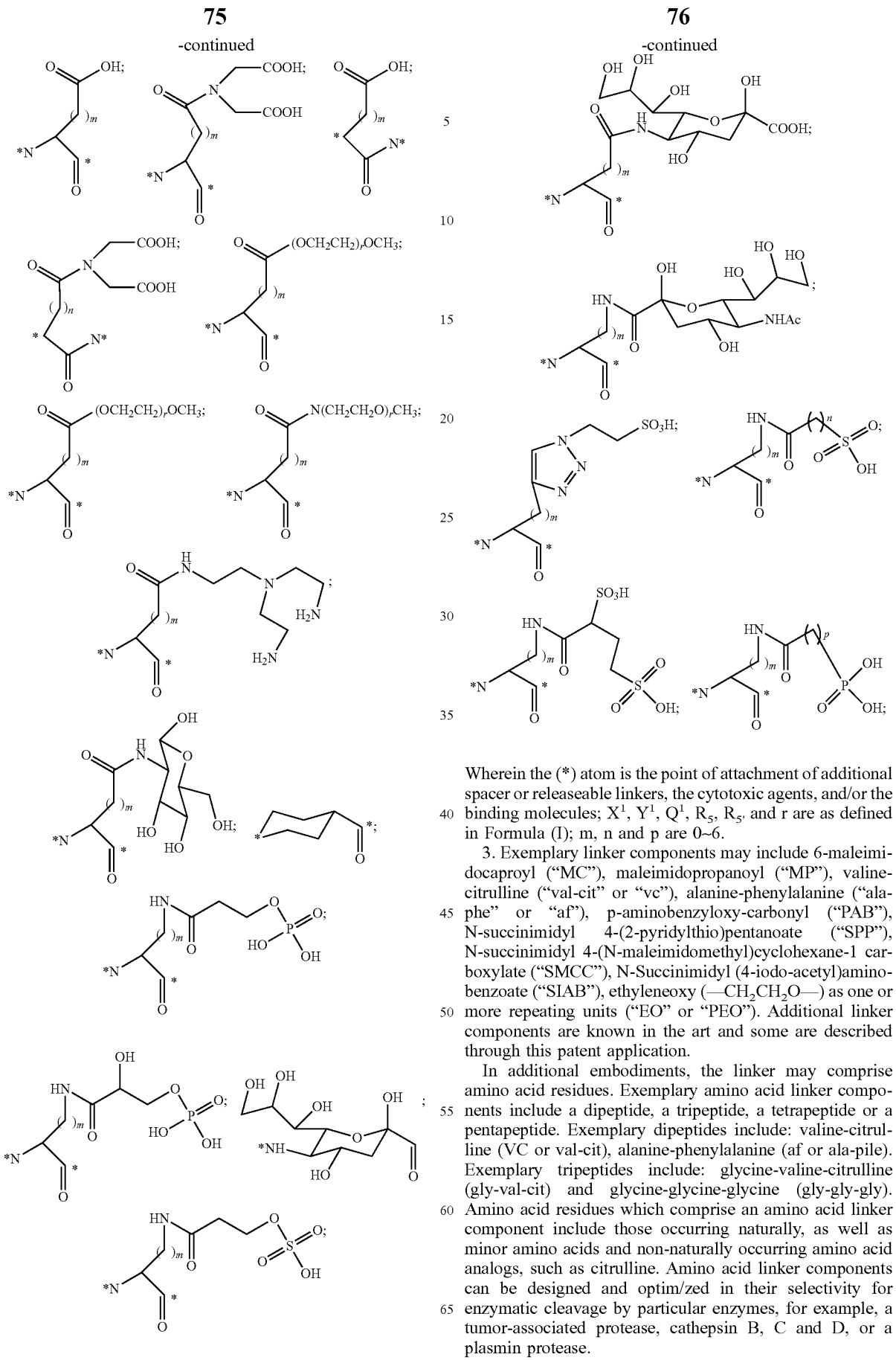

Wherein the (*) atom is the point of attachment of additional spacer or releaseable linkers, the cytotoxic agents, and/or the binding molecules; $X^1$, $Y^1$, $Q^1$, $R_5$, $R_{5'}$ and r are as defined in Formula (I); m, n and p are 0~6.

3. Exemplary linker components may include 6-maleimidocaproyl ("MC"), maleimidopropanoyl ("MP"), valine-citrulline ("val-cit" or "vc"), alanine-phenylalanine ("ala-phe" or "af"), p-aminobenzyloxy-carbonyl ("PAB"), N-succinimidyl 4-(2-pyridylthio)pentanoate ("SPP"), N-succinimidyl 4-(N-maleimidomethyl)cyclohexane-1 carboxylate ("SMCC"), N-Succinimidyl (4-iodo-acetyl)aminobenzoate ("SIAB"), ethyleneoxy (—$CH_2CH_2O$—) as one or more repeating units ("EO" or "PEO"). Additional linker components are known in the art and some are described through this patent application.

In additional embodiments, the linker may comprise amino acid residues. Exemplary amino acid linker components include a dipeptide, a tripeptide, a tetrapeptide or a pentapeptide. Exemplary dipeptides include: valine-citrulline (VC or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optim/zed in their selectivity for enzymatic cleavage by particular enzymes, for example, a tumor-associated protease, cathepsin B, C and D, or a plasmin protease.

In the cell-binding agent-drug conjugates of the invention, cell-binding agent (CBA) is conjugated to one or more drug moieties (Drug, or PBD derivatives), e.g. about 1 to about 20 drug moieties per cell-binding agent, through a bifunctional linker (L). The conjugate of Formula (IX), (X), (XI), (XII), (XIII), and (XIV) may be prepared by several routes, employing organic chemistry reactions, conditions, and reagents known to those skilled in the art, including: (1) the first modification of cell-binding agent (CBA) with a cross-linker (L) in an aqueous buffer pH 3~9 having optionally 0~30% organic co-solvents to introduce reactive disulfide, maleimido, haloacetyl, hydrazide, nitrile, alkynyl, alkyloxyamino or aldehyde groups on the cell-binding agent, to form a covalent bonded CBA-L. The CBA-L molecule then reacts with a drug moiety (Drug) of formula (I) to generate a cell binding agent-drug conjugate; or (2) the first modification of drug moiety (Drug) of the formula (I) with a crosslinker (L) in organic media or in an aqueous buffer pH 3~9 having optionally 0~99% organic co-solvents to introduce a reactive disulfide, maleimido, haloacetyl, hydrazide, nitrile, alkynyl, alkyloxyamino, aldehyde, N-hydroxysuccinimide (NHS) or pentafluorophenyl ester group on the drug moiety (a covalent bonded Drug-L molecule). The Drug-L molecule then reacts with a cell binding agent (CBA), or pre-modified CBA to generate a cell binding agent-drug conjugate; or (3) directly through reaction of a cell-binding agent with drug moieties of formula (I) bearing reactive function groups of disulfide, maleimido, haloacetyl, hydrazide, nitrile, alkynyl, alkyloxyamino, aldehyde, N-hydroxysuccinimide (NHS) or pentafluorophenyl esters in an aqueous buffer pH 3~9 having optionally 0~30% organic co-solvents.

The thiol or amine groups on a cell-binding agents, such as an antibody, are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimido groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Nucleophilic groups on antibodies or proteins can react to electrophilic groups on a function linker following by reaction with a cytotoxic agent, or directly react to a linker-cytotoxic agent moiety to form covalent bond conjugate of a cell binding agent-cytotoxic agent. Nucleophilic groups on antibodies or proteins include, but are not limited to: (i)N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker-cytotoxic agent moieties including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges which may be made reactive by treatment with a reducing agent such as DTT (dithiothreitol) or tricarbonylethylphosphine (TCEP) (Getz et al (1999) Anal. Biochem. Vol 273: 73-80; Soltec Ventures, Beverly, Mass.). Each cysteine bridge will thus form, theoretically, two reactive thiol nucleophiles. Alternatively, sulfhydryl groups can be introduced into antibodies through modification of lysine residues, e.g., by reacting lysine residues with 2-iminothiolane (Tract's reagent), resulting in conversion of an amine into a thiol. Reactive thiol groups may be introduced into an antibody by introducing one, two, three, four, or more cysteine residues (e.g., by preparing variant antibodies comprising one or more non-native cysteine amino acid residues). Thus free thiol on the cell binding agents can be conjugated to the thiol-reactive groups, such as, a maleimide, an iodoacetamide, a pyridyl disulfide, or other thiol-reactive groups on the cytotoxic agents, or linker-cytotoxic agent intermediates of the invention. Some unconjugated free thiols on the antibodies can be reoxidized to reform interchain and interchain disulfide bonds.

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such an aldehyde can be reacted with a drug moiety or linker nucleophile.

Examples of these kinds of two-step conjugations are depicted below:

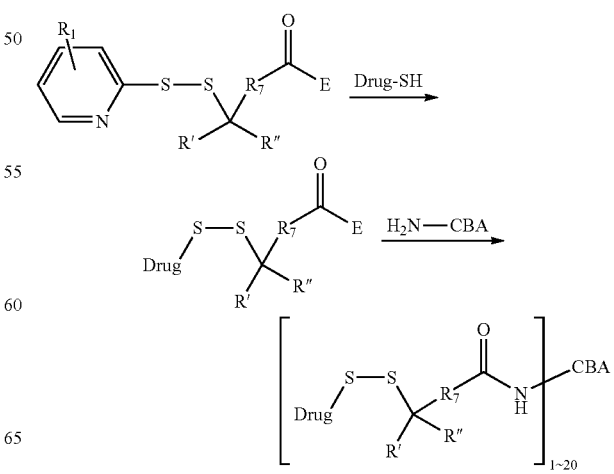

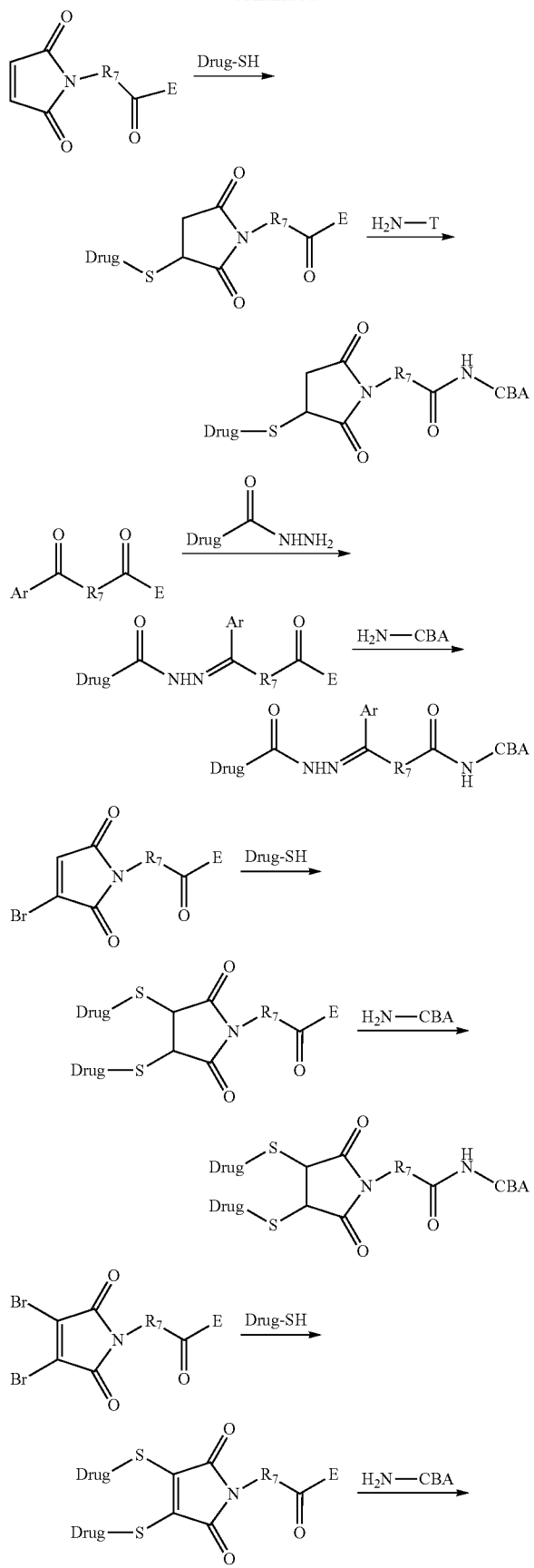

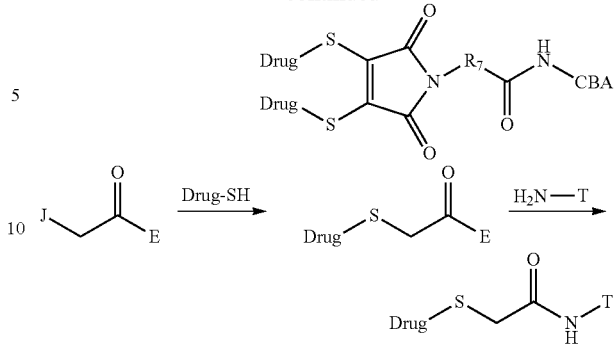

wherein E includes, but is not limited to, such as hydroxysuccinimidyl esters (NHS, Sulfo-NHS, etc), 4-nitrophenyl esters, pentafluorophenyl esters, tetrafluorophenyl (includes sulfo-tetrafluorophenyl) esters, anhydrides, acid chlorides, sulfonyl chlorides, isocyanates and isothiocyanates. R' and R" are independently H or $CH_3$, or $C_2H_5$; J is F, Cl, Br, I, tosylate (TsO), mesylate (MsO), nitrophenol, dinitrophenol, or pentaflourophenol.

It is to be understood that where more than one nucleophilic group on the cell binding agents, such as an antibody, reacts with a drug-linker intermediate or linker reagent followed by drug moiety reagent, then the resulting product is a mixture of the cell binding agent-cytoxic agent conjugates with a distribution of one or more drug moieties attached to an antibody. The average number of drugs per antibody may be calculated from the mixture by a dual ELISA antibody assay, which is specific for antibody and specific for the drug. Individual conjugate molecules may be identified in the mixture by mass spectroscopy and separated by HPLC, e.g. hydrophobic interaction chromatography. In certain embodiments, a homogeneous conjugate with a single loading value may be isolated from the conjugation mixture by electrophoresis or chromatography.

In the conjugation, The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of lysine or cysteine residues is modified for control of the number and/or position of linker-drug attachments (such as thioMab or thioFab).

Other further examplary methods for preparing ADC are described in FIGS. 5, 11, 12, 13, 14, 16, 17, 18, 19, 20, 21, 22, and 23 and examples in the description of the patent.

Cell-Binding Agent-Drug Conjugate Treatments

It is contemplated that the cell-binding agent drug conjugate, preferably antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune disorders.

In specific embodiment, the conjugates of the invention are used in accordance with the compositions and methods of the invention for the treatment of cancers. The cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metasatic Squamous Neck Cancer with Occult Primary, Multiple Myeloma, and Other Plasma Cell Neoplasms, Mycosis Fungoides, Myelodysplastic Syndrome, Myeloproliferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor In another specific embodiment, the compounds and the conjugates of the invention are used in accordance with the compositions and methods of the invention for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaff's encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostemyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barré syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Ménière's disease, Microscopic polyangiitis, Miller-Fisher syndrome, Mixed Connective Tissue Disease, Morphea, Mucha-Habermann disease, MuckleWells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate for the treatment or prevention of an autoimmune disease includes, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.subARNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial(M2) antibody; Rheumatoid factor antibody; Anti-MCV antibody; Anti-topoisomerase antibody; Anti-neutrophil cytoplasmic (cANCA) antibody.

In certain preferred embodiments, the binding molecule for the conjugate in the present invention, can bind to either a receptor or a receptor complex expressed on an activated lymphocyte which is associated with an autoimmune disease. The receptor or receptor complex can comprise an immunoglobulin gene superfamily member (e.g. CD2, CD3, CD4, CD8, CD19, CD22, CD28, CD79, CD90, CD152/CTLA-4, PD-1, or ICOS), a TNF receptor superfamily member (e.g. CD27, CD40, CD95/Fas, CD134/OX40, CD137/4-1BB, INF-R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuramimidase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g. a bacteria, fungi, pathogenic protozoa, or yeast polypeptide including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PRO542 which is a CD4 fusion antibody for the treatment of HIV infection; Ostavir which is a human antibody for the treatment of hepatitis B virus; PROTVIR which is a humanized IgG.sub.1 antibody for the treatment of cytomegalovirus; and anti-LPS antibodies.

The binding molecules-cytotoxic agent conjugates of this invention can be used in the treatment of infectious diseases. These infectious diseases include, but are not limited to, Acinetobacter infections, Actinomycosis, African sleeping sickness (African trypanosomiasis), AIDS (Acquired immune deficiency syndrome), Amebiasis, Anaplasmosis, Anthrax, *Arcanobacterium haemolyticum*infection, Argentine hemorrhagic fever, *Ascariasis, Aspergillosis, Astrovirus infection, Babesiosis, Bacillus cereus* infection, Bacterial pneumonia, Bacterial vaginosis, *Bacteroides* infection, Balantidiasis, Baylisascaris infection, BK virus infection, Black piedra, *Blastocystis hominis*infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, *Chlamydia, Chlamydophila pneumoniae* infection, Cholera, Chromoblastomycosis, Clonorchiasis, *Clostridium difficile* infection, Coccidioidomycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), Enterococcus infection, *Enterovirus* infection, Epidemic typhus, Erythema infectiosum (Fifth disease), Exanthem subitum, Fasciolopsiasis, Fasciolosis, Fatal familial insomnia, Filariasis, Food poisoning by *Clostridium perfringens*, Free-living amebic infection, *Fusobacterium* infection, Gas gangrene (Clostridial myonecrosis), Geotrichosis, Gerstmann-Straussler-Scheinker syndrome, Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), influenza, Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever, Measles, Melioidosis (Whitmore's disease), Meningitis, Meningococcal disease, Metagonimiasis, Microsporidiosis, Molluscum contagiosum, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCID), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis pneumonia*, Pneumonia, Poliomyelitis, *Prevotella* infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever, Rocky mountain spotted fever, Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White piedra (Tinea blanca), *Yersinia pseudotuberculosis* infection, Yersiniosis, Yellow fever, Zygomycosis.

The binding molecules, more preferred antibodies described in this patent that are against pathogenic strains include, but are not limit, *Acinetobacter baumannii, Actinomyces israelii, Actinomyces gerencseriae* and *Propionibacterium propionicus, Trypanosoma brucei*, HIV (Human immunodeficiency virus), *Entamoeba histolytica, Anaplasma* genus, *Bacillus anthracis, Arcanobacterium haemolyticum, Junin virus, Ascaris lumbricoides, Aspergillus* genus, Astroviridae family, *Babesia* genus, *Bacillus cereus*, multiple bacteria, *Bacteroides* genus, *Balantidium coli, Baylisascaris* genus, BK virus, *Piedraia hortae, Blastocystis hominis, Blastomyces dermatitides*, Machupo virus, *Borrelia* genus, *Clostridium botulinum*, Sabia, *Brucella* genus, usually *Burkholderia cepacia* and other *Burkholderia* species, *Mycobacterium ulcerans*, Caliciviridae family, *Campylobacter* genus, usually *Candida albicans* and other *Candida* species, *Bartonella henselae*, Group A *Streptococcus* and *Staphylococcus, Trypanosoma cruzi, Haemophilus ducreyi*, Varicella zoster virus (VZV), *Chlamydia trachomatis, Chlamydophila pneumoniae, Vibrio cholerae, Fonsecaea pedrosoi, Clonorchis sinensis, Clostridium difficile, Coccidioides immitis* and *Coccidioides posadasii*, Colorado tick fever virus, rhinoviruses, coronaviruses, CJD prion, Crimean-Congo hemorrhagic fever virus, *Cryptococcus neoformans, Cryptosporidium* genus, *Ancylostoma braziliense*; multiple parasites, *Cyclospora cayetanensis, Taenia solium*, Cytomegalovirus, Dengue viruses (DEN-1, DEN-2, DEN-3 and DEN-4) Flaviviruses, *Dientamoeba fragilis, Corynebacterium diphtheriae, Diphyllobothrium, Dracunculus medinensis*, Ebolavirus, *Echinococcus* genus, *Ehrlichia* genus, *Enterobius vermicularis, Enterococcus* genus, *Enterovirus* genus, *Rickettsia prowazekii*, Parvovirus B19, Human herpesvirus 6 and Human herpesvirus 7, *Fasciolopsis buski, Fasciola hepatica* and *Fasciola gigantica*, FFI priori, Filarioidea superfamily, *Clostridium perfringens, Fusobacterium* genus, *Clostridium perfringens*; other *Clostridium* species, *Geotrichum candidum*, GSS prion, *Giardia intestinalis, Burkholderia mallei, Gnathostoma spinigerum* and *Gnathostoma hispidum, Neisseria gonorrhoeae, Klebsiella granulomatis, Streptococcus pyogenes, Streptococcus agalactiae, Haemophilus influenzae*, Enteroviruses, mainly Coxsackie A virus and *Enterovirus* 71, Sin Nombre virus, *Helicobacter pylori, Escherichia coli* O157:H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, *Histoplasma capsulatum, Ancylostoma duodenale* and *Necator americanus*, Hemophilus influenzae, Human bocavirus, *Ehrlichia ewingii, Anaplasma phagocytophilum*, Human metapneumovirus, *Ehrlichia chaffeensis*, Human papillomavirus, Human parainfluenza viruses, *Hymenolepis nana* and *Hymenolepis diminuta*, Epstein-Barr Virus, Orthomyxoviridae family, *Isospora belli, Kingella kingae, Klebsiella pneumoniae, Klebsiella ozaenas, Klebsiella rhinoscleromotis*, Kuru prion, Lassa virus, *Legionella pneumophila, Legionella pneumophila, Leishmania* genus, *Mycobacterium leprae* and *Mycobacterium lepromatosis, Leptospira* genus, *Listeria monocytogenes, Borrelia burgdorferi* and other *Borrelia* species, *Wuchereria bancrofti* and *Brugia malayi*, Lymphocytic choriomeningitis virus (LCMV), *Plasmodium* genus, Marburg virus, Measles virus, *Burkholderia pseudomallei, Neisseria meningitides, Metagonimus yokagawai*, Microsporidia phylum, Molluscum contagiosum virus (MCV), Mumps virus, *Rickettsia typhi, Mycoplasma pneumoniae*, numerous species of bacteria (Actinomycetoma) and fungi (Eumycetoma), parasitic dipterous fly larvae, *Chlamydia trachomatis* and *Neisseria gonorrhoeae*, vCJD prion, *Nocardia asteroides* and other *Nocardia* species, *Onchocerca volvulus, Paracoccidioides brasiliensis, Paragonimus westermani* and other *Paragonimus* species, *Pasteurella* genus, *Pediculus humanus* capitis, *Pediculus humanus* corporis, *Phthirus*pubis, *Bordetella pertussis, Yersinia pestis, Streptococcus pneumoniae, Pneumocystis jirovecii*, Poliovirus, *Prevotella* genus, *Naegleria fowleri*, JC virus, *Chlamydophila psittaci, Coxiella burnetii*, Rabies virus, *Streptobacillus moniliformis* and Spirillum minus, Respiratory syncytial virus, *Rhinosporidium seeberi*, Rhinovirus, *Rickettsia* genus, *Rickettsia akari*, Rift Valley fever virus, *Rickettsia rickettsii*, Rotavirus, Rubella virus, *Salmonella* genus, SARS coronavirus, *Sarcoptes scabiei, Schistosoma* genus, *Shigella* genus, Varicella zoster virus, Variola major or Variola minor, *Sporothrix schenckii, Staphylococcus* genus, *Staphylococcus* genus, *Staphylococcus aureus, Streptococcus pyogenes, Strongyloides stercoralis, Treponema pallidum, Taenia* genus, *Clostridium tetani, Trichophyton* genus, *Trichophyton tonsurans, Trichophyton* genus, *Epidermophyton floccosum, Trichophyton rubrum*, and *Trichophyton mentagrophytes, Trichophyton rubrum, Hortaea werneckii, Trichophyton* genus, *Malassezia* genus, *Toxocara canis* or *Toxocara cati, Toxoplasma gondii, Trichinella spiralis, Trichomonas vaginalis, Trichuris trichiura, Mycobacterium tuberculosis, Francisella tularensis, Ureaplasma urealyticum*, Venezuelan equine encephalitis virus, *Vibrio coleraez*, Guanarito virus, West Nile virus, *Trichosporon beigelii, Yersinia pseudotuberculosis, Yersinia enterocolitica*, Yellow fever virus, Mucorales order (Mucormycosis) and Entomophthorales order (Entomophthoramycosis), *Pseudomonas aeruginosa, Campylobacter* (*Vibrio*) fetus, *Aeromonas hydrophile, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohernorrhagiae, Pneumocystis carinii, Brucella abortus, Brucella suis, Brucella melitensis, Mycoplasma* spp., *Rickettsia prowazeki, Rickettsia tsutsugumushi, Clamydia* spp.; pathogenic fungi (*Aspergillus fumigatus, Candida albicans, Histoplasma capsulatum*); protozoa (*Entomoeba histolytica, Trichomonas tenas, Trichomonas hominis, Tryoanosoma gambiense, Trypanosoma rhodesiense, Leishmania donovani, Leishmania tropica, Leishmania braziliensis, Pneumocystis pneumonia, Plasmodium vivax, Plasmodium falciparum, Plasmodium malaria*); or Helminiths (*Schistosoma japonicum, Schistosoma mansoni, Schistosoma haematobium*, and hookworms).

Other antibodies as a binding ligand in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytial virus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further embodiment, the present invention also concerns pharmaceutical compositions comprising the conjugate of the invention together with a pharmaceutically acceptable carrier for treatment of cancer and autoimmune disorders. The method for treatment of cancer, autoimmune disorders, infectious diseases or viral disease can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the narrow and reinfusion of the treated cells, the treated marrow cells are stored frozen in liquid nitrogen using standard medical equipment.

For clinical in vivo use, the cell binding agent-cytotoxic agent conjugates of this invention will be supplied as solutions or as a lyophilized solid that can be redissolved in sterile water for injection. Examples of suitable protocols of conjugate administration are as follows. Conjugates are given weekly for 8 weeks as an i.v. bolus. Bolus doses are given in 50 to 500 ml of normal saline to which human serum albumin (e.g. 0.5 to 1 mL of a concentrated solution of human serum albumin, 100 mg/mL) can be added. Dosages will be about 50 µg to 20 mg/kg of body weight per week, i.v. (range of 10 µg to 200 mg/kg per injection). 8 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the cell binding agent cytotoxic agent conjugates of this invention may be provided in an aqueous physiological buffer solution containing 0.1 to 10% w/v conjugates for parenteral administration. Typical dose ranges are from 1 µg/kg to 0.1 g/kg of body weight per day; a preferred dose range is from 0.01 mg/kg to 20 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The cell binding agent-cytotoxic agent conjugates of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably the unit dose range is from 1 to 500 mg administered one to four times a day, and even more preferably from 10 mg to 500 mg, once a day. Conjugatess provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches. The compositions may conveniently be administered in unit dosage form and may be prepared by any of the methods well known in the pharmaceutical art, for example, as described in Remington: The Science and Practice of Pharmacy, 21$^{th}$ ed.; Lippincott Williams & Wilkins: Philadelphia, Pa., 2005. Preferred formulations include pharmaceutical compositions in which a compound of the present invention is formulated for oral or parenteral administration. For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination. Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

In a specific embodiment, the cell binding agent cytotoxic agent conjugates of this invention are administered concurrently with the other known or will be known therapeutic agents such as the chemotherapeutic agent, the radiation therapy, immunotherapy agents, autoimmune disorder agents, anti-infectious agents or the other antibody-drug conjugates, resulting in a synergistic effect. In another specific embodiment, the synergistic drugs or radiation therapy are administered prior or subsequent to administration of a conjugate, in one aspect at least an hour, 12 hours, a day, a week, a month, in further aspects several months, prior or subsequent to administration of a conjugate of the invention.

In other embodiments, the synergistic drugs include, but not limited to:

1). Chemotherapeutic agents: a). Alkylating agents: such as [Nitrogen mustards:

(chlorambucil, cyclophosphamide, ifosfamide, mechlorethamine, melphalan, trofosfamide); Nitrosoureas: (carmustine, lomustine); Alkylsulphonates: (busulfan, treosulfan); Triazenes: (dacarbazine); Platinum containing compounds: (carboplatin, cisplatin, oxaliplatin)]; b). Plant Alkaloids: such as [Vinca alkaloids: (vincristine, vinblastine, vindesine, vinorelbine); Taxoids: (paclitaxel, docetaxol)]; c). DNA Topoisomerase inhibitors: such as [Epipodophyllins: (9-aminocamptothecin, camptothecin, crisnatol, etoposide, etoposide phosphate, irinotecan, teniposide, topotecan,); Mitomycins: (mitomycin C)]; d). Anti-metabolites: such as {[Anti-folate: DHFR inhibitors: (methotrexate, trimetrexate); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (5-Fluorouracil, doxifluridine, floxuridine, ratitrexed(Tomudex)); Cytosine analogs: (cytarabine, cytosine arabinoside, fludarabine); Purine analogs: (azathioprine, mercaptopurine, thioguanine)]}; e). Hormonal therapies: such as {Receptor antagonists: [Anti-estrogen: (megestrol, raloxifene, tamoxifen); LHRH agonists: (goscrclin, leuprolide acetate); Anti-androgens: (bicalutamide, flutamide)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxy-hypocrellin A); Cytokines: (Interferon-alpha, Interferon-gamma, tumor necrosis factor (TNFs), human proteins containing a TNF domain)]}; f). Kinase inhibitors, such as BMW 2992 (anti-EGFR/Erb2), imatinib, gefitinib, pegaptanib, sorafenib, dasatinib, sunitinib, erlotinib, nilotinib, lapatinib, axitinib, pazopanib, vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). Others: such as gemcitabine, epoxomicins (e. g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as Neomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), vismodegib, Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A. More detail lists of known and will be known anti-cancer drugs that can be used as a combination therapy (a synergistic effect) with the compounds and conjugates of the invention can be seen in National Cancer Institute (US) website (www.cancer.gov; www.cancer.gov/cancertopics/druginfo/alphalist), American Cancer Society (www.cancer.org/treatment/index) and Cancer Research UK (www.cancerrearchuk.org; (www.cancerresearchuk.org/cancer-help/about-cancer/treatment/cancer-drugs/)

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols: azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cetbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpim/zole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flornoxef, latamoxef); f). Glycopeptides: bleomycin, vancomycin (oritavancin, telavancin), teicoplanin (dalbavancin), ramoplanin; g). Glycylcyclines: e. g, tigecycline; g). β-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k), Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; l]. Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethylpenicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (e.g, tigecycline); u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensimycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides & nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2',3'-dideoxynucleoside analogues (e.g. 3'-fluoro-2',3'-dideoxythymidine (ELT) and 3'-fluoro-2',3'-dideoxyguanosine (FLG), fomivirsen, ganciclovir, idoxuridine, lamivudine (3TC), 1-nucleosides (e.g. β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (NA-950), tipranavir; h). Other types of anti-virus drugs: abzyme, arbidol, calanolide a, ceragenin, cyanovirin-n, diarylpyrimidines, epigallocatechin gallate (EGCG), foscarnet, grifthsin, taribavirin (viramidine), hydroxyurea, KP-1461, miltefosine, pleconaril, portmanteau inhibitors, ribavirin, seliciclib.

5). Other immunotheraphy drugs: e.g. imiquimod, interferons (e.g. α, β), granulocyte colony-stimulating factors, cytokines, Interleukins (IL-1~IL-35), antibodies (e. g. trastuzumab, pertuzumab, bevacizumab, cetuximab, panitumumab, infliximab, adalimumab, basiliximab, daclizumab, omalizumab), Protein-bound drugs Abraxane), an antibody conjugated with drugs selected from calicheamicin derivative, of maytansine derivatives (DM1 and DM4), CC-1065 and duocarmycin minor groove binders, potent taxol derivatives, doxorubicin, auristatin antimitotic drugs (e. g. Trastuzumab-DM1, Inotuzumab ozogamicin, Brentuximab vedotin, Glembatumumab vedotin, lorvotuzumab mertansine, AN-152 LMB2, TP-38, VB4-845, Cantuzumab mertansine, AVE9633, SAR341.9, CAT-8015 (anti-CD22), milatuzumab-doxorubicin, SGN-75 (anti-CD70), Anti-CD22-MCC-DM1, IMGN853, Anti-CD22-MMAE, Anti-CD22-MMAF, Anti-CD22-calicheamicin.

The invention is further illustrated but not restricted by the description in the following examples.

Example 1. Tris(2-(benzyloxy)ethyl)phosphine oxide (2)

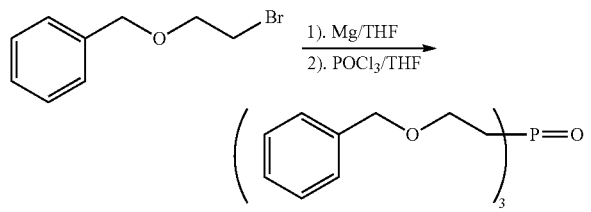

Mg turnings (1.50 g, 61.70 mmol) stirred in THF (80 ml) under Ar was added ((2-bromoethoxy)methyl)benzene (13.10 g, 61.21 mmol) dropwise for 2 h, then kept to stirring for another 3 h. To the mixture was added phosphorus(V) oxychloride (1.90 ml, 20.40 mmol) at −78° C. After stirred at −78° C. for 4 h, the mixture was diluted with 0.1 M NaHCO$_3$ solution (80 ml), NaCl (sat. 100 ml) and EtOAc (50 ml), separated, and the aqueous solution was extracted with EtOAc (2×50 ml). The organic layers were combined, dried over MgSO$_4$, filtered, concentrated and purified on SiO2 column eluted with EtOAc (1:10~1:6) to afford the title compound, 6.11 g (66.2% yield). ESI MS m/z+ 475.2 (M+Na).

Example 2. Tris(2-hydroxyethyl)phosphine oxide (3)

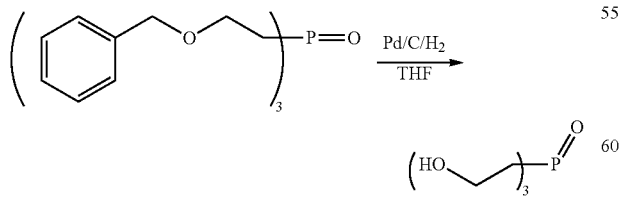

Tris(2-(benzyloxy)ethyl)phosphine oxide (6.03 g, 13.33 mmol.) in THF (100 ml) was added Pd/C (0.31 g, 10% Pd/C, 50% wet) in a hydrogenation bottle. The mixture was shaken for 4 h, filtered through Celite (filter aid), concentrated to afford the title compound (2.33 g, 96% yield) without further purification. ESI MS m/z+ 205.8 (M+Na).

Example 3. S-(2-(bis(2-hydroxyethyl)phosphoryl) ethyl) ethanethioate (8)

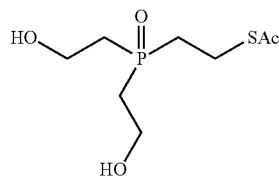

To a solution of PPh$_3$ (3.30 g, 12.59 mol), thioacetic acid (0.762 g, 10.0 mol), and tris(2-hydroxyethyl)phosphine oxide (2.30 g, 12.58 mmol) in THF (70 mL) was added, at 0-4° C., DIAD (2.5 mL, 12.69 mol) dropwise over a period of 1 h. The reaction mixture was stirred for 1 h at 0° C. and RT for 1 h. The mixture was diluted with EtOAc (100 ml), then poured into saturated Na$_2$CO$_3$ (100 mL). The mixture was separated and the aqueous solution was extracted with EtOAc (2×60 ml). The organic layers were combined, dried over Na$_2$SO$_4$, filtered, concentrated and purified on SiO$_2$ column eluted with MeOH/CH$_2$Cl$_2$ (1:15~1:8) to afford the title compound (1.75 g, 73% yield). ESI MS m/z+ 263.4 (M+Na).

Example 4. S-(2-(bis(2-bromoethyl)phosphoryl) ethyl) ethanethioate (9)

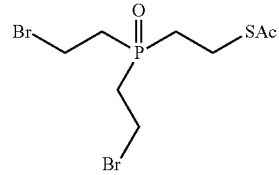

To a solution of S-(2-(bis(2-hydroxyethyl)phosphoryl) ethyl) ethanethioate (0.9 g, 3.75 mmol) in CH$_2$Cl$_2$ (50 ml) was added PPh$_3$ (2.00 g, 7.63 mol) and CBr$_4$(2.46 g, 7.50 mmol) and the reaction mixture was stirred for 6 h. The mixture was concentrated, diluted with EtOAc (80 ml), filtered through Celite, concentrated and purified on SiO$_2$ column eluted with ETOAc/hexane (1:8~1:3) to afford the title compound (1.21 g, 89% yield). ESI MS m/z+ 571.2 (M+Na).

Example 5. S-(2-(bis(2-(tosyloxy)ethyl)phosphoryl) ethyl) ethanethioate (10)

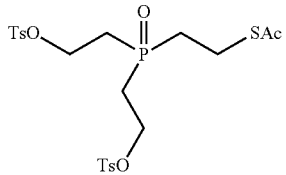

To a solution of S-(2-(bis(2-hydroxyethyl)phosphoryl)ethyl) ethanethioate (0.9 g, 3.75 mmol) in CH₂Cl₂ (30 ml) and pyridine (20 ml) was added TsCl (2.00 g, 10.52 mol) and the reaction mixture was stirred for 6 h. The mixture was concentrated and purified on SiO₂ column eluted with EtOAc/hexane (1:5~1:3) to afford the title compound (1.77 g, 86% yield). ESI MS m/z+ 386.8 (M+Na).

Example 6. Bis(2-hydroxyethyl)(2-(methylsulfinothioyl)ethyl)phosphine oxide (12)

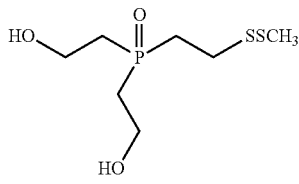

(2-(bis(2-hydroxyethyl)phosphoryl)ethyl) ethanethioate (1.25 g, 5.20 mmol) in CH₃OH (40 ml) and H₂O (20 ml) was added NaOH (0.5 M, 20 ml) at 4° C. The mixture was stirred at RT for 1 h, neutralized with HCl (6 M) to pH 7.0, and then MeSSO₂Me (1.0 g, 7.93 mmol) was added. The mixture was stirred for 4 h, concentrated, and purified on SiO₂ column eluted with MeOH/CH₂Cl₂ (1:15~1:8) to afford the title compound (1.09 g, 83% yield). ESI MS m/z+ 267.4 (M+Na).

Example 7. ((2-(methylsulfinothioyl)ethyl)phosphoryl)bis(ethane-2,1-diyl) bis(4-methylbenzenesulfonate) (13)

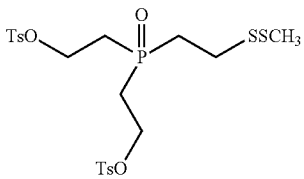

Bis(2-hydroxyethyl)(2-(methylsulfinothioyl)ethyl)phosphine oxide (1.01 g, 4.13 mmol) in CH₂Cl₂ (30 ml) and pyridine (15 ml) was added TsCl (2.00 g, 10.52 mmol). The mixture was stirred at RT for 6 h, concentrated and purified on SiO₂ column eluted with EtOAc/hexane (1:5~4:3) to afford the title compound (1.98 g, 87% yield). ESI MS m/z+ 575.2 (114+Na).

Example 8. Bis(2-hydroxyethyl)(2-(pyridin-2-yldisulfanyl)ethyl)phosphine oxide (14)

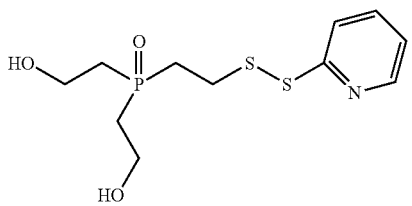 [SMILES: O=P(CCO)(CCO)CCSSc1ccccn1]

(2-(bis(2-hydroxyethyl)phosphoryl)ethyl) ethanethioate (1.25 g, 5.20 mmol) in CH₃OH (40 ml) and H₂O (20 ml) was added NaOH (0.5 M, 20 ml) at 4° C. The mixture was stirred at RT for 1 h, neutralized with HCl (6 M) to pH 7.5, and then 1,2-di(pyridin-2-yl)disulfane (4.20 g, 19.09 mmol) in CH₃OH (40 ml) was added. The mixture was stirred for 4 h, concentrated, and purified on SiO₂ column eluted with MeOH/CH₂Cl₂ (from 100% CH₂Cl₂ to ~1:8) to afford the title compound (1.26 g, 79% yield). ESI MS m/z+ 330.2 (M+Na).

Example 9. ((2-(pyridin-2-yldisulfanyl)ethyl)phosphoryl)bis(ethane-2,1-diyl) bis(4-methylbenzenesulfonate) (15)

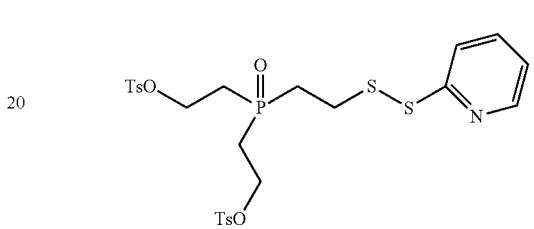

Bis(2-hydroxyethyl)(2-(pyridin-2-yldisulfanyl)ethyl) phosphine oxide (1.21 g, 3.94 mmol) in CH₂Cl₂ (30 ml) and pyridine (15 ml) was added TsCl (2.00 g, 10.52 mmol). The mixture was stirred at RT for 6 h, concentrated and purified on SiO₂ column eluted with EtOAc/hexane (1:5~1:3) to afford the title compound (1.98 g, 87% yield). ESI MS m/z+ 575.2 (M+Na).

Example 10. Trimethyl 3,3',3''-phosphinetriyltripropanoate (26)

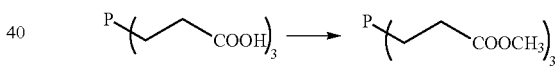

Tris(2-carboxyethyl)phosphine hydrochloride (TCEP) (7.0 g, 24.42 mmol) was co-evaporated with EtOH (2×100 ml), dissolved in CH₃OH (200 ml) at 4° C., and then thionyl chloride (9.0 mL, 122.29 mmol) was added. The resulting mixture was stirred for at RT overnight, concentrated, and dried over vacuum to provide the title compound (7.0 g, 98% yield), ESI MS m/z+ 293.2 (M+H).

Example 11. Tris(2-hydroxypropyl)phosphine oxide (27)

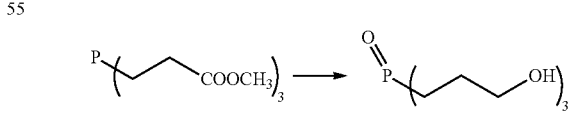

Trimethyl 3,3',3''-phosphinetriyltripropanoate (7.0 g, 23.96 mmol) in THF (100 ml) at 0° C. was added LiAlH₄ (2 M) in THF (70 ml), The reaction was stirred for 4 h at 0° C., quenched with cold water (5 ml), filtered, evaporated to dryness to afford crude 3,3',3''-phosphinetriyltris (propan-1-ol) (5.1 g, 102% yield) which was used directly for next step. This compound dissolved in HOAc (80 ml) was added H₂O, (20 ml, 33% in water). The mixture was stirred for overnight, concentrated, co-evaporated with water (2×100 ml) and toluene, and dried over vacuum to afford the title compound (4.88 g, 91% yield). ESI MS m/z+ 225.2 (M+H).

Example 12. S-(3-(bis(3-hydroxypropyl)phosphoryl) propyl) ethanethioate (28)

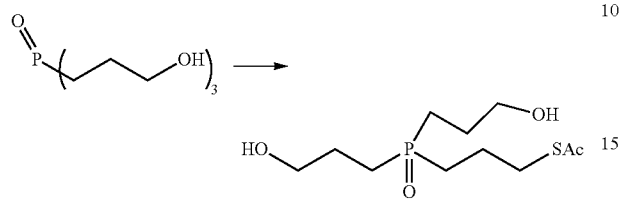

To a solution of PPh₃ (3.30 g, 12.59 mol), thioacetic acid (0.762 g, 10.0 mol), and tris(2-hydroxypropyl)phosphine oxide (2.82 g, 12.58 mmol) in THF (70 mL) was added, at 0-4° C., DIAD (2.5 mL, 12.69 mol) dropwise over a period of 1 h. The reaction mixture was stirred for 1 h at 0° C. and RT for 1 h. The mixture was diluted with EtOAc (100 ml), then poured into saturated Na₂CO₃ (100 mL). The mixture was separated and the aqueous solution was extracted with EtOAc (2×60 ml). The organic layers were combined, dried over Na₂SO₄, filtered, concentrated and purified on SiO₂ column eluted with MeOH/CH₂Cl₂ (1:15~1:8) to afford the title compound (1.77 g, 89% yield). ESI MS m/z+ 305.2 (M+Na).

Example 13. Bis(3-hydroxypropyl)(3-(methylsulfinothioyl)propyl)phosphine oxide (32)

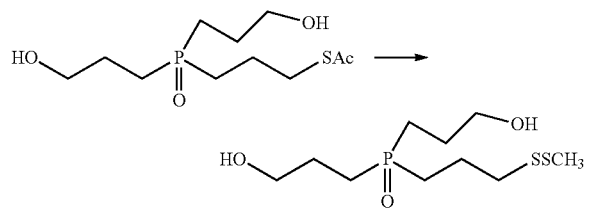

S-(3-(Bis(3-hydroxypropyl)phosphoryl)propyl) ethanethioate (1.75 g, 6.20 mmol) in CH₃OH (40 ml) and H₂O (20 ml) was added NaOH (0.5 M, 20 ml) at 4° C. The mixture was stirred at RT for 1 h, neutralized with HCl (6 M) to pH 7.0, and then MeSSO₂Me (1.0 g, 7.93 mmol) was added. The mixture was stirred for 4 h, concentrated, and purified on SiO₂ column eluted with MeOH/CH₂Cl₂ (1:15~1:8) to afford the title compound (1.56 g, 88% yield). ESI MS m/z+ 309.4 (M+Na).

Example 14. ((3-(methylsulfinothioyl)propyl)phosphoryl)bis(propane-3,1-diyl)bis(4-methylbenzenesulfonate) (33)

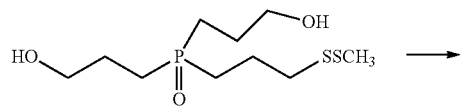

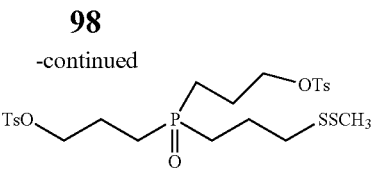

Bis(3-hydroxypropyl)(3-(methylsulfinothioyl)propyl) phosphine oxide (1.51 g, 5.35 mmol) in CH₂Cl₂ (30 ml) and pyridine (15 ml) was added TsCl (3.00 g, 15.78 mmol). The mixture was stirred at RT for 6 h, concentrated and purified on SiO₂ column eluted with EtOAc/hexane (1:5~1:3) to afford the title compound (2.73 g, 86% yield). ESI MS m/z+ 617.2 (M+Na).

Example 15. Methyl 4-(((bis(2-hydroxyethyl)phosphoryl)methyl)amino)-4-oxobutanoate (39)

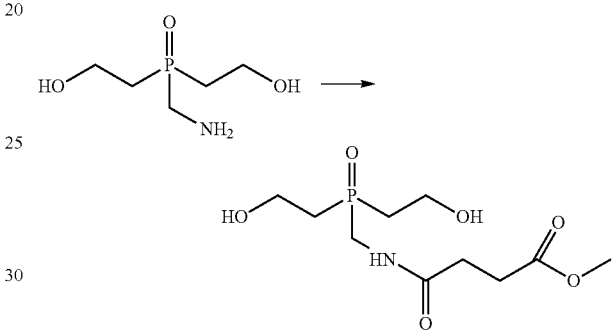

(Aminomethyl)bis(2-hydroxyethyl)phosphine oxide (1.00 g, 5.98 mmol) and 4-methoxy-4-oxobutanoic acid (0.79 g, 5.98 mmol) in DMA (50 ml) was added EDC (2.40 g, 12.50 mmol). The mixture was stirred for 8 h, concentrated and purified on SiO₂ column eluted with MeOH/CH₂Cl₂ (1:15~1:7) to afford the title compound (1.39 g, 83% yield). ESI MS m/z+ 304.2 (M+Na).

Example 16. Methyl 4-(((bis(2-(tosyloxy)ethyl) phosphoryl)methyl)amino)-4-oxobutanoate (40)

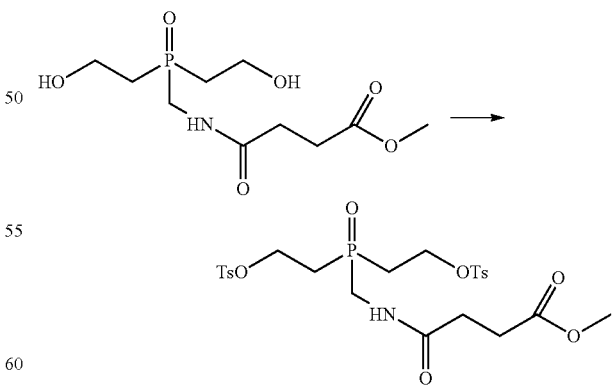

Methyl 4-(((bis(2-hydroxyethyl)phosphoryl)methyl) amino)-4-oxobutanoate (1.35 g, 4.80 mmol) in CH₂Cl₂ (30 ml) and pyridine (15 ml) was added TsCl (2.50 g, 13.15 mmol). The mixture was stirred at RT for 6 h, concentrated and purified on SiO₂ column eluted with EtOAc/hexane (1:5~1:3) to afford the title compound (2.34 g, 83% yield). ESI MS m/z+ 612.2 (M+Na).

Example 17. N-((bis(2-hydroxyethyl)phosphoryl)methyl)-4-methyl-4-(methyldisulfanyl)pentanamide (44)

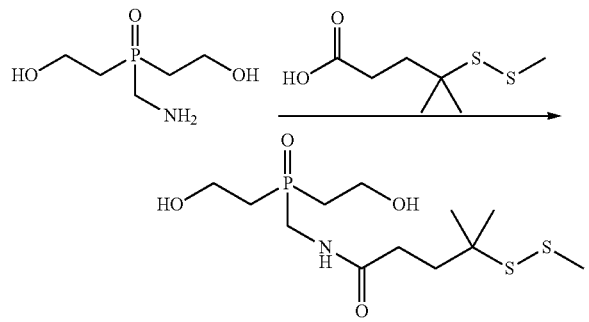

(Aminomethyl)bis(2-hydroxyethyl)phosphine oxide (1.00 g, 5.98 mmol) and 4-methyl-4-(methyldisulfanyl)pentanoic acid (1.16 g, 5.98 mmol) in DMA (50 ml) was added EDC (2.40 g, 12.50 mmol). The mixture was stirred for 8 h, concentrated and purified on SiO$_2$ column eluted with MeOH/CH$_2$Cl$_2$ (1:15~1:7) to afford the title compound (1.66 g, 81% yield). ESI MS m/z+ 366.2 (M+Na).

Example 18. (((4-methyl-4-(methyldisulfanyl)pentanamido)methyl)phosphoryl)-bis(ethane-2,1-diyl) dimethanesulfonate (45)

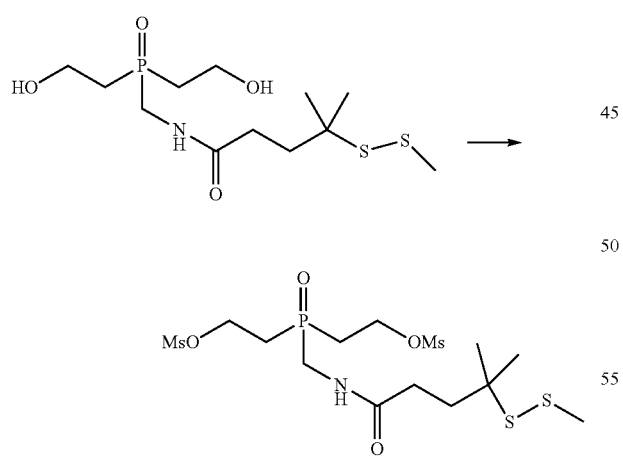

N-((bis(2-hydroxyethyl)phosphoryl)methyl)-4-methyl-4-(methyldisulfanyl)pentanamide (1.20 g, 3.49 mmol) in CH$_2$Cl$_2$ (30 ml) and pyridine (15 ml) was added MsCl (1.50 g, 13.16 mmol). The mixture was stirred at RT for 6 h, concentrated and purified on SiO$_2$ column eluted with EtOAc/hexane (1:5~1:3) to afford the title compound 1.44 g, 83% yield). ESI MS m/z+ 522.1 (M+Na).

Example 19. 4-(benzyloxy)-3-methoxybenzoic acid

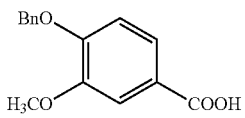

4-Hydroxy-3-methoxybenzoic acid (50.0 g, 297.5 mmol) in the mixture of ethanol (350 ml) and NaOH solution (2.0 M, 350 ml) was added BnBr (140.0 g, 823.5 mmol). The mixture was stirred at 65° C., for 8 h, concentrated, co-evaporated with water (2×400 ml) to ~400 ml, acidified with 6 M HCl to pH 3.0, filtered the solid, crystallized with EtOH, dried over the oven at 45° C. with vacuum to afford the title compound (63.6 g, 83% yield). ESI MS m/z+ 281.2 (M+Na).

Example 20. 4-(benzyloxy)-5-methoxy-2-nitrobenzoic acid

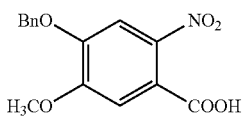

4-(Benzyloxy)-3-methoxybenzoic acid (63.5 g, 246.0 mmol) in the mixture of CH$_2$Cl$_2$ (400 ml) and HOAc (100 ml) was added HNO$_3$ (fuming, 25.0 ml, 528.5 mmol). The mixture was stirred for 6 h, concentrated, crystallized with EtOH, dried over the oven at 40° C. with vacuum to afford the title compound (63.3 g, 85% yield). ESI MS m/z+ 326.1 (M+Na).

Example 21. (2S,4R)-methyl 4-hydroxypyrrolidine-2-carboxylate, hydrochloric salt

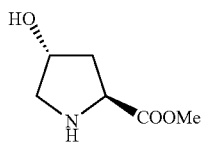

Trans-4-hydroxy-L-proline (15.0 g, 114.3 mmol) in dry methanol (250 mL) at 0~4° C., was added dropwise thionyl chloride (17 mL, 231 mmol). The resulting mixture was stirred for at RT overnight, concentrated, crystallized with EtOH/hexane to provide the title compound (18.0 g, 87% yield), ESI MS m/z+ 168.2 (M+Na).

Example 22. (2S,4R)-1-tert-butyl 2-methyl 4-hydroxypyrrolidine-1,2-dicarboxylate

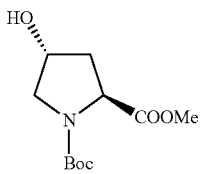 [SMILES: COC(=O)[C@@H]1C[C@@H](O)CN1C(=O)OC(C)(C)C]

To a solution of trans-4-hydroxy-L-proline methyl ester (18.0 g, 107.0 mmol) in the mixture of MeOH (150 ml) and sodium bicarbonate solution (2.0 M, 350 ml) was added (BOC)$_2$O (30.0 g, 137.6 mmol) in three portions in 4 h. After stiffing for an additional 4 h, the reaction was concentrated to ~350 nil and extracted with EtOAc (4×80 mL). The combined organic layers were washed with brine (100 mL), dried (MgSO$_4$), filtered, concentrated and purified by SiO$_2$ chromatography (1:1 hexanes/EtOAc) to give the title compound (22.54 g, 86% yield). ESI MS m/z+ 268.2 (M+Na).

Example 23. (S)-1-tert-butyl 2-methyl 4-oxopyrrolidine-1,2-dicarboxylate

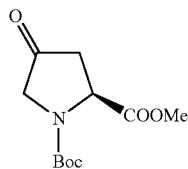 [SMILES: COC(=O)[C@@H]1CC(=O)CN1C(=O)OC(C)(C)C]

The title compound prepared through Dess-Martin oxidation was described in: Franco Manfre et al. *J. Org. Chem.* 1992, 57, 2060-2065. Alternatively Swern oxidation procedure is as following: A solution of (COCl)$_2$ (13.0 ml, 74.38 mmol) in CH$_2$Cl$_2$ (350 ml) cooled to −78° C. was added dry DMSO (26.0 mL). The solution was stirred at −78° C. for 15 min and then (2S,4R)-1-tert-butyl 2-methyl 4-hydroxypyrrolidine-1,2-dicarboxylate (8.0 g, 32.63 mmol) in CH$_2$Cl$_2$ (100 ml). After stirred at −78° C. for 2 h, triethylamine (50 ml, 180.3 mmol) was added dropwise, and the solution was warmed to room temperature (RT). The mixture was diluted with NaH$_2$PO$_4$ (400 ml, 1.0 M) solution, separated, and the aqueous layer was extracted with CH$_2$Cl$_2$ (2×60 ml). The organic layers were combined, dried over MgSO$_4$, filtered, concentrated and purified by SiO$_2$ chromatography (7:3 hexanes/EtOAc) to give the title compound (6.73 g, 85% yield). ESI MS m/z+ 266.2 (M+Na).

Example 24. (S)-1-tert-butyl 2-methyl 4-methylenepyrrolidine-1,2-dicarboxylate

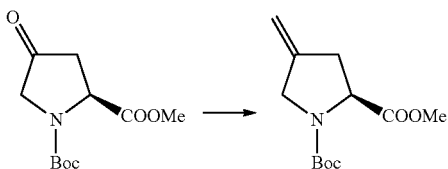 [SMILES: COC(=O)[C@@H]1CC(=O)CN1C(=O)OC(C)(C)C ; C=C1C[C@@H](C(=O)OC)N(C(=O)OC(C)(C)C)C1]

A solution of methyltriphenylphosphonium bromide (19.62 g, 55.11 mmol.) in THF (150 mL) at 0° C. was potassium-t-butoxide (6.20 g, 55.30 mmol) in anhydrous THF (80 mL). After stirred at 0° C. for 2 h, the resulting yellow ylide suspension was added the solution of (S)-1-tert-butyl 2-methyl 4-oxopyrrolidine-1,2-dicarboxylate (6.70 g, 27.55 mmol) in THF (40 mL). After stirring at RT for 1 h, the reaction mixture was concentrated, diluted with EtOAc (200 mL), washed with H$_2$O (150 mL), brine (150 mL), dried over MgSO$_4$, concentrated purified on SiO$_2$ flash chromatography (9:1 hexanes/EtOAc) to yield the title compound (5.77 g, 87% yield). EIMS m/z+ 264 (M+Na).

Example 25. (S)-methyl 4-methylenepyrrolidine-2-carboxylate

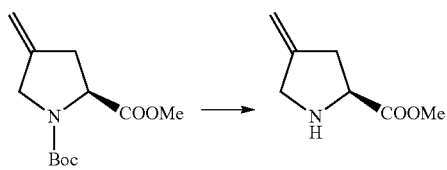

(S)-1-tert-butyl 2-methyl 4-methylenepyrrolidine-1,2-dicarboxylate (5.70 g, 23.63 mmol) in EtOAc (40 ml) at 4° C. was added. HCl (10 ml, 12 M). The mixture was stirred for 1 h, diluted with toluene (50 ml), concentrated, and crystallized with EtOH/hexane to yield the title compound as HCl salt (3.85 g, 92% yield). EIMS m/z+ 142.2 (M+H).

Example 26. (S)-methyl 1-(4-(benzyloxy)-5-methoxy-2-nitrobenzoyl)-4-methylenepyrrolidine-2-carboxylate

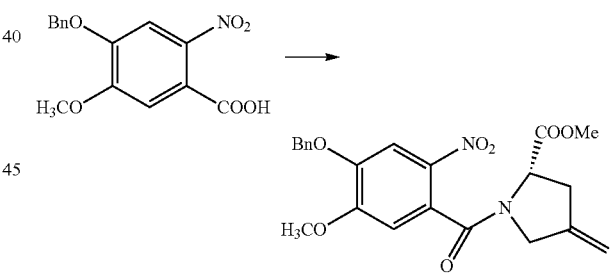

A catalytic amount of DMF (30 ul) was added to a solution of 4-(benzyloxy)-5-methoxy-2-nitrobenzoic acid (2.70 g, 8.91 mmol) and oxalyl chloride (2.0 mL, 22.50 mmol) in anhydrous CH$_2$Cl$_2$ (70 mL) and the resulting mixture was stirred at room temperature (RT) for 2 h. Excess CH$_2$Cl$_2$ and oxalyl chloride was removed with rotavap. The actyl chloride was resuspended in fresh CH$_2$Cl$_2$ (70 mL) and was added dropwise to a solution of 4-methylene-L-proline methyl ester HCl salt (1.58 g, 8.91 mmol), Et$_3$N (6 mL) at 0° C. under argon atmosphere. The reaction mixture was allowed to warm to RT and stirring was continued for 8 h. After removal of CH$_2$Cl$_2$ and Et$_3$N, the residue was partitioned between H$_2$O and EtOAc (70/70 mL). The aqueous layer was further extracted with EtOAc (2×60 mL). The combined organic layers were washed with brine (40 mL), dried (MgSO$_4$) and concentrated. Purification of the residue with flash chromatography (silica gel, 2:8 hexanes/EtOAc)

yielded (S)-methyl 1-(4-(benzyloxy)-5-methoxy-2-nitrobenzoyl)-4-methylenepyrrolidine-2-carboxylate (2.88 g, 76.1% yield); EIMS m/z 449.1 ([M]⁺+Na).

Example 27. (S)-1-(4-(benzyloxy)-5-methoxy-2-nitrobenzoyl)-4-methylenepyrrolidine-2-carbaldehyde

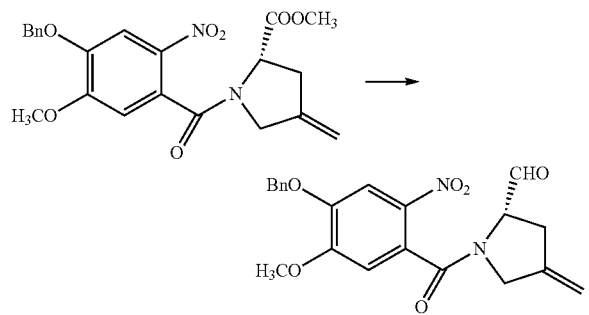

To a vigorously stirred solution of (S)-methyl 1-(4-(benzyloxy)-5-methoxy-2-nitrobenzoyl)-4-methylenepyrrolidine-2-carboxylate (2.80 g, 6.57 mmol) in anhydrous CH₂Cl₂ (60 mL) was added dropwise solution of DIBAL-H (10 mL of a 1M solution in CH₂Cl₂) at −78° C. under argon atmosphere. After the mixture was stirred for an additional 90 min, excess reagent was decomposed by addition of 2 ml of methanol followed by 5% HCl (10 mL). The resulting mixture was allowed to warm to 0° C. Layers were separated and the aqueous layer was further extracted with CH₂Cl₂ (3×50 mL). Combined organic layers were washed with brine, dried (MgSO₄) and concentrated. Purification of the residue with flash chromatography (silica gel, 95:5 CHCl₃/MeOH) yielded (S)-1-(4-(benzyloxy)-5-methoxy-2-nitrobenzoyl)-4-methylenepyrrolidine-2-carbaldehyde (2.19 g, 84% yield). EIMS m/z 419.1 ([M]⁺+Na).

Example 28. (S)-8-(benzyloxy)-7-methoxy-2-methylene-2,3-dihydro-1H-benzo[e]-pyrrolo[1,2-a]azepin-5(11aH)-one

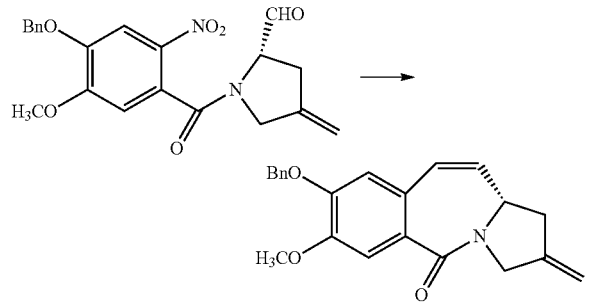

(S)-1-(4-(benzyloxy)-5-methoxy-2-nitrobenzoyl)-4-methylenepyrrolidine-2-carbaldehyde (2.18 g, 5.50 mmol) and Na₂S₂O₄ (8.0 g, 45.97 mmol) in the mixture of THF (60 ml) and H₂O (40 ml) were stirred at RT for 20 h. Solvents were removed under high vacuum. The residue was re-suspended in MeOH (60 mL), and HCl (6M) was added dropwise until pH~2. The resulting mixture was stirred at RT for 1 h. The reaction was work-up by removing most of MeOH, then diluted with EtOAc (100 mL). The EtOAc solution was washed with sat. aq. NaHCO₃, brine, dried (MgSO₄), and concentrated. Purification of the residue with flash chromatography (silica gel, 97:3 CHCl₃/MeOH) yielded (S)-8-(benzyloxy)-7-methoxy-2-methylene-2,3-dihydro-1H-benzo[e]pyrrolo[1,2-a]azepin-5(11aH)-one (1.52 g, 80%). EIMS m/z 370.1 ([M]⁺+Na).

Example 29. (S)-8-hydroxy-7-methoxy-2-methylene-2,3-dihydro-1H-benzo[e]pyrrolo[1,2-a]azepin-5(11aH)-one

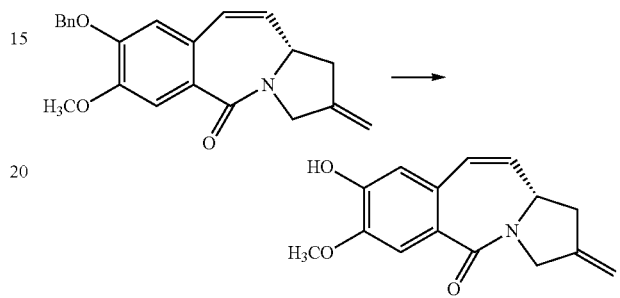

(S)-8-(benzyloxy)-7-methoxy-2-methylene-2,3-dihydro-1H-benzo[e]pyrrolo[1,2-a]azepin-5(11aH)-one (1.50 g, 4.32 mmol) in 70 ml of CH₂Cl₂ at 0° C. was added 25 ml of CH₂SO₃H. The mixture was stirred at 0° C. for 10 min then RT for 2 h, diluted with CH₂Cl₂, neutralized with cold 1.0 M NaHCO₃ to pH 4, filtered. The aqueous layer was extracted with CH₂Cl₂ (3×60 ml). The organic layers were combined, dried over Na₂SO₄, filtered, evaporated and purified on SiO₂ chromatography eluted with CH₃OH/CH₂Cl₂ (1:15) to afford 811 mg (73%) of the title product. EIMS m/z 280.1 ([M]⁺+Na).

Example 30. (S)-Methyl piperidine-2-carboxylate, HCl salt

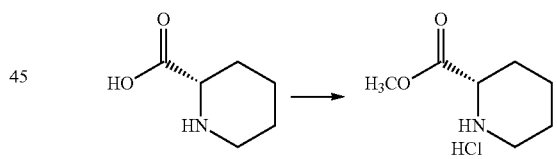

(S)-Piperidine-2-carboxylic acid (10.00 g, 77.46 mmol) in methanol (200 ml) at 0° C. was added thionyl chloride (15.0 ml, 205.61 mmol) under Ar. The mixture was stirred at 0° C. for 30 min, then RT overnight, evaporated and crystallized with EtOH to afford the title product (9.90 g, 92% yield). EIMS m/z 144.1 ([M]⁺+H).

Example 31. (S)-Methyl 1-(4-(benzyloxy)-5-methoxy-2-nitrobenzoyl)piperidine-2-carboxylate

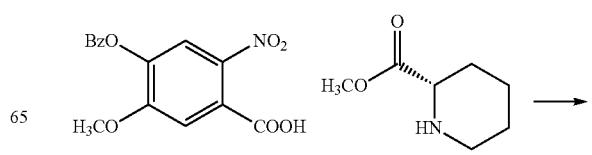

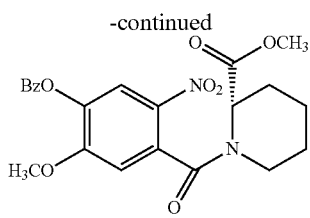

A catalytic amount of DMF (20 ul) was added to a solution of 4-(benzyloxy)-5-methoxy-2-nitrobenzoic acid (1.35 g, 4.45 mmol) and oxalyl chloride (1.0 mL, 11.25 mmol) in anhydrous CH$_2$Cl$_2$ (40 mL) and the resulting mixture was stirred at room temperature (RT) for 2 h. Excess CH$_2$Cl$_2$ and oxalyl chloride was removed with rotavap. The chloride compound was resuspended in fresh CH$_2$Cl$_2$ (40 mL) and was added dropwise to a solution of (S)-methyl piperidine-2-carboxylate HCl salt (0.80 g, 4.46 mmol), Et$_3$N (4 mL) at 0° C. under argon atmosphere. The reaction mixture was allowed to warm to RT and stirring was continued for 8 h. After removal of CH$_2$Cl$_2$ and Et$_3$N, the residue was partitioned between H$_2$O and EtOAc (70/70 mL). The aqueous layer was further extracted with EtOAc (2×60 mL). The combined organic layers were washed with brine (30 mL), dried (MgSO$_4$) and concentrated. Purification of the residue with flash chromatography (silica gel, 2:8 hexanes/EtOAc) (R)-methyl 1-(4-(benzoyloxy)-5-methoxy-2-nitrobenzoyl)piperidine-2-carboxylate (1.51 g, 73.1% yield); EIMS m/z 465.1 ([M]$^+$+Na).

Example 32. (S)-1-(4-(benzyloxy)-5-methoxy-2-nitrobenzoyl)piperidine-2-carbaldehyde

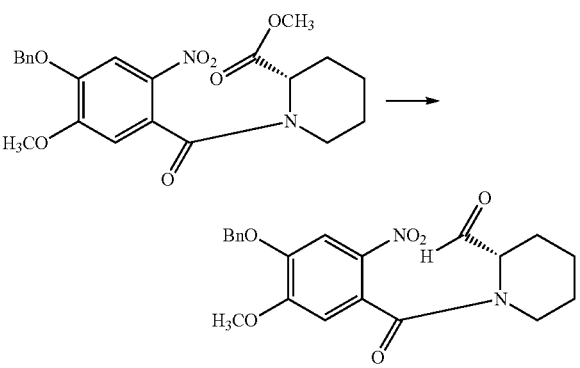

(S)-Methyl 1-(4-(benzoyloxy)-5-methoxy-2-nitrobenzoyl)piperidine-2-carboxylate (1.50 g, 3.50 mmol) in CH$_2$Cl$_2$ (50 ml) at −78° C. was added DIBAL (7.5 ml, 1.0 M) in toluene under Ar in 30 min. The mixture was stirred at −78° C. for 3 hr and the reaction was quenched with 0.5 ml of methanol. The mixture was diluted with EtAc (150 ml) and HCl (100 ml, 0.2 M). The organic was separated and the aqueous was extracted with EtAc (3×80 ml). The organics were combined, dried over MgSO$_4$, filtered, concentrated and purified on SiO$_2$ chromatography eluted with EtAc/hexane (3:2) to afford 1.52 g (90% yield) of the title product. $^1$H NMR (CDCl$_3$), 9.60 (s, 1H), 7.70 (s, 1H), 7.65-7.28 (m, 5H), 6.78 (m, 1H), 5.16 (s, 2H), 3.92 (s, 3H), 3.22, (m, 1H), 3.01 (m, 1H), 2.20 (m, 1H), 1.84 (m, 1H), 1.65-1.40 (m, 4H); $^{13}$C NMR 200.24, 171.31, 155.13, 154.78, 148.41, 146.20, 137.57, 135.47, 129.03, 128.73, 127.31, 109.83, 109.41, 71.61, 64.50, 56.96, 45.98, 25.25, 23.42, 18.70; MS m/z+ 421.1 (M+Na).

Example 33. (S)-3-(benzyloxy)-2-methoxy-7,8,9,10-tetrahydrobenzo[e]pyrido[1,2-a][1,4]diazepin-12(6aH)-one

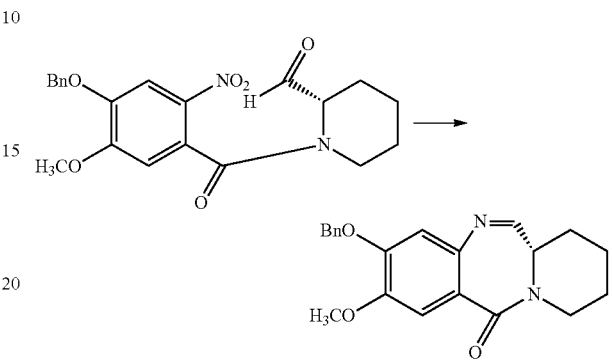

(S)-1-(4-(benzyloxy)-5-methoxy-2-nitrobenzoyl)piperidine-2-carbaldehyde (1.50 g, 3.77 mmol) in a mixture solution of THF (50 ml) and water (50 ml) was added Na$_2$S$_2$O$_4$ (5.0 g, 28.73 mmol). The mixture was stirred for 8 h, diluted with dioxane (50 ml), evaporated and co-evaporated with dioxane (3×60 ml) to dryness. The solid was sonicated with a mixture of CH$_3$OH/CH$_2$Cl$_2$ (1:1, 80 ml), filtered and evaporated to solid. The yield solid was dissolved in CH$_3$OH (100 ml) followed added 0.4 ml of HCl (conc). The mixture was stirred for 1 h, neutralized to pH 3.0 with 0.1 M NaHCO$_3$, concentrated, and extracted with CH$_2$Cl$_2$ (4×60 ml). The organic layers were combined, washed with 1M NaHCO$_3$/NaCl (conc), dried over Na$_2$SO$_4$, filtered, evaporated and purified on SiO$_2$ chromatography eluted with EtAc/CH$_2$Cl$_2$ (1:3) to afford the title product (950 mg, 72% yield). $^1$H. NMR (CDCl$_3$), 7.81 (d, 1H, J=5.7 Hz), 7.38~7.23 (m, 6H), 6.74 (s, 1H), 5.12 (dd, 2H, J=2.3, 21.8 Hz), 4.18 (m, 1H), 3.88 (d, 3H), 3.69 (m, 1H), 3.15 (m, 1H), 1.99 (m, 1H), 1.87 (m, 1H), 1.79~1.65 (m, 4H); $^{13}$C NMR 167.76, 163.31, 150.72, 148.48, 140.09, 136.46, 128.87, 128.28, 127.53, 121.77, 111.01, 71.02, 56.41, 49.84, 39.93, 24.76, 23.21, 18.62; MS m/z+ 373.2 (M+Na), 391.2 (M+Na+H$_2$O).

Example 34. (S)-3-hydroxy-2-methoxy-7,8,9,10-tetrahydrobenzo[e]pyrido[1,2-a][1,4]diazepin-12(6aH)-one

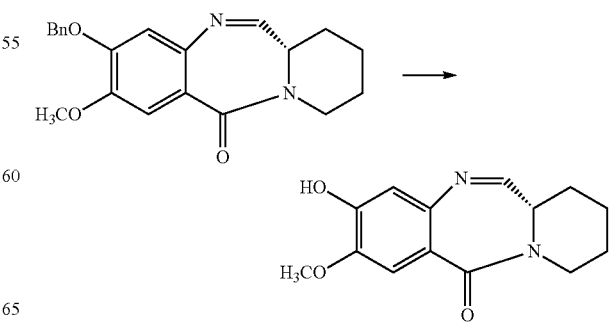

(S)-3-(benzyloxy)-2-methoxy-7,8,9,10-tetrahydrobenzo[e]pyrido[1,2-a][1,4]diazepin-12(6aH)-one (925 mg, 2.64 mmol) in CH$_2$Cl$_2$ (50 ml) at 0° C., was added CH$_2$SO$_3$H (25 ml). The mixture was stirred at 0° C. for 10 min then RT for 2 h, diluted with CH$_2$Cl$_2$, neutralized with cold 1.0 M NaHCO$_3$, extracted with CH$_2$Cl$_2$, dried over Na$_2$SO$_4$, filtered, evaporated and purified on SiO$_2$ chromatography eluted with CH$_3$OH/CH$_2$Cl$_2$ (1:15) to afford the title product (555 mg, 81% yield). $^1$H NMR (CDCl$_3$), 7.75 (d, 1H, J=5.7 Hz), 7.28 (s, 1H), 6.70 (s, 1H), 4.08 (m, 1H), 3.83 (d, 3H), 3.61 (m, 1H), 3.08 (m, 1H), 1.91 (m, 1H), 1.81 (m, 1H), 1.71~1.55 (m, 4H); $^{13}$C NMR 167.81, 163.46, 148.53, 145.71, 140.84, 121.23, 111.89, 111.39, 56.45, 49.83, 39.96, 24.71, 23.22, 18.60; MS m/z+ 283.7 (M+Na).

Example 35. (S)-methyl 1-(4-(benzyloxy)-5-methoxy-2-nitrobenzoyl)pyrrolidine-2-carboxylate

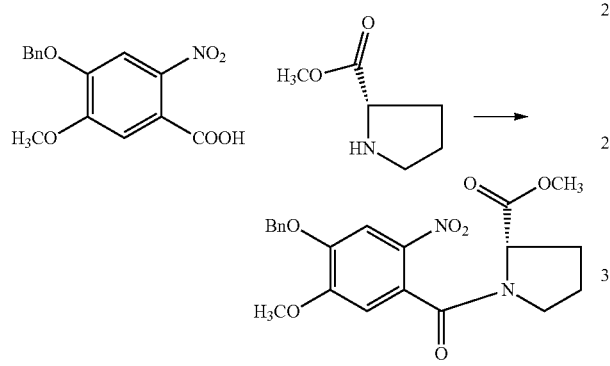

4-(benzyloxy)-5-methoxy-2-nitrobenzoic acid (2.00 g, 6.60 mmol), L-proline methyl ester HCl salt (1.09 g, 6.60 mmol), EDC (3.50 g, 18.22 mmol) and DIPEA (1.0 ml, 5.75 mmol) was stirred in 25 ml of DMA over night. The mixture was evaporated, diluted with DCM, washed with washed 1M NaH$_2$PO$_4$/NaCl (conc) and 0.1 M NaHCO$_3$/NaCl (conc) separately. The organic was dried over MgSO$_4$, filtered, concentrated and purified on SiO$_2$ chromatography eluted with EtOAc/DCM (1:15) to afford 1.96 g (72%) of the title product. EIMS m/z 437.1 (M+Na).

Example 36. (S)-1-(4-(benzyloxy)-5-methoxy-2-nitrobenzoyl)pyrrolidine-2-carbaldehyde

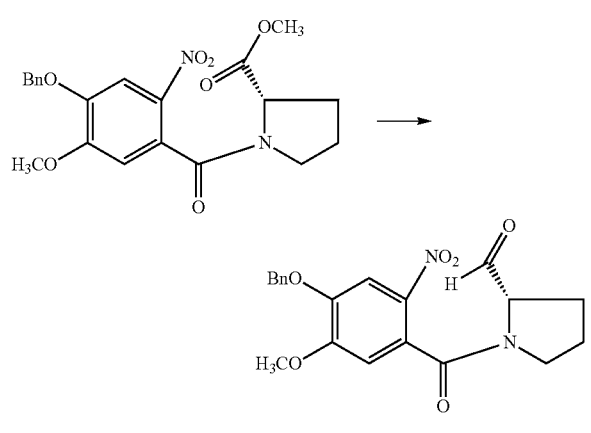

(S)-methyl 1-(4-(benzyloxy)-5-methoxy-2-nitrobenzoyl)pyrrolidine-2-carboxylate (1.90 g, 4.59 mmol) in CH$_2$Cl$_2$ (50 ml) at −78° C. was added DIBAL (7.5 ml, 1.0 M) in toluene under Ar in 30 min. The mixture was stirred at −78° C. for 3 hr and the reaction was quenched with 0.5 ml of methanol. The mixture was diluted with EtAc (150 ml) and HCl (100 ml, 0.2 M). The organic was separated and the aqueous was extracted with EtAc (3×80 ml), The organics were combined, dried over MgSO$_4$, filtered, concentrated and purified on SiO$_2$ chromatography eluted with EtAc/hexane (3:2) to afford the title product (1.34 g, 76% yield). MS m/z+ 407.1 (M+Na).

Example 37. (S)-8-(benzyloxy)-7-methoxy-2,3-dihydro-1H-benzo[e]pyrrolo[1,2-a][1,4]diazepin-5(11aH)-one

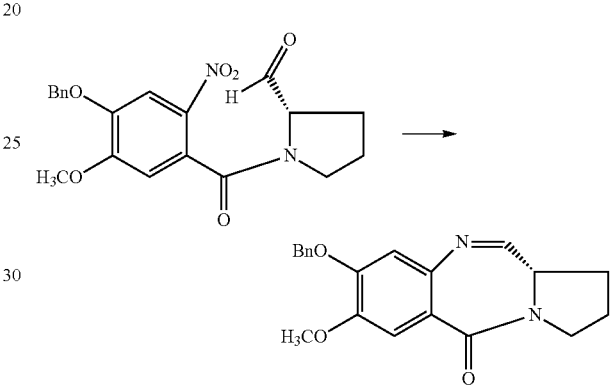

(S)-1-(4-(benzyloxy)-5-methoxy-2-nitrobenzoyl)pyrrolidine-2-carbaldehyde (1.30 g, 3.38 mmol) in a mixture solution of THF (50 ml) and water (50 ml) was added Na$_2$S$_2$O$_4$ (5.0 g, 28.73 mmol). The mixture was stirred for 8 h, diluted with dioxane (50 ml), evaporated and co-evaporated with dioxane (3×60 ml) to dryness. The solid was sonicated with a mixture of CH$_3$OH/CH$_2$Cl$_2$ (1:1, 80 ml), filtered and evaporated to solid. The yield solid was dissolved in CH$_3$OH (100 ml) followed added 0.4 ml of HCl (conc). The mixture was stirred for 1 h, neutralized to pH 3.0 with 0.1 M NaHCO$_3$, concentrated, and extracted with CH$_2$Cl$_2$ (4×60 ml). The organic layers were combined, washed with 1M NaHCO$_3$/NaCl (conc), dried over Na$_2$SO$_4$, filtered, evaporated and purified on SiO$_2$ chromatography eluted with EtAc/CH$_2$Cl$_2$ (1:3) to afford the title product (807 mg, 71% yield). EIMS m/z+ 359.2 (M+Na), 377.2 (M+Na+H$_2$O).

Example 38. (S)-8-hydroxy-7-methoxy-2,3-dihydro-1H-benzo[e]pyrrolo[1,2-a][1,4]diazepin-5(11aH)-one

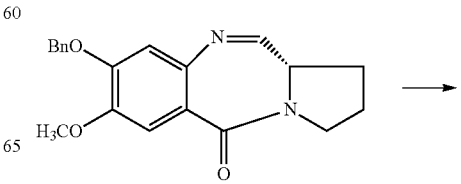

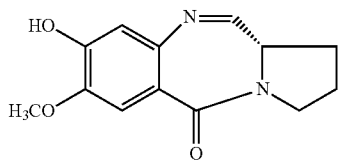

(R)-8-(benzyloxy)-7-methoxy-2,3-dihydro-1H-benzo[e]pyrrolo[1,2-a][1,4]diazepin-5(11aH)-one (795 mg, 2.36 mmol) in CH$_2$Cl$_2$ (30 ml) at 0° C. was added CH$_2$SO$_3$H (15 ml). The mixture was stirred at 0° C. for 10 min then RT for 2 h, diluted with CH$_2$Cl$_2$, neutralized with cold 1.0 M NaHCO$_3$, extracted with CH$_2$Cl$_2$, dried over Na$_2$SO$_4$, filtered, evaporated and purified on SiO$_2$ chromatography eluted with CH$_3$OH/CH$_2$Cl$_2$ (1:15) to afford the title product (477 mg, 82% yield). EIMS m/z+ 269.2 (M+Na), 287.2 (M+Na+H$_2$O), 301.2 (M+Na+CH$_3$OH).

Example 39. (11aS,11a'S)-8,8'-((((2-(methylsulfinothioyl)ethyl)phosphoryl)bis(ethane-2,1-diyl)bis(oxy))-bis(7-methoxy-2-methylene-2,3-dihydro-1H-benzo[e]pyrrolo[1,2-a][1,4]diazepin-5(11aH)-one)

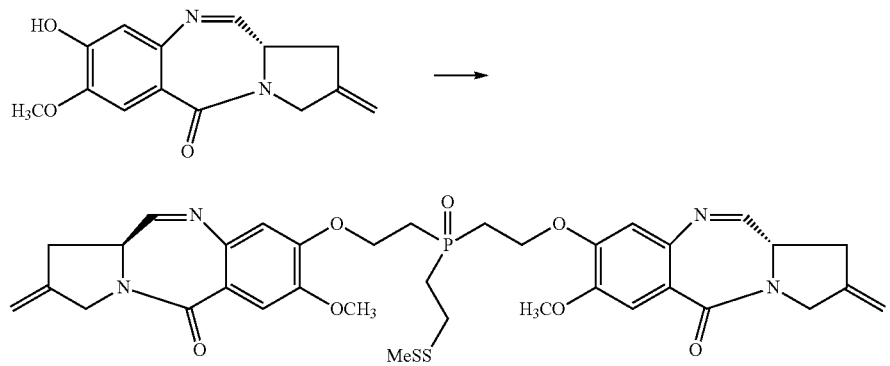

To the stirring solution of (S)-8-hydroxy-7-methoxy-2-methylene-2,3-dihydro-1H-benzo[e]pyrrolo[1,2-a][1,4]diazepin-5(11aH)-one (60.1 mg, 0.232 mmol), Cs$_2$CO$_3$ (100 mg, 0.307 mmol), KI (3.2 mg, 0.018 mmol) in 5 ml of acetone was added ((2-(methylsulfinothioyl)-ethyl)phosphoryl)-bis(ethane-2,1-diyl) bis(4-methylbenzenesulfonate) (13) (67.2 mg, 0.121 mmol). The mixture was stirred over night, evaporated and purified on HPLC preparative C-18 column (Φ10 mm×200 mm column, flow rate 9 mL/min and a gradient solvent system going from 80:20 solvent A:B at time 0-5 min to 50:50 A:B at 15 min then to 30:70 A:B at 25 min until to 10:90 A:B at 30 min. Solvent A—water, solvent B—dioxane) and lyophilized to afford a white solid 54.6 mg (64%) of the title compound. EIMS m/z+ 747.2 (M+Na), 763.3 (M+K), 781.3 (M+K+H$_2$O); MS m/z– 723.2 (M–H).

The compound was highly potent towards Raji cells, with IC$_{50}$ values between 5.0-11 pM measured at 37° C., 5 days incubation.

Example 40. Sodium (11S,11aS,11'S,11a'S)-8,8'4 (((2-mercaptoethyl)phosphoryl)bis-(ethane-2,1-diyl))bis(oxy))bis(7-methoxy-2-methylene-5-oxo-2,3,5,10,11,11a-hexahydro-1H-benzo[e]pyrrolo[1,2-a][1,4]diazepine-11-sulfonate)

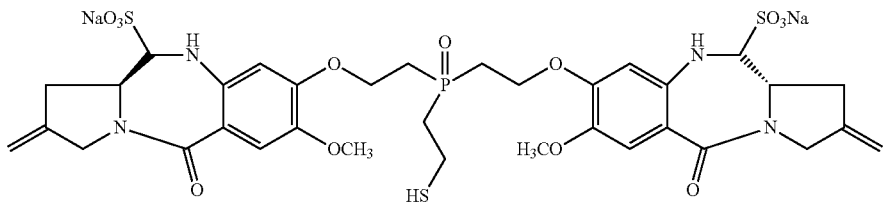

(11aS,11a'S)-8,8'-((((2-(methylsulfinothioyl)ethyl)phosphoryl)bis(ethane-2,1-diyl))bis(oxy))-bis(7-methoxy-2-methylene-2,3-dihydro-1H-benzo[e]pyrrolo[1,2-a][1,4]diazepin-5(11aH)-one) (25 mg, 0.034 mmol) in the mixture of isopropanol (5 ml) and H$_2$O (5 mL) was added NaHSO$_3$ (9 mg, 0.086 mmol) and the mixture was stirred at RT for 4 hr. Then TCEP (29.1 mg, 0.102 mmol) and NaH$_2$PO$_4$ (3.0 ml, 2.5 M, pH 7.5) were added. After stirred for 4 h, the mixture was concentrated, purified on HPLC (C-18 column, mobile phase A: water, mobile phase B: methanol from 10% of B to 75% of B in 30 mmin). The fractions were pooled and lyophilized to give the title compound (14.5 mg, 49.3% yield), ESI m/z– 841.2 ([M]–H); and a side product of (11aS,11a'S)-8,8'-((((2-mercaptoethyl)phosphoryl)bis(ethane-2,1-diyl))bis(oxy))bis(7-methoxy-2-methylene-2,3-dihydro-1H-benzo[e]pyrrolo[1,2-a][1,4]diazepin-5(11aH)-one) (2.5 mg, 10% yield), ESI m/z–+ 701.2 ([M]+Na), 717.2 ([M]+Na+K)

Example 41. Sodium (11S,11aS,11'S,11a'S)-8,8'-((((2-((1-(4-((2,5-dioxopyrrolidin-1-yl)oxy)-4-oxobutyl)-2,5-dioxopyrrolidin-3-yl)thio)ethyl)phosphoryl)bis(ethane-2,1-diyl))bis(oxy))bis(7-methoxy-2-methylene-5-oxo-2,3,5,10,11,11a-hexahydro-1H-benzo[e]pyrrolo[1,2-a][1,4]diazepine-11-sulfonate)

dine, 1% sucrose, 0.01% Tween-20, 50 μM sodium bisulfite formulation buffer, pH 6.0, using NAP desalting columns (Illustra Sephadex G-25 DNA Grade, GE Healthcare), Dialysis was performed in the same buffer for 4 hours at room temperature utilizing Slide-a-Lyzer dialysis cassettes (ThermoScientific 20,000 MWCO). The purified conjugate was found to have an average of 3.8 PBD derivative

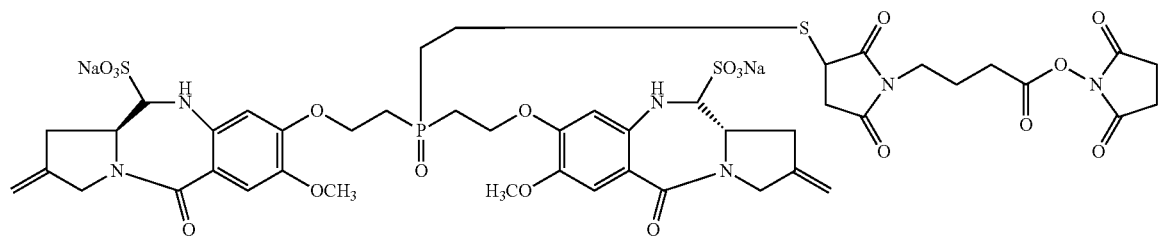

Succinimidyl 4-(N-maleimido) butyrate (3.4 mg, 0.012 mmol) in DMA (0.5 mL) was added sodium (11S,11aS,11'S,11a'S)-8,8'-((((2-mercaptoethyl)phosphoryl)bis(ethane-2,1-diyl))bis(oxy))bis(7-methoxy-2-methylene-5-oxo-2,3,5,10,11,11a-hexahydro-1H-benzo[e]pyrrolo[1,2-a][1,4]diazepine-11-sulfonate) (5.0 mg, 0.0059 mmol), After stirred for 2 h, the mixture was concentrated, purified on HPLC (C-18 column, mobile phase A: water, mobile phase B: dioxane, from 10% of B to 75% of B in 30 mmin). The fractions were pooled and lyophilized to give the title compound (4.9 mg, 72% yield), ESI MS m/z– 1165.2 ([M]–H).

Example 42. A Conjugate of a PBD Derivative to an Antibody with a Thioether Linkage and its Specific Antitumor Activity of the Patent molecules linked per antibody (by LC-MS), 99% monomer (by size exclusion chromatography), <0.1% unconjugated drug (by dual-column reverse-phase HPLC analysis) and a final protein concentration of 1.1 mg/ml.

In vitro potency measurements for conjugates of antiCD20 antibody with the PBD derivative dimer. The conjugates were highly potent towards antigen-positive Raji cells, with $IC_{50}$ values between 1.0-2.1 pM. Antigen blocking with 1 μM unconjugated antiCD20 antibody significantly diminished the potency, demonstrating the antigen specificity of the cytotoxic effect.

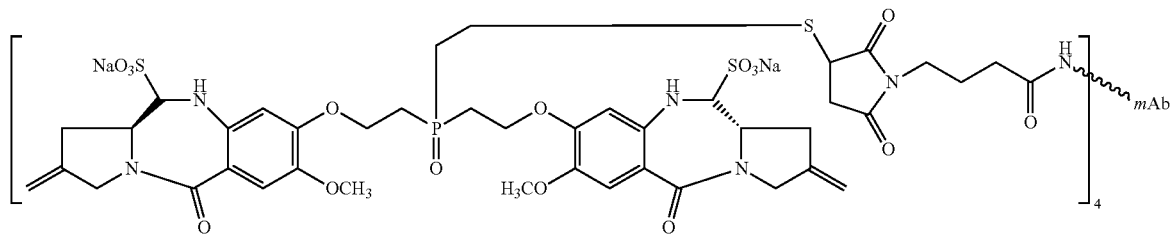

A reaction containing 2.5 mg/mL anti-CD20 antibody and 5 molar equivalents of sodium (11S,11aS,11'S,11a'S)-8,8'-((((2-((1-(4-((2,5-dioxopyrrolidin-1-yl)oxy)-4-oxobutyl)-2,5-dioxopyrrolidin-3-yl)thio)ethyl)phosphoryl)bis(ethane-2,1-diyl))bis(oxy))bis(7-methoxy-2-methylene-5-oxo-2,3,5,10,11,11a-hexahydro-1H-benzo[e]pyrrolo[1,2-a][1,4]diazepine-11-sulfonate) in 50 mM HEPES (4-(2-hydroxyethyl)-1-piperazine ethanesulfonic acid) pH 7.5 buffer containing 10% v/v DMA (N,N-Dimethylacetamide) was stirred for 6 hours at 30° C. The conjugate was purified and buffer exchanged into 250 mM Glycine, 10 mM Histi- In Vitro potency measurement against Raji cells in 37° C., 5 day incubation

| Conjugate Drug/ mAb ratio | $IC_{50}$ values | $IC_{50}$ with 1 μM unconjugated antiCD20 antibody blocking | Specificity window |
|---|---|---|---|
| 3.8 | 1.0~2.1 pM | 1.6~2.4 nM | 760~2400 |

Example 43. (11aS)-7-Methoxy-8-(2-((2-(((S)-7-methoxy-2-methylene-5-oxo-2,3,5,10,11,11a-hexahydro-1H-benzo[e]pyrrolo[1,2-a][1,4]diazepin-8-yl)oxy)ethyl)(2-(methylsulfinothioyl)ethyl)phosphoryl)-ethoxy)-2-methylene-2,3-dihydro-1H-benzo[e]pyrrolo[1,2-a][1,4]diazepin-5(11aH)-one

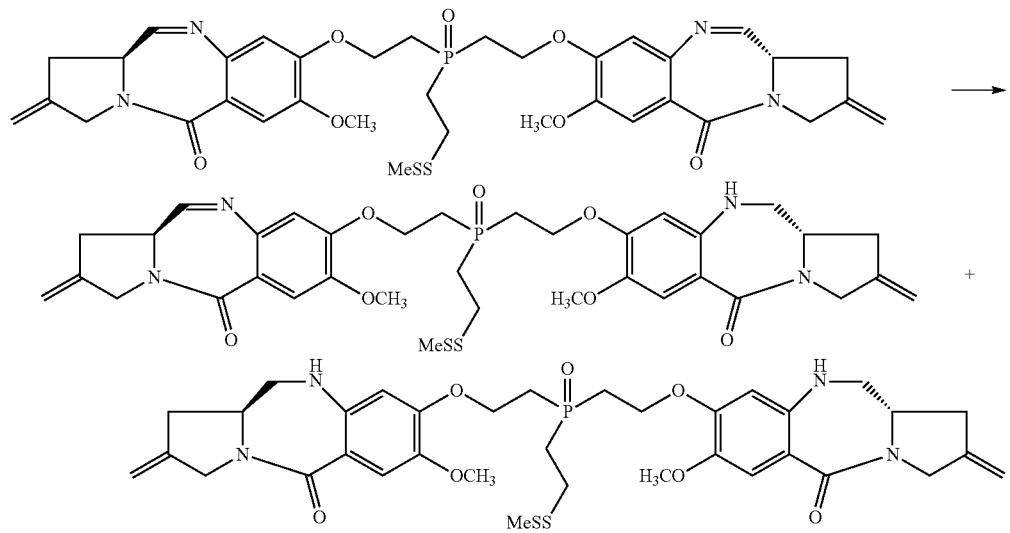

To a stirred solution of (11aS,11a'S)-8,8'-(((((2-(methyl-sulfinothioyl)ethyl)phosphoryl)-bis(ethane-2,1-diyl))bis(oxy))bis(7-methoxy-2-methylene-2,3-dihydro-1H-benzo[e]pyrrolo-[1,2-a][1,4]diazepin-5(11aH)-one) (150 mg, 0.207 mmol) in anhydrous dichloromethane (1 mL) and absolute ethanol (1.5 mL) was added sodium borohydride in methoxyethyl ether (82 µl, 0.5 M, 0.041 mmol) at 0° C. The ice bath was removed after 5 minutes and the mixture was stirred at room temperature for 3 hours, then cooled to 0° C., quenched with saturated ammonium chloride, diluted with dichloromethane, and separated. The organic layer was washed with brine, dried over anhydrous $Na_2SO_4$ and filtered through Celite and concentrated. The residue was purified by reverse phase HPLC (C18 column, acetonitrile/water). The corresponding fractions were extracted with dichloromethane and concentrated to afford (11 aS)-7-Methoxy-8-(2-((2-(((S)-7-methoxy-2-methylene-5-oxo-2,3,5,10,11,11a-hexahydro-1H-benzo[e]pyrrolo[1,2-a][1,4]-diazepin-8-yl)oxy)ethyl)(2-(methylsulfinothioyl)-ethyl)phosphoryl)-ethoxy)-2-methylene-2,3-dihydro-1H-benzo[e]pyrrolo[1,2-a][1,4]diazepin-5(11aH)-one (63.1 mg, 42%), MS m/z+ 749.2 (M+Na), 765.3 (M+K), 767.2 (M+Na+$H_2O$); and (11aS,11a'S)-8,8'-(((((2-(methylsulfino-thioyl)ethyl)phosphoryl)bis(ethane-2,1-diyl))bis(oxy))bis(7-methoxy-2-methylene-2,3,11,11a-tetrahydro-1H-benzo[e]pyrrolo[1,2-a][1,4]diazepin-5(10H)-one) (16.5 mg, 10.9%), MS m/z+ 751.2 (M+Na), 767.2 (M+K), 769.2 (M+Na+$H_2O$); and the unreacted starting material (10.2 mg, 6.8%), MS m/z+ 747.2 (M+Na), 765.2 (M+Na+$H_2O$).

Example 44. (11aS)-8-(2-((2-mercaptoethyl)(2-(((S)-7-methoxy-2-meth ylene-5-oxo-2,3,5,10,11,11a-hexahydro-1H-benzo[e]pyrrolo[1,2-a][1,4]diazepin-8-yl)oxy)ethyl)phosphoryl)ethoxy)-7-methoxy-2-methylene-2,3-dihydro-1H-benzo[e]pyrrolo[1,2-a][1,4]diazepin-5(11aH)-one

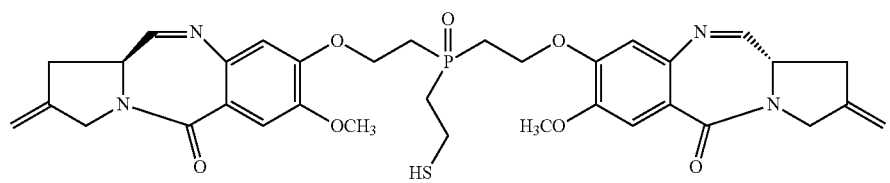

To a stirred solution of (11aS)-7-Methoxy-8-(2-((2-(((S)-7-methoxy-2-methylene-5-oxo-2,3,5,10,11,11a-hexahydro-1H-benzo[e]pyrrolo[1,2-a][1,4]-diazepin-8-yl)oxy)ethyl)(2-(methylsulfinothioyl)ethyl)phosphoryl)-ethoxy)-2-methylene-2,3-dihydro-1H-benzo[e]pyrrolo[1,2-a][1,4]diazepin-5(11aH)-one (30 mg, 0.041 mmol) in acetonitrile (2 mL) and methanol (5 mL) was added freshly prepared TCEP solution (30 mg of TCEP HCl salt was neutralized with saturated sodium bicarbonate to pH 6.5 then diluted with 0.4 mL, 1.0 M of pH 6.5 phosphate buffer) at room temperature. The mixture was stirred at room temperature for 3.5 hours and then diluted with dichloromethane and deionized water, separated. The organic layer was concentrated and purified by reverse phase HPLC (C18 column, acetonitrile/water) to give the title compound as a white solid (20.2 mg, 72% yield). ESI MS m/z+ 703.2 (M+Na), 721.2 (M+Na+$H_2O$), m/z− 697.2 (M+$H_2O$—H).

Example 45. 2,5-Dioxopyrrolidin-1-yl 4-((2-((2-
(((S)-7-methoxy-2-methylene-5-oxo-2,3,5,10,11,11a-
hexahydro-1H-benzo[e]pyrrolo[1,2-a][1,4]diazepin-
8-yl)oxy)ethyl)(2-(((S)-7-methoxy-2-methylene-5-
oxo-2,3,5,11a-tetrahydro-1H-benzo[e]pyrrolo[1,2-a]
[1,4]diazepin-8-yl)oxy)ethyl)phosphoryl)ethyl)
disulfanyl)-4-methylpentanoate (((S)-7-methoxy-2-methylene-5-oxo-2,3,5,10,11,11a-hexa-
hydro-1H-benzo[e]pyrrolo[1,2-a][1,4]diazepin-8-yl)oxy)
ethyl)(2-(((S)-7-methoxy-2-methylene-5-oxo-2,3,5,11a-
tetrahydro-1H-benzo[e]pyrrolo[1,2-a][1,4]diazepin-8-yl)
oxy)ethyl)phosphoryl)ethyl)-disulfanyl)-4-
methylpentanoate in 50 mM HEPES (4-(2-hydroxyethyl)-
1-piperazine ethanesulfonic acid) pH 7.5 buffer containing
10% v/v DMA and 1 mM sodium bisulfate was stirred for 6

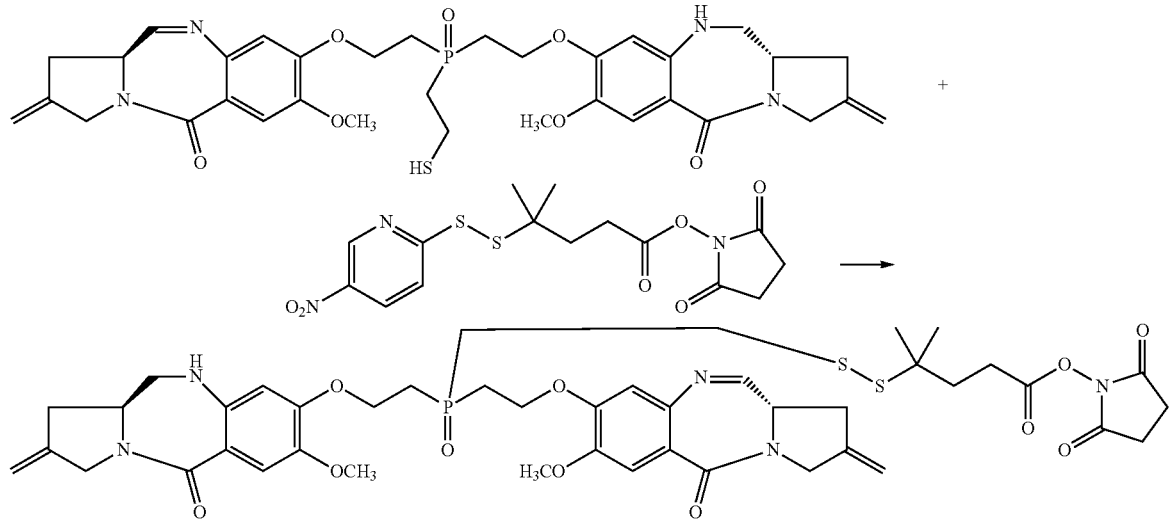

2,5-Dioxopyrrolidin-1-yl 4-methyl-4-((5-nitropyridin-2-yl)disulfanyl)pentanoate linker (5.2 mg, 0.013 mol) in DMA (0.5 mL) was added (11aS)-8-(2-((2-mercaptoethyl)(2-(((S)-7-methoxy-2-methylene-5-oxo-2,3,5,10,11,11a-hexahydro-1H-benzo[e]pyrrolo[1,2-a][1,4]diazepin-8-yl)oxy)ethyl)phosphoryl)ethoxy)-7-methoxy-2-methylene-2,3-dihydro-1H-benzo[e]pyrrolo[1,2-a][1,4]diazepin-5(11aH)-one (5.0 mg, 0.0073 mmol) and $NaH_2PO_4$ buffer (0.5 M, 0.3 ml, pH 6.0). After stirred for 2 h, the mixture was concentrated, purified on HPLC (C-18 column, mobile phase A: water, mobile phase B: dioxane, from 10% of B to 65% of B in 30 mmin). The fractions were pooled and lyophilized to give the title compound (4.9 mg, 73% yield), ESI MS m/z+ 946.3 ([M]+Na), 964.3 ([M]+Na+$H_2O$).

Example 46. A Conjugate of a PBD Derivative to
an Antibody with a Disulfide Bond Linkage and its
Specific Antitumor Activity of the Patent A reaction containing 2.5 mg/mL anti-CD20 antibody and 5 molar equivalents of 2,5-Dioxopyrrolidin-1-yl 4-((2- hours at 30° C. The conjugate was purified and buffer exchanged into 250 mM Glycine, 10 mM Histidine, 1% sucrose, 0.01% Tween-20, 50 μM sodium bisulfite formulation buffer, pH 6.0, using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO). The purified conjugate was found to have an average of 3.6 PBD derivative molecules linked per antibody (by LC-MS), 99% monomer (by size exclusion chromatography), <0.1% unconjugated drug (by dual-column reverse-phase HPLC analysis) and a final protein concentration of 1.5 mg/ml.

In vitro potency measurements for conjugates of antiCD20 antibody with the PBD derivative dimer. The conjugates were highly potent towards antigen-positive Raji cells, with $IC_{50}$ values between 1.6-2.5 pM, Antigen blocking with 1 μM unconjugated antiCD20 antibody signifi-

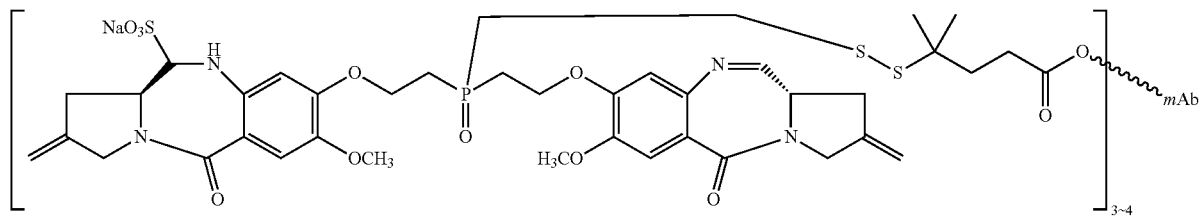

cantly diminished the potency, demonstrating the antigen specificity of the cytotoxic effect.

In Vitro Potency Measurement Against Raji Cells in 37° C., 5 Day Incubation

| Conjugate Drug/ mAb ratio | $IC_{50}$ values | $IC_{50}$ with 1 μM unconjugated antiCD20 antibody blocking | Specificity window |
|---|---|---|---|
| 3.6 | 1.6~2.5 pM | 1.5~2.3 nM | 600~1440 |

Example 47. (6aS,6a'S)-3,3'-((((2-(methylsulfinothioyl)ethyl)phosphoryl)bis(ethane-2,1-diyl))bis(oxy))-bis(2-methoxy-7,8,9,10-tetrahydrobenzo[e]pyrido[1,2-a][1,4]diazepin-12(6aH)-one)

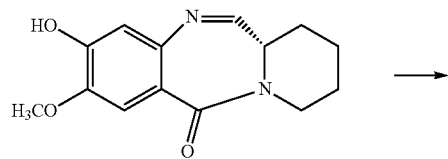

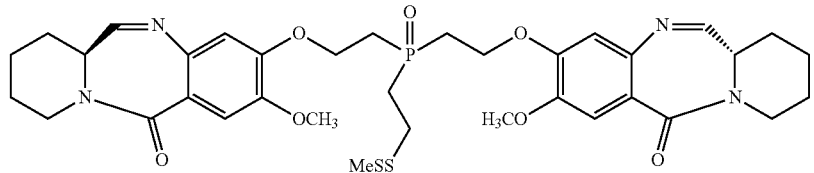

To the stirring solution of (S)-3-hydroxy-2-methoxy-7,8,9,10-tetrahydrobenzo[e]pyrido [1,2-a][1,4]diazepin-12 (6aH)-one (65 mg, 0.25 mmol), $Cs_2CO_3$ (100 mg, 0.307 mmol), KI (3.2 mg, 0.018 mmol) in 5 ml of acetone was added ((2-(methylsulfinothioyl)ethyl)-phosphoryl)bis(ethane-2,1-diyl) bis(4-methylbenzenesulfonate) (13) (71 mg, 0.123 mmol). The mixture was stirred over night, evaporated and purified on HPLC preparative C-18 column (Φ10 mm×200 mm column, flow rate 9 mL/min and a gradient solvent system going from 80:20 solvent A:B at time 0-5 min to 50:50 A:B at 15 min then to 30:70 A:B at 25 min until to 10:90 A:B at 30 min. Solvent A—water, solvent B—dioxane) and lyophilized to afford a white solid 54.7 mg (61%) of the title compound. EIMS m/z+ 751.2 (M+Na), 767.3 (M+K), 785.3 (M+K+$H_2O$); MS m/z– 727.2 (M–H).

Example 48. (11aS,11a'S)-8,8'-((((2-(methylsulfinothioyl)ethyl)phosphoryl)bis(ethane-2,1-diyl))bis(oxy))bis(7-methoxy-2,3-dihydro-1H-benzo[e]pyrrolo[1,2-a][1,4]diazepin-5(11aH)-one)

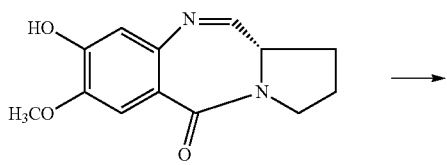

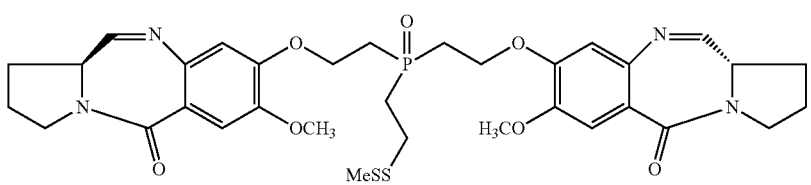

To the stirring solution of (S)-8-hydroxy-7-methoxy-2,3-dihydro-1H-benzo[e]pyrrolo[1,2-a][1,4]diazepin-5(11aH)-one (60.4 mg, 0.245 mmol), Cs$_2$CO$_3$ (100 mg, 0.307 mmol), KI (3.2 mg, 0.018 mmol) in 5 ml of acetone was added ((2-(methylsulfinothioyl)ethyl)phosphoryl)-bis(ethane-2,1-diyl)bis(4-methylbenzenesulfonate) (71 mg, 0.123 mmol). The mixture was stirred over night, evaporated and purified on HPLC preparative C-18 column (Φ10 mm×200 mm column, flow rate 9 mL/min and a gradient solvent system going from 80:20 solvent A:B at time 0-5 min to 50:50 A:B at 15 min then to 30:70 A:B at 25 min until to 10:90 A:B at 30 min. Solvent A—water, solvent B—dioxane) and lyophilized to afford a white solid 54.7 mg (61%) of the title compound. EIMS m/z+ 723.2 (M+Na), 739.3 (M+K), 757.3 (M+K+H$_2$O); MS m/z– 699.2 (M–H).

Example 49. Bis(2-bromoethyl)phosphinic acid

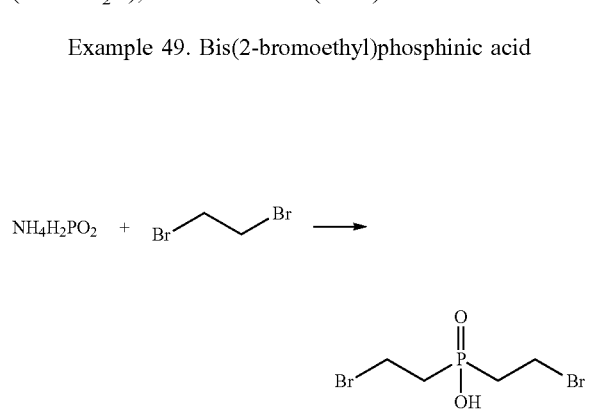

A mixture of ammonium hypophosphite (8.00 g, 96 mmol) and hexamethydisilazane (20.0 mL, 96 mmol) was heated at 120° C. for 1 h under argon. After the mixture was cooled to RT, dibromoethane (60.0 mL) was added, and the mixture was stirred for 8 h at 120° C. The formed trimethylbromosilane and excess dibromoethane were removed under vacuum. Then 100 mL of aqueous ethanol (1:1) were added dropwise to the residue and refluxed for 0.5 h. Then the solvent was removed under vacuum and extracted with ethyl acetate. The organic layer was dried over magnesium sulfate and the solvent was removed under vacuum to give the title compound (16.53 g, 61% yield). ESI MS m/z– C$_4$H$_8$Br$_2$O$_2$P (M–H), cacl. 276.8. found 276.8.

Example 50. Ethyl bis(2-bromoethyl)phosphinate

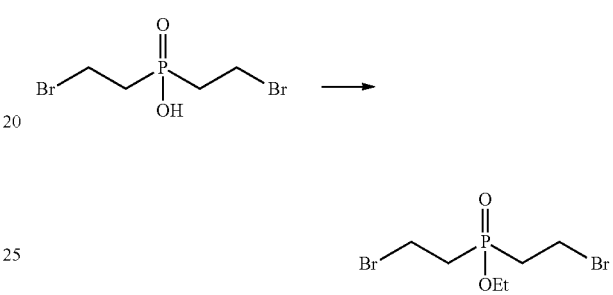

Bis(2-bromoethyl)phosphinic acid (5.00 g, 18.0 mmol) in triethyl orthoformate (100.0 mL) was refluxed with a Dean-Stark trap to remove ethanol and ethyl formate. Excess triethyl orthoformate was removed under vacuum. The mixture was purified with SiO2 column eluted with EtOAc/Hexane (1:15 to 1:4) to give the title compound (2.86 g, 52% yield). ESI MS m/z+ 328.9 (M+Na), 330.9 (M+Na+2), 332.9 (M+Na+4).

Example 51. Ethyl bis(2-(((S)-7-methoxy-5-oxo-2,3,5,11a-tetrahydro-1H-benzo[e]pyrrolo[1,2-a][1,4]diazepin-8-yl)oxy)ethyl)phosphinate

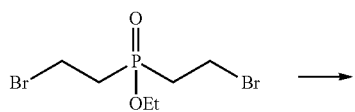

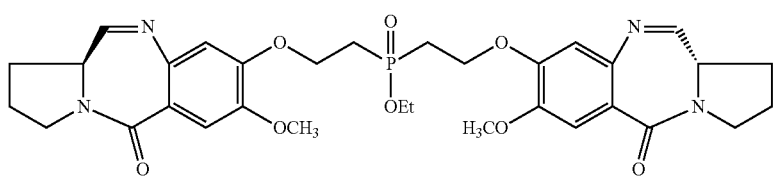

To the stirring solution of (S)-8-hydroxy-7-methoxy-2,3-dihydro-1H-benzo[e]pyrrolo[1,2-a][1,4]diazepin-5(11aH)-one (60.1 mg, 0.244 mmol), Cs₂CO₃ (100 mg, 0.307 mmol), KI (3.2 mg, 0.018 mmol) in 5 ml of butanone was added ethyl bis(2-bromoethyl)phosphinate (37.1 mg, 0.122 mmol). The mixture was stirred over night, evaporated and purified on HPLC preparative C-18 column (Φ10 mm×200 mm column, flow rate 9 mL/min and a gradient solvent system going from 80:20 solvent A:B at time 0-5 min to 50:50 A:B at 15 min then to 30:70 A:B at 25 min until to 10:90 A:B at 30 min. Solvent A—water, solvent B—dioxane) and lyophilized to afford the title compound as a white solid (52.9 mg, 68% yield). ESI MS m/z+ 661.2 (M+Na), 677.3 (M+K), 679. (M+Na+H₂O).

Example 52. Ethyl (2-(((S)-7-methoxy-5-oxo-2,3,5,10,11,11a-hexahydro-1H-benzo[e]pyrrolo[1,2-a][1,4]diazepin-8-yl)oxy)ethyl)(2-(((S)-7-methoxy-5-oxo-2,3,5,11a-tetrahydro-1H-benzo[e]pyrrolo[1,2-a][1,4]diazepin-8-yl)oxy)ethyl)phosphinate quenched with saturated ammonium chloride, diluted with dichloromethane, separated. The organic layer was washed with brine, dried over anhydrous Na₂SO₄ and filtered through Celite and concentrated. The residue was purified by reverse phase HPLC (C18 column, acetonitrile/water). The corresponding fractions were extracted with dichloromethane and concentrated to afford ethyl (2-(((S)-7-methoxy-5-oxo-2,3,5,10,11,11a-hexahydro-1H-benzo[e]pyrrolo[1,2-a][1,4]diazepin-8-yl)oxy)ethyl)(2-(((S)-7-methoxy-5-oxo-2,3,5,11a-tetrahydro-1H-benzo[e]pyrrolo[1,2-a][1,4]diazepin-8-yl)oxy)ethyl)-phosphinate (43.1 mg, 43% yield), MS m/z+ 663.3 (M+Na), 679.3 (M+K), 681.3 (M+Na+H₂O); and ethyl bis(2-(((S)-7-methoxy-5-oxo-2,3,5,10,11,11a-hexahydro-1H-benzo[e]pyrrolo[1,2-a][1,4]diazepin-8-yl)oxy)ethyl)phosphinate (9.2 mg, 9.2%) yield), MS m/z+ 665.2 (M+Na), 681.3 (M+K), 683.2 (M+Na+H₂O); and the unre-

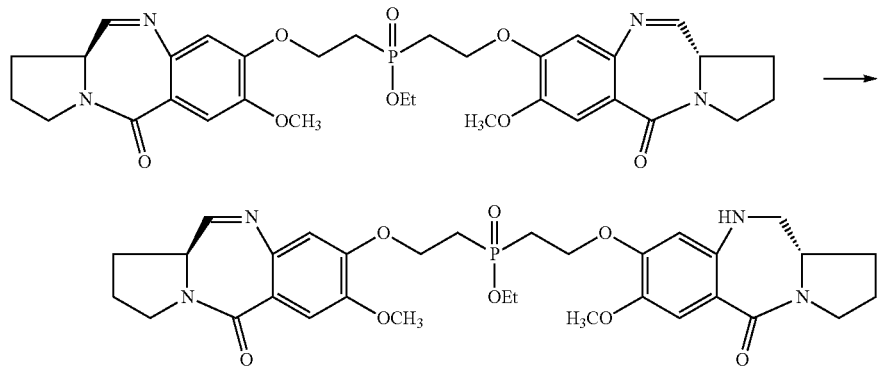

To a stirred solution of ethyl bis(2-(((S)-7-methoxy-5-oxo-2,3,5,11a-tetrahydro-1H-benzo[e]pyrrolo[1,2-a][1,4]diazepin-8-yl)oxy)ethyl)phosphinate (100 mg, 0.156 mmol) in anhydrous dichloromethane (1 mL) and absolute ethanol (1.5 mL) was added sodium borohydride in methoxyethyl ether(63 μl, 0.5 M, 0.031 mmol) at 0° C. The ice bath was removed after 5 minutes and the mixture was stirred at room temperature for 3 hours and then cooled to 0° C. and acted starting material (9.6 mg, 9.6% yield), MS m/z+ 661.2 (M+Na), 679.2 (M+Na+H₂O).

Example 53. Ethyl (2-(((S)-7-methoxy-5-oxo-10-(4-(pyridin-2-yldisulfanyl)butanoyl)-2,3,5,10,11,11a-hexahydro-1H-benzo[e]pyrrolo[1,2-a][1,4]diazepin-8-yl)oxy)ethyl)(2-(((S)-7-methoxy-5-oxo-2,3,5,11a-tetrahydro-1H-benzo[e]pyrrolo[1,2-a][1,4]diazepin-8-yl)oxy)ethyl)phosphinate

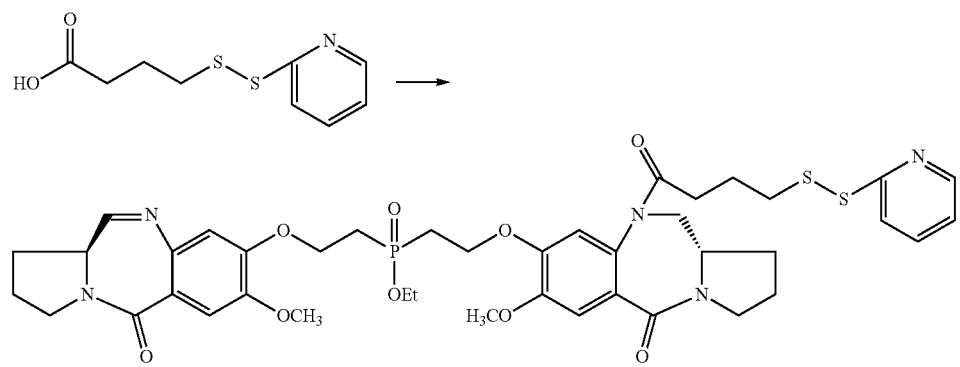

A catalytic amount of DMF (5 ul) was added to a solution of 4-(pyridin-2-yldisulfanyl)butanoic acid (51.1 mg, 0.223 mmol) and oxalyl chloride (0.10 mL, 1.125 mmol) in anhydrous $CH_2Cl_2$ (4.0 mL) and the resulting mixture was stirred at room temperature (RT) for 2 h. Excess $CH_2Cl_2$ and oxalyl chloride was removed with rotavap. The yielded chloride compound was resuspended in fresh $CH_2Cl_2$ (3.0 mL) and was added Ethyl (2-(((S)-7-methoxy-5-oxo-2,3,5,10,11,11a-hexahydro-1H-benzo[e]pyrrolo[1,2-a][1,4]diazepin-8-yl)oxy)ethyl)(2-(((S)-7-methoxy-5-oxo-2,3,5,11a-tetrahydro-1H-benzo[e]pyrrolo[1,2-a][1,4]diazepin-8-yl)oxy)ethyl)phosphinate (40.0 mg, 0.062 mmol) $Et_3N$ (0.4 mL) at 0° C. under argon atmosphere. The reaction mixture was allowed to warm to RT and stirring was continued for 8 h. After removal of $CH_2Cl_2$ and $Et_3N$, the residue was partitioned between $H_2O$ and EtOAc (6/6 mL). The aqueous layer was further extracted with EtOAc (2×6 mL). The combined organic layers were washed with brine (3 mL), dried ($MgSO_4$) and concentrated. Purification of the residue with flash chromatography (silica gel, EtOAc/$CH_2Cl_2$ 1:20 to 1:8) afforded the title compound (38.1 mg, 72.1% yield); EIMS m/z+ 874.2 ([M]$^+$+Na), 892.2 ([M]$^+$+Na+$H_2O$).

Example 54. A Conjugate of a PBD Derivative to an Antibody with a Disulfide Bond Linkage and its Specific Antitumor Activity of the Patent

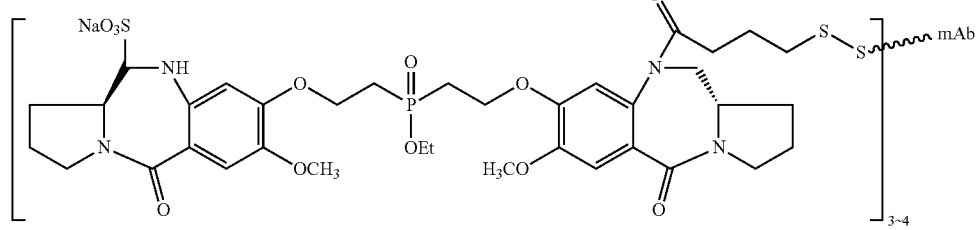

The mAbs (5 mg/mL, especially engineered cysteine-riched CD22 or CD20 antibodies) in PBS buffer containing 50 mM sodium borate, pH 7.8, were treated with dithiothreitol (DDT) (10 mM final) at 37° C. for 30 min. After gel filtration (G-25, PBS containing 1 mM DTPA), thiol determination using 5,5'-dithiobis(2-nitrobenzoic acid) indicated that there were approximately 7~8 thiols per mAb. To the reduced mAb in a PBS buffer pH 7.5 containing 10% v/v DMA and 1 mM sodium bisulfite at 4° C. was added the ethyl (2-(((S)-7-methoxy-5-oxo-10-(4-(pyridin-2-yldisulfanyl)butanoyl)-2,3,5,10,11,11a-hexahydro-1H-benzo[e]pyrrolo[1,2-a][1,4]diazepin-8-yl)oxy)ethyl)(2-(((S)-7-methoxy-5-oxo-2,3,5,11a-tetrahydro-1H-benzo[e]pyrrolo[1,2-a][1,4]diazepin-8-yl)oxy)ethyl)-phosphinate at the drug derivatives (1.2 equiv/SH group). The reaction was stirred for 6 hours at 30° C. The reactions were quenched with excess cysteine. The conjugate was purified and buffer exchanged into 250 mM Glycine, 10 mM Histidine, 1% sucrose, 0.01% Tween-20, 50 µM sodium bisulfite formulation buffer, pH 6.0, using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO). The purified conjugate was found to have an average of 3~4 PBD derivative molecules linked per antibody (by LC-MS), 99% monomer (by size exclusion chromatography), <0.2% unconjugated cysteine-quenched drug (by dual-column reverse-phase HPLC analysis) and a final protein concentration of 2.5 mg/ml (Protein concentration and drug loading were determined by spectral analysis at 280 and 254 nm, respectively)

In Vitro Potency Measurement Against Raji Cells in 37° C., 5 Day Incubation

| Conjugate Drug/ mAb ratio | IC$_{50}$ values | IC$_{50}$ with 1 µM unconjugated antiCD20 antibody blocking | Specificity window |
|---|---|---|---|
| 3.4 | 4.1~21.5 pM | 1.2~2.1 nM | 55~512 |

Example 55. Bis(2-(benzyloxy)ethyl)phosphine oxide

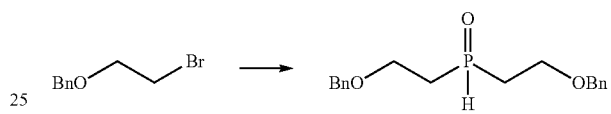

In a three-neck flask was fixed with a dropping funnel, reflux condenser and charged with Mg turnings (1.20 g, 50.0 mmol) and $Et_2O$ was added (50 mL). The dropping funnel was charged with ((2-bromoethoxy)methyl)benzene (10.70 g, 50.0 mmol) in $Et_2O$ (50 mL). The solution in the dropping funnel was added dropwise to the Mg slurry and gently heated to initiate the reaction. Once initiated heating was no longer required and the solution was added at such a rate to maintain refluxing conditions. After the solution has been completely added to the Mg slurry, the flask was heated for 1 hour to reflux. After, 1 hour, the solution was cooled to 0° C. and a solution of diethylphosphite (3.10 mL, 24.0 mmol) was added to the dropping funnel in $Et_2O$ (10 tint). Once added the ice bath was removed and heated to reflux for 1 hour. After 1 hour, the mixture was cooled with an ice bath and 10% HCl solution (50 mL) and $H_2O$ (50 mL) were added slowly with stirring. The ether layer was separated, dried over $MgSO_4$, filtered, evaporated and purified on $SiO_2$ column eluted with EtOAc/$CH_2Cl_2$ (1:20~1:10) to provide the title product (6.26 g, 82% yield). MS (ESI) m/z+ for $C_{18}H_{23}NaO_3P$ calcd. 341.1 (M+Na). found 341.1.

Example 56. P,P-bis(2-hydroxyethyl)-N-(3-(pyridin-2-yldisulfanyl)propyl)phosphinic amide

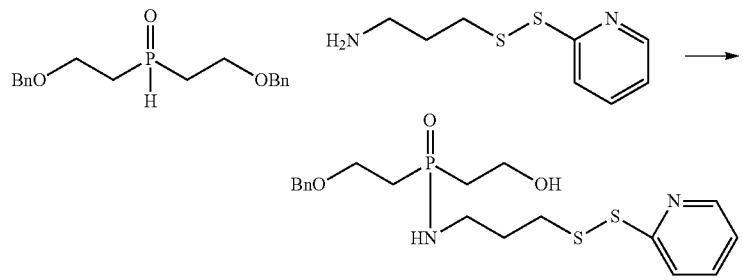

Bis(2-(benzyloxy)ethyl)phosphine oxide (1.0 g, 3.14 mmol) and Pd/C (0.20 g, 10% Pd on C) in THF (30 ml) in a 250 ml hydrogenation bottle was conducted with $H_2$ (30 psi). After shaken for 2 h, the mixture was filtered through Celite bed, concentrated and co-evaporated with $CH_2Cl_2$/toluene. The mixture was redissolved in $CH_2Cl_2$ (30 ml) and $CCl_4$ (3 ml) on ice bath, followed by dropwise addition of 3-(pyridin-2-yldisulfanyl)propan-1-amine (1.10 g, 5.50 mol) in a 20% aqueous solution of NaOH (10 ml). The reaction mixture was stirred at 20-25° C. for 2 h. The organic layer was separated, washed with a saturated solution of $K_2CO_3$ (2×30 mL) and water (3×30 mL), dried with $Na_2SO_4$, concentrated in vacuo and chromatographed on silica gel to afford the title compound (665 mg, 63% yield). MS (ESI) m/z+ for $C_{12}H_{21}N_2NaO_3PS_2$. calcd. 359.1 (M+Na). found 359.1.

Example 57. P,P-bis(2-(benzyloxy)ethyl)-N-methyl-N-(3-(methylamino)propyl)-phosphinic amide

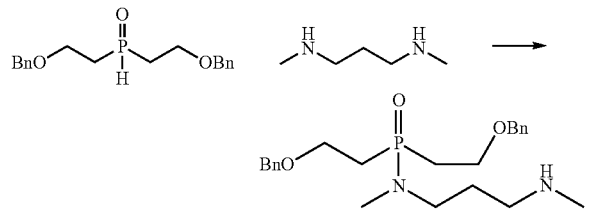

To a mixture of optically pure bis(2-(benzyloxy)ethyl) phosphine oxide (1.00 g, 3.14 mmol), $Et_3N$ (5 ml), and $CCl_4$ (25 mL) was added N,N-dimethylpropane-1,3-diamine (1.80 g, 17.6 mmol) at 0° C. The resulted mixture was kept at 0° C. for 30 min and then warmed up to room temperature. After the mixture was stirred overnight, solvent was removed under a reduced pressure, and water was added. The mixture was extracted with EtOAc, and the organic layers were dried over anhydrous $MgSO_4$. After filtration and removal of the solvent, the residues were purified with flash $SiO_2$ chromatography to afford the title compound (1.09 g, 83% yield). MS (ESI) m/z+ for $C_{23}H_{35}N_2NaO_3P$ calcd. 441.2 (M+Na). found 441.2.

Example 58. P,P-bis(2-hydroxyethyl)-N-methyl-N-(3-(methylamino)propyl)phosphinic amide

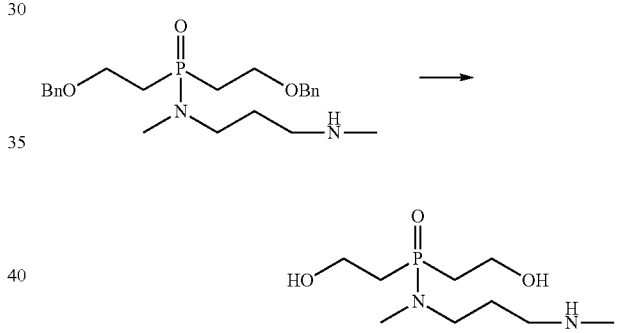

P,P-bis(2-(benzyloxy)ethyl)-N-methyl-N-(3-(methylamino)propyl)phosphinic amide (1.00 g, 2.39 mmol) and Pd/C (0.20 g, 10% Pd on C) in methanol (40 ml) in a hydrogenation bottle was conducted $H_2$ (30 psi). The mixture was shaken for 4 h, filtered through celite bed, concentrated and used for the next step reaction without further purification. Yield 0.566 g, 99% crude yield). MS (ESI) m/z+ for $C_9H_{23}N_2NaO_3P$ calcd. 261.1 (M+Na). found 261.1.

Example 59. N-(3-((bis(2-hydroxyethyl)phosphoryl)(methyl)amino)propyl)-4-(2,5-dioxo-2,5-dihydro-1H-pyrrol-1-yl)-N-methylbutanamide

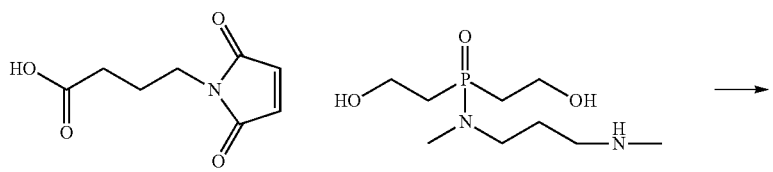

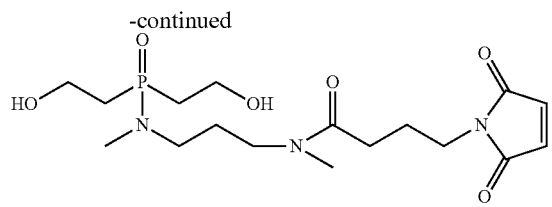

4-(2,5-dioxo-2,5-dihydro-1H-pyrrol-1-yl)butanoic acid (0.60 g, 3.27 mmol) in CH$_2$Cl$_2$) (25 ml) was added (COCl$_2$ (1.00 g, 7.87 mmol) and DMF (20 μl). The mixture was stirred for 2 h, evaporated to dryness and then redissolved in THF (20 ml). To the fresh made P,P-bis(2-hydroxyethyl)-N-methyl-N-(3-(methylamino)propyl)phosphinic amide (0.566 g, ~2.38 mmol) in the mixture of THF (20 ml) and saturated Na$_2$HPO$_3$buffer (60 ml, pH 10) at 4° C. was added dropwise the fresh made 4-(2,5-dioxo-2,5-dihydro-1H-pyrrol-1-yl)butanoic acid chloride mixture in THF (20 ml) in 1 h. After addition, the mixture was stirred at RT for 3 h, neutrated with H$_3$PO$_4$ (conc.) to pH ~7.5, concentrated to ~65 ml, and extracted with CH$_2$Cl$_2$ (3×40 ml). The organic layers were combined, dried over Na$_2$SO$_4$, filtered, concentrated and purified on a SiO$_2$ column eluted with MeOH/CH$_2$Cl$_2$ (1:10~1:5) to afford the title compound (601 mg, 63% yield). MS (ESI) m/z+ for C$_{17}$H$_{30}$N$_3$NaO$_6$P calcd. 426.2 (M+Na). found 426.2.

Example 60. (((3-(4-(2,5-dioxo-2,5-dihydro-1H-pyrrol-1-yl)-N-methylbutanamido)-propyl)(methyl)-amino)phosphoryl)bis(ethane-2,1-diyl)dimethanesulfonate

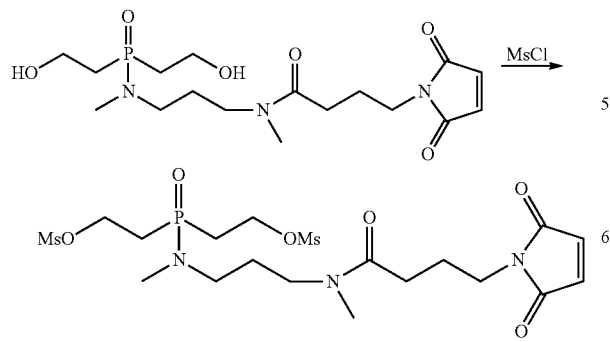

N-(3-((bis(2-hydroxyethyl)phosphoryl)(methyl)amino)propyl)-4-(2,5-dioxo-2,5-dihydro-1H-pyrrol-1-yl)-N-methylbutanamide (590 mg, 1.46 mmol) in the mixture of CH$_2$Cl$_2$ (20 ml) and Et$_3$N (5 ml) was added mesyl chloride (0.40, 5.16 mmol). The mixture was stirred for 4 h, concentrated and purified on a SiO$_2$ column eluted with EtOAc/CH$_2$Cl$_2$ (1:15~1:10) to afford the title compound (710 mg, 87% yield). MS (ESI) m/z+ for C$_{19}$H$_{34}$N$_3$NaO$_{10}$PS$_2$ calcd. 582.1 (M+Na). found 582.1.

Example 61. N-(3-((bis(2-hydroxyethyl)phosphoryl)(methyl)amino)propyl)-N-methyl-4-(pyridin-2-yldisulfanyl)butanamide

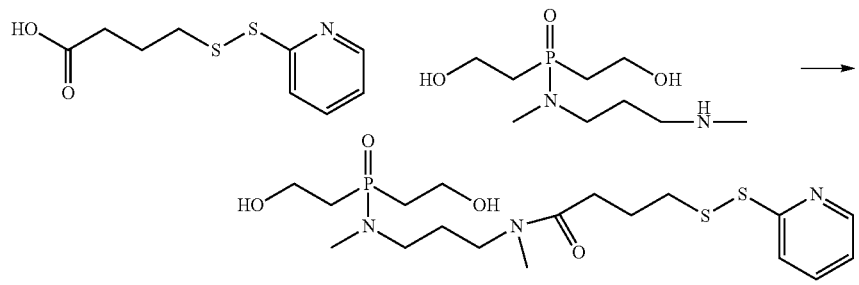

4-(pyridin-2-yldisulfanyl)butanoic acid (1.05 g, 4.58 mmol) in CH$_2$Cl$_2$ (40 ml) was added (COCl)$_2$ (1.20 g, 9.44 mmol) and DMF (20 μl). The mixture was stirred for 2 h, evaporated to dryness and then redissolved in THF (30 ml). To the fresh made P,P-bis(2-hydroxyethyl)-N-methyl-N-(3-(methylamino)propyl)phosphinic amide (0.566 g, ~2.38 mmol) in the mixture of THF (20 ml) and saturated Na$_2$HPO$_3$buffer (70 ml, pH 10) at 4° C. was added dropwise the fresh made 4-(pyridin-2-yldisulfanyl)butanoic acid chloride mixture in THF (30 ml) in 1 h. After addition, the mixture was stirred at RT for 3 h, neutrated with H$_3$PO$_4$ (conc.) to pH ~7.5, concentrated to ~75 ml, and extracted with CH$_2$Cl$_2$ (3×50 ml). The organic layers were combined, dried over Na$_2$SO$_4$, filtered, concentrated and purified on a SiO$_2$ column eluted with MeOH/CH$_2$Cl$_2$ (1:10~1:5) to afford the title compound (640 mg, 60% yield). MS (ESI) m/z+ for C$_{18}$H$_{32}$N$_3$NaO$_4$PS$_2$ calcd. 472.2 (M+Na). found 472.2.

Example 62. ((Methyl(3-(N-methyl-4-(pyridin-2-yldisulfanyl)butanamido)propyl)-amino)phosphoryl)-bis(ethane-2,1-diyl) dimethanesulfonate

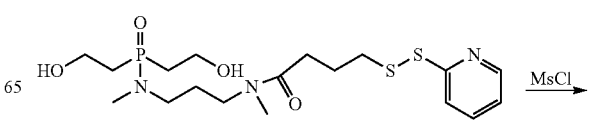

-continued

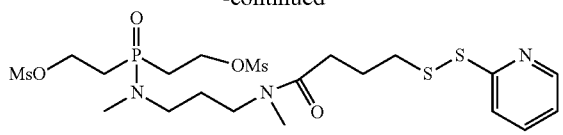

N-(3-((bis(2-hydroxyethyl)phosphoryl)(methyl)amino) propyl)-N-methyl-4-(pyridin-2-yldisulfanyl)butanamide (630 mg, 1.40 mmol) in the mixture of CH$_2$Cl$_2$ (20 ml) and Et$_3$N (5 ml) was added mesyl chloride (0.40 ml, 5.16 mmol). The mixture was stirred for 4 h, concentrated and purified on a SiO$_2$ column eluted with EtOAc/CH$_2$Cl$_2$ (1:15~1:10) to afford the title compound (720 mg, 85% yield). MS (EST) m/z+ for C$_{20}$H$_{36}$N$_3$NaO$_8$PS$_4$ calcd. 628.1 (M+Na). found 628.1.

Example 63. (((3-(pyridin-2-yldisulfanyl)propyl) amino)phosphoryl)bis(ethane-2,1-diyl) bis(4-methylbenzenesulfonate)

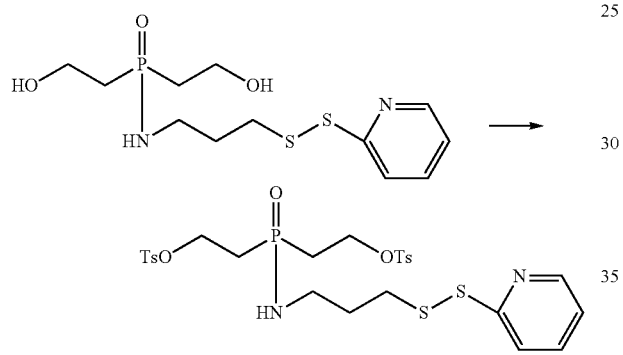

P,P-bis(2-hydroxyethyl)-N-(3-(pyridin-2-yldisulfanyl) propyl)phosphinic amide (502 mg, 1.50 mmol) in the mixture of CH$_2$Cl$_2$ (20 ml) and Et$_3$N (5 ml) was added tosyl chloride (1.15 g, 6.03 mmol). The mixture was stirred for 4 h, concentrated and purified on a SiO$_2$ column eluted with EtOAc/CH$_2$Cl$_2$ (1:15~1:10) to afford the title compound (802 mg, 83% yield). MS (ESI) m/z+ for C$_{26}$H$_{33}$N$_2$NaO$_7$PS$_4$ calcd. 667.1 (M+Na). found 667.1.

Example 64. Dimethyl 2,2'-(chlorophosphoryl)diacetate

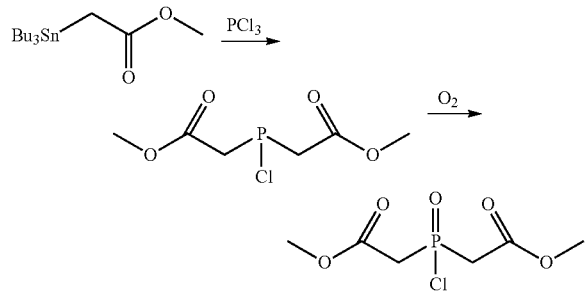

To a stirred solution of PCl$_3$ (5 ml, 2.0 M in CH$_2$Cl$_2$) in benzene (100 ml) was added Bu$_3$SnCH$_2$CO$_2$Me (7.29 g, 20.0 mmol) under Ar. After refluxed 30 min, the mixture gave ~85% ClP(CH$_2$CO$_2$Me)$_2$, which was confirmed by NMR and GC-MS after small portion was worked-up. Then reaction mixture was filtered through a thick celite bed, washed the bed with benzene, cooled to 0° C., and bubbled with dry oxygen through the solution for 6 h. Then the solution was quickly evaporated at 0° C., purged with argon and used without any purification. The mixture was around ~85% pure of the title product checked by NMR. MS (ESI) m/z+ for C$_6$H$_{10}$ClNaO$_5$P calcd. 251.0 (M+Na). found 251.0.

Example 65. Trimethyl 2,2',2''-phosphoryltriacetate

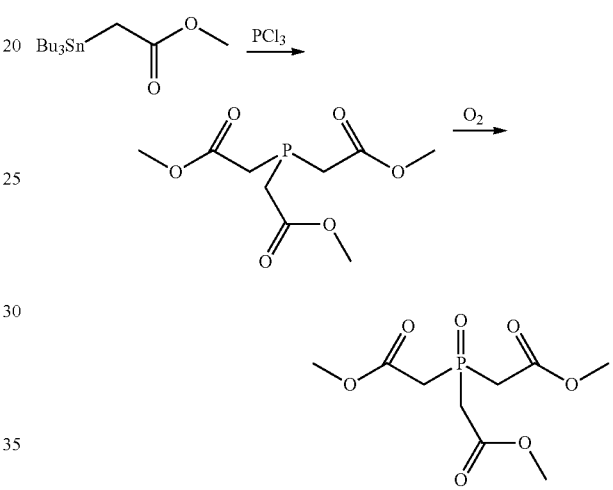

To a stirred solution of PCl$_3$ (5 ml, 2.0 M in CH$_2$Cl$_2$) in benzene (100 ml) was added Bu$_3$SnCH$_2$CO$_2$Me (11.67 g, 32.0 mmol) under Ar. After refluxed 30 min, the mixture gave ~93% P(CH$_2$CO$_2$Me)$_3$, which was checked by NMR and GC after small portion was worked-up. Then reaction mixture was filtered through a thick celite bed, washed the bed with benzene, cooled to 0° C., and bubbled with dry oxygen through the solution for 6 h. Then the solution was evaporated, purified on SiO$_2$ column eluted with EtAc/CH$_2$Cl$_2$ (1:15~1:8) to afford the title compound (2.31 g, 87%). MS (ESI) m/z+ for C$_9$H$_{15}$NaO$_7$P calcd. 289.0 (M+Na). found 289.0.

Alternatively, To a stirred solution of P(SiMe$_3$)$_3$ (2.50 g, 10.0 mmol) in benzene (100 ml) was added BrCH$_2$CO$_2$CH$_3$ (4.70 g, 30.90 mmol) under Ar. After refluxed 30 min, the mixture gave ~89% P(CH$_2$CO$_2$Me)$_3$, which was checked by NMR and GC after small portion was worked-up. Then reaction mixture was filtered through a thick celite bed, washed the bed with CH$_2$Cl$_2$, evaporated, redissolved in CH$_2$Cl$_2$, charged with m-CPBA (2.07 g, 12.1 mmol), and then vigorously stirred for 1 h at room temperature. 6 h. Then the solution was evaporated, purified on SiO2 column eluted with EtAc/CH$_2$Cl$_2$ (1:15~1:8) to afford the title compound (2.25 g, 85% yield). MS (ESI) m/z+ for C$_9$H$_{15}$NaO$_7$P calcd. 289.0 (M+Na). found 289.0.

Example 66. Tris(2-hydroxyethyl)phosphine oxide

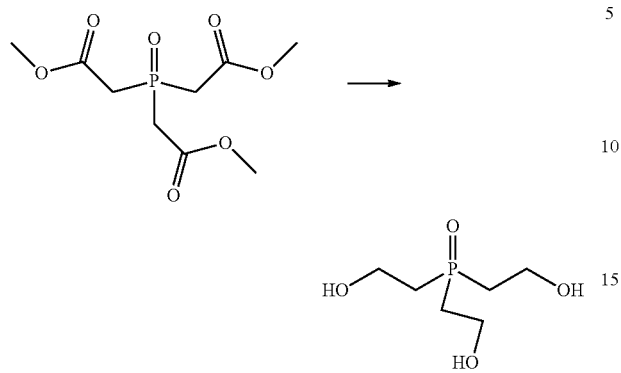

Trimethyl 2,2',2''-phosphoryltriacetate (2.20 g, 8.27 mmol) in THF (50 ml) at 0° C. was added LiAlH$_4$ (20 ml, 1.0 M in THF, 20 mmol). The mixture was stirred at 0° C. for 2.5 h, then quenched with MeOH (5 ml), diluted with CH$_2$Cl$_2$ (100 ml), filtered through a short SiO$_2$ column eluted with MeOH/CH$_2$Cl$_2$, concentrated and crystallized with EtOH/Hexane to afford the title compound (1.23 g, 82% yield). MS (ESI) m/z+ for C$_6$H$_{15}$NaO$_4$P calcd. 205.07 (M+Na). found 205.07.

Example 67. P,P-bis(chloromethyl)-N-(3-(pyridin-2-yldisulfanyl)propyl)phosphinic amide

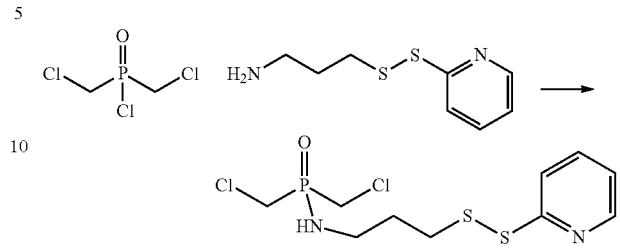

To 3-(pyridin-2-yldisulfanyl)propan-1-amine (0.60 g, 3.00 mmol) in the mixture of CH$_2$Cl$_2$ (20 ml) and Et$_3$N (5 ml) at 0~4° C. was added dropwise bis(chloromethyl)phosphinic chloride (0.54 g, 3.00 mmol from FCH Group) in CH$_2$Cl$_2$ (5 ml) in 30 min. After addition, the mixture was stirred at RT for 1 h, evaporated, and purified on SiO$_2$ column eluted with EtAc/CH$_2$Cl$_2$ (1:20~1:10) to afford the title compound (887 mg, 86% yield). MS (ESI) m/z+ for C$_{10}$H$_{15}$Cl$_2$N$_2$NaOPS$_2$ calcd. 367.0 (M+Na). found 367.0.

Example 68. P,P-Bis((2S,3aR)-2-fluoro-8-methoxy-10-oxo-1,2,3,3a,10,10a-hexahydro-benzo[b]cyclopenta[e]azepin-7-yl)oxy)methyl)-N-(3-(pyridin-2-yldisulfanyl)propyl)-phosphinic amide

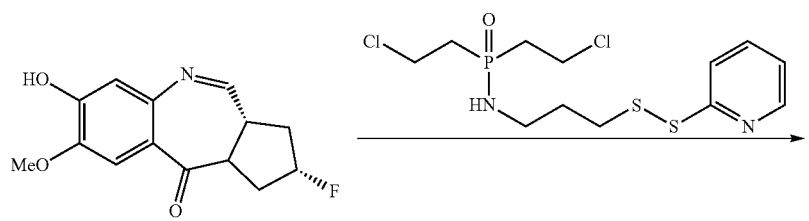

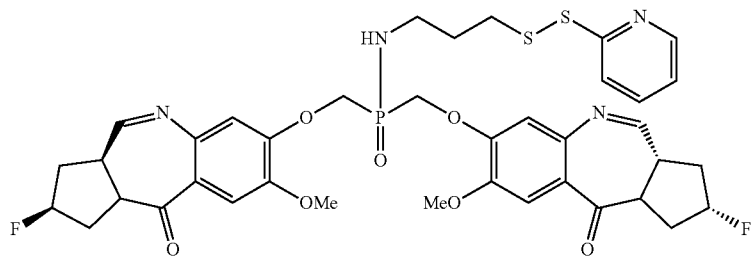

(2S,3aR)-2-fluoro-7-hydroxy-8-methoxy-1,3,3a,10a-tetrahydrobenzo[b]cyclopenta[e]-azepin-10(2H)-one (C2-fluoro substituted pyrrolo[2,1-c][1,4]benzodiazepines, Ref: Kamal, A. et al, Bioorg. Med. Chem. Lett. (2004), 14, 2669-2672) (80 mg, 0.30 mmol) and $Cs_2CO_3$ (112 mg, 0.34 mmol) were stirred in butanone (5 ml) for 5 min, followed by addition of P,P-bis(chloromethyl)-N-(3-(pyridin-2-yldisulfanyl)propyl)phosphinic amide (50 mg, 0.145 mmol) and KI (4 mg, 0.024 mmol). The mixture was stirred under Ar for 24 h, concentrated and purified on preparative HPLC C-18 column (25×2 cm) eluted with $H_2O/CH_3CN$ (from 5% $CH_3CN$ to 60% $CH_3CN$ in 45 min, v=9 ml/min) to afford the title compound (73 mg, 63% yield). MS (ESI) m/z+ for $C_{38}H_{41}F_2N_4O_7PS_2$ calcd. 821.2 (M+Na). found 821.2, 837.3 (M+K), 839.2 (M+Na+$H_2O$), 857.2 (M+Na+2$H_2O$).

The in vitro potency measurement against Ramos cells in 37° C., 5 day incubation was $IC_{50}$=0.1~0.5 nM.

(2S,3aR)-2-fluoro-7-hydroxy-8-methoxy-1,3,3a,10a-tetrahydrobenzo[b]cyclopenta[e]-azepin-10(2H)-one (80 mg, 0.30 mmol) and $Cs_2CO_3$ (110 mg, 0.33 mmol) were stirred in butanone (5 ml) for 5 min, followed by addition of (((3-(4-(2,5-dioxo-2,5-dihydro-1H-pyrrol-1-yl)-N-methylbutanamido)propyl)(methyl)amino)phosphoryl)bis(ethane-2,1-diyl) dimethanesulfonate (82 mg, 0.146 mmol) and KI (4 mg, 0.024 mmol). The mixture was stirred under Ar for 24 h, concentrated and purified on preparative HPLC C-18 column (25×2 cm) eluted with $H_2O/CH_3CN$ (from 5% $CH_3CN$ to 60% $CH_3CN$ in 45 min, v=9 ml/min) to afford the title compound (79 mg, 61% yield). MS (ESI) m/z+ $C_{45}H_{54}F_2N_5NaO_{10}P$ calcd. 916.3 (M+Na). found 916.3, 932.3 (M+K), 934.3 (M+Na+$H_2O$), 952.3 (M+Na+2$H_2O$).

Example 69. N-(3-((bis(2-(((2S,3aR)-2-fluoro-8-methoxy-10-oxo-1,2,3,3a,10,10a-hexahydrobenzo[b]cyclopenta[e]azepin-7-yl)oxy)ethyl)phosphoryl)(methyl)amino-propyl)-4-(2,5-dioxo-2,5-dihydro-1H-pyrrol-1-yl)-N-methylbutanamide Example 70. N-(3-((bis(2-(((2S,3aR)-2-fluoro-8-methoxy-10-oxo-1,2,3,3a,10,10a-hexahydrobenzo[b]cyclopenta[e]azepin-7-yl)oxy)ethyl)phosphoryl)(methyl)amino)-propyl)-N-methyl-4-(pyridin-2-yldisulfanyl)butanamide

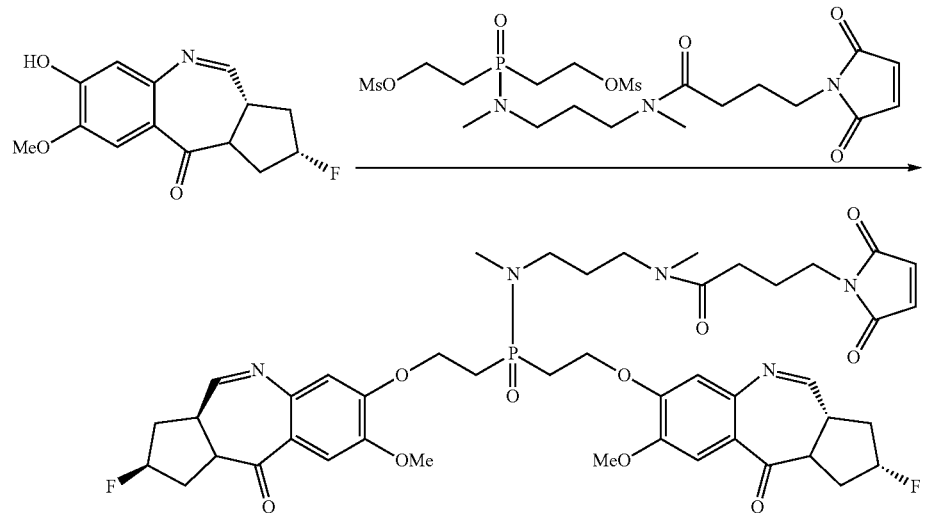

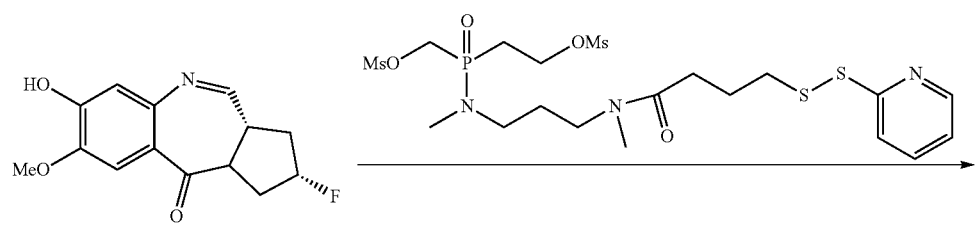

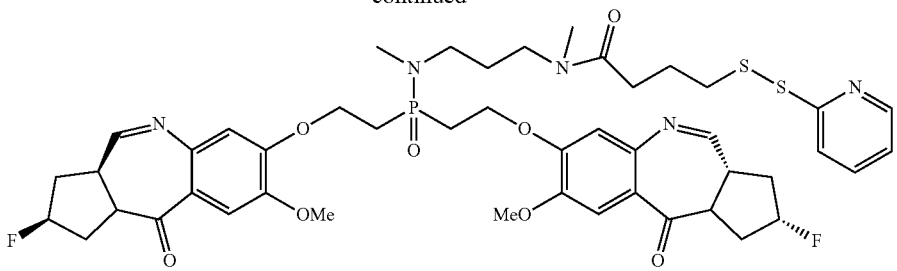

(2S,3aR)-2-fluoro-7-hydroxy-8-methoxy-1,3,3a,10a-tetrahydrobenzo[b]cyclopenta[e]-azepin-10(2H)-one (80 mg, 0.30 mmol) and $Cs_2CO_3$ (110 mg, 0.33 mmol) were stirred in butanone (5 ml) for 5 min, followed by addition of ((methyl(3-(N-methyl-4-(pyridin-2-yldisulfanyl)-butanamido)propyl)amino)phosphoryl)bis(ethane-2,1-diyl) dimethanesulfonate (87 mg, 0.144 mmol) and KI (4 mg, 0.024 mmol). The mixture was stirred under Ar for 24 h, concentrated and purified on preparative HPLC C-18 column (25×2 cm) eluted with $H_2O/CH_3CN$ (from 5% $CH_3CN$ to 60% $CH_3CN$ in 45 min, v=9 ml/min) to afford the title compound (82 mg, 61% yield). MS (ESI) m/z+ $C_{46}H_{56}F_2N_5O_8PS_2$ calcd. 962.3 (M+Na). found 962.3 (M+Na), 978.3 (M+K), 980.3 (M+Na+$H_2O$), 996.3 (M+Na+2$H_2O$).

Example 71. Sodium (2R,2'R,3aR,3a'R,4S,4'S)-7,7'-(((((3-(4-mercapto-N-methylbutan-amido)propyl)(methyl)amino)phosphoryl)bis(ethane-2,1-diyl))bis(oxy))bis(2-fluoro-8-methoxy-10-oxo-1,2,3,3a,4,5,10,10a-octahydrobenzo[b]cyclopenta[e]azepine-4-sulfonate)

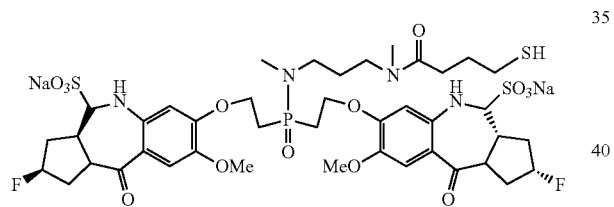

N-(3-((bis(2-(((2S,3aR)-2-fluoro-8-methoxy-10-oxo-1,2,3,3a,10,10a-hexahydrobenzo[b]-cyclopenta[e]azepin-7-yl)oxy)ethyl)phosphoryl)(methyl)amino)propyl)-N-methyl-4-(pyridin-2-sulfanyl)butanamide (70 mg, 0.074 mmol) in $Na_2HPO_4$ (50 mM, 5 ml) buffer containing 10% DMA (v/v), and 2 mM sodium bisulfite pH 7.8 was stirred for 1 h, followed by treated with TCEP (40 mg, 0.139 mmol, neutralized with $NaHCO_3$ sat.). The mixture was stirred for 1, concentrated and purified on preparative HPLC C-18 column (25×2 cm) eluted with $H_2O/CH_3CN$ (from 2% $CH_3CN$ to 50% $CH_3CN$ in 45 min, v=9 ml/min) to afford the title compound (52 mg, 68% yield). MS (ESI) m/z– $C_{41}H_{54}F_2N_4Na_2O_{14}PS_3$ calcd. 1037.2 (M–H). found 1037.2.

Example 72. Preparation of Conjugates of the PBD Derivative Dimers Containing Free Thiol to an Antibody as Shown Below

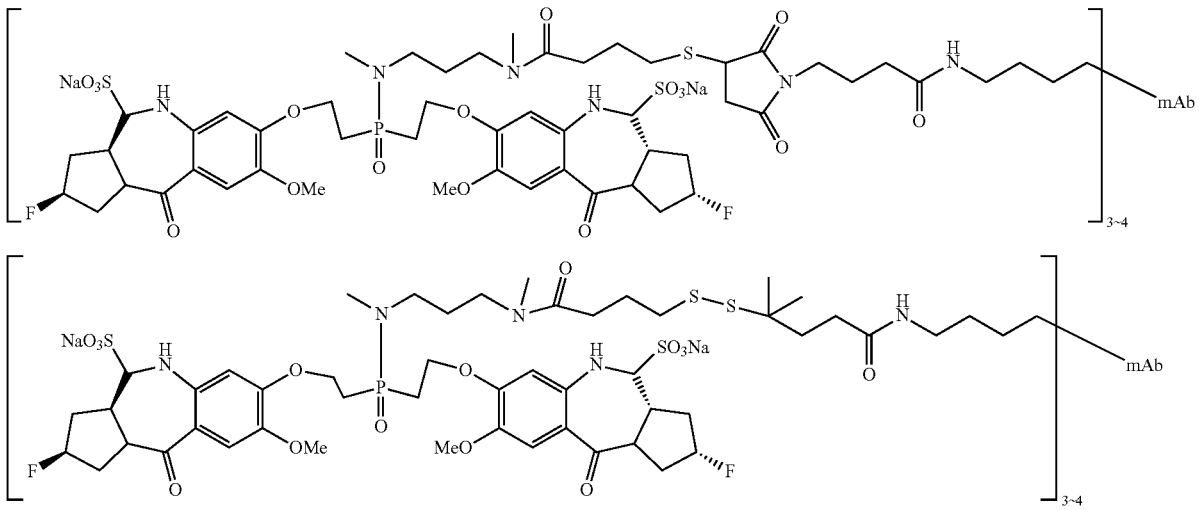

An amount of 1.0 equiv of linkers (SMCC or SMPDP, ~2 mM) in DMA was added to PBS buffer (pH 6.0) containing 1.5 equiv of Sodium (2R,2'R,3aR,3a'R,4S,4'S)-7,7'-(((((3-(4-mercapto-N-methylbutanamido)propyl) (methyl)amino) phosphoryl)bis(ethane-2,1-diyl))bis(oxy))bis(2-fluoro-8-methoxy-10-oxo-1,2,3,3a,4,5,10,10a-octahydrobenzo[b]cyclopenta[e]azepine-4-sulfonate), and the mixtures were incubated for 45~120 min at 4~20° C. Then 0.1~0.25 equiv of mAb in a buffer solution (~pH 8) was added to the linker-drug mixture and the final pH adjusted to 7.0~8.0. After incubating for 2~24 h at room temperature, the mixture was purified using a Sephadex G25 column equilibrated with PBS, pH 6.5. The number of PBD derivative dimer molecules incorporated was determined by UV at 254 nm and 280 nm, or by QTOF mass spectrum.

In Vitro Potency Measurement Against Ramos Cells in 37° C., 5 Day Incubation

| With Linker | Conjugate Drug/antiCD20 antibody ratio | $IC_{50}$ values | $IC_{50}$ with 1 μM unconjugated antiCD20 antibody blocking | Specificity window |
|---|---|---|---|---|
| SMCC | 3.4 | 3.7~28 pM | 1.7~3.7 nM | 61~1000 |
| SMPDP | 3.5 | 2.8~31 pM | 2.1~4.5 nM | 68~1607 |

Example 73. In Vitro Cytotoxicity Assays

General Procedure Used: Samples of unconjugated free drug compounds or drug conjugates were added to 96-well flat bottomed tissue culture plates and titrated using serial dilutions to cover the desired molar range. Antigen positive ($Ag^+$) or Antigen negative ($Ag^-$) cells were added to the wells in specific cell densities (1000~10000 cells/wall) in such a way that there were triplicate samples for each drug concentration for each corresponding cell line. All other cell lines were grown in RPMI-1640 (catalog no. 11875-085, Invitrogen), supplemented with 10% fetal bovine serum and gentamycin. The plates were then incubated at 37° C. in an atmosphere of 5% $CO_2$ for 5 days. At the end of the incubation period cytotoxic potencies were then assessed using a WST-8 based cell viability assay and surviving cells were measured by developing with WST-8 (2-7 hours). The absorbance in each well was measured and the surviving fraction of cells at each concentration was plotted to reveal the cytotoxicity and/or antigen specificity (of the conjugates). The potency and specificity of the antibody-drug conjugates were measured against antigen-expressing cells, with and without the additions of an excess amount of blocking unconjugated antibody to show specificity of the killing effect.

REFERENCES (1) Ma, C.; et al. *Acta Crystallogr Sect E Struct Rep Online* 2012, 68, o126.
(2) Kamal, A.; et al. *Bioorg Med Chem Lett* 2012, 22, 571.
(3) Hartley, J. A.; et al. *Invest New Drugs* 2012, 30, 950.
(4) Bose, D. S.; et al. *Eur J Med Chem* 2012, 50, 27.
(5) Shankaraiah, N.; et al. *J Org Chem* 2011, 76, 7017.
(6) Rahman, K. M.; et al. *Nucleic Acids Res* 2011, 39, 5800.
(7) Ourahou, S.; et al. *Acta Crystallogr Sect E Struct Rep Online* 2011, 67, o1906.
(8) Kamal, A.; et al. *Chem Med Chem* 2011, 6, 1665.
(9) Kamal, A.; et al, *Bioorg Med Chem* 2011, 19, 2565.
(10) Kamal, A.; et al. *Eur J Med Chem* 2011, 46, 3820.
(11) Jebani, A.; et al. *Acta Crystallogr Sect E Struct Rep Online* 2011, 67, o2003.
(12) Hsieh, M. C.; et al. *Toxicol Appl Pharmacol* 2011, 255, 150.
(13) Hopton, S. R.; Thompson, A. S. *Biochemistry* 2011, 50, 4720.
(14) Guerrini, G.; et al. *Bioorg Med Chem* 2011, 19, 3074.
(15) Araujo A. C.; et al. *J Med Chem* 2011, 54, 1266.
(16) Antonow, D.; Thurston, D. E. *Chem. Rev* 2011, 111, 2815.
(17) Rettig, M.; et al. *Org Biomol Chem* 2010, 8, 3179.
(18) Ourahou, S.; et al. *Acta Crystallogr Sect E Struct Rep Online* 2010, 66, o1653.
(19) Ourahou, S.; et al. *Acta Crystallogr Sect E Struct Rep Online* 2010, 66, o732.
(20) Kamal, A.; et al. *Bioorg Med Chem Lett* 2010, 20, 3310.
(21) Kamal, A.; et al. *Bioorg Med Chem* 2010, 18, 526.
(22) Kamal, A.; et al. *Bioorg Med Chem* 2010, 18, 4747.
(23) Kamal, A.; et al. *Eur J Med Chem* 2010, 45, 3924.
(24) Kamal, A.; et al. *Bioorg Med Chem Lett* 2010, 20, 5232.
(25) Kamal, A.; et al, *Bioorg Med Chem* 2010, 18, 6666.
(26) Kamal, A.; et al. *Eur J Med Chem.* 2010, 45, 3870.
(27) Kamal, A.; et al. *Mini Rev Med Chem* 2010, 10, 405.
(28) Antonow, D.; et al. *J Med Chem* 2010, 53, 2927.
(29) Rettig, M.; et al. *Biochemistry* 2009, 48, 12223.
(30) Rettig, M.; et al. *Bioorg Med Chem* 2009, 17, 919.
(31) Lee, C. H.; et al. *Chem Biol Interact* 2009, 180, 360.
(32) Kamal, A.; et al. *Bioorg Med Chem* 2009, 17, 1557.
(33) Kamal, A.; et al. *Chemistry* 2009, 15, 7215,
(34) Hu, W. P.; et al. *Bioorg Med Chem* 2009, 17, 1172.
(35) Howard, P. W.; et al. *Bioorg Med Chem. Lett* 2009, 19, 6463.
(36) Doyle, M.; et al. *J Antimicrob Chemother* 2009, 64, 949.
(37) Cipolla, L.; et al. *Anticancer Agents Med Chem* 2009, 9, 1.
(38) Benzeid, H.; et al. *Acta Crystallogr Sect E Struct Rep Online* 2009, 65, o2322.
(39) Wells, G.; et al. *Bioorg Med Chem Lett* 2008, 18, 2147.
(40) Wade Calcutt, M.; et al. *J Mass Spectrom* 2008, 43, 42.
(41) Tiberghien, A. C.; et al. *Bioorg Med Chem Lett* 2008, 18, 2073.
(42) Tamazyan, R.; et al. *Acta Crystallogr Sect E Struct Rep Online* 2008, 64, o587.
(43) Kamal, A.; et al. *Bioorg Med Chem Lett* 2008, 18, 3769.
(44) Kamal, A.; et al. *Chem Med Chem* 2008, 3, 794.
(45) Kamal, A.; et al. *Bioorg Med Chem Lett* 2008, 18, 2434.
(46) Kamal, A.; et al. *Bioorg Med Chem* 2008, 16, 7218.
(47) Kamal, A.; et al, *Bioorg Med Chem Lett* 2008, 18, 2594.
(48) Kamal, A.; et al. *Bioorg Med Chem* 2008, 16, 3895.
(49) Kamal, A.; et al. *Bioorg Med Chem* 2008, 16, 7804.
(50) Hu, W. P et. al. *Chem Res Toxicol* 2008, 21, 1330.
(51) Antonow, D.; et al. *Biochemistry* 2008, 47, 11818.
(52) Zhao, D. M.; et al. *Acta Crystallogr Sect E Struct Rep Online* 2007, 64, o266.
(53) Kamal, A.; et al. *J Comb Chem* 2007, 9, 29.
(54) Kamal, A.; et al. *Bioorg Med Chem* 2007, 15, 6868.
(55) Kamal, A.; et al. *Bioorg Med Chem Lett* 2007, 17, 5345.
(56) Hu, W. P.; et al. *Chem Res Toxicol* 2007, 20, 905.
(57) Antonow, D.; et al. *Bioorg Med Chem* 2007, 15, 3041.
(58) Antonow, D.; et al. *J Comb Chem,* 2007, 9, 437.
(59) Wang, J. J.; et al. *J Med Chem* 2006, 49, 1442.
(60) Masterson, L. A.; et al. *Bioorg Med Chem Lett* 2006, 16, 252.
(61) Khom, S.; et al. *Mol Pharmacol* 2006, 69, 640.
(62) Kamal, A.; et al *Bioorg Med Chem Lett* 2006, 16, 1160.

(63) Venkatesan, A. M.; et al. *Bioorg Med Chem Lett* 2005, 15, 5003.
(64) Platt, D. M.; et al. *J Pharmacol Exp Ther* 2005, 313, 658.
(65) Kamal, A.; et al. *Bioorg Med Chem* 2005, 13, 2021.
(66) Kamal, A.; et al. *Bioorg Med Chem Lett* 2005, 15, 2621.
(67) Hadjivassileva, T.; et al. *J Antimicrob Chemother* 2005, 56, 513.
(68) Correa, A.; et al. *J Org Chem* 2005, 70, 2256.
(69) Clingen, P. H.; et al. *Nucleic Acids Res* 2005, 33, 3283.
(70) Cheung, A.; et al. *J Chromatogr B Analyt Technol Biomed Life Sci* 2005, 822, 10.
(71) Tiberghien, A. C.; et al. *Bioorg Med Chem Lett* 2004, 14, 5041.
(72) Mischiati, C.; et al. *Biochem Pharmacol* 2004, 67, 401.
(73) Masterson, L. A.; et al. *Bioorg Med Chem Lett* 2004, 14, 901.
(74) Kamal, A.; et al. *Bioorg Med Chem* 2004, 12, 4337.
(75) Kamal, A.; et al. *Bioorg Med Chem Lett* 2004, 14, 4107.
(76) Kamal, A.; et al. *Bioorg Med Chem. Lett* 2004, 14, 4791.
(77) Kamal, A.; et al. *Bioorg Med Chem Lett* 2004, 14, 4907.
(78) Kamal, A.; et al. *Bioorg Med Chem Lett* 2004, 14, 471.
(79) Gregson, S. J.; et al. *J Med Chem* 2004, 47, 1161.
(80) Chen, Z.; et al. *Bioorg Med Chem Lett* 2004, 14, 1547.
(81) Alley, M. C.; et al. *Cancer Res* 2004, 64, 6700.
(82) Tercel, M.; et al. *J Med Chem* 2003, 46, 2132.
(83) Smellie, M.; et al. *Biochemistry* 2003, 42, 8232.
(84) Kumar, R.; Lown, J. W. *Oncol Res* 2003, 13, 221.
(85) Kumar, R.; Lown, J. W. *Mini Rev Med Chem* 2003, 3, 323.
(86) Kumar, R.; Lown, J. W. *Org Biomol Chem* 2003, 1, 3327.
(87) Kamal, A.; et al. *Bioorg Med Chem Lett* 2003, 13,3577.
(88) Kamal, A.; et al. *Bioorg Med Chem Lett* 2003, 13, 3955.
(89) Kamal, A.; et al. *Bioorg Med Chem. Lett* 2003, 13, 3451.
(90) James, A. M.; et al. *Eur J Biochem* 2003, 270, 2827.
(91) Hu, W. P.; et al. *Kaohsiung J Med Sci* 2003, 19, 6.
(92) Gregson, S. J.; et al. *Bioorg Med Chem Lett* 2003, 13, 2277.
(93) Lisowski, V.; et al. *J Enzyme Inhib Med Chem* 2002, 17, 403.
(94) Kamal, A.; Reddy et. al. *Bioorg Med Chem Lett* 2002, 12, 1933.
(95) Kamal, A.; et al. *Curr Med Chem Anticancer Agents* 2002, 2, 215.
(96) Kamal, A.; et al. *Bioorg Med Chem Lett* 2002, 12, 1917.
(97) Berry, J. M.; et al. *Bioorg Med Chem Lett* 2002, 12, 1413,
(98) Li, M.; et al. *Eur J Pharmacol* 2001, 413, 63.
(99) Langlois, N.; et al. *J Med Chem* 2001, 44, 3754.
(100) Kamal, A.; et al. *Bioorg Med Chem Lett* 2001, 11, 387.
(101) Hu, W. P.; et al. *J Org Chem* 2001, 66, 2881.
(102) Gregson, S. J.; et al. *Bioorg Med Chem Lett* 2001, 11, 2859.
(103) Reddy, B. S.; et al. *Anticancer Drug Des* 2000, 15, 225.
(104) Kamal, A.; et al. *Bioorg Med Chem Lett* 2000, 10, 2311.
(105) Gregson, S. J.; et al. *Bioorg Med Chem Lett* 2000, 10, 1845.
(106) Gregson, S. J.; et al. *Bioorg Med Chem Lett* 2000, 10, 1849.
(107) Baraldi, P. G.; et al. *Nucleosides Nucleotides Nucleic Acids* 2000, 19, 1219.
(108) Ashwell, M. A.; et al. *Bioorg Med Chem Lett* 2000, 10, 783.
(109) Wilson, S. C.; et al. *J Med Chem* 1999, 42, 4028.
(110) Thurston, D. E.; et al. *J Med Chem* 1999, 42, 1951.
(111) Reddy, B. S.; Sondhi, S. M.; Lown, J. W. *Pharmacol Ther* 1999, 84, 1.
(112) Ohtake, Y.; et al. *Bioorg Med Chem* 1999, 7, 1247.
(113) Damayanthi, Y.; et al. *J Org Chem* 1999, 64, 290.
(114) Baraldi, P. G.; et al. *Farmaco* 1999, 54, 15.
(115) Baraldi, P. G.; et al. *J Med Chem* 1999, 42, 5131.
(116) Aranapakam, V.; et al. *Bioorg Med Chem Lett* 1999, 9, 1737.
(117) Aranapakam, V.; et al. *Bioorg Med Chem Lett* 1999, 9, 1733.
(118) Guiotto, A.; et al. *Bioorg Med Chem Lett* 1998, 8, 3017.
(119) Baraldi, P. G.; et al. *Curr Pharm Des* 1998, 4, 249.
(120) Baraldi, P. G.; et al. *Bioorg Med Chem Lett* 1998, 8, 3019.
(121) Puvvada, M. S.; et al. *Biochemistry* 1997, 36, 2478.
(122) Kossakowski, J.; et al. *Acta Pol Pharm* 1997, 54, 483.
(123) Walton, M. I.; et al. *Cancer Chemother Pharmacol* 1996, 38, 431.
(124) Thurston, D. E.; et al. *J Org Chem* 1996, 61, 8141.
(125) Mickelson, J. W.; et al. *J Med Chem* 1996, 39, 4654.
(126) Aoyama, T.; Shioiri, T. *Yakugaku Zasshi* 1995, 115, 446.
(127) Acri, J, B.; et al. *Eur J Pharmacol* 1995, 278, 213.
(128) TenBrink, R. E.; et al. *J Med Chem* 1994, 37, 758.
(129) Baraldi, P. G.; et al. *J Med Chem* 1994, 37, 4329.
(130) Puvvada, M. S.; et al. *Nucleic Acids Res* 1993, 21, 3671.
(131) Serra, Ni.; et al. *J Pharmacol Exp Ther* 1992, 263, 1360.
(132) Massa, S.; et al. *J Med Chem* 1992, 35, 4533.
(133) Werner, W.; et al. *Biophys Chem* 1990, 35, 271.
(134) Trapani, G.; et al. *Farmaco* 1990, 45, 577.
(135) Osada, H.; et al. *Agric Biol Chem* 1990, 54, 2883.
(136) Morris, S. J.; et al. *J Antibiot* (Tokyo) 1990, 43, 1286.
(137) Jones, G. B.; et al. *Anticancer Drug Des* 1990, 5, 249.
(138) Kaneko, T.; et al. *J Med Chem* 1985, 28, 388.
(139) Konishi, M.; et al. *J Antibiot* (Tokyo) 1984, 37, 200.
(140) Wright, W. B., Jr.; et al, *J Med Chem* 1980, 23, 462.
(141) Porretta, G. C.; et al. *Farmaco Sci* 1979, 34, 914.
(142) Wright, W. B., Jr.; et al. *J Med Chem* 1978, 21, 1087.
(143) Scalzo, M.; et al. *Farmaco Sci* 1977, 32, 579.
(144) Chimenti, F.; et al. *Farmaco Sci* 1977, 32, 339.
(145) Vomero, S.; et al. *Farmaco Sci* 1976, 31, 681.
(146) De Martino, G.; et al. *Farmaco Sci* 1976, 31, 785.
(147) Scalzo, M.; et al. *Farmaco Sci* 1974, 29, 459.

The invention claimed is:
1. A compound of Formula (I)

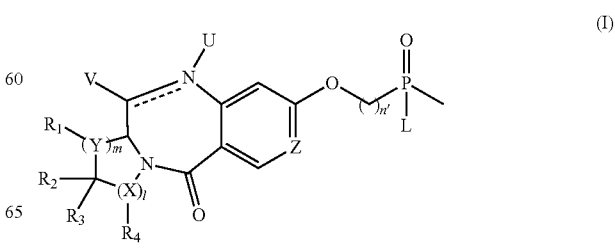

-continued

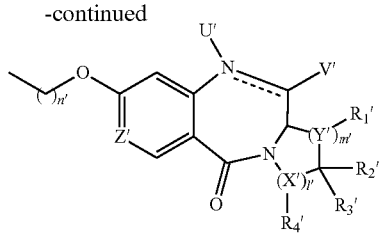

wherein
═ represents either a single bond or a double bond;
provided that when ═ represents a single bond, U and U' are the same or different, and independently represent H, $R_5$, or an amine protecting moiety, or a linking group L';
V and V' are the same or different, and are independently selected from the group consisting of H, OH, —NHOH; —$OR_5$; —$OCOR_5$; —$OCOOR_5$; —$NR_5R_5'$, —$NR_5COR_5'$, —$NR_5NR_5'NR_5''$; —$OCONR_5R_5'$; —$NR_5(C=NH)NR_5'R_5''$; an optionally substituted 5- or 6-membered nitrogen-containing heterocycle selected from the group consisting of piperidine, tetrahydropyrrole, pyrazole, morpholine; —$NR_5CONR_5'R_5''$; —$OCSNHR_5$; —SH; —$SR_5$; —$SOR_5$; —$SOOR_5$: —$SO_3$, —$HSO_3$, —$HSO_2$, or a sodium or potassium salt of —$HSO^{3-}$, —$SO_3^{2-}$, —$HSO_2$, or —$OSO_3^-$; —$NR_5SOOR_5'$; $H_2S_2O_5$ or a sodium or potassium salt of —$S_2O_5^{2-}$; —$PO_3SH_3$, —$PO_2S_2H_2$, —$POS_3H_2$, —$PS_4H_2$ or a sodium or potassium salt of —$PO_3S^{3-}$, —$PO_2S_2^{3-}$, —$POS_3^{3-}$, —$PS_4^{3-}$; —$(R_5O)_2POSR_5'$; —$HS_2O_3$ or a sodium or potassium salt of —$S_2O_3^{2-}$; —$HS_2O_4$ or a sodium or potassium salt of —$S_2O_4^{2-}$; —$P(=S)(OR_5)(S)(OH)$ or a sodium or potassium salt thereof; —$NR_5OR_5'$; —$R_5C(=O)NOH$ or a sodium or potassium salt thereof; $HOCH_2SO_2$—, or a sodium or potassium salt thereof; —$NR_5COR_5'$; —$N_3$; a cyano; a halo; a trialkylphosphoramidate (phosphoramidic acid), or triarylphosphonium; and a linking group L';
and when ═ represents a double bond, U and U' are absent; V and V' represent H, a linear or branched alkyl having 1 to 4 carbon atoms;
n and n' are 0, 1,2, 3,4, 5 or 6; l, m, l' and m' are 1 or 2;
X, X', Y and Y' are the same or different, and independently, represent $CH_2$, $CHR_5$, =CH—, =$CR_5$—, or —$C(OR_5)H$—;
Z and Z' are the same or different, and independently, represent CH, C—$R_5$, COH or $COR_5$;
$R_1$, $R_2$, $R_3$, $R_4$, $R_1'$, $R_2'$, $R_3'$, and $R_4'$ are the same or different and are independently selected from the group consisting of —H, an optionally substituted linear, branched or cyclic alkyl, alkenyl, alkynyl or aryl having from 1 to 10 carbon atoms, a polyethylene glycol unit —$(OCH_2CH_2)_nR_5$, halogen, —$NH(C=NH)NH_2$, —$OR_5$, —$NR_5R_5'$, —$NO_2$, —NCO, —$NR_5COR_5'$, —$SR_5$, —$SOR_5$, —$SO_2R_5$, —$SO_3'M^+$, —$SO_3H$, —$OSO_3'M^+$, $OSO_3H$, —$SO_2NR_5R_5'$, cyano, an azido, —$COR_5$, —$OCOR_5$, —$OCONR_5R_5'$, $CF_3$, $OR_5$, aryl, heterocycle, $P(O)R_5R_5'R_5''$, a linking group (L') with a reactive group, and a cell binding agent bonded thereto; $R_2$ and $R_3$ may join together, or $R_2'$ and $R_3'$ may join together to form a = (double bond), =O (ketone), =S, =$NR_5$, —$C(=O)R_5$, or a double bond containing group =$CR_5R_5'$; and $R_1$ and $R_2$ may join together, or $R_1'$ and $R_2'$ may join together, or $R_3$ and $R_4$ may join together or $R_3'$ and $R_4'$ may join together to form an aromatic, heterocyclic, or heteroaryl ring;
$R_5$, $R_5'$ and $R_5''$ are independently selected from the group consisting of H, linear, branched or cyclic alkyl, alkenyl alkynyl or aryl having from 1 to 10 carbon atoms, a polyethylene glycol unit —$(CH_2CH_2O)_r$—$R_{11}$, an optionally substituted aryl having 6 to 18 carbon atoms, an optionally substituted 5- to 18-membered heteroaryl ring containing one or more heteroatoms independently selected from the group consisting of nitrogen, oxygen, and sulfur, and an optionally substituted 3- to 18-membered heterocyclic ring containing 1 to 6 heteroatoms independently selected from the group consisting of O, S, N and P; $R_5$, $R_5'$, and $R_5''$ may be substituted with at least one substituent selected from the group consisting of —$N(R_1)(R_2)$, —$CO_2H$, —$SO_3H$, —$OR_{11}$, —$CO_2R_{11}$, —$CONR_{11}$, —$PO_2R_{11}R_{12}$, —$POR_{11}R_{12}R_{13}$ and —$PO_3H$, and pharmaceutical salts, $R_{11}$, $R_{12}$, and $R_{13}$ being independently a linear, branched or cyclic alkyl having from 1 to 10 carbon atoms;
q=0, 1 or 2;
L and L' are the same or different and are independently a linker or a linker-cell binding molecule (Q) covalently bound cluster, or a linker which has a functional group on the linker that enables reaction of the compound with a cell-binding agent (CBA), wherein the linker for L has a formula of: -Ww-(Aa)r-Tt-; or -Ww-(Aa)r-Tt-Q; or Q-Ww-(Aa)r-Tt-; wherein: W is a Stretcher unit: w is 0 or 1; Aa is independently an amino acid unit selected from the group consisting of *valine-citrulline*, *alanine-phenylalanine*, *glycine-valine-citrulline* or *glycine-glycine-glycine*, wherein * is a point of attachment; r is an integer ranging from 0 to 100; the Stretcher unit W contains a self-immolative or a non-self-immolative component, a peptidyl unit, a hydrazone unit (—NH—NH—), a disulfide unit (—S—S—), an ester unit (—COO—), an oxime unit (—NH—O—), an amide unit

or a thioether unit (—S—); the self-immolative component is para-aminobenzylcarbamoyl (PAB) unit, 2-aminoimidazol-5-methanol unit, a heterocyclic PAB unit, beta-glucuronide unit, or an ortho or para-aminobenzylacetal unit;

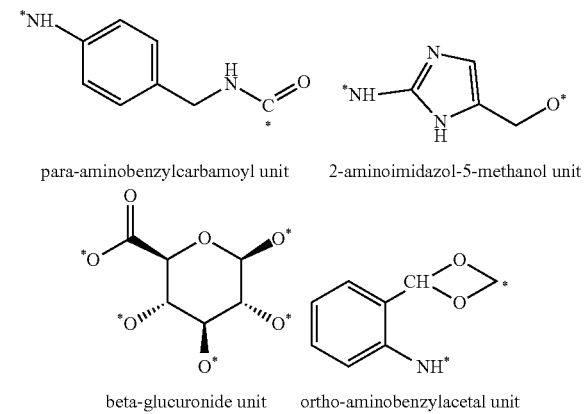

para-aminobenzylcarbamoyl unit     2-aminoimidazol-5-methanol unit beta-glucuronide unit     ortho-aminobenzylacetal unit -continued

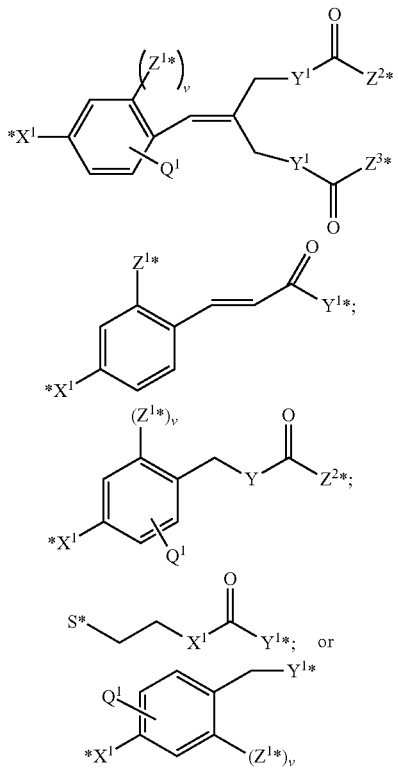

para-aminobenzylacetal unit or the self-immolative component has any one of following structures:

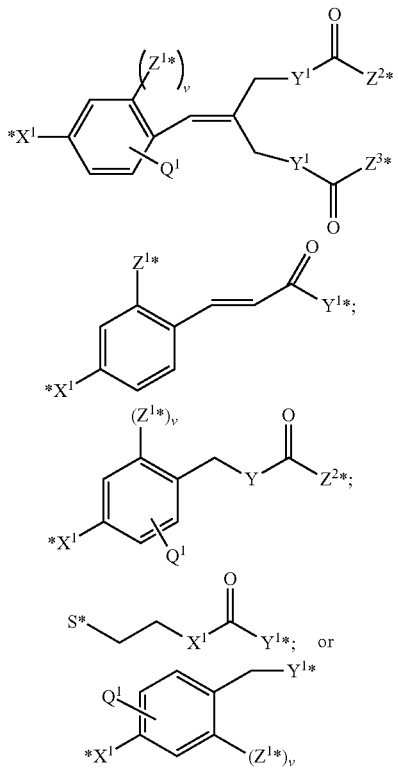

wherein the (*) atom is a point of attachment of additional spacer or releasable linker unit, or a cytotoxic agent, and/or a binding molecule (CBA); $X^1$, $Y^1$, $Z^2$ and $Z^3$ are independently NH, or O, or S; $Z^1$ is H, or NH, or O or S independently; v is 0 or 1; $Q^1$ is independently H, OH, $C_1$-$C_6$ alkyl, $(OCH_2CH_2)_nCH_3$, F, Cl, Br, I, $OR_5$, or $SR_5$, $NR_5R_{5'}$, N=$NR_5$, N=$R_5$, $NR_5R_5'$, $NO_2$, $SOR_5R_5'$, $SO_2R_5$, $SO_3R_5$, $OSO_3R_5$, $PR_5R_5'$, $POR_5R_5'$, $PO_2R_5R_5'$, $OPO(OR_5)(OR_5')$, or $OCH_2PO(OR_5(OR_5'))$, wherein $R_5$ and $R_5'$ are as defined above;

the non-self-immolative component is any one of following structures:

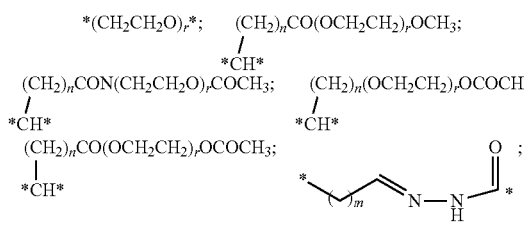

-continued

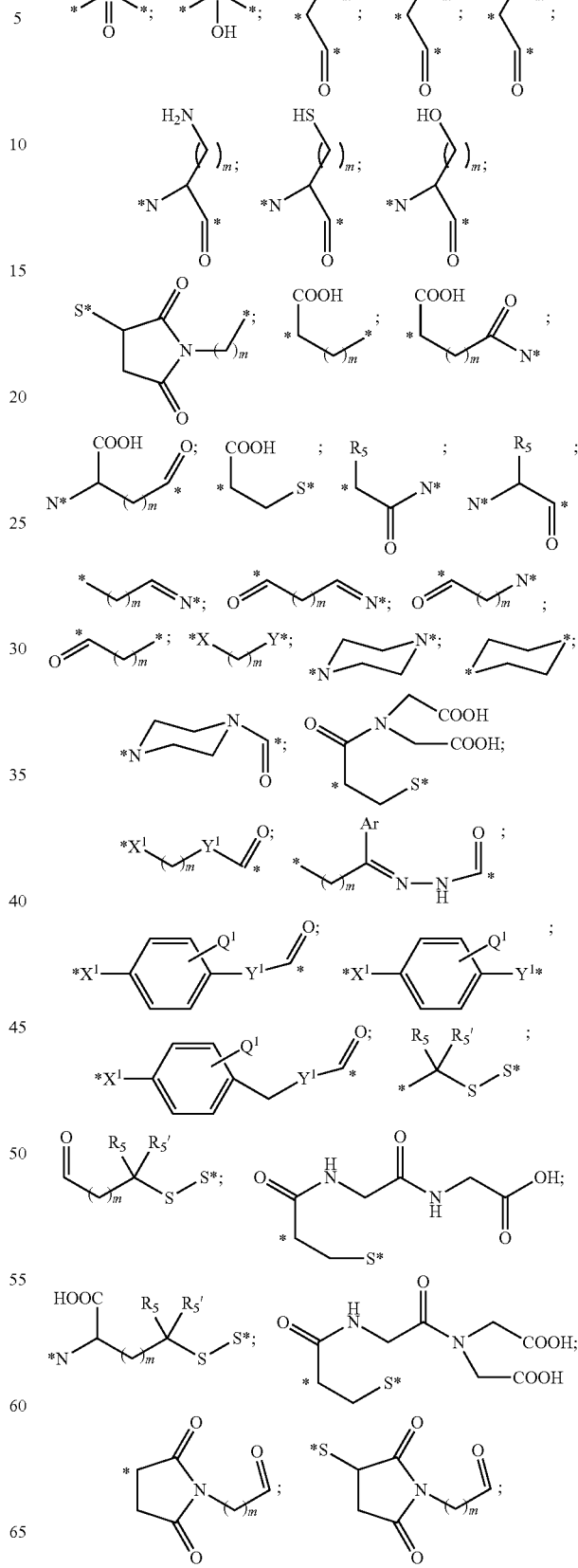

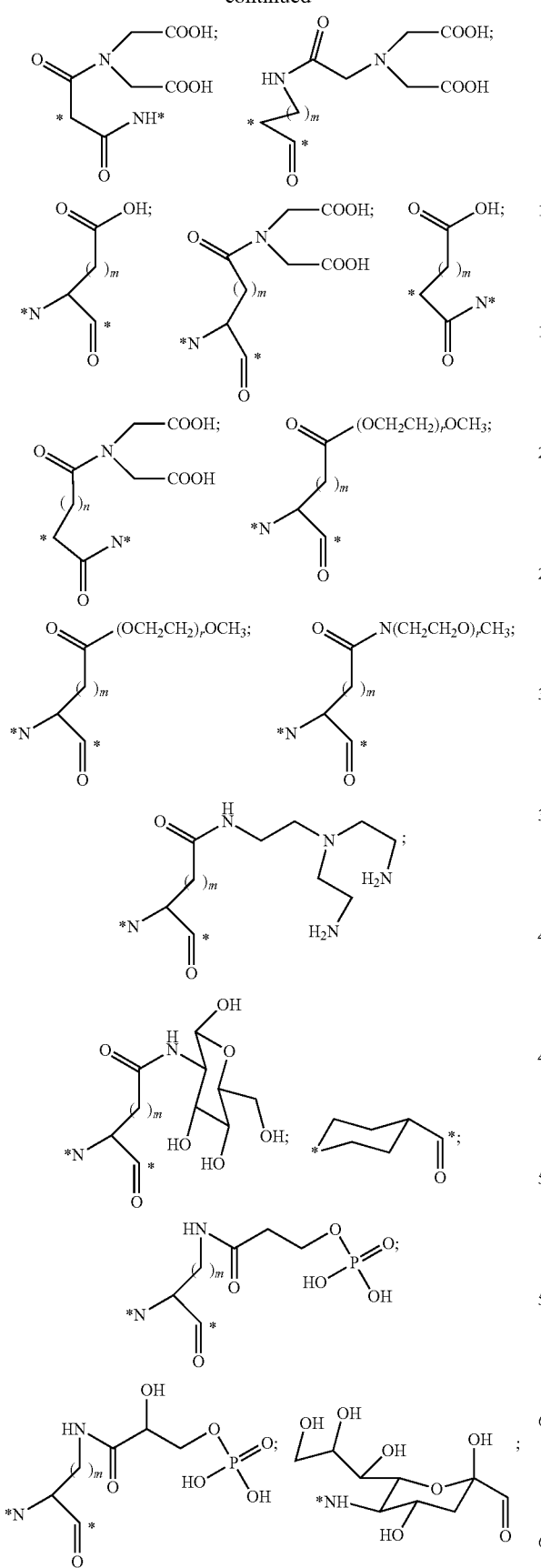
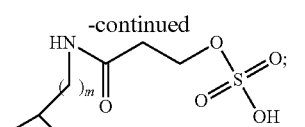
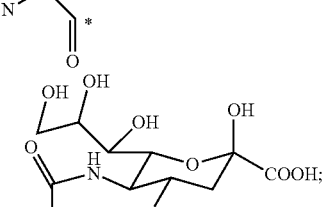
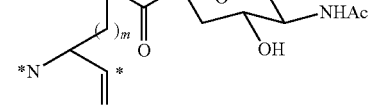
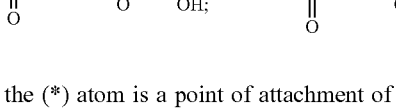
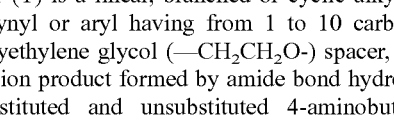
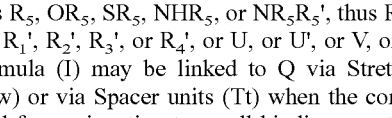

wherein the (*) atom is a point of attachment of additional spacer or releaseable linker, a cytotoxic agents, and/or a binding molecules; $X^1$, $Y^1$, $Q^1$, $R_5$, $R_5'$ are as defined above; r is 0-100; m, n and p are 0-6;

spacer (T) is a linear, branched or cyclic alkyl, alkenyl, alkynyl or aryl having from 1 to 10 carbon atoms, polyethylene glycol (—CH$_2$CH$_2$O-) spacer, or a cyclization product formed by amide bond hydrolysis of a substituted and unsubstituted 4-aminobutyric acid amide, substituted bicyclo[2.2.1] and bicyclo[2.2.2] ring system, or 2-aminophenylpropionic acid amide; and t is 0, or 1-100;

or L is $R_5$, $OR_5$, $SR_5$, $NHR_5$, or $NR_5R_5'$, thus $R_1$, $R_2$, $R_3$, $R_4$, $R_1'$, $R_2'$, $R_3'$, or $R_4'$, or U, or U', or V, or V' in the Formula (I) may be linked to Q via Stretcher units (Ww) or via Spacer units (Tt) when the compound is used for conjugation to a cell binding agent;

Q is a cell binding molecule (CBA), or a functional group that enables reaction of the compound with a cell-binding agent, or a functional group capable of reacting the compound with a linker attached on a cell binding agent, the function group is selected from the group consisting of a thiol group, an amine group, a hydrazine group, an alkoxylamino group, a disulfide group, a maleimido group, a haloacetyl group, a carboxy acid group, an N-hydroxy succinimide ester group, a ketone group, an ester group, an aldehyde group, an alkynyl group, an alkenyl group, and a protected thiol or disulfide group of SAc, SSR₁ or SSAr; Ar is an aromatic group or hetero aromatic group, or a pharmaceutically acceptable salt thereof, or an optical isomer, racemate, diastereomer or enantiomer.

2. The compound according to claim 1 having following entiomer Formula (Ia), (Ib) or (Ic):

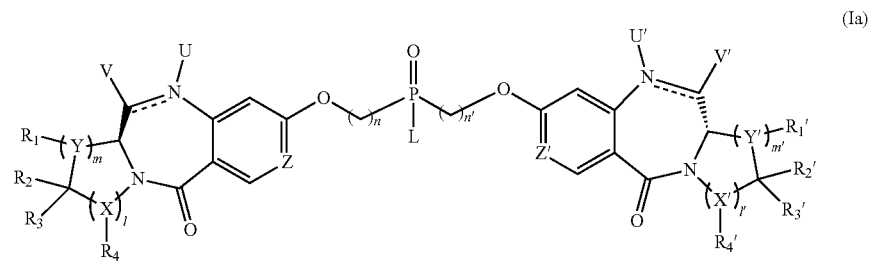
(Ia)

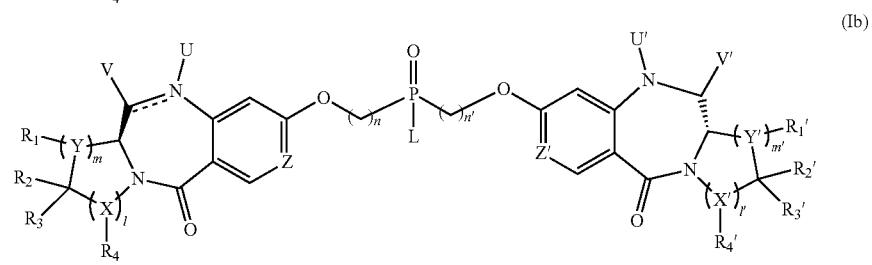
(Ib)

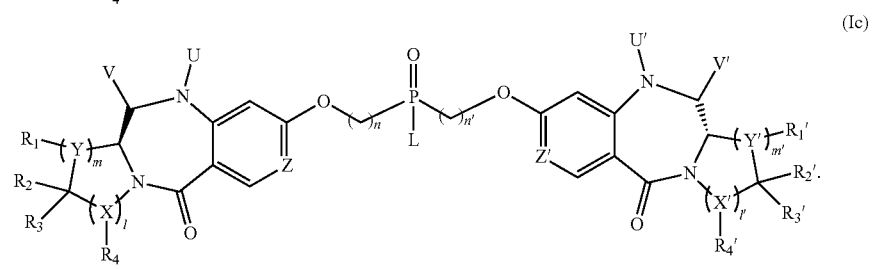
(Ic)

3. The compound according to claim 1 having following Formula (II), (III), or (IV):

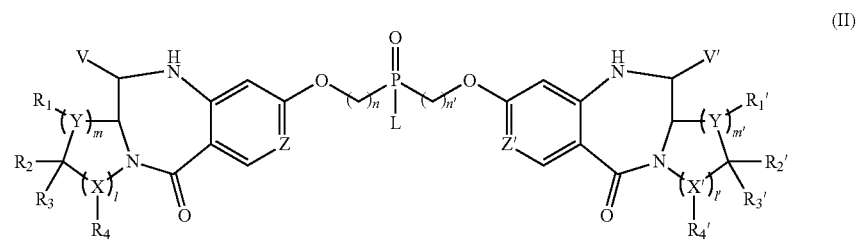
(II)

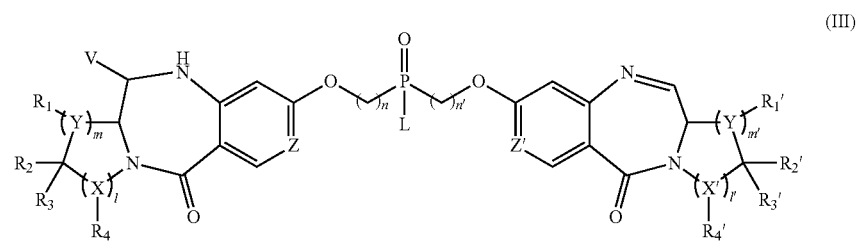
(III)

-continued (IV)

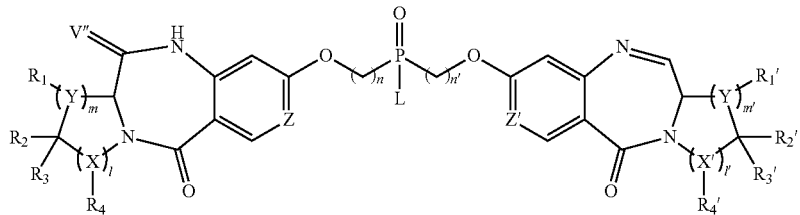

wherein
V and V' are the same or different and are independently selected from the group consisting of OH, —OR$_5$, —OCOR$_5$, —COOR$_5$, —OCOOR$_5$, —OCONR$_5$R$_5$', —NRCONR$_5$R$_5$', —OCSNHR$_5$, —SH, —SR$_5$, —SOR$_5$, —SOOR$_5$, a sodium or potassium salt of —SO$_3^-$, or —OSO$_3^-$, —NRSOOR, —NRR', —NR$_5$OR$_5$', —NR$_5$COR$_5$', —NR$_5$CONR$_5$'R$_5$", —N$_3$, —CN, a halo, a trialkyl or triarylphosphonium, and an aminoacid group;
V''' is (=)O, (=)NH, (=)N-CONR$_5$R$_5$', (=)N-COR$_5$, (=)N-COOR$_5$, or (=)N—O-R$_5$,
R$_5$, R$_5$' and R$_5$" are independently selected from the group consisting of H, C$_1$-C$_8$ of alkyl, alkenyl, alkynyl, heteroalkyl, aryl, arylalkyl, carbonylalkyl, and pharmaceutical salts; R$_5$, R$_5$' and R$_5$" are optionally substituted with at least one substituent selected from the group consisting of —N(R$_{11}$)(R$_{12}$), —CO$_2$H, —SO$_3$H, —OR$_{11}$, —CO$_2$R$_{11}$, —CONR$_{11}$, —PO$_2$R$_{11}$R$_{12}$, —POR$_{11}$R$_{12}$R$_{13}$, —PO$_3$H and a pharmaceutically acceptable salt thereof, or are linked a cell binding agent via Stretcher units (Ww) or via Spacer units (Tt);
or a pharmaceutically acceptable salt thereof,
or an optical isomer, racemate, diastereomer or enantiomer.

4. The compound according to claim 1 having following Formula (V), (VII), (VIII), (IX), (X), (XI), (XII), (XIII), (XIV), (XVI), or (XVII):

(V)

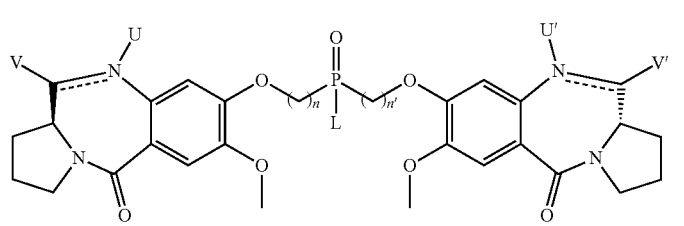

(VII)

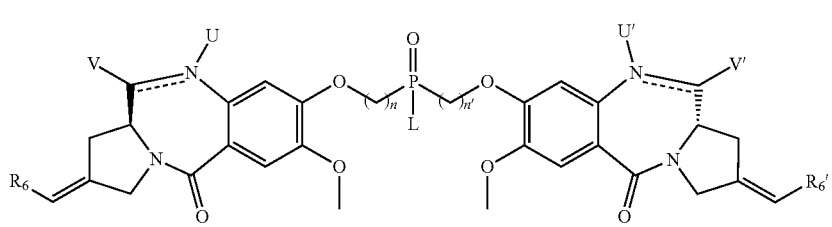

(VIII)

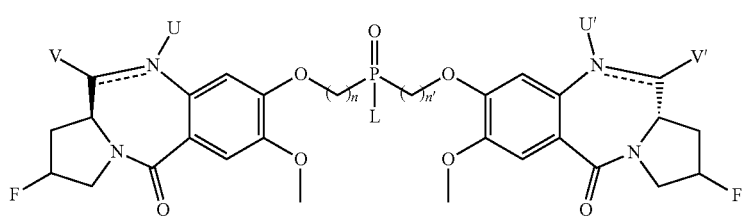

(IX)

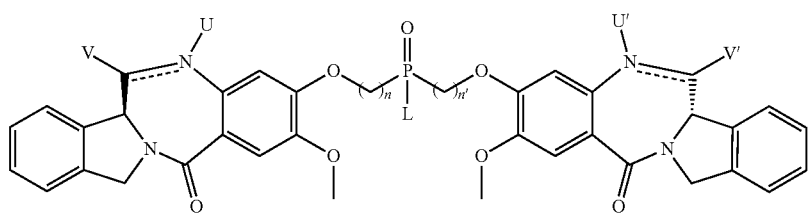

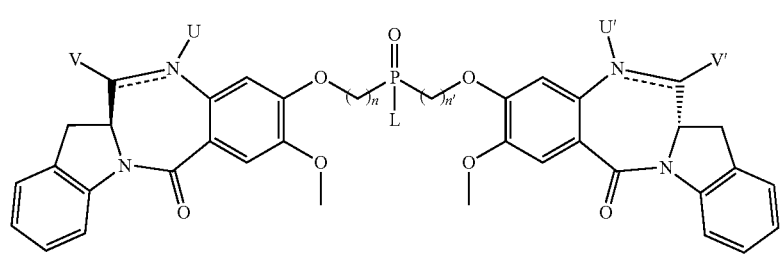
(X)
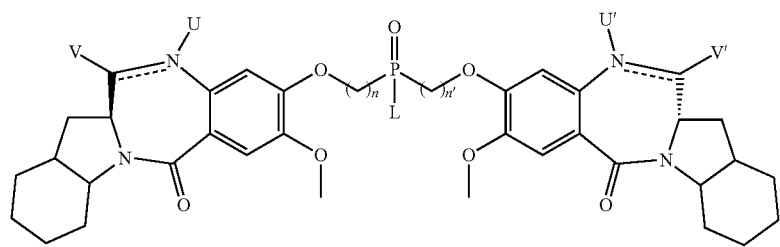
(XI)
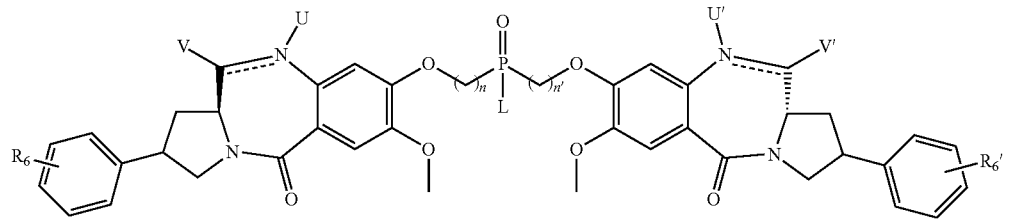
(XII)
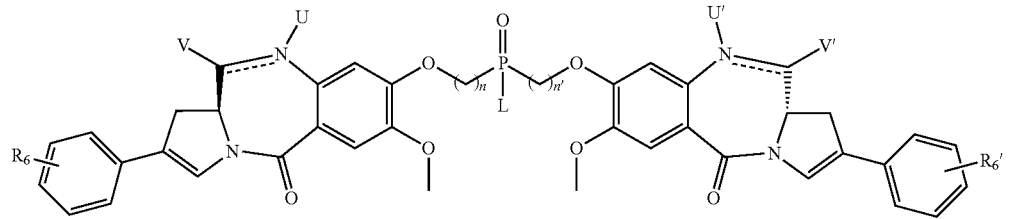
(XIII)
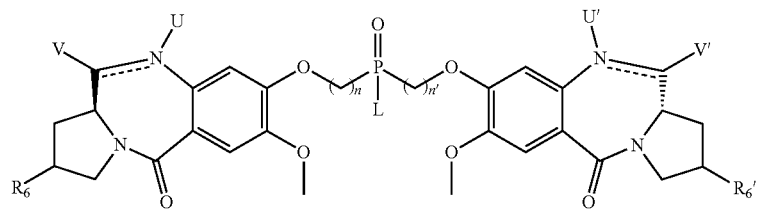
(XIV)
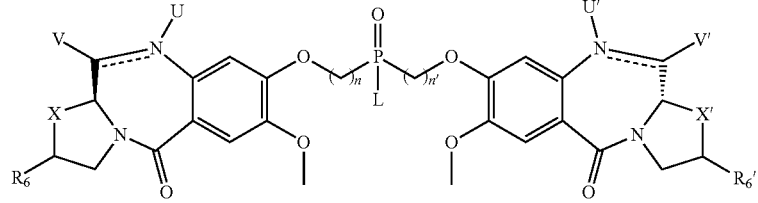
(XVI)
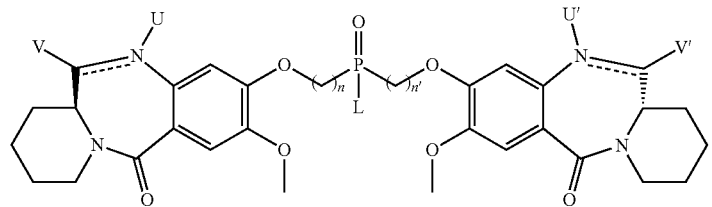
(XVII)

wherein $R_6$ and $R_6'$ are the same as $R_5$, or selected independently from $C_1$-$C_{10}$ of alkyl, alkenyl, alkinyl, aryl, cyclic, cyclohetero, haloalkyl, alkoxy, haloalkoxy or of alkylamino; or halogen, or dihalogens, —CF;, —NO$_2$, —CN or H; or linked a cell binding agent via Stretcher units (Ww) or via Spacer units (Ti);

or a pharmaceutically acceptable salt thereof, or an optical isomer, racemate, diastereomer or enantiomer.

5. The compound according to claim 1 wherein the linker l is selected from the group consisting of —$R_5$, —$OR_5$, —$SR_5$, —$NR_5R_5'$, —$(CR_5R_6)_m(Aa)_r(CR_7R_8)_n(OCH_2CH_2)_rQ$, —$(CR_5R_6)_m(CR_7R_8)_n(Aa)_r(CH_2CH_2)_rQ$, -$(Aa)_r(CR_5R_6)_m(CR_7R_8)_n(OCH_2CH_2)_rQ$, —$(CR_5R_6)_m(CR_7R_8)_n(OCH_2CH_2)_r(Aa)_rQ$, —$(CR_5R_6)_m$—$(CR_7=CR_8)(CR_9R_{10})_n(Aa)(OCH_2CH_2)_rQ$, —$(CR_5R_6)_m(NR_{11}CO)(Aa)_t(CR_9R_{10})_n(OCH_2CH_2)_rQ$, —$(CR_5R_6)_m(Aa)_t(NR_{11}CO)(CR_9R_{10})_n(OCH_2CH_2)_rQ$, —$(CR_5R_6)_m(OCO)(Aa)_t(CR_9R_{10})_n(OCH_2CH_2)_rQ$, —$(CR_5R_6)_m(OCNR_7)(Aa)_t(CR_9R_{10})_n(OCH_2CH_2)_rQ$, —$(CR_5R_6)_m(CO)(Aa)_t$-$(CR_9R_{10})_n(OCH_2CH_2)_rQ$, —$(CR_5R_6)_m(NR_{11}CO)(Aa)_t(CR_9R_{10})_n(OCH_2CH_2)_rQ$, —$(CR_5R_6)_m(OCO)(Aa)_t(CR_9R_{10})_n(OCH_2CH_2)_rQ$, —$(CR_5R_6)_m(OCNR_7)(Aa)(CR_9R_{10})_n(OCH_2CH_2)_rQ$, —$(CR_5R_6)_m(CO)(Aa(CR_9R_{10})_n(OCH_2CH_2)_rQ$, —$(CR_5R_6)_m$-phenyl-$CO(Aa)_t(CR_7R_8)_nQ$, —$(CR_5R_6)_m$-furyl-$CO$-$(Aa)_t(CR_7R_8)_nQ$, —$(CR_5R_6)_m$-oxazolyl-$CO(Aa)_t(CR_7R_8)_nQ$, —$(CR_5R_6)_m$-thiazolyl-$CO(Aa)_t$-$(CCR_7R_8)_nQ$, —$(CR_5R_6)_t$-thienyl-$CO(CR_7R_8)_nQ$, —$(CR_5R_6)_t$-imidazolyl-$CO(CR_7R_8)_nQ$, —$(CR_5R_6)_t$-morpholino-$CO(Aa)_t(CR_7R_8)_nQ$, —$(CR_5R_6)_t$piperazino-$CO(Aa)_t(CR_7R_8)_nQ$, —$(CR_5R_5)_t$—N-methylpiperazin-$CO(Aa)_t(CR_7R_8)_nQ$, —$(CR_5R)_m(Aa)_t$phenyl-Q, —$(CR_5R_6)_m$-$(Aa)_t$furyl-Q, —$(CR_5R_6)_m$-oxazolyl$(Aa)_t$-Q, —$(CR_5R_6)_m$-thiaxolyl$(Aa)_t$-Q, —$(CR_5R_6)_m$-thienyl-$(Aa)_tQ$, —$(CR_5R_6)_m$-imidazolyl$(Aa)_t$-Q, —$(CR_5R_6)_m$-morpholino-$(Aa)_tQ$, —$(CR_5R_6)_m$-piperazino-$(Aa)_tQ$, —$(CR_5R_6)_m$—N-methylpiperazino-$(Aa)_tQ$, —$K(CR_5R_6)_m(Aa)_r(CR_7R_8)_n(OCH_2CH_2)_tQ$, —$K(CR_5R_6)_m(CR_7R_8)_n(Aa)_r(OCH_2CH_2)_tQ$, —$K(Aa)_r(CR_5R_6)_m(CR_7R_8)_n(OCH_2CH_2)_rQ$, —$K(CR_5R_6)_m(CR_7R_8)_n(OCH_2CH_2)_r(Aa)_tQ$, —$K(CR_5R_6)_m(CR_7=CR_8)(CR_9R_{10})_n(Aa)_t(OCH_2CH_2)_rQ$, —$K(CR_5R_6)_m(NR_{11}CO)(Aa)_t(CR_9R_{10})_n(OCH_2CH_2)_rQ$, —$K(CR_5R_6)_m(Aa)_t(NR_{11}CO)(CR_9R_{10})_n(OCH_2CH_2)_rQ$, —$K(CR_5R_6)_m(OCO)(Aa)_t(CR_9R_{10})_n(OCH_2CH_2)_rQ$, —$K(CR_5R_6)_m(OCNR_7)(Aa)_t(CR_9R_{10})_n(OCH_2CH_2)_rQ$, —$K(CR_5R_6)_m(CO)(Aa)_t(CR_9R_{10})_n(OCH_2CH_2)_rQ$, —$K(CR_5R_6)_m(NR_{11}CO)(Aa)_t(CR_9R_{10})_n(OCH_2CH_2)_rQ$, —$K(CR_5R_6)_m(OCO)(Aa)_t(CR_9R_{10})_n(OCH_2CH_2)_rQ$, —$K(CR_5R_6)_m(OCNR_7)(Aa)_t(CR_9R_{10})_n(OCH_2CH_2)_rQ$, —$K(CR_5R_6)_m(CO)(Aa)_t(CR_9R_{10})_n(OCH_2CH_2)_rQ$, —$K(CR_5R_6)_m$-phenyl-$CO(Aa)_t(CR_7R_8)_nQ$, —$K(CR_5R_6)_m$-furyl-$CO(Aa)_t(CR_7R_8)_nQ$, —$K(CR_5R_6)_m$-oxazolyl-$CO(Aa)_t(CR_7R_8)_nQ$, —$K(CR_5R_6)_m$-thiazolyl-$CO(Aa)_t(CCR_7R_8)_nQ$, —$K(CR_5R_6)_m$-thienyl-$CO(CR_7R_8)_nQ$, —$K(CR_5R_6)_t$-imidazolyl-$CO(CR_7R_8)_nQ$, —$K(CR_5R_6)_t$morpholino-$CO(Aa)_t(CR_7R_8)_nQ$, —$K(CR_5R_6)_t$piperazano-$CO(Aa)_tCR_7R_8)_nQ$, —$K(CR_5R_6)_t$—N-methylpiperazin-$CO(Aa)_t(CR_7R_8)_nQ$, —$K(CR_5R_6)_m$-$(Aa)_t$phenyl-Q, —$K(CR_5R_6)_m$-$(Aa)_t$furyl-Q, —$K(CR_5R_6)_m$-oxazolyl$(Aa)_t$-Q, —$K(CR_5R_6)_m$-thiazolyl$(Aa)_t$-Q, —$K(CR_5R_6)$-thienyl-$(Aa)_tQ$, —$K(CR_5R_6)_m$-imidazolyl$(Aa)_t$-Q, —$K(CR_5R_6)_m$-morpholino-$(Aa)_tQ$, —$K(CR_5R_6)_m$-piperazino-$(Aa)_tQ$, and —$K(CR_5R_6)_m$N-methylpiperazino-$(Aa)_tQ$;

wherein $R_6$, $R_7$, and $R_8$ are the same or different and are independently selected from the group consisting of H; halide: $C_1$-$C_8$ of alkyl, aryl, alkenyl, alkynyl, ether, ester, amine and amide, which are optionally substituted by one or more halide, CN, $NR_1R_2$, $CF_3$, $OR_1$, Aryl, heterocycle, $S(O)R_1$, $SO_2R_1$, —$CO_2H$, —$SO_3H$, —$OR_1$, —$CO_2R_1$, —$CONR_1$, —$PO_2R_1R_2$, —$PO_3H$ or $P(O)R_1R_2R_3$; K is $NR_1$, O, S, Se, B or heterocycle.

6. The compound of claim 1, wherein when L is $R_5$, $OR_5$, $SR_5$ or $NR_5R_5'$, one of U, U', V, V', $R_1$, $R_1'$, $R_2$, $R_2'$, $R_3$, $R_3'$, $R_4$, $R_4'$, $R_6$, $R_6'$ is a linking group independently selected from the group consisting of —$(CR_5R_6)_m(Aa)r(CR_7R_8)_n(OCH_2CH_2)_rQ$, —$(CR_5R_6)_m(CR_7R_8)_n(Aa)_r(CH_2CH_2)_rQ$, -$(Aa)r(CR_5R_6)_m(CR_7R_8)_n(OCH_2CH_2)_rQ$, —$(CR_5R_6)_m(CR_7R_8)_n(OCH_2CH_2)_r(Aa)_rQ$, —$(CR_5R_6)_m(CR_7=CR_8)(CR_9R_{10})_n(Aa)_t(OCH_2CH_2)_rQ$, —$(CR_5R_6)_m(NR_{11}CO)(Aa)_t(CR_9R_{10})_n(OCH_2CH_2)_rQ$, —$(CR_5R_6)_m(Aa)_t(NR_{11}CO)(CR_9R_{10})_n(OCH_2CH_2)_rQ$, —$(CR_5R_6)_m(OCO)(Aa)_t(CR_9R_{10})_n(OCH_2CH_2)_rQ$, —$(CR_5R_6)_m(OCNR_7)(Aa)_t(CR_9R_{10})_n(OCH_2CH_2)_rQ$, —$(CR_5R_6)_m(CO)(Aa)_r(CR_9R_{10})_n(OCH_2CH_2)_rQ$, —$(CR_5R_6)_m(NR_{11}CO)(Aa)_t(CR_9R_{10})_n(OCH_2CH_2)_rQ$, —$(CR_5R_6)_m(OCO)(Aa)_t(CR_9R_{10})_n(OCH_2CH_2)_rQ$, —$(CR_5R_6)_m(OCNR_7)(Aa)_t(CR_9R_{10})_n(OCH_2CH_2)_rQ$, —$(CR_5R_6)_m(CO)(Aa)_t(CR_9R_{10})_n(OCH_2CH_2)_rQ$, —$(CR_5R_6)_m$-phenyl-$CO(Aa)_t(CR_7R_8)_nQ$, —$(CR_5R_6)_m$-furyl-$CO$-$(Aa)_t(CR_7R_8)_nQ$, —$(CR_5R_6)_m$-oxazolyl-$CO(Aa)_t(CR_7R_8)_nQ$, —$(CR_5R_6)_m$-thiazolyl-$CO(Aa)_t$-$(CCR_7R_8)_nQ$, —$(CR_5R_6)_t$-thienyl-$CO(CR_7R_8)_nQ$, —$(CR_5R_6)_t$imidazolyl-$CO(CR_7R_4)_nQ$, —$(CR_5R_6)_t$morpholino-$CO(Aa)_t(CR_7R_8)_nQ$, —$(CR_5R_6)_t$piperazino-$CO(Aa)_t(CR_7R_8)_nQ$, —$(CR_5R_6)_t$—N-methylpiperazin-$CO(Aa)_t(CR_7R_8)_nQ$, —$(CR_5R_6)_m$-$(Aa)_t$phenyl-Q, —$(CR_5R_6)_m$-$(Aa)_t$furyl-Q, —$(CR_5R_6)_m$-oxazolyl$(Aa)_t$-Q, —$(CR_5R_6)_m$-thiazolyl$(Aa)_t$-Q, —$(CR_5R_6)_m$-thienyl-$(Aa)_tQ$, —$(CR_5R_6)_m$-imidazolyl$(Aa)_t$-Q, —$(CR_5R_6)_m$-morpholino-$(Aa)_tQ$, —$(CR_5R_6)_m$-piperazino-$(Aa)_tQ$, —$(CR_5R_6)_m$—N-methylpiperazino-$(Aa)_tQ$, —$K(CR_5R_6)_m(Aa)r(CR_7R_8)_n(OCH_2CH_2)_tQ$, —$K(CR_5R_6)_m(CR_7R_8)_n(Aa)_r(OCH_2CH_2)_tQ$, —$K(Aa)r(CR_5R_6)_m(CR_7R_8)_n(OCH_2CH_2)_rQ$, —$K(CR_5R_6)_m(CR_7R_8)_n(OCH_2CH_2)_r(Aa)_tQ$, —$K(CR_5R_6)_m(CR_7=CR_8)(CR_9R_{10})_n(Aa)(OCH_2CH_2)_rQ$, —$K(CR_5R_6)_m(NR_{11}CO)(Aa)_t(CR_9R_{10})_n(OCH_2CH_2)_rQ$, —$K(CR_5R_6)_m(Aa)_t(NR_{11}CO)(CR_9R_{10})_n(OCH_2CH_2)_rQ$, —$K(CR_5R_6)_m(OCO)(Aa)_t(CR_9R_{10})_n(OCH_2CH_2)_rQ$, —$K(CR_5R_6)_m(OCNR_7)(Aa)_t(CR_9R_{10})_n(OCH_2CH_2)_rQ$, —$K(CR_5R_6)_m(CO)(Aa)_t(CR_9R_{10})_n(OCH_2CH_2)_rQ$, —$K(CR_5R_6)_m(NR_{11}CO)(Aa)_t(CR_9R_{10})_n(OCH_2CH_2)_rQ$, —$K(CR_5R_6)_m(OCO)(Aa)_t(CR_9R_{10})_n(OCH_2CH_2)_rQ$, —$K(CR_5R_6)_m(OCNR_7)(Aa)_t(CR_9R_{10})_n(OCH_2CH_2)_rQ$, —$K(CR_5R_6)_m(CO)(Aa)_t(CR_9R_{10})_n(OCH_2CH_2)_rQ$, —$K(CR_5R_6)_m$-phenyl-$CO(Aa)_t(CR_7R_8)_nQ$, —$K(CR_5R_6)_m$-furyl-$CO(Aa)_t(CR_7R_8)_nQ$, —$K(CR_5R_6)_m$-oxazolyl-$CO(Aa)_t(CR_7R_8)_nQ$, —$K(CR_5R_6)_m$-thiazolyl-$CO(Aa)_t(CCR_7R_8)_nQ$, —$K(CR_5R_6)_t$-thienyl-$CO(CR_7R_8)_nQ$, —$K(CR_5R_6)_t$-imidazoyl-$CO(CR_7R_8)_nQ$, —$K(CR_5R_6)_t$morpholino-$CO(Aa)_t(CR_7R_8)_nQ$, —$K(CR_5R_6)_t$piperazino-$CO(Aa)_t(CR_7R_8)_nQ$, —$K(CR_5R_6)_t$—N-methylpiperazin-$CO(Aa)_t(CR_7R_8)_nQ$, —$K(CR_5R)_m$-$(Aa)_t$phenyl-Q, —$K(CR_5R_6)_m$-$(Aa)_t$furyl-Q, —$K(CR_5R_6)_m$-oxazolyl$(Aa)_t$-Q, —$K(CR_5R_6)_m$-thiazolyl$(Aa)_t$-Q, —$K(CR_5R_6)_m$-thienyl-$(Aa)_tQ$, —$K(CR_5R_6)_m$-imidazolyl$(Aa)_t$-Q, —$K(CR_5R_6)_m$-morpholino-$(Aa)_tQ$, —$K(CR_5R_6)_m$-piperazino-$(Aa)_tQ$, and —$K(CR_5R_6)_m$N-methylpiperazino-$(Aa)_tQ$;

wherein $R_6$, $R_7$, and $R_5$ are the same or different and are independently chosen from the group consisting of H; halide; $C_1$-$C_5$ alkyl, aryl, alkenyl, alkynyl, ether, ester, amine or amide, which are optionally substituted by one or more halide, CN, $NR_1R_2$, $CF_3$, $OR_1$, Aryl, heterocycle, $S(O)R_1$, $SO_2R_1$, —$CO_2H$, —$SO_3H$, —$OR_1$, —$CO_2R_1$, —$CONR_1$, —$PO_2R_1R_2$, —$PO_3H$ or $P(O)R_1R_2R_3$; K is $NR_1$, O, S, Se, B or heterocycle.

7. The compound according to claim 1 having one of following formulae (XVIII-1)-(XVIII-79):
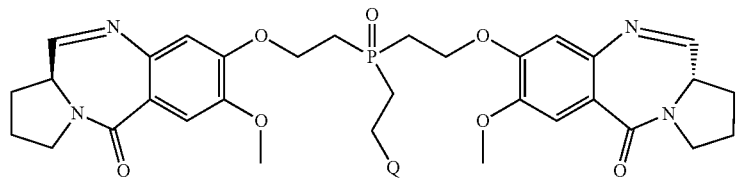
(XVIII-1)
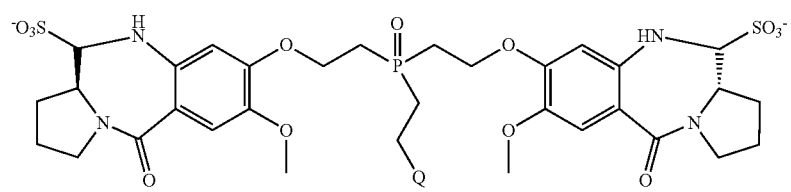
(XVIII-2)
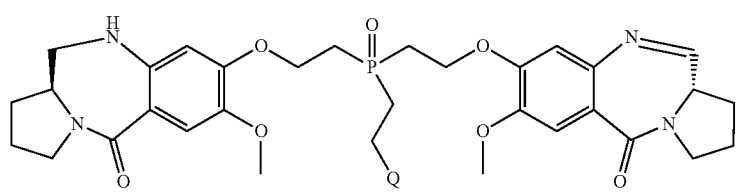
(XVIII-3)
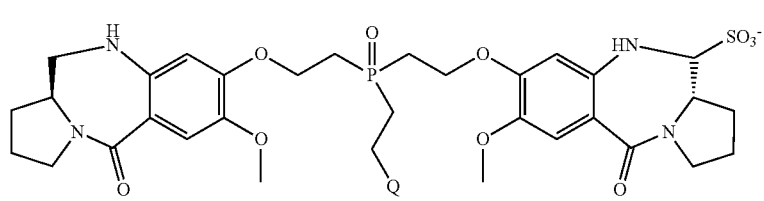
(XVIII-4)
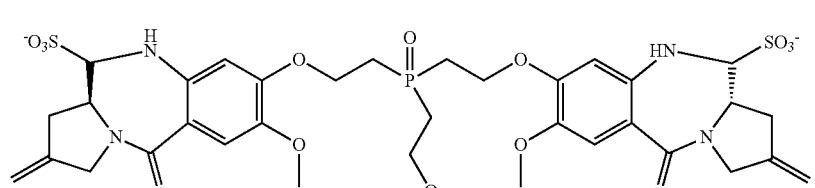
(XVIII-5)
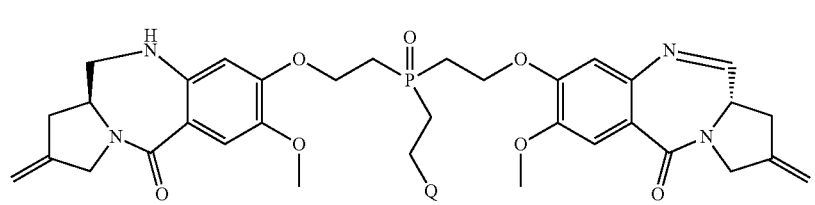
(XVIII-6)
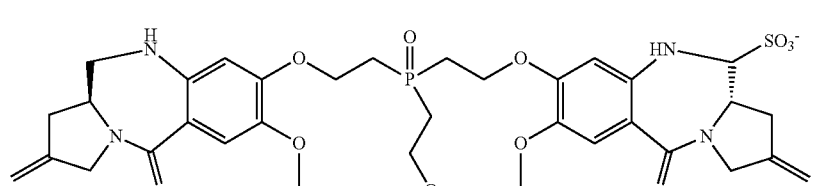
(XVIII-7)
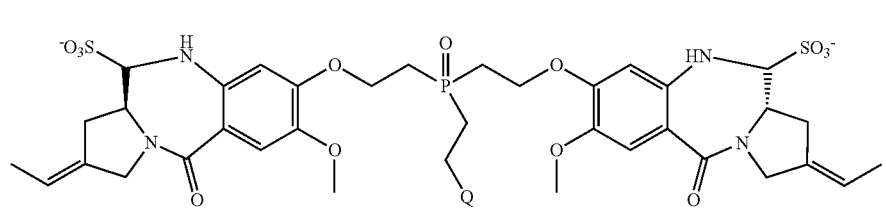
(XVIII-8)

-continued
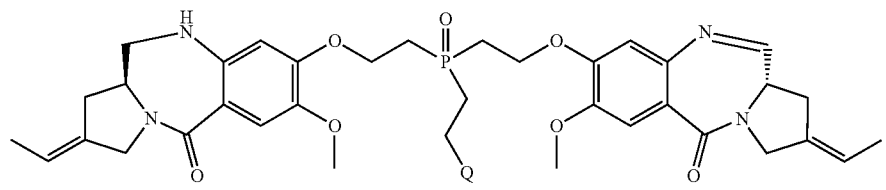
(XVIII-9)
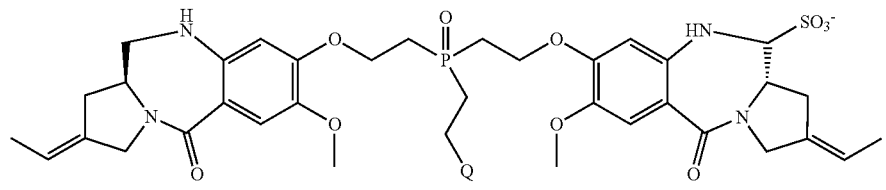
(XVIII-10)
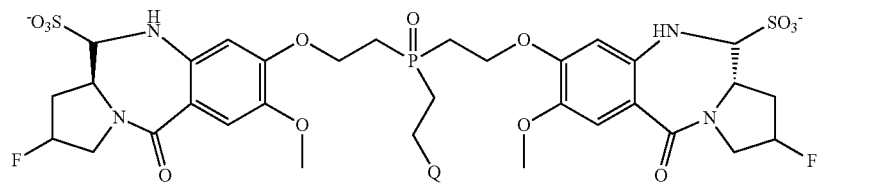
(XVIII-11)
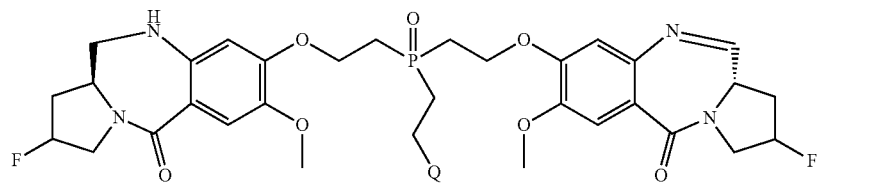
(XVIII-12)
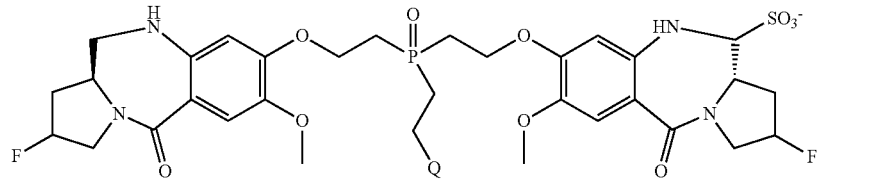
(XVIII-13)
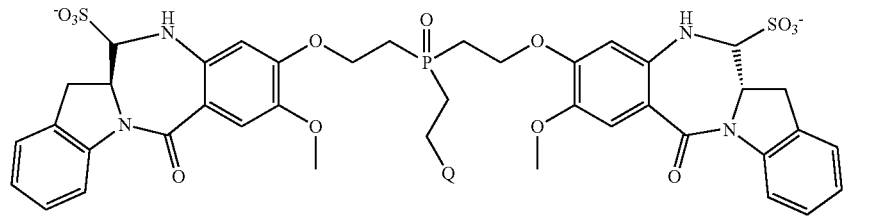
(XVIII-14)
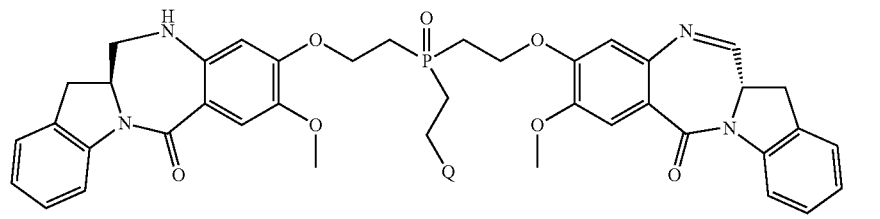
(XVIII-15)
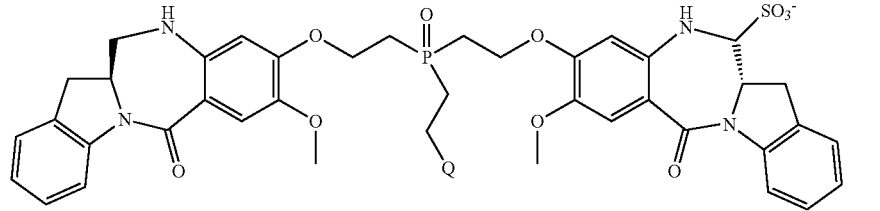
(XVIII-16)

-continued
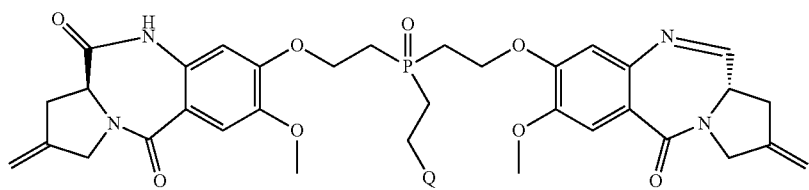
(XVIII-17)
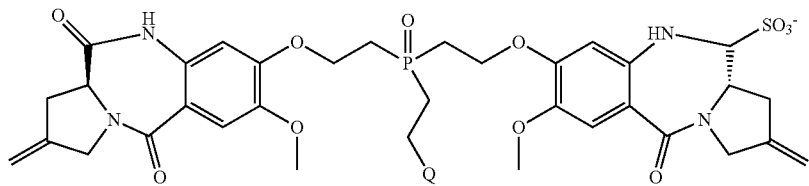
(XVIII-18)
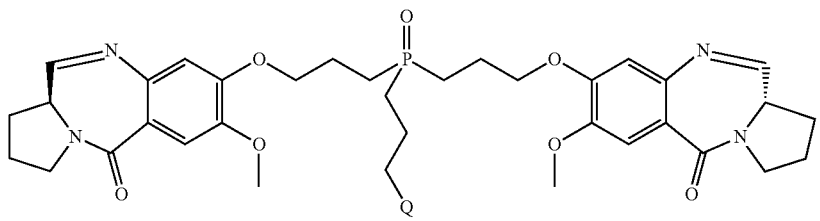
(XVIII-19)
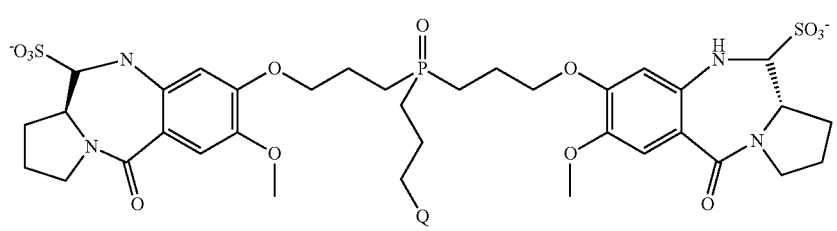
(XVIII-20)
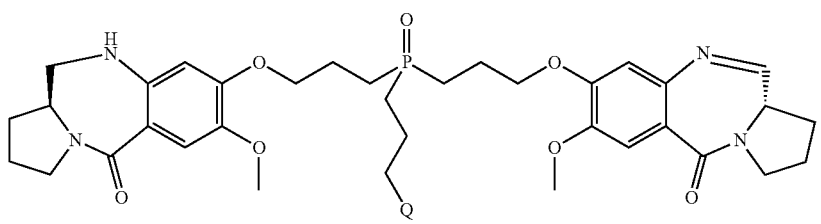
(XVIII-21)
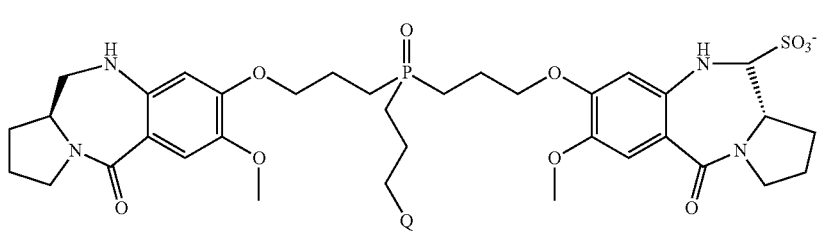
(XVIII-22)
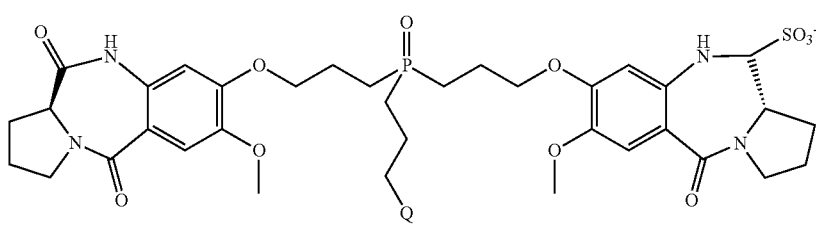
(XVIII-23)

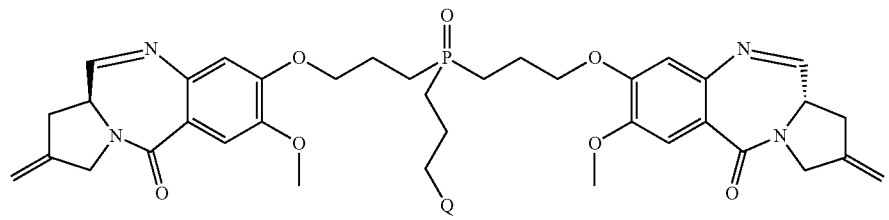
(XVIII-24)
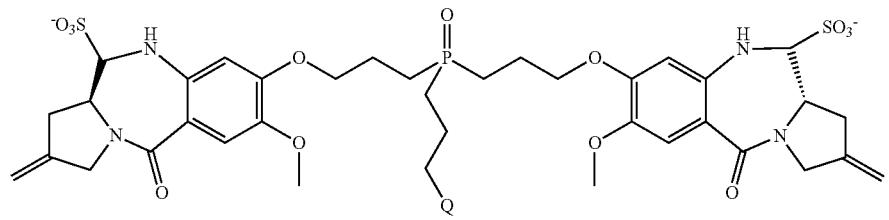
(XVIII-25)
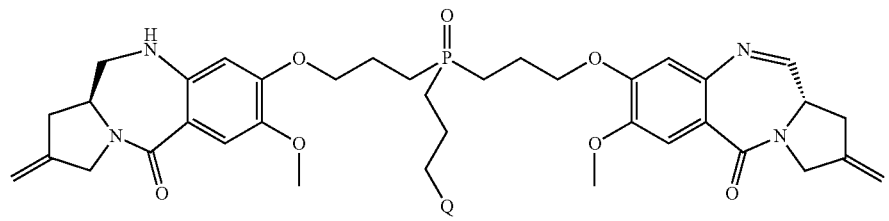
(XVIII-26)
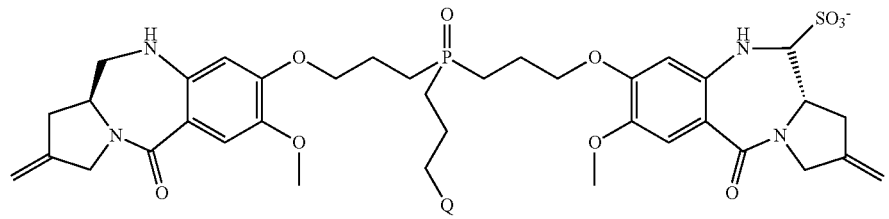
(XVIII-27)
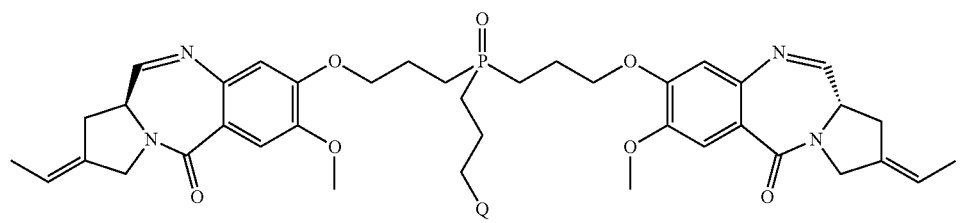
(XVIII-28)
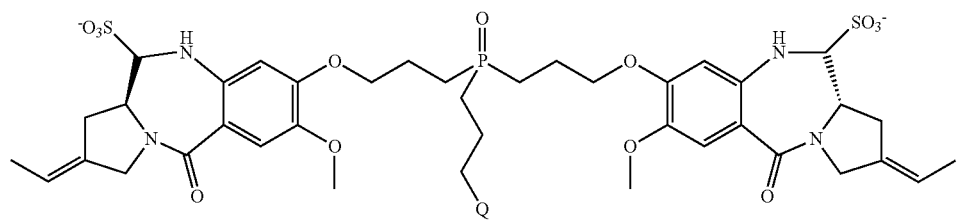
(XVIII-29)
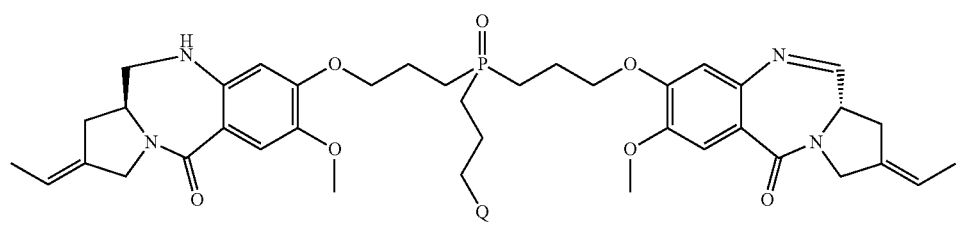
(XVIII-30)

-continued
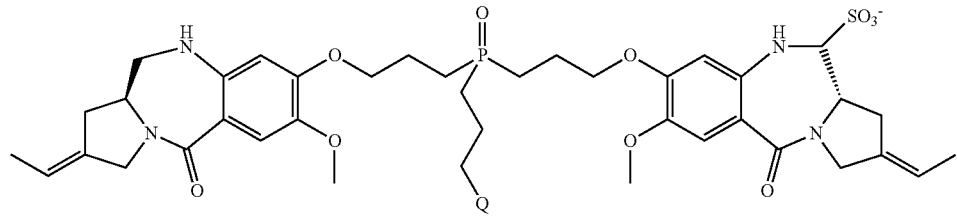
(XVIII-31)
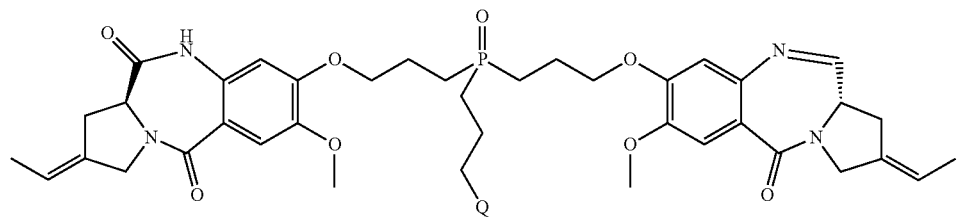
(XVIII-32)
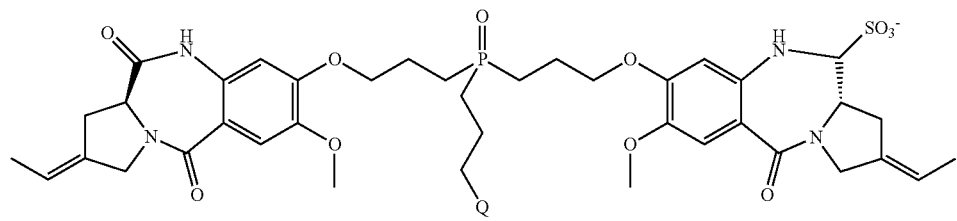
(XVIII-33)
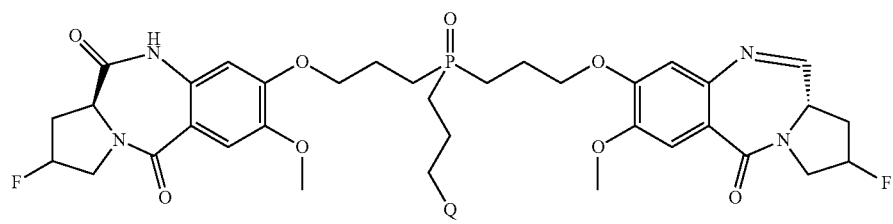
(XVIII-34)
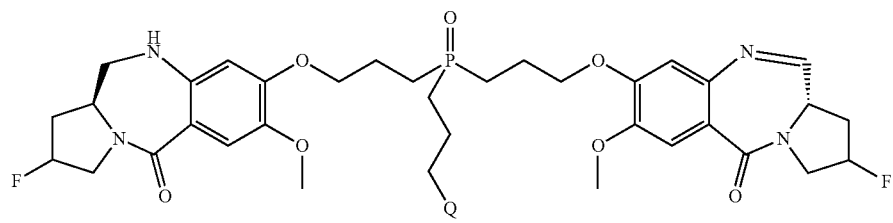
(XVIII-35)
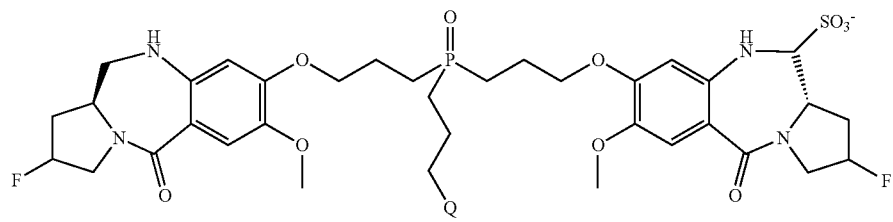
(XVIII-36)
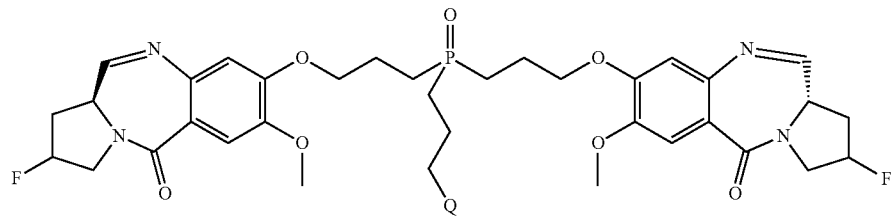
(XVIII-37)

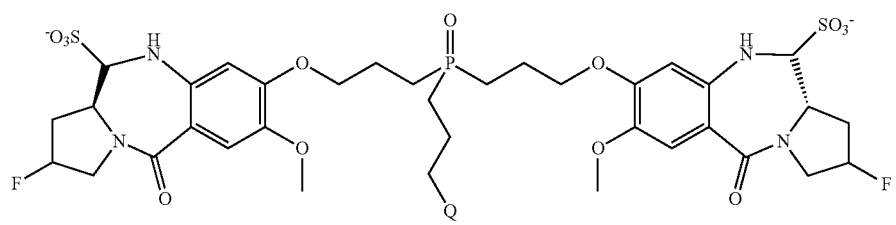
(XVIII-38)
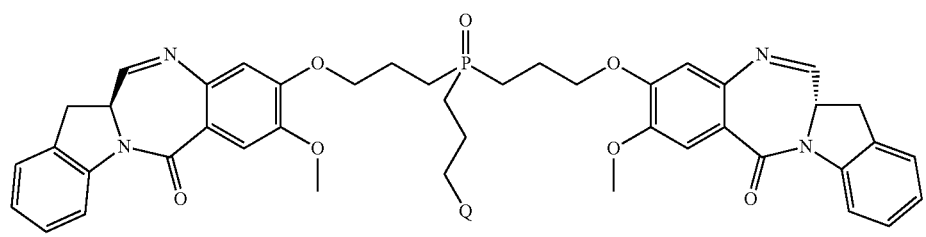
(XVIII-39)
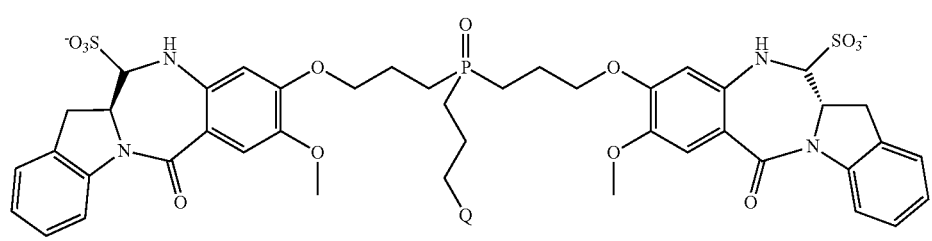
(XVIII-40)
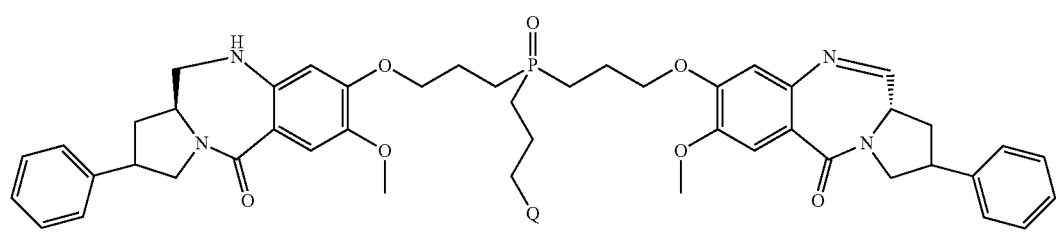
(XVIII-41)
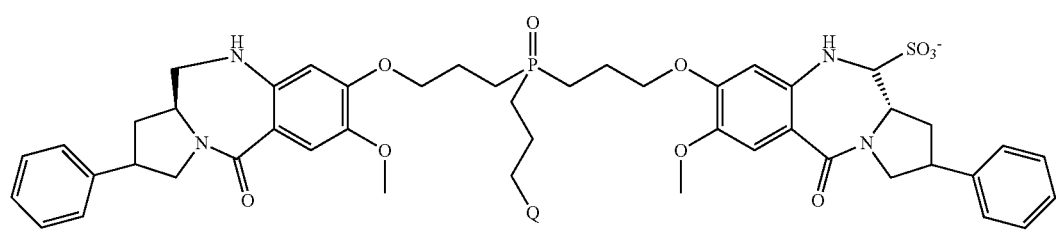
(XVIII-42)
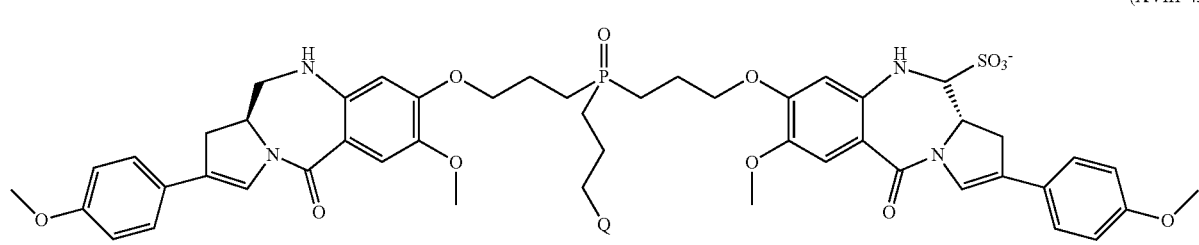
(XVIII-43)

(XVIII-44)
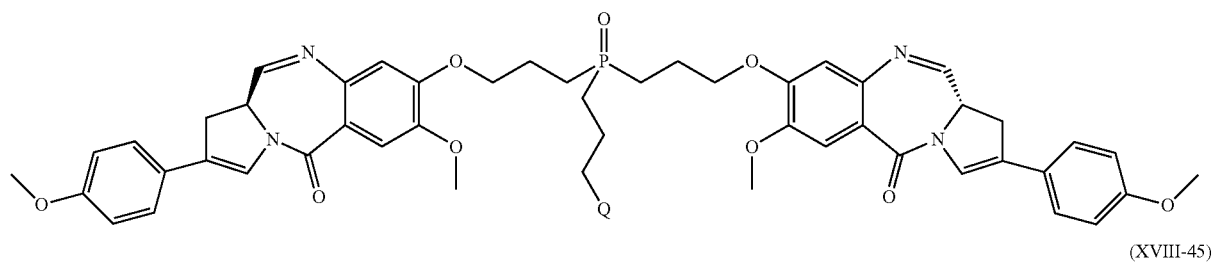
(XVIII-45)
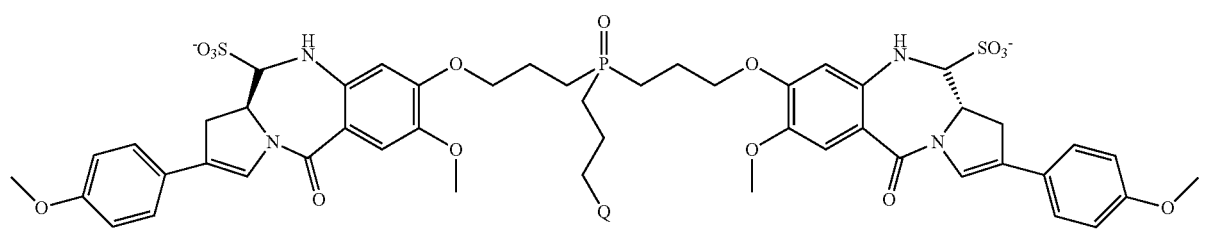
(XVIII-46)
(XVIII-47)
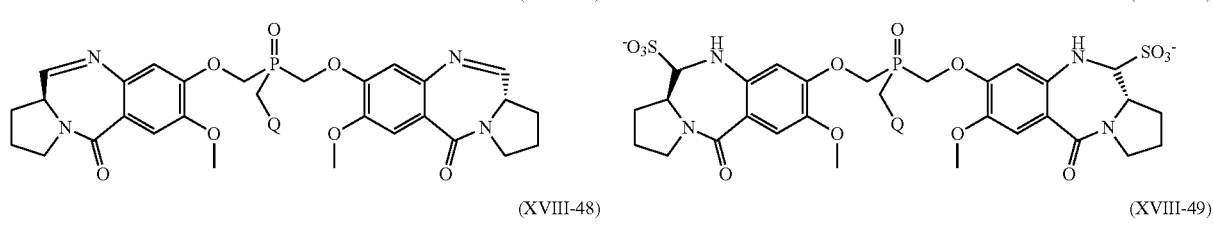
(XVIII-48)
(XVIII-49)
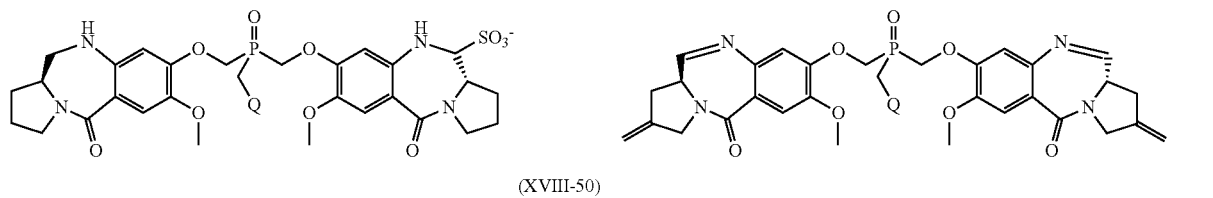
(XVIII-50)
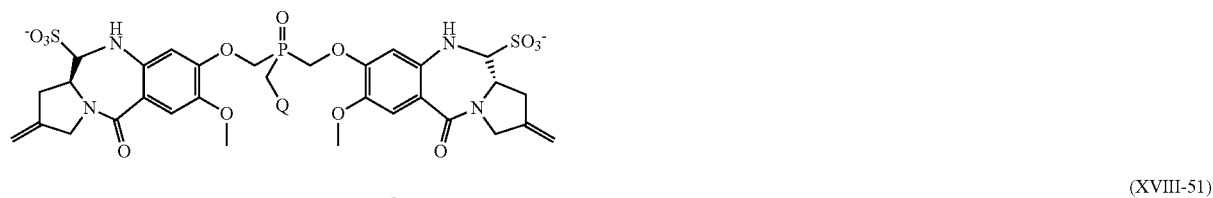
(XVIII-51)
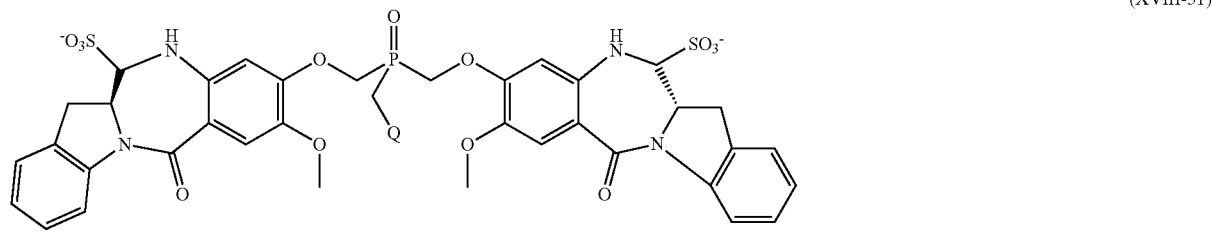
(XVIII-52)
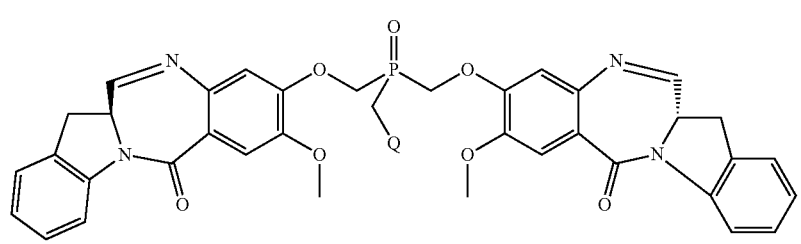

-continued
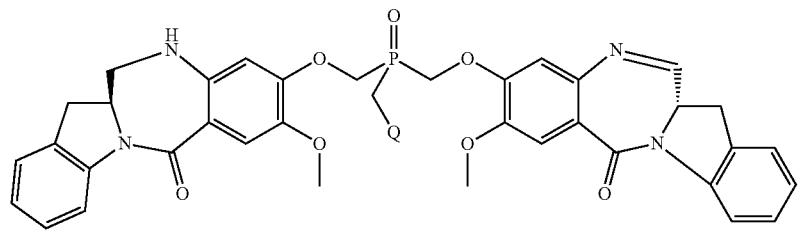
(XVIII-53)
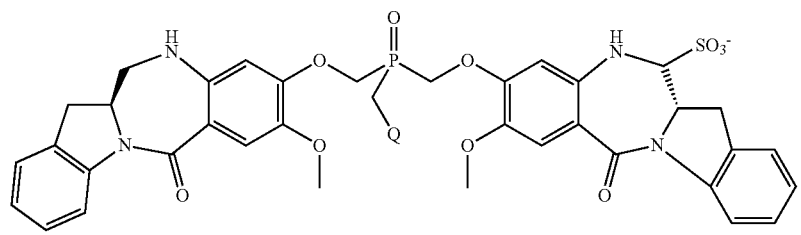
(XVIII-54)
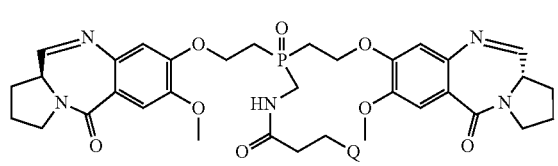
(XVIII-55)
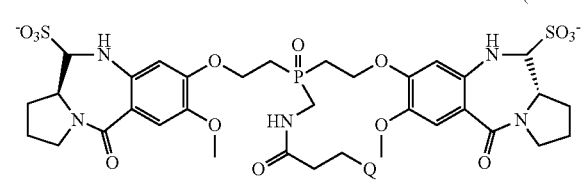
(XVIII-56)
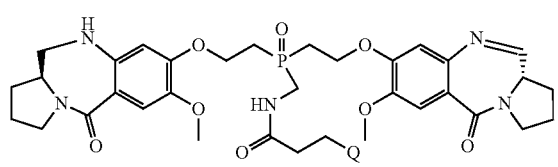
(XVIII-57)
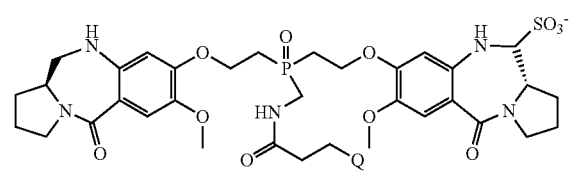
(XVIII-58)
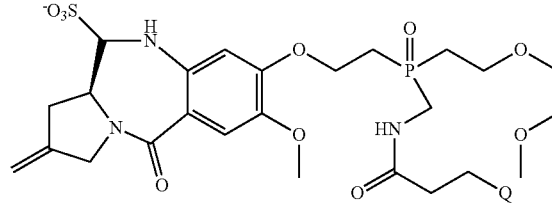
(XVIII-59)
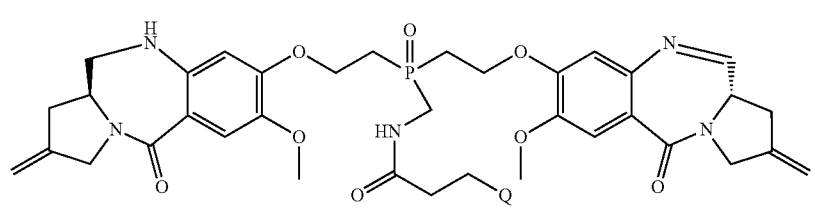
(XVIII-60)
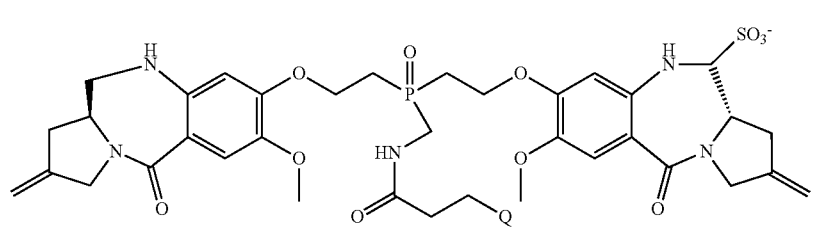
(XVIII-61)

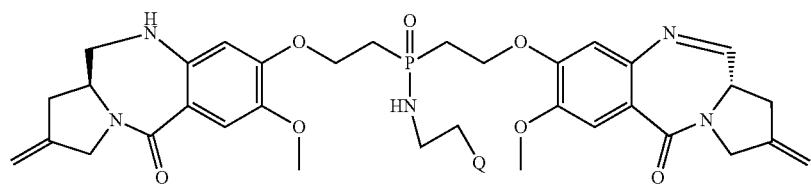
(XVIII-62)
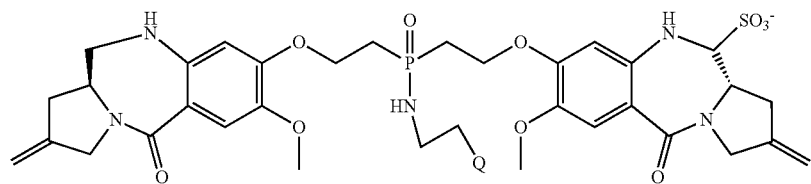
(XVIII-63)
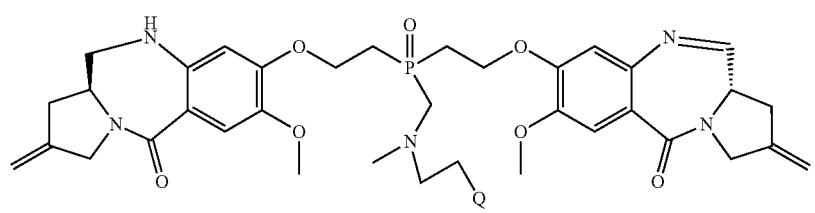
(XVIII-64)
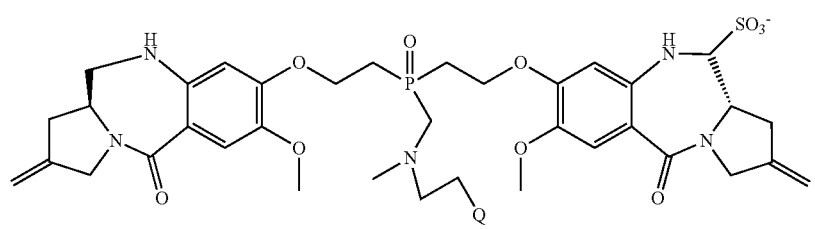
(XVIII-65)
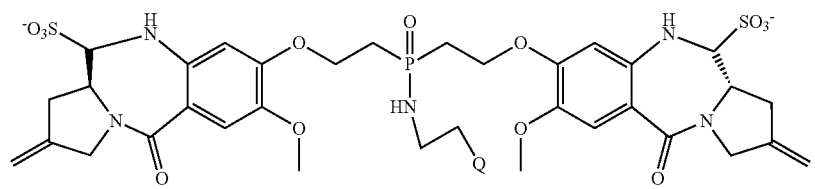
(XVIII-66)
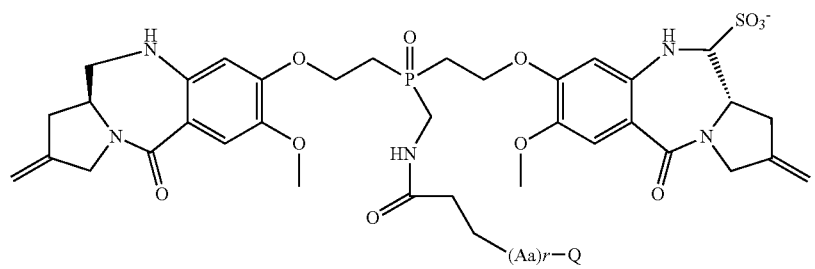
(XVIII-67)
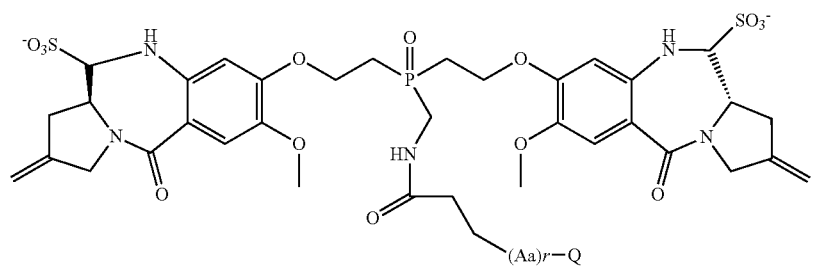
(XVIII-68)

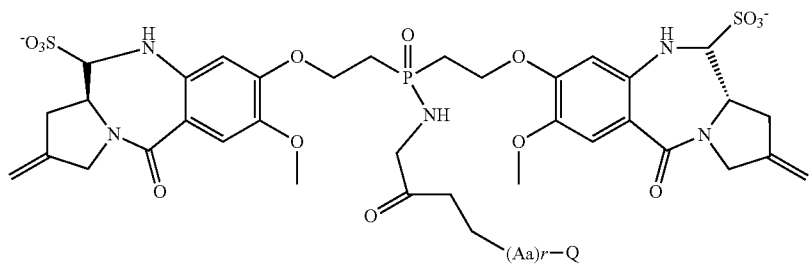
(XVIII-69)
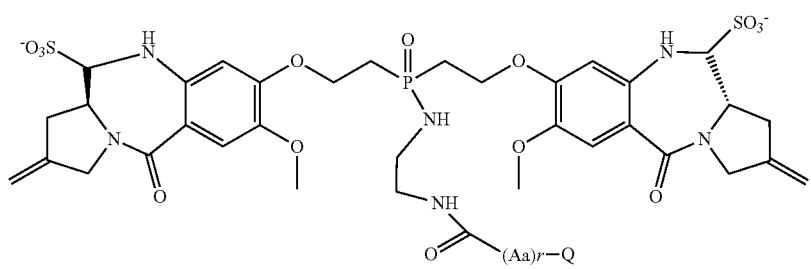
(XVIII-70)
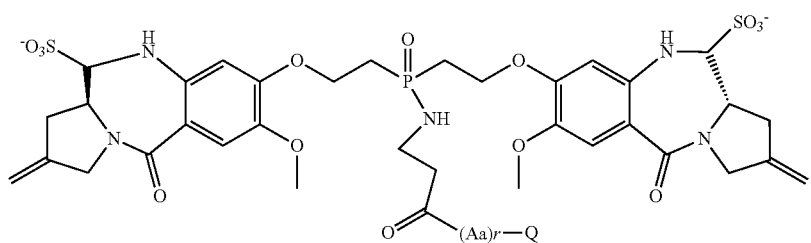
(XVIII-71)
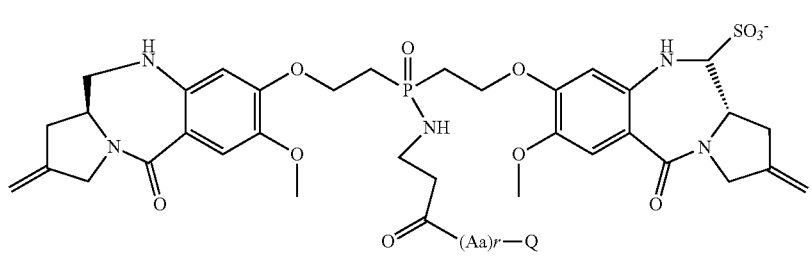
(XVIII-72)
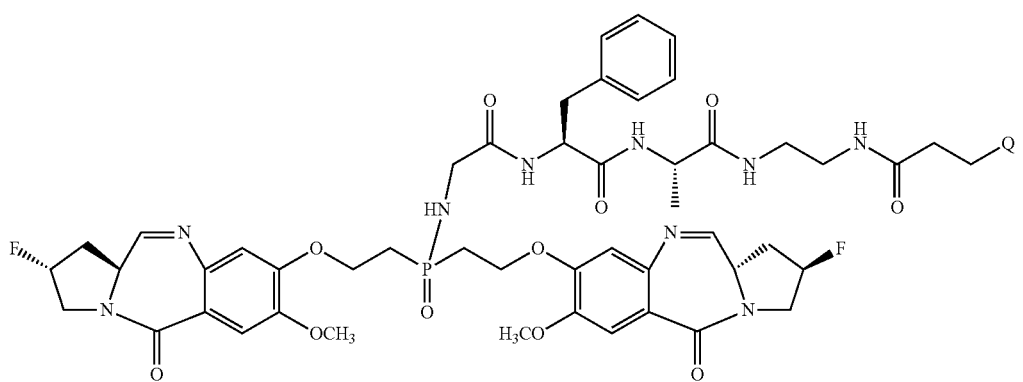
(XVIII-73)

(XVIII-74)
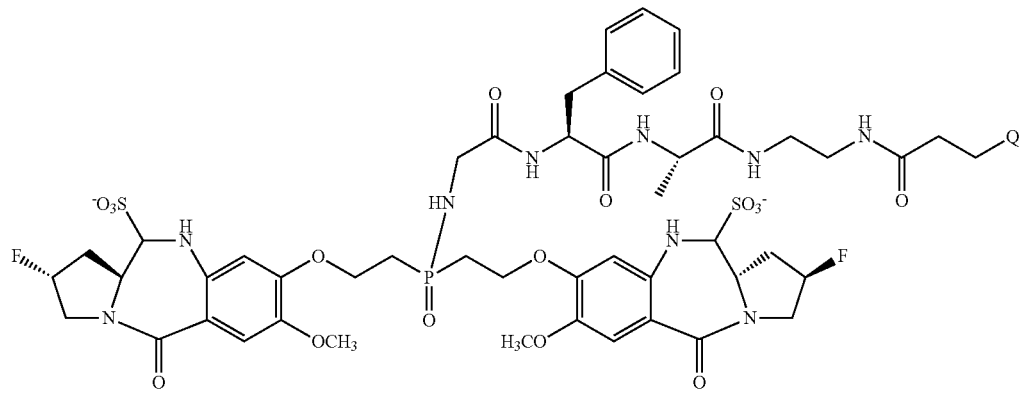
(XVIII-75)
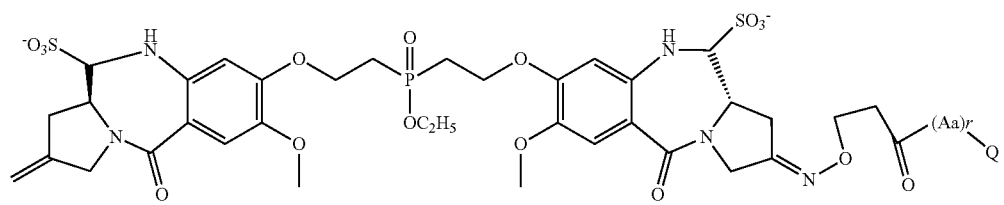
(XVIII-76)
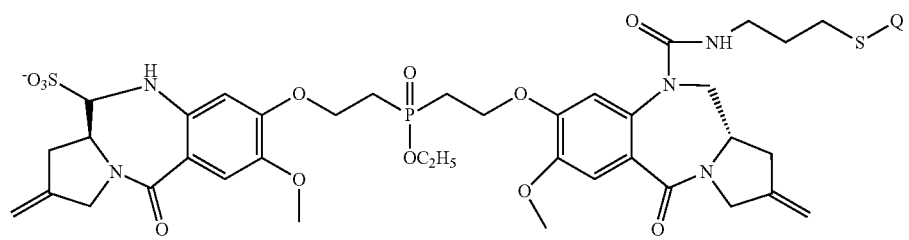
(XVIII-77)
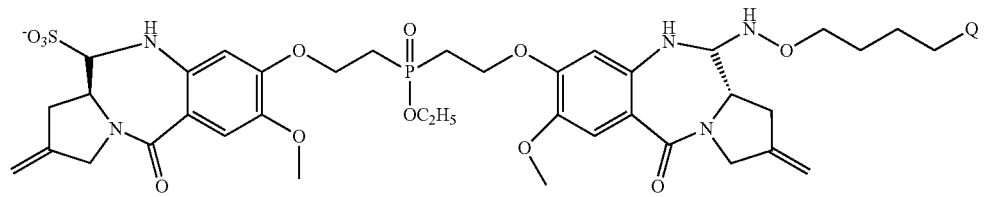
(XVIII-78)
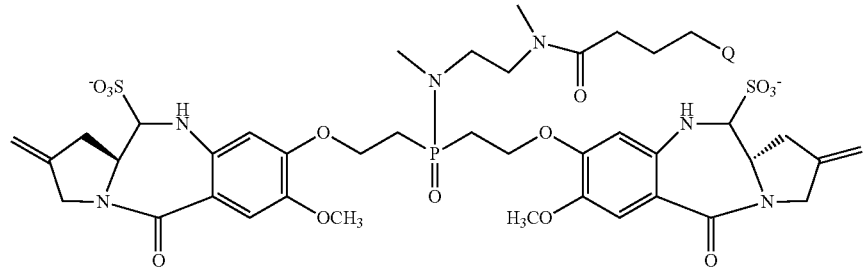
(XVIII-79)
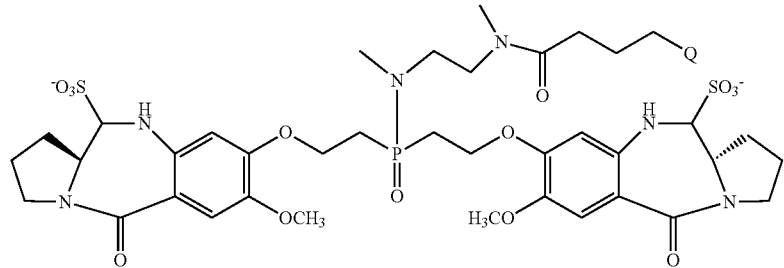

8. The compound according to claim 1 having following formula (XIX), (XX), (XXI), (XXII), (XXIII), or (XXIV):
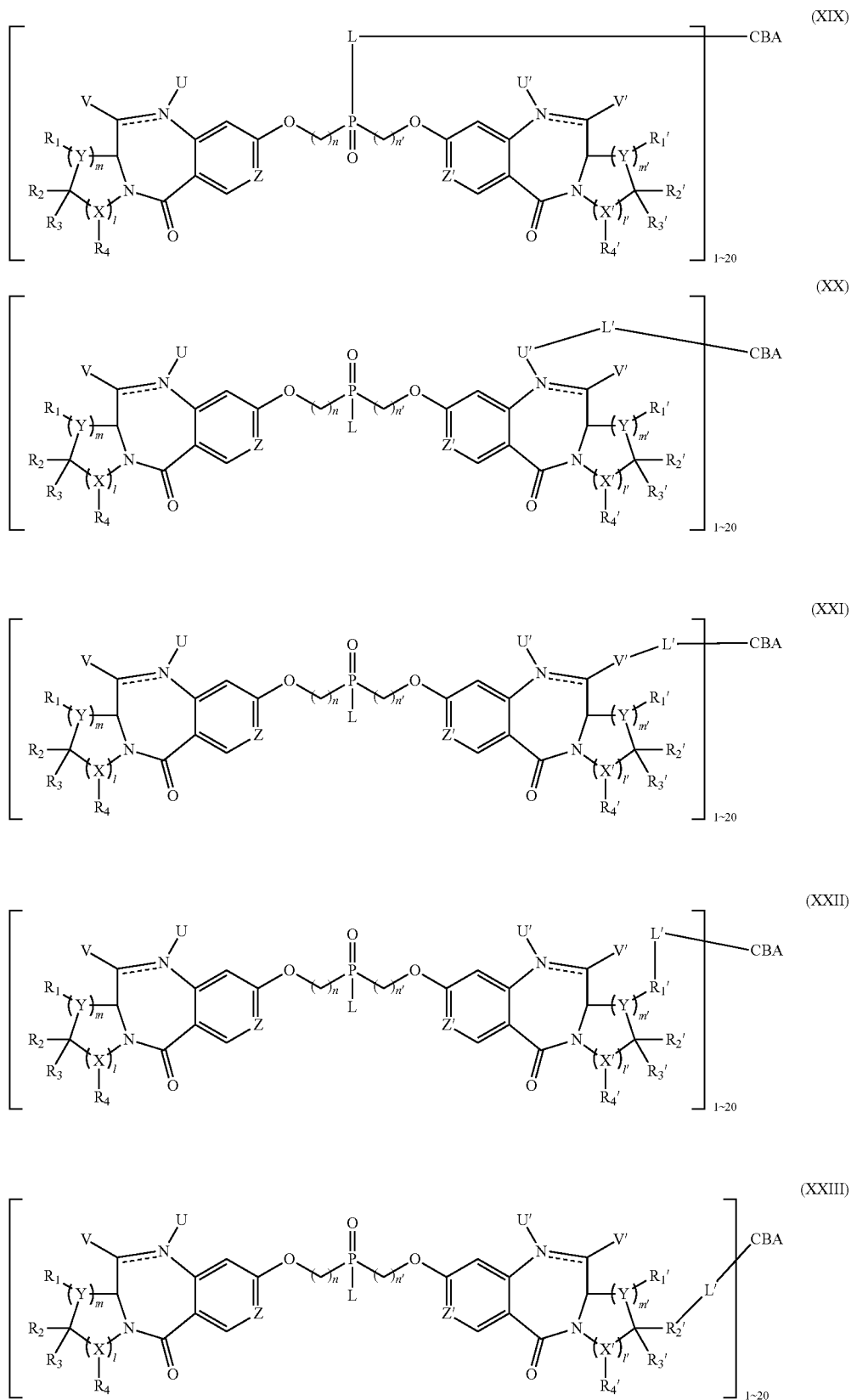

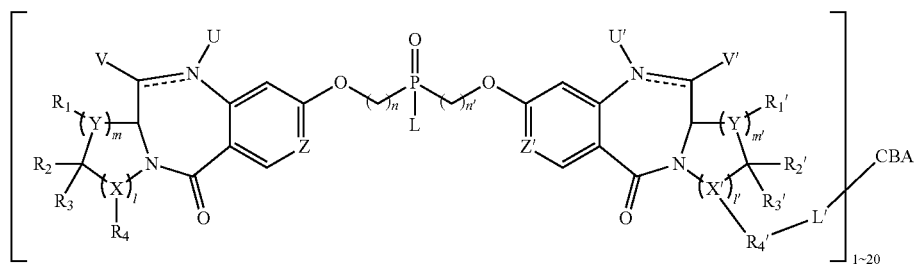

(XXIV)

wherein CBA is a cell binding agent;

L and L' independently have formula of: -Ww-(Aa)r-Tt-; or -Ww-(Aa)r-Tt-Q; or Q-Ww-(Aa)r-Tt-.

9. The compound according to claim 1, wherein the cell binding agent (CBA) is a full-length polyclonal or monoclonal antibody; a single chain antibody; a diabody, a triabody, a fragment of antibody (Fab, Fab', F(ab')$_2$, F$_v$, a fragment produced by a Fab expression library, an anti-idiotypic (anti-Id) antibody, CDR's, and an epitope-binding fragment of any of the above which immuno-specifically bind to cancer cell antigens, viral antigens or microbial antigens; interferon (type I, II, III); a peptide: a lymphokine IL-2, IL-3, IL-4, IL-6, GM-CSF, interferon-gamma (IFN-γ); a hormone, insulin, TRH (thyrotropin releasing hormone), MSH (melanocyte-stimulating hormone), a steroid hormone, androgens, estrogens, melanocyte-stimulating hormone (MSH); a growth factor and a colony-stimulating factor, an epidermal growth factors (EGF), a granulocyte-macrophage colony-stimulating factor (GM-CSF), a transforming growth factors (TGF), TGFα, TGFβ; an insulin and insulin like growth factor (IGF-I, IGF-II) G-CSF, M-CSF and GM-CSF; a vaccinia growth factor (VGF); a fibroblast growth factor (FGFs); a smaller molecular weight protein, poly-peptide, peptide and peptide hormone, bombesin, gastrin, gastrin-releasing peptide; a platelet-derived growth factor; an interleukin and a cytokine, interleukin-2 (IL-2), interleukin-6 (IL-6), a leukemia inhibitory factor, a granulocyte-macrophage colony-stimulating factor (GM-CSF); a vitamin, folate; an apoprotein and a lycoproteis; transferrin; a sugar-binding protein or a lipoprotein, a lectin: a cell nutrient-transport molecule (transferrin); and a small molecular inhibitor, prostate-specific membrane antigen (PSMA) inhibitor and small molecular tyrosine kinase inhibitor (TKI); peptide, or peptide analog, protein including conjugated protein that is able to bind a targeted cell; and a non-peptide or any other cell binding molecule or substance in forms of bioactive polymer, bioactive dendrimer, nanoparticle, liposome, or viral capside.

10. A pharmaceutical composition comprising the compound of claim 1, and a pharmaceutically ac table carrier.

11. The pharmaceutical composition of claim 10, further comprising a synergistic drug, which is a chemotherapeutic agent, or an anti-autoimmune disease agent, or an anti-infectious disease agent, or an anti-viral drug, or an immunotherapeutic agent.

12. The compound according to claim 1, wherein the cell binding agent (CBA) is an antibody, an antibody fragment, a diabody, a tri(a)body, an epidermal growth factor (EGF), a prostate specific membrane antigen (PSMA) inhibitor, a melanocyte stimulating hormone (MSH), a thyroid stimulating hormone (TSH), a polyclonal antibody, a somatostatin, a folate, a matriptase inhibitor, an estrogen, an estrogen analogue, a designed ankyrin repeat proteins (DARPins), an androgen, or an androgen analogue.

13. The compound of claim 12, wherein the antibody is a resurfaced antibody, a resurfaced single chain antibody, or a resurfaced antibody fragment.

14. The compound of claim 12, wherein the antibody is a humanized antibody, a humanized single chain antibody, a humanized antibody fragment, a chimeric antibody, a chimeric antibody fragment, a domain antibody, or a domain antibody fragment.

15. The compound of claim 1, wherein the cell is selected from the group consisting of tumor cells; virus infected cells; microorganism infected cells; parasite infected cells; autoimmune cells; activated cells; myeloid cells; activated T-cells, B cells, or melanocytes; or cells expressing the CD4, CD6, CD19, CD20, CD22, CD30, CD33, CD37, CD38, CD40, CD44, CD51, CD56, CD66, CD70, CD74, CD79b, CD80, CD98, CD105, CD106, CD125, CD221, CD227, CD262, CD309, CD326, CEACAM3, CEACAM5, DLL4, cMet, EpCAM, CanAg, CALLA, EGFR, CTLA4, CXCR4, Endoglin, ERBB2, FCGR1, FOLR, GD2, G-28, GD3 idiotype, Heat shock proteins, HER1, HLA-DR10, HLA-DRB, IGF1R, IL-2 receptor, IL-6R, Integrins (αvβ3, α5β1, α6β4, α11β3, α5β5, αvβ5), MAGE-1, MAGE-2, MAGE-3, MAGE 4, anti-transferrin receptor, p97, MS4A1, MUC1 or MUC1-KLH, MUC16, CA125, CEA, gp100, MART1, MPG, Nucleolin, Neu oncogene product, P21, Paratope of anti-N-glycolylneuraminic acid, PLAP-like testicular alkaline phosphatase, PSMA, PSA, ROBO4, TAG 72, T cell transmembrane protein, Tie (CD202b), TNFRSF10B, TNFRSF13B, TPBG, TRAIL-R1, VCAM-1, VEGF, VEGF-A, VEGF-2 (CD309), Her-2 antigens, Her-3 antigens; and cells expressing insulin growth factor receptors, epidermal growth factor receptors, or folate receptors.

16. A method for preparing the compound of claim 8 comprising:
   forming a covalent bonded CBA-L molecule by modification of a cell-binding agent (CBA) with a crosslinker (L) in an aqueous buffer having pH 3-9 and having 0-30% organic co-solvent to introduce reactive disulfide, maleimido, haloacetyl, hydrazide, nitrile, alkynyl, alkyloxyamino or aldehyde group on the cell-binding agent; and
   reacting the CBA-L molecule with a drug moiety (Drug) of formula (I) in an aqueous buffer having pH 3-9 and having 0-30% organic co-solvent to generate a cell binding agent-drug conjugate.

17. A method for preparing the compound of claim 8 comprising:
   forming a covalent bonded Drug-L molecule by modification of drug moiety (Drug) of the formula (I) with a crosslinker (L) in an organic media or in an aqueous buffer having pH 3-9 and having 0-99% organic co-solvent to introduce a reactive disulfide, maleimido, haloacetyl, hydrazide, nitrile, alkynyl, alkyloxyamino, aldehyde, N-hydroxysuccinimide (NHS) ester or pentafluorophenyl ester group on the drug moiety; and
reacting the Drug-L molecule with a cell binding agent (CBA), or pre-modified CBA in an aqueous buffer having pH 3-9 and having 0-30% organic co-solvent to generate a cell binding agent-drug conjugate.

18. A method for preparing the compound of claim 8 comprising reacting a cell-binding agent with drug moieties of formula (I) bearing reactive function groups of disulfide, maleimido, haloacetyl, hydrazide, nitrile, alkynyl, alkyloxyamino, aldehyde, N-hydroxysuccinimide (NHS) ester or pentafluorophenyl ester in an aqueous buffer having pH 3-9 and having 0-30% organic co-solvent.

\* \* \* \* \*